US010703712B2

(12) United States Patent
Smith et al.

(10) Patent No.: US 10,703,712 B2
(45) Date of Patent: Jul. 7, 2020

(54) FARNESOID X RECEPTOR AGONISTS AND USES THEREOF

(71) Applicant: Metacrine, Inc., San Diego, CA (US)

(72) Inventors: Nicholas D. Smith, San Diego, CA (US); Steven P. Govek, San Diego, CA (US); Johnny Y. Nagasawa, San Diego, CA (US)

(73) Assignee: METACRINE, INC., San Diego, CA (US)

( * ) Notice: Subject to any disclaimer, the term of this patent is extended or adjusted under 35 U.S.C. 154(b) by 0 days.

(21) Appl. No.: 15/758,707

(22) PCT Filed: Sep. 16, 2016

(86) PCT No.: PCT/US2016/052270
§ 371 (c)(1),
(2) Date: Mar. 8, 2018

(87) PCT Pub. No.: WO2017/049173
PCT Pub. Date: Mar. 23, 2017

(65) Prior Publication Data
US 2018/0282263 A1  Oct. 4, 2018

Related U.S. Application Data

(60) Provisional application No. 62/219,430, filed on Sep. 16, 2015.

(51) Int. Cl.
| *C07C 233/80* | (2006.01) |
| *A61K 31/44* | (2006.01) |
| *C07D 333/32* | (2006.01) |
| *C07D 239/34* | (2006.01) |
| *C07D 241/18* | (2006.01) |
| *C07D 263/32* | (2006.01) |
| *C07D 205/04* | (2006.01) |
| *C07D 207/27* | (2006.01) |
| *C07D 275/03* | (2006.01) |
| *C07D 277/34* | (2006.01) |
| *C07D 213/65* | (2006.01) |
| *A61K 45/06* | (2006.01) |
| *C07D 207/12* | (2006.01) |
| *C07D 213/75* | (2006.01) |
| *C07D 207/08* | (2006.01) |
| *C07D 213/68* | (2006.01) |
| *C07D 211/42* | (2006.01) |
| *C07D 211/46* | (2006.01) |

(Continued)

(52) U.S. Cl.
CPC .......... *C07C 233/80* (2013.01); *A61K 31/167* (2013.01); *A61K 31/216* (2013.01); *A61K 31/381* (2013.01); *A61K 31/397* (2013.01); *A61K 31/40* (2013.01); *A61K 31/4015* (2013.01); *A61K 31/421* (2013.01); *A61K 31/425* (2013.01); *A61K 31/426* (2013.01); *A61K 31/445* (2013.01); *A61K 31/4418* (2013.01); *A61K 31/4965* (2013.01); *A61K 31/505* (2013.01); *A61K 45/06* (2013.01); *C07C 233/59* (2013.01); *C07C 233/62* (2013.01); *C07C 233/63* (2013.01); *C07C 237/22* (2013.01); *C07C 237/42* (2013.01); *C07C 271/20* (2013.01); *C07D 205/04* (2013.01); *C07D 207/08* (2013.01); *C07D 207/12* (2013.01); *C07D 207/24* (2013.01); *C07D 207/27* (2013.01); *C07D 211/42* (2013.01); *C07D 211/46* (2013.01); *C07D 211/94* (2013.01); *C07D 213/40* (2013.01); *C07D 213/64* (2013.01); *C07D 213/65* (2013.01); *C07D 213/68* (2013.01); *C07D 213/75* (2013.01); *C07D 213/80* (2013.01); *C07D 239/34* (2013.01); *C07D 241/18* (2013.01); *C07D 263/32* (2013.01); *C07D 275/03* (2013.01); *C07D 277/34* (2013.01); *C07D 333/32* (2013.01); *C07C 2601/04* (2017.05); *C07C 2601/14* (2017.05)

(58) Field of Classification Search
CPC ... C07C 233/80; C07C 2601/04; A61K 31/40; A61K 45/06
See application file for complete search history.

(56) References Cited

U.S. PATENT DOCUMENTS 6,645,980 B1   11/2003  Cuny et al.
7,671,085 B2    3/2010  Downes et al.
(Continued)

FOREIGN PATENT DOCUMENTS

EP    0656355 A1    6/1995
FR    2839974 A1   11/2003
(Continued)

OTHER PUBLICATIONS

Ali et al. Recent advances in the development of farnesoid X receptor agonists. Ann Transl Med 3(1):5 (2015).
(Continued)

*Primary Examiner* — Michael G. Hartley
*Assistant Examiner* — Jagadishwar R Samala
(74) *Attorney, Agent, or Firm* — Wilson Sonsini Goodrich & Rosati

(57) ABSTRACT

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

16 Claims, No Drawings

(51) Int. Cl.

| | | |
|---|---|---|
| *C07D 213/40* | (2006.01) | |
| *C07D 213/64* | (2006.01) | |
| *C07D 213/80* | (2006.01) | |
| *C07C 271/20* | (2006.01) | |
| *C07C 233/63* | (2006.01) | |
| *C07C 237/22* | (2006.01) | |
| *C07C 237/42* | (2006.01) | |
| *C07C 233/59* | (2006.01) | |
| *C07C 233/62* | (2006.01) | |
| *A61K 31/167* | (2006.01) | |
| *A61K 31/216* | (2006.01) | |
| *A61K 31/381* | (2006.01) | |
| *A61K 31/397* | (2006.01) | |
| *A61K 31/40* | (2006.01) | |
| *A61K 31/4015* | (2006.01) | |
| *A61K 31/421* | (2006.01) | |
| *A61K 31/425* | (2006.01) | |
| *A61K 31/426* | (2006.01) | |
| *A61K 31/4418* | (2006.01) | |
| *A61K 31/445* | (2006.01) | |
| *A61K 31/4965* | (2006.01) | |
| *A61K 31/505* | (2006.01) | |
| *C07D 207/24* | (2006.01) | |
| *C07D 211/94* | (2006.01) | |

(56) References Cited

U.S. PATENT DOCUMENTS

| | | |
|---|---|---|
| 2006/0009459 A1 | 1/2006 | Chakka et al. |
| 2008/0081824 A1 | 4/2008 | Zheng et al. |
| 2008/0280916 A1 | 11/2008 | Bilich et al. |
| 2012/0115869 A1* | 5/2012 | Crosignani .......... C07D 257/04 514/236.2 |
| 2015/0258052 A1 | 9/2015 | Evans et al. |
| 2017/0066724 A1 | 3/2017 | Evans et al. |
| 2018/0244606 A1 | 8/2018 | Smith et al. |
| 2018/0251429 A1 | 9/2018 | Smith et al. |
| 2019/0062277 A1 | 2/2019 | Smith et al. |

FOREIGN PATENT DOCUMENTS

| | | |
|---|---|---|
| JP | 2006199656 A | 8/2006 |
| MY | 144229 A | 8/2011 |
| WO | WO-0069810 A1 | 11/2000 |
| WO | WO-0071518 A2 | 11/2000 |
| WO | WO-0185694 A2 | 11/2001 |
| WO | WO-0192226 A1 | 12/2001 |
| WO | WO-0224649 A1 | 3/2002 |
| WO | WO-0230927 A1 | 4/2002 |
| WO | WO-02098852 A2 | 12/2002 |
| WO | WO-03037865 A1 | 5/2003 |
| WO | WO-2004009549 A2 | 1/2004 |
| WO | WO-2004026823 A1 | 4/2004 |
| WO | WO-2004009549 A3 | 6/2004 |
| WO | WO-2004045511 A2 | 6/2004 |
| WO | WO-2004046162 A2 | 6/2004 |
| WO | WO-2004096771 A1 | 11/2004 |
| WO | WO-2005011655 A2 | 2/2005 |
| WO | WO-2005037216 A2 | 4/2005 |
| WO | WO-2005058822 A1 | 6/2005 |
| WO | WO-2007093603 A1 | 8/2007 |
| WO | WO-2007110237 A2 | 10/2007 |
| WO | WO-2008066097 A1 | 6/2008 |
| WO | WO-2008073936 A1 | 6/2008 |
| WO | WO-2008156715 A1 | 12/2008 |
| WO | WO-2009076747 A1 | 6/2009 |
| WO | WO-2009106991 A2 | 9/2009 |
| WO | WO-2011006935 A2 | 1/2011 |
| WO | WO-2011008915 A1 | 1/2011 |
| WO | WO-2012011081 A1 | 1/2012 |
| WO | WO-2012129495 A1 | 9/2012 |
| WO | WO-2014133414 A2 | 9/2014 |
| WO | WO-2015040425 A1 | 3/2015 |
| WO | WO-2015138969 A1 | 9/2015 |
| WO | WO-2016149111 A1 | 9/2016 |
| WO | WO-2017049172 A1 | 3/2017 |
| WO | WO-2017049173 A1 | 3/2017 |
| WO | WO-2017049176 A1 | 3/2017 |
| WO | WO-2017049177 A1 | 3/2017 |
| WO | WO-2018170165 A1 | 9/2018 |
| WO | WO-2018170166 A1 | 9/2018 |
| WO | WO-2018170167 A1 | 9/2018 |
| WO | WO-2018170173 A1 | 9/2018 |
| WO | WO-2018170182 A1 | 9/2018 |

OTHER PUBLICATIONS

Berge et al. Pharmaceutical Salts. Journal of Pharmaceutical Sciences 66(1):1-19 (Jan. 1977).

Bundgaard. Design and Application of Prodrugs. Textbook of Drug Design and Development. Krosgaard-Larsen and Bundgaard. Chapter 5. pp. 113-191 (1991).

Bundgaard. Means to Enhance Penetration: Prodrugs as a Means to Improve the Delivery of Peptide Drugs. Advanced Drug Delivery Review 8:1-38 (1992).

Chemical Abstract compound, STN express RN 1026708-50-8 (Entered STN: Jun. 9, 2008).

Chemical Abstract compound, STN express. RN 1347920-07-3 (Entered STN: Dec. 4, 2011).

Costantino et al. Molecular Dynamics Simulation of the Ligand Binding Domain of Farnesoid X Receptor. Insights into Helix-12 Stability and Coactivator Peptide Stabilization in Response to Agonist Binding. J Med Chem 48:3251-3259 (2005).

Downes et al. A Chemical, Genetic, and Structural Analysis of the Nuclear Bile Acid Receptor FXR. Molecular Cell 11:1079-1092 (2003).

Erb et al. Sequential One-Pot Access to Molecular Diversity through Aniline Aqueous Borylation. J Organ Chem 79:10568-10580 (2014).

Fang et al. Intestinal FXR agonism promotes adipose tissue browning and reduces obesity and insulin resistance. Nat Med 21(2):159-165 (2015).

Fu et al. Discovery of new non-steroidal FXR ligands via a virtual screening workflow based on Phase shape and induced fit docking. Bioorg Med Chem Lett 22(22):6848-6853 (2012).

Fu et al. Fibroblast growth factor 19 increases metabolic rate and reverses dietary and leptin-deficient diabetes. Endocrinology 145:2594-2603 (2004).

Gege et al. Knocking on FXR's Door: The "Hammerhead"-Structure Series of FXR Agonists—Amphiphilic Isoxazoles with Potent In Vitro and In Vivo Activi-ties. Current Topics in Medicinal Chemistry 14:2143-2158 (2014).

Hambruch et al. On the Pharmacology of Farnesoid X Receptor Agonists: Give me an "A", Like an "Acid". Nuclear Receptor Research 3:Article ID 101207 (2016).

Honorio et al. 3D QSAR Comparative molecular field analysis on nonsteroidal farnesoid X receptor activators. J Mol Graph Model 25:921-927 (2007).

Honorio et al. Hologram quantitative structure-activity relationships for a series of farnesoid X receptor activators. Bioorg Med Chem Letts 15:3119-3125 (2005).

Hu et al. Predicting biological Functions of Compounds based on Chemical-Chemical Interactions. PLoS One 6(12):e29491 (2011).

Inagaki et al. Regulation of antibacterial defense in the small intestine by the nuclear bile acid receptor. PNA USA 103:3920-3925 (2006).

Kim et al. Inhibitory Effects of Bile Acides and Synthetic Farnesoid X Receptor Agonists on Rotavirus Replication. J Virol 85(23):12570-12577 (2011).

Lam et al. Bile acids inhibit duodenal secretin expression via orphan nuclear receptor small heterodimer partner (SHP). Am J Physiol Gastrointest Liver Physiol 287:G90-G97 (2009).

Li et al. Microbiome remodelling leads to inhibition of intestinal farnesoid X receptor signalling and decreased obesity. Nat Commun 4:2384 (2013).

(56) References Cited

OTHER PUBLICATIONS

Li et al. Progress in the ligands and their complex structures of farnesoid X receptor. Acta Pharmaceutica Sinica 47(6):704-715 (2012) (English Abstract).

Misawa et al. Discovery and structural development of small molecules that enhance transport activity of bile salt export pump mutant associated with progressive familial intrahepatic cholestasis type 2. Bioorg Med Chem 20:2940-2949 (2012).

Morkved. Intramolecular O→N acyl migration. Preparation of unsymmetrical imides derived from isoquinoline-1-carboxylic acid and substituted picolinic acids. Acta Chemica Scandinavica B 33(7):544-546 (1979).

Nicolaou et al. Discovery and optimization of non-steroidal FXR agonists from natural product-like libraries. Org Biomol Chem 1:908-920 (2003).

PCT/US2016/052270 International Preliminary Report on Patentability dated Mar. 29, 2018.

PCT/US2016/052270 International Search Report and Written Opinion dated Mar. 3, 2017.

Reschly et al. Ligand specificity and evolution of liver X receptors. J Steroid Biochem Mol Biol 110(1-2):83-94 (2008).

Schuster et al. Pharmacophore-based discovery of FXR agonists. Part I: Model development and experimental validation. Bioorg Med Chem 19:7168-7180 (2011).

Science IP—The CAS Search Service. Jul. 17, 2015 (316 pgs).

Steri et al. Antidiabetic sulfonylureas modulate farnesoid X receptor activation and target gene transcription. Future Med Chem 2(4):575-589 (2010).

Widder et al. Section III: Prodrugs Kinetics. Method in Enzymology. 112:309-396 (1985).

Yang et al. Syntheses of nicotinamide riboside and derivatives: effective agents for increasing nicotinamide adenine dinucleotide concentrations in mammalian cells. J. Med. Chem. 50:6458-61 (2007).

Zhang et al. 3D-QSAR studies with the aid of molecular docking for a series of non-steroidal FXR agonists. 17(8):2156-2160 (2007).

Beaulieu et al., Preparation of 2-amido benzoic acid compounds as viral polymerase inhibitors. Chemical Abstracts Service. XP002791354. Database accession No. 2009:771969 (2009).

Boss et al., Preparation of N-benzyl N-piperidin-4-yl benzamides as inhibitors of parasitic aspartyl protease. Chemical Abstracts Service. XP002791357. Database accession No. 2005:570873 (2005).

Boss et al., Preparation of piperidines for the treatment of central nervous system disorders. Chemical Abstracts Service. XP002791361. Database accession No. 2004:80651 (2004).

Boss et al., Preparation of substituted amino-aza-cycloalkanes as anti-malarial agents. Chemical Abstracts Service. XP002791363. Database accession No. 2002:240729 (2002).

Boss et al., Achiral, cheap, and potent inhibitors of Plasmepsins I, II, and IV. ChemMedChem. 1(12):1341-1345 (2006).

Brauer et al., Evolutionary chemistry approach toward finding novel inhibitors of the type 2 diabetes target glucose-6-phosphate translocase. Journal of Combinatorial Chemistry. 7(2):218-226 (2005).

Bromidge et al., Preparation of biaryl compounds having activity at the 5-HT5A receptor. Chemical Abstracts Service. XP002791359. Database accession No. 2004:965222 (2004).

Brough et al., Preparation of resorcinol N-Aryl amide compounds, for use as pyruvate dehydrogenase kinase inhibitors. Chemical Abstracts Service. XP002791352 Database accession No. 2015:512259 (2015).

Fett et al., Preparation of oxadiazole and pyridazine derivatives as inhibitors of biosynthesis of triglycerides. Chemical Abstracts Service. XP002791353 Database accession No. 2012:125764 (2012).

Johnson et al., Preparation of arylheterocyclylamides as motilin antagonists. Chemical Abstracts Service. XP002791364. Database accession No. 2001:833284 (2001).

Ling et al., Preparation of 3-(benzoylamino)propionic acid derivatives as glucagon antagonists/inverse agonists. Chemical Abstracts Service. XP002791365. Database accession No. 2000:824211 (2000).

Mueller et al., Synthesis of plasmepsin II inhibitors as potential antimalarial agents. Chemical Abstracts Service. XP002791362. Database accession No. 2003:524478 (2003).

O'Keefe et al., Preparation of amide and sulfonamidel igands for the estrogen receptor. Chemical Abstracts Service. XP002791360. Database accession No. 2004:267292 (2004).

Poondra et al., Discovery of Indoline-Based, Natural-Product-like Compounds as Probes of Focal Adhesion Kinase Signaling Pathways. Chemical Abstracts Service. XP002791355 Database accession No. 2009:61531 (2009).

Zheng et al., Preparation of substituted piperidines as modulators of chemokine receptor activity. Chemical Abstracts Service. XP002791356. Database accession No. 2008:419604 (2008).

Merk et al. Medicinal chemistry of farnesoid X receptor ligands: from agonists and antagonists to modulators. Future Med Chem 4(8):1015-1036 (2012).

Mueller et al. Synthesis of plasmepsin II inhibitors—potential antimalarial agents. Molecules 8(7):556-564 (2003).

\* cited by examiner

FARNESOID X RECEPTOR AGONISTS AND USES THEREOF

CROSS-REFERENCE

This application is a U.S. National Stage entry of International Application No. PCT/US2016/052270, filed Sep. 16, 2016, which claims benefit of Provisional Application No. 62/219,430, filed Sep. 16, 2015, which are hereby incorporated by reference in their entirety.

FIELD OF THE INVENTION

Described herein are compounds that are farnesoid X receptor agonists, methods of making such compounds, pharmaceutical compositions and medicaments comprising such compounds, and methods of using such compounds in the treatment of conditions, diseases, or disorders associated with farnesoid X receptor activity.

BACKGROUND OF THE INVENTION

Farnesoid X receptor (FXR) is a nuclear receptor highly expressed in the liver, intestine, kidney, adrenal glands, and adipose tissue. FXR regulates a wide variety of target genes involved in the control of bile acid synthesis and transport, lipid metabolism, and glucose homeostasis. FXR agonism is a treatment modality for many metabolic and liver conditions.

SUMMARY OF THE INVENTION

In one aspect, described herein are farnesoid X receptor agonists and uses thereof.

In some embodiments, the farnesoid X receptor agonists described herein have the structure of Formula (I), or a pharmaceutically acceptable salt thereof:

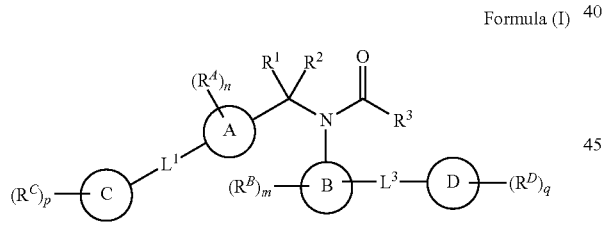

Formula (I)

wherein
- $R^1$ and $R^2$ are each independently selected from H, D, F, $C_1$-$C_4$alkyl, or $C_1$-$C_4$fluoroalkyl;
- or $R^1$ and $R^2$ are taken together with the carbon atom to which they are attached to form a substituted or unsubstituted $C_3$-$C_{10}$cycloalkyl, or substituted or unsubstituted $C_2$-$C_{10}$heterocycloalkyl;
- or $R^1$ and $R^2$ are taken together with the carbon atom to which they are attached to form a carbonyl (C=O);
- $R^3$ is selected from substituted or unsubstituted $C_1$-$C_{10}$alkyl, substituted or unsubstituted $C_2$-$C_{10}$alkenyl, substituted or unsubstituted $C_2$-$C_{10}$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl, wherein if $R^3$ is substituted then $R^3$ is substituted with one or more $R^{12}$ groups;
- each $R^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -L$^5$-L$^6$-R$^{13}$;
- L$^5$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;
- L$^6$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;
- R$^{13}$ is H, halogen, —N(R$^{10}$)$_2$, unsubstituted or substituted $C_1$-$C_{10}$alkyl, unsubstituted or substituted $C_2$-$C_{10}$alkenyl, unsubstituted or substituted $C_2$-$C_{10}$alkynyl, unsubstituted or substituted $C_3$-$C_{10}$cycloalkyl, unsubstituted or substituted $C_2$-$C_{10}$heterocycloalkyl, unsubstituted or substituted aryl, or unsubstituted or substituted heteroaryl;
- ring A is a monocyclic carbocycle, monocyclic heterocycle, or bicyclic heterocycle;
- each $R^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;
- L$^1$ is —X$^1$-L$^2$- or -L$^2$-X$^1$—;
- X$^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;
- L$^2$ is absent or substituted or unsubstituted $C_1$-$C_4$alkylene;
- ring C is monocyclic carbocycle, bicyclic carbocycle, monocyclic heterocycle, or bicyclic heterocycle;
- each $R^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C (=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl, and substituted or unsubstituted monocyclic heteroaryl;

ring B is a monocyclic carbocycle, bicyclic carbocycle, monocyclic heterocycle, or bicyclic heterocycle;

each R$^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

L$^3$ is —X$^2$-L$^4$- or -L$^4$-X$^2$—;

X$^2$ is absent, —O—, —S—, —S(=O)—, —S(=O)$_2$-, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

L$^4$ is absent or substituted or unsubstituted C$_1$-C$_4$alkylene;

ring D is phenyl, bicyclic carbocycle, monocyclic N-containing heterocycloalkyl, monocyclic heteroaryl, or bicyclic heterocycle;

each R$^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, unsubstituted or substituted C$_3$-C$_{10}$cycloalkyl, and substituted or unsubstituted C$_2$-C$_{10}$heterocycloalkyl;

each R$^{10}$ is independently selected from H, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

or two R$^{10}$ on the same N atom are taken together with the N atom to which they are attached to form a N-containing heterocycle;

each R$^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4;
q is 0, 1, 2, 3, or 4.

In some embodiments, the farnesoid X receptor agonists described herein have the structure of Formula (IV), or a pharmaceutically acceptable salt or solvate thereof:

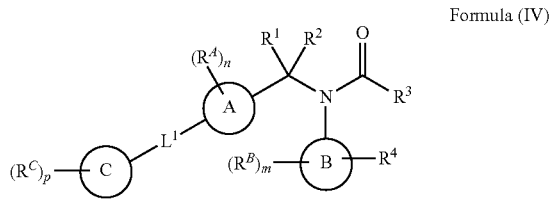

Formula (IV)

wherein
R$^1$ and R$^2$ are each independently selected from H, D, F, C$_1$-C$_4$alkyl, or C$_1$-C$_4$fluoroalkyl;

or R$^1$ and R$^2$ are taken together with the carbon atom to which they are attached to form a substituted or unsubstituted C$_3$-C$_{10}$cycloalkyl, or substituted or unsubstituted C$_2$-C$_{10}$heterocycloalkyl;

or R$^1$ and R$^2$ are taken together with the carbon atom to which they are attached to form a carbonyl (C=O);

R$^3$ is selected from substituted or unsubstituted C$_1$-C$_{10}$alkyl, substituted or unsubstituted C$_2$-C$_{10}$alkenyl, substituted or unsubstituted C$_2$-C$_{10}$alkynyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, wherein if R$^3$ is substituted then R$^3$ is substituted with one or more R$^{12}$ groups;

each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^5$-L$^6$-R$^{13}$ L$^5$ is absent, —O—, —S—, —S(=O)—, —S(=O)$_2$, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;

L$^6$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;

R$^{13}$ is H, halogen, —N(R$^{10}$)$_2$, unsubstituted or substituted C$_1$-C$_{10}$alkyl, unsubstituted or substituted C$_2$-C$_{10}$alkenyl, unsubstituted or substituted C$_2$-C$_{10}$alkynyl, unsubstituted or substituted C$_3$-C$_{10}$cycloalkyl, unsubstituted or substituted C$_2$-C$_{10}$heterocycloalkyl, unsubstituted or substituted aryl, or unsubstituted or substituted heteroaryl;

ring A is a monocyclic carbocycle, monocyclic heterocycle, or bicyclic heterocycle;

each R$^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

L$^1$ is —X$^1$-L$^2$- or -L$^2$-X$^1$—;

X$^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

L$^2$ is absent or substituted or unsubstituted C$_1$-C$_4$alkylene;

ring C is monocyclic carbocycle, bicyclic carbocycle, monocyclic heterocycle, or bicyclic heterocycle;

each R$^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;

ring B is a monocyclic carbocycle, bicyclic carbocycle, monocyclic heterocycle or bicyclic heterocycle;

each R$^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

R$^4$ is C$_2$-C$_{10}$alkenyl; or

R$^4$ is —N(R$^9$)$_2$, -(substituted or unsubstituted C$_1$-C$_6$alkylene)-N(R$^9$)$_2$, —NR$^9$—C(R$^7$)(R$^8$)—CO$_2$R$^{10}$, —NR$^9$-(Substituted or unsubstituted C$_1$-C$_6$alkylene)-N(R$^9$)$_2$—, or -L$^3$-Y;

L$^3$ is —C(R$^5$)(R$^6$)— or —C(R$^5$)(R$^6$)—C(R$^7$)(R$^9$)—;

R$^5$ and R$^7$ are each independently selected from H, D, C$_1$-C$_4$alkyl and C$_3$-C$_6$cycloalkyl;

or R$^5$ and R$^7$ are taken together with the intervening atoms to form a double bond;

or R$^5$ and R$^7$ are taken together with the intervening atoms to form an epoxide or a substituted or unsubstituted C$_3$-C$_6$cycloalkyl;

R$^6$ and R$^8$ are each independently selected from H, D, C$_1$-C$_4$alkyl or C$_3$-C$_6$cycloalkyl;

Y is —CH$_2$N(R$^9$)$_2$, —C(=O)N(R$^9$)$_2$,

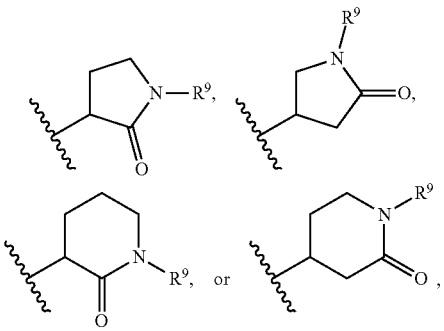

each R$^9$ is independently selected from H, substituted or unsubstituted C$_1$-C$_6$alkyl, substituted or unsubstituted C$_1$-C$_6$heteroalkyl, substituted or unsubstituted C$_2$-C$_6$alkenyl, substituted or unsubstituted C$_3$-C$_6$cycloalkyl, substituted or unsubstituted heterocycle, —S(=O)$_2$R$^{11}$, —S(=O)$_2$N(R$^{10}$)$_2$, —C(=O)R$^{11}$, —CO$_2$R$^{10}$, or —C(=O)N(R$^{10}$)$_2$;

or two R$^9$ on the same N atom are taken together with the N atom to which they are attached to form a N-containing heterocycle;

each R$^{10}$ is independently selected from H, substituted or unsubstituted C$_1$-C$_6$alkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

or two R$^{10}$ on the same N atom are taken together with the N atom to which they are attached to form a N-containing heterocycle;

each R$^{11}$ is independently selected from substituted or unsubstituted C$_1$-C$_6$alkyl, substituted or unsubstituted C$_1$-C$_6$heteroalkyl, substituted or unsubstituted C$_1$-C$_6$fluoroalkyl, substituted or unsubstituted C$_3$-C$_6$cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In another aspect, described herein is a method of treating a disease or condition in a mammal that would benefit from FXR agonism comprising administering a compound as described herein, or pharmaceutically acceptable salt, or solvate thereof, to the mammal in need thereof. In some embodiments, the disease or condition is a metabolic condition. In some embodiments, the disease or condition is a liver condition.

In some embodiments, the compound is administered to the mammal by intravenous administration, subcutaneous administration, oral administration, inhalation, nasal administration, dermal administration, or ophthalmic administration.

In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In one aspect, described herein is a method for the treatment or prevention of a metabolic or liver condition in a mammal comprising administering a therapeutically effective amount of a compound described herein, or a pharmaceutically acceptable salt, or solvate thereof, to the mammal in need thereof. In other embodiments, the metabolic or liver condition is amenable to treatment with a FXR agonist. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound of Formula (I) described herein, or a pharmaceutically acceptable salt thereof. In various embodiments, each agent is administered in any order, including simultaneously.

In any of the embodiments disclosed herein, the mammal or subject is a human.

In some embodiments, compounds provided herein are administered to a human.

In some embodiments, compounds provided herein are orally administered.

In some embodiments, described herein is method of treating or preventing a metabolic disorder in a subject, comprising: administering to a gastrointestinal tract of the subject a therapeutically effective amount of one or more of the compounds described herein, or a pharmaceutically acceptable salt or solvate thereof, thereby activating farnesoid X receptors (FXR) in the intestines, and treating or preventing a metabolic disorder in the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound. In some embodiments, the method reduces or prevents diet-induced weight gain. In some embodiments, the method increases a metabolic rate in the subject. In some embodiments, the increasing the metabolic rate comprises enhancing oxidative phosphorylation in the subject. In some embodiments, the method further comprises improving glucose and/or lipid homeostasis in the subject. In some embodiments, the method results in no substantial change in food intake and/or fat consumption in the subject. In some embodiments, the method results in no substantial change in appetite in the subject. In some embodiments, the metabolic disorder is selected from obesity, diabetes, insulin resistance, dyslipidemia or any combination thereof. In some embodiments, the metabolic disorder is non-insulin dependent diabetes mellitus. In some embodiments, the method protects against diet-induced weight gain, reduces inflammation, enhances thermogenesis, enhances insulin sensitivity in the liver, reduces hepatic steatosis, promotes activation of BAT, decreases blood glucose, increases weight loss, or any combination thereof. In some embodiments, the method enhances insulin sensitivity in the liver and promotes brown adipose tissue (BAT) activation. In some embodiments, the method further comprises administering to the subject an insulin sensitizing drug, an insulin secretagogue, an alpha-glucosidase inhibitor, a glucagon-like peptide (GLP) agonist, a dipeptidyl peptidase-4 (DPP-4) inhibitor, nicotinamide ribonucleoside, an analog of nicotinamide ribonucleoside, or combinations thereof.

In some embodiments, described herein is a method of treating or preventing inflammation in an intestinal region of a subject, comprising: administering to a gastrointestinal tract of the subject a therapeutically effective amount of one or more of the compounds described herein, or a pharmaceutically acceptable salt or solvate thereof, thereby activating FXR receptors in the intestines, and thereby treating or preventing inflammation in the intestinal region of the subject. In some embodiments, the compound's absorption is preferentially restricted to within the intestines. In some embodiments, the method substantially enhances FXR target gene expression in the intestines while not substantially enhancing FXR target gene expression in the liver or kidney. In some embodiments, the inflammation is associated with a clinical condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis or any combination thereof. In some embodiments, the one or more FXR target genes comprises IBABP, OSTα, Per1, FGF15, FGF19, SHP or combinations thereof. In some embodiments, the method further comprises administering a therapeutically effective amount of an antibiotic therapy to the subject, wherein the method treats or prevents inflammation associated with pseudomembranous colitis in the subject. In some embodiments, the method further comprises administering to the subject a therapeutically effective amount of an oral corticosteroid, other anti-inflammatory or immunomodulatory therapy, nicotinamide ribonucleoside, an analog of nicotinamide ribonucleoside, or combinations thereof. In some embodiments, the method increases HSL phosphorylation and β3-adrenergic receptor expression. In some embodiments, a serum concentration of the compound in the subject remains below its $EC_{50}$ following administration of the compound.

In some embodiments, described herein is a method of treating or preventing a cell proliferation disease in a subject, comprising administering to a gastrointestinal tract of the subject a therapeutically effective amount of one or more of the compounds described herein or a pharmaceutically acceptable salt or solvate thereof. In some embodiments, the cell proliferation disease is an adenocarcinoma. In some embodiments, the adenocarcinoma is a colon cancer. In some embodiments, the treating the adenocarcinoma reduces the size of the adenocarcinoma, the volume of the adenocarcinoma, the number of adenocarcinomas, cachexia due to the adenocarcinoma, delays progression of the adenocarcinoma, increases survival of the subject, or combinations thereof. In some embodiments, the method further comprises administering to the subject an additional therapeutic compound selected from the group consisting of a chemotherapeutic, a biologic, a radiotherapeutic, or combinations thereof.

In some embodiments, described herein is a method of treating or preventing a liver disease or condition in a subject, comprising administering to the subject a therapeutically effective amount of one or more of the compounds described herein, or a pharmaceutically acceptable salt or solvate thereof. In some embodiments, the liver disease or condition is an alcoholic or non-alcoholic liver disease. In some embodiments, the liver disease or condition is primary biliary cirrhosis, primary sclerosing cholangitis, cholestasis, nonalcoholic steatohepatitis (NASH), or nonalcoholic fatty liver disease (NAFLD). In some embodiments, the alcoholic liver disease or condition is fatty liver (steatosis), cirrhosis, or alcoholic hepatitis. In some embodiments, the non-alcoholic liver disease or condition is nonalcoholic steatohepatitis (NASH), or nonalcoholic fatty liver disease (NAFLD). In some embodiments, the non-alcoholic liver disease or condition is intrahepatic cholestasis or extrahepatic cholestasis.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for the treatment, prevention or amelioration of one or more symptoms of a disease or condition that would benefit from FXR agonism, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

The nuclear hormone receptor farnesoid X receptor (also known as FXR or nuclear receptor subfamily 1, group H, member 4 (NR1H4)) (OMIM: 603826) functions as a regulator for bile acid metabolism. FXR is a ligand-activated transcriptional receptor expressed in diverse tissues including the adrenal gland, kidney, stomach, duodenum, jejunum, ileum, colon, gall bladder, liver, macrophages, and white and brown adipose tissue. Bile acids function as endogenous ligands for FXR such that enteric and systemic release of bile acids induces FXR-directed changes in gene expression networks. Bile acids are the primary oxidation product of cholesterol, and in some cases, upon secretion into the intestines, are regulators of cholesterol absorption. The rate-limiting step for conversion of cholesterol into bile acids is catalyzed by cytochrome p450 enzyme cholesterol 7-α-hydroxylase (CYP7A1) and occurs in the liver. Activation of FXR represses the transcription of CYP7A1 by increasing the expression level of the hepatic small heterodimer partner (SHP) (also known as nuclear receptor subfamily 0, group B, member 2; or NR0B2) and intestinal expression of fibroblast growth factor 15 (FGF15) in mice and fibroblast growth factor 19 (FGF19) in human. SHP represses the liver receptor homolog (LRH-1), a nuclear receptor necessary for CYP7A1 gene expression, through its interaction with LRH-1 to form a non-functional heterodimer. In some cases, FGF15/19 released from the intestine then activates the fibroblast growth factor receptor 4 in the liver, leading to activation of the mitogen-activated protein kinase (MAPK) signaling pathway which suppress Cyp7A1.

In some embodiments, elevated levels of bile acids have been associated with insulin resistance. For example, insulin resistance sometimes leads to a decreased uptake of glucose from the blood, and increased de novo glucose production in the liver. In some instances, intestinal sequestration of bile acids has been shown to improve insulin resistance by promoting the secretion of glucagon-like peptide-1 (GLP1) from intestinal L-cells. GLP-1 is an incretin derived from the transcription product of the proglucagon gene. It is released in response to the intake of food and exerts control in appetite and gastrointestinal function, and promotes insulin secretion from the pancreas. The biologically active forms of GLP-1 include GLP-1-(7-37) and GLP-1-(7-36)$NH_2$, which result from selective cleavage of the proglucagon molecule.

In such cases, activation of FXR leading to decreased production of bile acids correlates to a decrease in insulin resistance.

In some embodiments, the activation of FXR also correlates to the secretion of pancreatic polypeptide-fold such as peptide YY (PYY or PYY3-36). In some instances, peptide YY is a gut hormone peptide that modulates neuronal activity within the hypothalamic and brainstem, regions of the brain involved in reward processing. In some instances, reduced level of PYY correlates to increased appetite and weight gain.

In some instances, the activation of FXR indirectly leads to a reduction of plasma triglycerides. The clearance of triglycerides from the bloodstream is due to lipoprotein lipase (LPL). LPL activity is enhanced by the induction of its activator apolipoprotein CII, and the repression of its inhibitor apolipoprotein CIII in the liver occurs upon FXR activation.

In some cases, the activation of FXR further modulates energy expenditure such as adipocyte differentiation and function. Adipose tissue comprises adipocytes or fat cells. In some instances, adipocytes are further differentiated into brown adipose tissue (BAT) or white adipose tissue (WAT). The function of BAT is to generate body heat, while WAT functions as fat storing tissues.

In some instances, FXR is widely expressed in the intestine. In some cases, the activation of FXR has been shown to induce the expression and secretion of FGF19 (or FGF15 in mouse) in the intestine. FGF19 is a hormone that regulates bile acid synthesis as well as exerts an effect on glucose metabolism, lipid metabolism, and on energy expenditure. In some instances, FGF19 has also been observed to modulate adipocyte function and differentiation. Indeed, a study has shown that the administration of FGF19 to high-fat diet-fed mice increased energy expenditure, modulated adipocytes differentiation and function, reversed weight gain, and improved insulin resistance (see, Fu et al., "Fibroblast growth factor 19 increases metabolic rate and reverses dietary and leptin-deficient diabetes." Endocrinology 145: 2594-2603 (2004)).

In some cases, intestinal FXR activity has also been shown to be involved in reducing overgrowth of the microbiome, such as during feeding (Li et al., *Nat Commun* 4:2384, 2013). For example, a study had shown that activation of FXR correlated with increased expression of several genes in the ileum such as Ang2, iNos, and Il8, which have established antimicrobial actions (Inagaki et al., *Proc Natl Acad Sci USA* 103:3920-3925, 2006).

G protein-coupled bile acid receptor 1 (also known as GPBAR2, GPCR19, membrane-type receptor for bile acids or M-BAR, or TGR5) is a cell surface receptor for bile acids. Upon activation with bile acid, TGR5 induces the production of intracellular cAMP, which then triggers an increase in triiodothyronine due to the activation of deiodinase (DIO2) in BAT, resulting in increased energy expenditure.

Hence in some embodiments, regulation of metabolic processes such as bile acid synthesis, bile-acid circulation, glucose metabolism, lipid metabolism, or insulin sensitivity is modulated by the activation of FXR. Furthermore, in some embodiments, dis-regulation of metabolic processes such as bile acid synthesis, bile-acid circulation, glucose metabolism, lipid metabolism, or insulin sensitivity results in metabolic diseases such as diabetes or diabetes-related conditions or disorders, alcoholic or non-alcoholic liver disease or condition, intestinal inflammation, or cell proliferative disorders.

Disclosed herein, in certain embodiments, are compounds that have activity as FXR agonists. In some embodiments, the FXR agonists described herein are structurally distinct from bile acids, other synthetic FXR ligands, and other natural FXR ligands.

In some embodiments, also disclosed herein are methods of treating or preventing a metabolic disorder, such as diabetes, obesity, impaired glucose tolerance, dyslipidemia, or insulin resistance by administering a therapeutically effective amount of an FXR agonist. In some instances, the compounds are administered to the GI tract of a subject.

In additional embodiments, disclosed herein are methods for treating or preventing alcoholic or non-alcoholic liver disease or conditions (e.g., cholestasis, primary biliary cirrhosis, steatosis, cirrhosis, alcoholic hepatitis, non-alcoholic steatohepatitis (NASH), non-alcoholic fatty liver disease (NAFLD), primary sclerosing cholangitis (PSC) or elevated liver enzymes) by administering a therapeutically effective amount of an FXR agonist to a subject in need thereof (e.g., via the GI tract). In additional embodiments, disclosed herein include methods for treating or preventing cholestasis, cirrhosis, primary biliary cirrhosis, non-alcoholic steatohepatitis (NASH), non-alcoholic fatty liver disease (NAFLD), or primary sclerosing cholangitis (PSC) by administering a therapeutically effective amount of an FXR agonist to a subject in need thereof. In some embodiments, disclosed herein include methods for treating or preventing cholestasis by administering a therapeutically effective amount of an FXR agonist to a subject in need thereof. In some embodiments, disclosed herein include methods for treating or preventing primary biliary cirrhosis by administering a therapeutically effective amount of an FXR agonist to a subject in need thereof. In some embodiments, disclosed herein include methods for treating or preventing NASH by administering a therapeutically effective amount of an FXR agonist to a subject in need thereof. In some embodiments, disclosed herein include methods for treating or preventing NAFLD by administering a therapeutically effective amount of an FXR agonist to a subject in need thereof.

In further embodiments, disclosed herein include methods for treating or preventing inflammation in the intestines and/or a cell proliferative disorder, such as cancer, by administering a therapeutically effective amount of an FXR agonist to a subject in need thereof (e.g., via the GI tract).

In still further embodiments, disclosed herein include FXR agonists that modulate one or more of the proteins or genes associated with a metabolic process such as bile acid synthesis, glucose metabolism, lipid metabolism, or insulin sensitivity, such as for example, increase in the activity of FGF19 (FGF15 in mouse), increase in the secretion of GLP-1, or increase in the secretion of PYY.

Metabolic Disorders

Disclosed herein, in certain embodiments, are methods of treating a metabolic disorder in a subject in need thereof. Also described herein include methods of preventing a metabolic disorder in a subject in need thereof. In some instances, these methods include administering to the subject in need thereof a therapeutically effective amount of one or more of the compounds disclosed herein. In some instances, the one or more compounds disclosed herein are absorbed in the gastrointestinal (GI) tract. In additional instances, the one or more disclosed compounds absorbed in the GI tract activates FXR receptors thereby treating or preventing a metabolic disorder in the subject.

In some embodiments, the disclosed compounds demonstrate systemic exposure. In some instances, the disclosed compounds have local exposure in the intestines, but limited exposure in the liver or systemically. In some embodiments, local exposure of the disclosed compounds in the intestines maybe demonstrated by regulation of FXR target genes in the intestines. In some embodiments, the target genes may include: SHP, FGF19 (FGF15), IBABP, C3, OST α/β. In some embodiments, exposure of the disclosed compounds is about 40%, 50%, 55%, 60%, 65%, 70%, 75%, 80%, 85%, 90%, 95%, 99%, 99.5%, or more in the intestines. In some instances, exposure of the disclosed compounds is about 0.5%, 1%, 5%, 10%, 15%, 20%, 25%, 30%, 40%, 50%, or less in the systemic circulation. In some embodiments, the exposure of the FXR agonists in the intestinal lumen reduces the chance of side effects which results from systemic action, thereby improving the safety profile of the therapy. In additional embodiments, the disclosed compounds enhance FXR target gene expression in the intestines. In additional embodiments, the disclosed compounds further modulate gene expressions in the FXR-mediated pathway, such as for example, FGF19 (FGF15) which inhibits CYP7A1 gene expression in the liver. In some instances, the disclosed compounds enhance gene expression in the FXR-mediated pathway. In other instances, the disclosed compounds reduce or inhibit gene expression in the FXR-mediated pathway. In some instances, enhancing is about 1%, 5%, 10%, 15%, 20%, 25%, 30%, 40%, 50%, 60%, 70%, 80%, 90%, 100%, 200%, 300%, 500%, 1,000%, 5,000%, 10,000%, 50,000%, 100,000%, 500,000% or higher in gene expression in the intestines, liver, kidney, or other tissues relative to the gene expression in the absence of the disclosed compound. In some cases, reducing is about 100%, 90%, 80%, 70%, 60%, 50%, 40%, 30%, 25%, 20%, 15%, 10%, 5%, 1%, or less in gene expression in the intestines, liver, kidney, or other tissues relative to the gene expression in the absence of the disclosed compound.

In some embodiments, the method substantially enhances FXR target gene expression in the intestines while minimizing systemic plasma levels of the delivered compound. In some embodiments, the method substantially enhances FXR target gene expression in the intestines and the liver while minimizing systemic plasma levels of the delivered compound. In some embodiments, the method substantially enhances FXR target gene expression in the intestines while not substantially enhancing FXR target gene expression in the liver or kidney, and while minimizing systemic plasma levels. In some embodiments, the method substantially enhances FXR target gene expression in the intestines and the liver and provides sustained systemic plasma levels of the delivered compound.

In some embodiments, metabolic disorder refers to any disorder that involves an alteration in the normal metabolism of carbohydrates, lipids, proteins, nucleic acids or a combination thereof. In some instances, a metabolic disorder is associated with either a deficiency or excess in a metabolic pathway resulting in an imbalance in metabolism of nucleic acids, proteins, lipids, and/or carbohydrates. Factors affecting metabolism include, but are not limited to, the endocrine (hormonal) control system (e.g., the insulin pathway, the enteroendocrine hormones including GLP-1, oxyntomodulin, PYY or the like), or the neural control system (e.g., GLP-1 in the brain). Exemplary metabolic disorders include, but are not limited to, diabetes, insulin resistance, dyslipidemia, liver disease, inflammation related intestinal conditions, cell proliferative disorders, or the like.

Diabetes Mellitus and Diabetes-Related Conditions or Disorders

In some embodiments, disclosed herein are methods of treating a subject having diabetes mellitus or diabetes-related condition or disorder with administration of a FXR agonist described herein. In some instances, diabetes is type II diabetes or non-insulin-dependent diabetes mellitus (NIDDM). In some instances, diabetes-related conditions or disorders include obesity, impaired glucose tolerance, dyslipidemia, and insulin resistance. In some instances, diabetes-related conditions or disorders further include secondary complications such as atherosclerosis, stroke, fatty liver disease, blindness, gallbladder disease, or polycystic ovary disease. In some cases, a FXR agonist is administered for the treatment of type II diabetes, obesity, impaired glucose tolerance, dyslipidemia, insulin resistance, or secondary complications such as atherosclerosis, stroke, fatty liver disease, blindness, gallbladder disease, or polycystic ovary disease.

In some embodiments, a diabetic subject (e.g., a type II diabetic subject) is further characterized with a body mass index (BMI) of 25 or greater, 30 or greater, 35 or greater, 40 or greater, such as a BMI of 25 to 29, 30 to 34, or 35 to 40.

In some examples, a FXR agonist described herein reduces or prevents weight gain in a subject. In some instances, the weight gain is diet-induced weight gain. In other instances, the weight gain is non diet-related, such as familial/genetic obesity or obesity resulting from medication. In some examples, such methods reduce or prevent weight gain in the subject by at least 5%, at least 10%, at least 15%, at least 20%, at least 30%, at least 40%, at least 50%, or more. In some instances, weight gain is reduced or prevented by about 5% to about 50%, by about 5% to about 25%, by about 10% to about 20%, or by about 10% to about 30%. In some cases, the reduction or prevention of weight gain is relative to the reduction or prevention of weight gain observed in a subject not treated with the FXR agonist.

Similarly, in some cases, the FXR agonist reduces the BMI of a subject. In some examples, such methods reduce the BMI of a subject by at least 5%, at least 10%, at least 15%, at least 20%, at least 25%, at least 30%, or more, relative to a subject not treated with the FXR agonist. In some instances, the subject is overweight but not obese. In other instances, the subject is neither overweight nor obese.

In some instances, administration of a FXR agonist results in a decrease in the amount of serum lipids. In some examples, the decrease in the amount of serum lipids is by at least 5%, at least 10%, at least 15%, at least 20%, at least 30%, at least 50%, at least 60%, at least 70%, at least 75%, or more. In some cases, the decrease in the amount of serum lipids is by about 5% to about 50%, by about 5% to about 25%, by about 10% to about 20%, by about 10% to about 70%, or by about 10% to about 30%. In some cases, the decrease in the amount of serum lipids is relative to the amount of serum lipids observed in a subject not treated with the FXR agonist.

In some examples, administration of a FXR agonist results in a decrease in triglyceride (e.g., hepatic triglyceride) level. In some instances, the decrease in triglyceride (e.g., hepatic triglyceride) level is by at least 5%, at least 10%, at least 15%, at least 20%, at least 30%, at least 50%, at least 60%, at least 70%, at least 75%, or more. In some instances, the decrease in triglyceride (e.g., hepatic triglyceride) level is by about 5% to about 50%, by about 5% to about 25%, by about 10% to about 20%, by about 10% to about 70%, or by about 10% to about 30%. In some cases, the decrease in triglyceride (e.g., hepatic triglyceride) level is relative to the triglyceride (e.g., hepatic triglyceride) level observed in a subject not treated with the FXR agonist.

In some examples, administration of a FXR agonist results in an increased insulin sensitivity to insulin in the liver. In some instances, the increase in insulin sensitivity is by at least 5%, at least 10%, at least 15%, at least 20%, at least 30%, at least 40%, at least 50%, or more. In some cases, the increase in insulin sensitivity is by about 5% to about 50%, by about 5% to about 25%, by about 10% to about 20%, or by about 10% to about 30%. In some cases, the increase in insulin sensitivity is relative to sensitivity observed in a subject not treated with the FXR agonist.

In some embodiments, administration of a FXR agonist results in a decrease in the amount of serum insulin in the subject. In some examples, the decrease in serum insulin is by at least 5%, at least 10%, at least 15%, at least 20%, at least 30%, at least 50%, at least 60%, at least 70%, at least 75%, or more. In some instances, serum insulin is decreased by about 5% to about 50%, by about 5% to about 25%, by about 10% to about 20%, by about 10% to about 70%, or by about 10% to about 30%. In some cases, the decrease in serum insulin level is relative to levels observed in a subject not treated with the FXR agonist.

In some embodiments, administration of a FXR agonist results in a decrease in the amount of serum glucose in the subject. In some examples, the decrease in serum glucose is by at least 5%, at least 10%, at least 15%, at least 20%, at least 30%, at least 50%, at least 60%, at least 70%, at least 75%, or more. In some instances, serum glucose is decreased by about 5% to about 50%, by about 5% to about 25%, by about 10% to about 20%, by about 10% to about 70%, or by about 10% to about 30%. In some cases, the decrease in serum glucose level is relative to levels observed in a subject not treated with the FXR agonist.

In some examples, a FXR agonist described herein increases browning of white adipose tissue in a subject. In some examples, the rate of increase of browning of white adipose tissue in the subject is by at least 5%, at least 10%, at least 15%, at least 20%, at least 30%, at least 40%, at least 50%, or more, relative to a subject not treated with the FXR agonist.

In some embodiments, administration of a FXR agonist does not result in substantial change in food intake and/or fat consumption in the subject. In some instances, food intake and/or fat consumption is reduced, such as by less than 15%, less than 10%, or less than 5%. In some embodiments, no substantial change in appetite in the subject results. In other embodiments, reduction in appetite is minimal as reported by the subject.

In some embodiments, administration of a FXR agonist results in an increase in the metabolic rate in the subject. In some instances, the FXR agonist increases the metabolic rate in a subject. In some cases, the metabolic rate in the subject is increased by at least 5%, at least 10%, at least 15%, at least 20%, at least 30%, at least 40%, at least 50%, at least 60%, at least 70%, at least 75%, or more. In some instances, the metabolic rate is increased by about 5% to about 50%, by about 5% to about 25%, by about 10% to about 20%, by about 10% to about 70%, or by about 10% to about 30%). In some cases, the increase in metabolic rate is relative to the rate observed in a subject not treated with the FXR agonist.

In some embodiments, the increase in metabolism results from enhanced oxidative phosphorylation in the subject, which in turn leads to increased energy expenditure in tissues (such as BAT). In such instances, the FXR agonist helps to increase the activity of BAT. In some examples, the activity of BAT is increased by at least 5%, at least 10%, at least 15%, at least 20%, at least 30%, at least 50%, at least 60%, at least 70%, at least 75%, or more. In some instances, the activity of BAT is increased by about 5% to about 50%, by about 5% to about 25%, by about 10% to about 20%, by about 10% to about 70%, or by about 10% to about 30%. In some cases, the increase in BAT activity is relative to the activity of BAT observed in a subject not treated with the FXR agonist.

Alcoholic and Non-Alcoholic Liver Disease or Condition

Disclosed herein include methods of preventing and/or treating alcoholic or non-alcoholic liver diseases or conditions. Exemplary alcoholic or non-alcoholic liver diseases or conditions include, but are not limited to cholestasis, cirrhosis, steatosis, alcoholic hepatitis, non-alcoholic steatohepatitis (NASH), non-alcoholic fatty liver disease (NAFLD), primary sclerosing cholangitis (PSC), elevated liver enzymes, and elevated triglyceride levels. In some embodiments, a FXR agonist is used in the prevention or treatment of alcoholic or non-alcoholic liver diseases. In some embodiments, a FXR agonist is used in the prevention or treatment of cholestasis, cirrhosis, steatosis, alcoholic hepatitis, non-alcoholic steatohepatitis (NASH), non-alcoholic fatty liver disease (NAFLD), or primary sclerosing cholangitis (PSC).

Cholestasis

In some embodiments, a FXR agonist disclosed herein is used in the treatment of cholestasis in a subject. Cholestasis, an impairment or cessation in the flow of bile, which in some cases, causes hepatotoxicity due to the buildup of bile acids and other toxins in the liver. In some instances, cholestasis is a component of many liver diseases, including cholelithiasis, cholestasis of pregnancy, primary biliary cirrhosis (PBC), and primary sclerosing cholangitis (PSC). In some instances, the obstruction is due to gallstone, biliary trauma, drugs, one or more additional liver diseases, or to cancer. In some cases, the enterohepatic circulation of bile acids enables the absorption of fats and fat-soluble vitamins from the intestine and allows the elimination of cholesterol, toxins, and metabolic by-products such as bilirubin from the liver. In some cases, activation of FXR induces expression of the canalicular bile transporters BSEP (ABCB11) and multidrug resistance-related protein 2 (MRP2; ABCC2, cMOAT), and represses genes involved in bile acid biosynthesis, such as for example sterol 12α-hydroxylase (CYP8B1) and CYP7A1.

In some examples, the FXR agonist reduces cholestasis in the subject by at least 5%, at least 10%, at least 15%, at least 20%, at least 30%, at least 40%, at least 50%, or more. In some cases, cholestasis is reduced by about 5% to about 50%, by about 5% to about 25%, by about 10% to about 20%, or by about 10% to about 30%. In some instances, the level of cholestasis is relative to the level of cholestasis in a subject not treated with the FXR agonist.

Primary Biliary Cirrhosis and Cirrhosis

In some embodiments, a FXR agonist disclosed herein is used in the treatment of primary biliary cirrhosis (PBC) in a subject. PBC is a liver disease that primarily results from autoimmune destruction of the bile ducts that transport bile acids (BAs) out of the liver, resulting in cholestasis. As PBC progresses, persistent toxic buildup of BAs causes progressive liver damage. Chronic inflammation and fibrosis can advance to cirrhosis. In some examples, the FXR agonist reduces PBC in the subject by at least 5%, at least 10%, at least 15%, at least 20%, at least 30%, at least 40%, at least 50%, or more. In some cases, PBC is reduced by about 5% to about 50%, by about 5% to about 25%, by about 10% to about 20%, or by about 10% to about 30%. In some instances, the level of PBC is relative to the level of PBC in a subject not treated with the FXR agonist.

In some embodiments, a FXR agonist disclosed herein reduces cirrhosis in a subject. In some examples, the FXR agonist reduces cirrhosis in the subject by at least 5%, at least 10%, at least 15%, at least 20%, at least 30%, at least 40%, at least 50%, or more. In some cases, cirrhosis is reduced by about 5% to about 50%, by about 5% to about 25%, by about 10% to about 20%, or by about 10% to about 30%. In some instances, the level of cirrhosis is relative to the level of cirrhosis in a subject not treated with the FXR agonist.

Non-Alcoholic Fatty Liver Disease and Non-Alcoholic Steatohepatitis

Non-alcoholic fatty liver disease (NAFLD) is associated with excessive fat in the liver (steatosis) and in some cases progresses to NASH, which is defined by the histologic hallmarks of inflammation, cell death, and fibrosis. In some instances, primary NASH is associated with insulin resistance, while secondary NASH is caused by medical or surgical conditions, or drugs such as, but not limited to, tamoxifen. In some cases, NASH progresses to advanced fibrosis, hepatocellular carcinoma, or end-stage liver disease requiring liver transplantation.

In some instances, NASH develops as a result of triglyceride (TGs) imbalance. For example, dysfunctional adipocytes secrete pro-inflammatory molecules such as cytokines and chemokines leading to insulin resistance and a failure of lipolysis suppression in the adipocytes. In some instances, this failure of lipolysis suppression leads to a release of free fatty acids (FFAs) into the circulation and uptake within the liver. In some cases, overaccumulation of FFAs in the form of triglycerides (TGs) in lipid droplets leads to oxidative stress, mitochondrial dysfunction, and upregulation of pro-inflammatory molecules.

In some instances, activation of FXR inhibits triglyceride (TG)/fatty acid (FA) synthesis facilitated by suppressing sterol regulatory element-binding protein 1c (SREBP1c) via activation of SHP. In some cases, FXR additionally increases the clearance of TG by stimulating lipoprotein lipase (LPL) activity as well as the hepatic uptake of remnants and low-density lipoprotein by inducing syndecan 1 (SDC1) and the VLDL receptor (VLDLR).

In some embodiments, a FXR agonist disclosed herein is used in the treatment of non-alcoholic steatohepatitis (NASH). In some examples, the FXR agonist reduces NASH the subject by at least 5%, at least 10%, at least 15%, at least 20%, at least 30%, at least 40%, at least 50%, or more. In some cases, NASH is reduced by about 5% to about 50%, by about 5% to about 25%, by about 10% to about 20%, or by about 10% to about 30%. In some instances, the level of NASH is relative to the level of NASH in a subject not treated with the FXR agonist.

In some embodiments, a FXR agonist disclosed herein is used in the treatment of NAFLD. In some examples, the FXR agonist reduces NAFLD in the subject by at least 5%, at least 10%, at least 15%, at least 20%, at least 30%, at least 40%, at least 50%, or more. In some cases, NAFLD is reduced by about 5% to about 50%, by about 5% to about 25%, by about 10% to about 20%, or by about 10% to about 30%. In some instances, the level of NAFLD is relative to the level of NAFLD in a subject not treated with the FXR agonist.

Steatosis

In some embodiments, a FXR agonist disclosed herein reduces fatty liver (steatosis) in a subject. In some examples, the FXR agonist reduces steatosis in the subject by at least 5%, at least 10%, at least 15%, at least 20%, at least 30%, at least 40%, at least 50%, or more. In some instances, steatosis is reduced by about 5% to about 50%, by about 5% to about 25%, by about 10% to about 20%, or by about 10% to about 30%. In some instances, the level of steatosis is relative to the level of steatosis in a subject not treated with the FXR agonist.

Alcoholic Hepatitis

In some embodiments, a FXR agonist disclosed herein reduces alcoholic hepatitis in a subject. In some examples, the FXR agonist reduces alcoholic hepatitis in the subject by at least 5%, at least 10%, at least 15%, at least 20%, at least 30%, at least 40%, at least 50%, or more. In some instances, the level of alcoholic hepatitis is reduced by about 5% to about 50%, by about 5% to about 25%, by about 10% to about 20%, or by about 10% to about 30%. In some instances, the level of alcoholic hepatitis is relative to the level of alcoholic hepatitis in a subject not treated with the FXR agonist.

Primary Sclerosing Cholangitis

In some embodiments, a FXR agonist disclosed herein is used in the treatment of primary sclerosing cholangitis (PSC). PSC is a chronic and progressive cholestatic liver disease. PSC is characterized by progressive inflammation, fibrosis, and stricture formation in liver ducts. Common symptoms include pruritus and jaundice. The disease is strongly associated with inflammatory bowel disease (IBD)—about 5% of patients with ulcerative colitis will have PSC. Up to 70% of patients with PSC also have IBD, most commonly ulcerative colitis.

Additional Alcoholic and Non-Alcoholic Liver Diseases or Conditions

In some embodiments, a FXR agonist disclosed herein reduces liver enzymes in a subject. In some examples, the FXR agonist reduce liver enzymes (e.g., serum ALT and/or AST levels) in the subject by at least 5%, at least 10%, at least 15%, at least 20%, at least 30%, at least 40%, at least 50%, or more. In some instances, the level of liver enzymes is reduced by about 5% to about 50%, by about 5% to about 25%, by about 10% to about 20%, or by about 10% to about 30%. In some instances, the level of liver enzymes is relative to the level of liver enzymes in a subject not treated with the FXR agonist.

In some embodiments, a FXR agonist disclosed herein reduces liver triglycerides in a subject. In some examples, the FXR agonist reduces liver triglycerides in the subject by at least 5%, at least 10%, at least 15%, at least 20%, at least 30%, at least 40%, at least 50%, or more. In some instances, the level of liver triglycerides is reduced by about 5% to about 50%, by about 5% to about 25%, by about 10% to about 20%, or by about 10% to about 30%. In some instances, the level of liver triglycerides is relative to the level of liver triglycerides in a subject not treated with the FXR agonist.

Inflammatory Intestinal Condition

Disclosed herein are methods of treating or preventing an inflammatory intestinal condition. Exemplary inflammatory conditions include necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection. In some embodiments, the inflammatory condition is NEC and the subject is a newborn or prematurely born infant. In some embodiments, the subject is enterally-fed infant or formula-fed infant.

In some embodiments, a FXR agonist disclosed herein is administered to a subject having an inflammatory intestinal condition. In some embodiments, a FXR agonist disclosed herein is administered to a subject having necrotizing enterocolitis (NEC), gastritis, ulcerative colitis, inflammatory bowel disease, irritable bowel syndrome, pseudomembranous colitis, gastroenteritis, radiation induced enteritis, chemotherapy induced enteritis, gastro-esophageal reflux disease (GERD), peptic ulcer, non-ulcer dyspepsia (NUD), celiac disease, intestinal celiac disease, gastrointestinal complications following bariatric surgery, gastric carcinogenesis, or gastric carcinogenesis following gastric or bowel resection.

In some embodiments, a FXR agonist disclosed herein reduces inflammation of the intestines in a subject (such as a human). In some examples, the FXR agonist reduces intestinal inflammation in the subject by at least 5%, at least 10%, at least 15%, at least 20%, at least 30%, at least 40%, at least 50%, or more. In some instances, intestinal inflammation is reduced by about 5% to about 50%, by about 5% to about 25%, by about 10% to about 20%, or by about 10% to about 30%. In some instances, the level of intestinal inflammation is relative to the level of intestinal inflammation in a subject not treated with the FXR agonist.

Cell Proliferation Disease

Further disclosed herein are methods of preventing or treating cell proliferation diseases, for example, in certain types of cancer. In some embodiments, the FXR agonists disclosed herein are used in the prevention or treatment of adenocarcinomas, or a carcinoma derived from glandular tissue or in which the tumor cells form recognizable glandular structures. In some embodiments, adenocarcinomas are classified according to the predominant pattern of cell arrangement, as papillary, alveolar, or according to a particular product of the cells, as mucinous adenocarcinoma. In some instances, adenocarcinomas are observed for example, in colon, kidney, breast, cervix, esophagus, gastric, pancreas, prostate, or lung.

In some embodiments, the compounds disclosed herein are used in the prevention or treatment of a cancer of the intestine, such as colon cancer, e.g. cancer that forms in the tissues of the colon (the longest part of the large intestine), or a cancer of another part of the intestine, such as the jejunum, and/or ileum. In some instances, colon cancer is also referred to as "colorectal cancer." In some instances, the most common type of colon cancer is colon adenocarcinoma.

In some cases, cancer progression is characterized by stages, or the extent of cancer in the body. Staging is usually based on the size of the tumor, the presence of cancer in the lymph nodes, and the presence of the cancer in a site other than the primary cancer site. Stages of colon cancer include stage I, stage II, stage III and stage IV. In some embodiments, colon adenocarcinoma is from any stage. In other embodiments, colon adenocarcinoma is a stage I cancer, a stage II cancer or a stage III cancer.

In some embodiments, a FXR agonist described herein is administered to a subject having a stage I, stage II, stage III, or stage IV cancer. In some instances, a FXR agonist described herein is administered to a subject having a stage I, stage II, or stage III colon adenocarcinoma.

In some embodiments, a FXR agonist disclosed herein further reduces the tumor burden in a subject. In some examples, the FXR agonist reduces tumor burden (such as colon tumor burden) in the subject by at least 5%, at least 10%, at least 15%, at least 20%, at least 30%, at least 40%, at least 50%, or more. In some instances, tumor burden is reduced by about 5% to about 50%, by about 5% to about 25%, by about 10% to about 20%, or by about 10% to about 30%. In some instances, the level of tumor burden is relative to the level of tumor burden in a subject not treated with the FXR agonist.

In some instances, a FXR agonist disclosed herein further reduces tumor size and/or volume in a subject. In some cases, the FXR agonist reduces tumor size and/or volume (such as a colon tumor) in the subject by at least 5%, at least 10%, at least 15%, at least 20%, at least 30%, at least 40%, at least 50%, or more. In some instances, tumor size is reduced by about 5% to about 50%, by about 5% to about 25%, by about 10% to about 20%, or by about 10% to about 30%. In some instances, the tumor size is relative to the tumor size in a subject not treated with the FXR agonist.

In additional embodiments, a FXR agonist disclosed herein reduces effects of cachexia due to a tumor in a subject. In some examples, the FXR agonist reduce the effect of cachexia (such as due to a colon tumor) in the subject by at least 5%, at least 10%, at least 15%, at least 20%, at least 30%, at least 40%, at least 50%, or more. In some instances, the effect of cachexia is reduced by about 5% to about 50%, by about 5% to about 25%, by about 10% to about 20%, or by about 10% to about 30%. In some instances, the effect of cachexia is relative to the effect of cachexia in a subject not treated with the FXR agonist.

In other embodiments, a FXR agonist disclosed herein increases survival rates of a subject with a tumor. In some cases, the FXR agonist increases the survival rate of a subject with a tumor (such as a colon cancer) in the subject by at least 5%, at least 10%, at least 15%, at least 20%, at least 30%, at least 40%, at least 50%, or more. In some instances, survival rate is increased by about 5% to about 50%, by about 5% to about 25%, by about 10% to about 20%, or by about 10% to about 30%. In some instances, the survival rate is relative to the survival rate in a subject not treated with the FXR agonist.

Compounds

Compounds described herein, including pharmaceutically acceptable salts, prodrugs, active metabolites and pharmaceutically acceptable solvates thereof, are farnesoid X receptor agonists.

In one aspect, described herein is a compound of Formula (I), or a pharmaceutically acceptable salt, or solvate thereof:

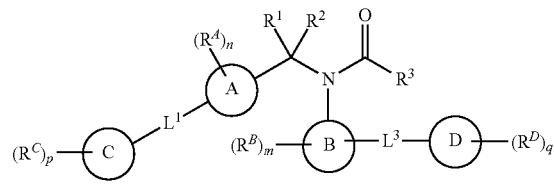

Formula (I)

wherein
  $R^1$ and $R^2$ are each independently selected from H, D, F, $C_1$-$C_4$alkyl, or $C_1$-$C_4$fluoroalkyl;
  or $R^1$ and $R^2$ are taken together with the carbon atom to which they are attached to form a substituted or unsubstituted $C_3$-$C_{10}$cycloalkyl, or substituted or unsubstituted $C_2$-$C_{10}$heterocycloalkyl;

or $R^1$ and $R^2$ are taken together with the carbon atom to which they are attached to form a carbonyl (C=O);

$R^3$ is selected from substituted or unsubstituted $C_1$-$C_{10}$alkyl, substituted or unsubstituted $C_2$-$C_{10}$alkenyl, substituted or unsubstituted $C_2$-$C_{10}$alkynyl, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl, wherein if $R^3$ is substituted then $R^3$ is substituted with one or more $R^{12}$ groups;

each $R^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NHC(=O)R$^{11}$, —NHC(=O)OR$^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -L$^5$-L$^6$-R$^{13}$ $L^5$ is absent, —O—, —S—, —S(=O)—, —S(=O)$_2$, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;

$L^6$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;

$R^{13}$ is H, halogen, unsubstituted or substituted $C_1$-$C_{10}$alkyl, unsubstituted or substituted $C_2$-$C_{10}$alkenyl, unsubstituted or substituted $C_2$-$C_{10}$alkynyl, unsubstituted or substituted $C_1$-$C_{10}$cycloalkyl, unsubstituted or substituted $C_1$-$C_{10}$heteroalkyl, unsubstituted or substituted aryl, or unsubstituted or substituted heteroaryl;

ring A is a monocyclic carbocycle, monocyclic heterocycle, or bicyclic heterocycle;

each $R^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

$L^1$ is —X$^1$-L$^2$- or -L$^2$-X$^1$—;

$X^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

$L^2$ is absent or substituted or unsubstituted $C_1$-$C_4$alkylene;

ring C is monocyclic carbocycle, bicyclic carbocycle, monocyclic heterocycle, or bicyclic heterocycle;

each $R^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, substituted or unsubstituted phenyl, and substituted or unsubstituted monocyclic heteroaryl;

ring B is a monocyclic carbocycle, bicyclic carbocycle, monocyclic heterocycle, or bicyclic heterocycle;

each $R^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, and substituted or unsubstituted $C_1$-$C_6$heteroalkyl;

$L^3$ is —X$^2$-L$^4$- or -L$^4$-X$^2$—;

$X^2$ is absent, —O—, —S—, —S(=O)—, —S(=O)$_2$-, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;

$L^4$ is absent or substituted or unsubstituted $C_1$-$C_4$alkylene;

ring D is phenyl, bicyclic carbocycle, monocyclic N-containing heterocycloalkyl, monocyclic heteroaryl, or bicyclic heterocycle;

each $R^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4;

q is 0, 1, 2, 3, or 4.

For any and all of the embodiments, substituents are selected from among a subset of the listed alternatives. For example, in some embodiments, $R^1$ and $R^2$ are each independently selected from H, D, F, $C_1$-$C_4$alkyl, and $C_1$-$C_4$fluoroalkyl. In other embodiments, $R^1$ and $R^2$ are each independently selected from H, D, F, $CH_3$, and $CF_3$. In some other embodiments, $R^1$ and $R^2$ are each independently selected from H or D. In some other embodiments, $R^1$ and $R^2$ are each H.

In some embodiments, ring B is a monocyclic carbocycle or monocyclic heterocycle wherein the groups

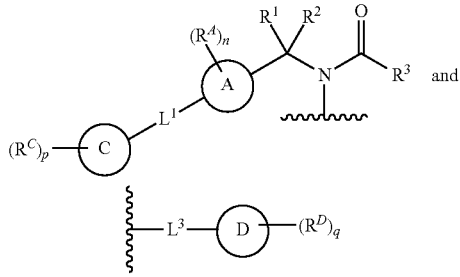

and are in a 1,3-relationship on ring B.

In some embodiments, ring B is a monocyclic carbocycle or monocyclic heterocycle wherein the groups

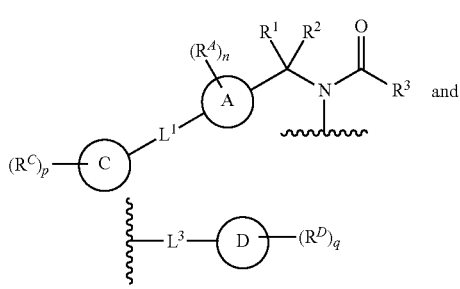

and are in a 1,4-relationship on ring B.

In some embodiments, ring B is phenyl.

In some embodiments, ring B is monocyclic heteroaryl.

In some embodiments, ring B is monocyclic 6-membered heteroaryl selected from pyridinyl, pyrimidinyl, pyrazinyl, and pyridazinyl.

In some embodiments,

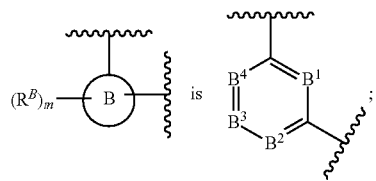

$B^1$ is $CR^B$ or N; $B^2$ is $CR^B$ or N;

$B^3$ is $CR^B$ or N; $B^4$ is $CR^B$ or N.

In some embodiments, $B^1$ is $CR^B$; $B^2$ is $CR^B$; $B^3$ is $CR^B$; $B^4$ is $CR^B$.

In some embodiments, $B^1$ is N; $B^2$ is $CR^B$ or N; $B^3$ is $CR^B$; $B^4$ is $CR^B$.

In some embodiments, $B^1$ is $CR^B$ or N; $B^2$ is $CR^B$; $B^3$ is $CR^B$ or N; $B^4$ is $CR^B$.

In some embodiments, $B^1$ is $CR^B$ or N; $B^2$ is $CR^B$; $B^3$ is $CR^B$; $B^4$ is $CR^B$ or N.

In some embodiments, $B^1$ is $CR^B$ or N; $B^2$ is N; $B^3$ is $CR^B$; $B^4$ is $CR^B$ or N.

In some embodiments,

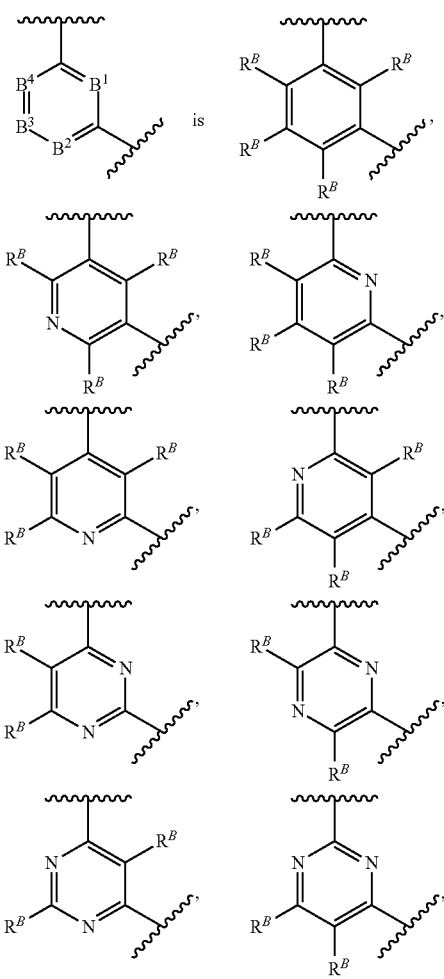

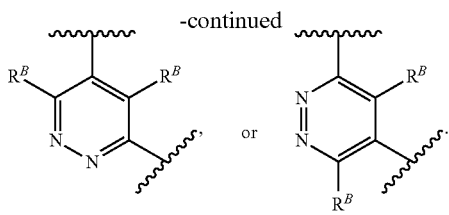

In some embodiments, ring D is phenyl, bicyclic carbocycle, monocyclic N-containing heterocycle, or bicyclic heterocycle.

In some embodiments, ring D is phenyl, bicyclic carbocycle, monocyclic heteroaryl, or bicyclic heterocycle.

In some embodiments, ring D is phenyl or monocyclic heteroaryl.

In some embodiments, ring D is monocyclic heteroaryl.

In some embodiments, ring D is monocyclic heteroaryl selected from furanyl, thienyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, and pyridazinyl.

In some embodiments, ring D is phenyl, bicyclic carbocycle, monocyclic N-containing heterocycloalkyl, monocyclic heteroaryl, or bicyclic heterocycle.

In some embodiments, ring D is phenyl, indanyl, indenyl, or naphthyl.

In some embodiments, ring D is phenyl.

In some embodiments, ring D is monocyclic N-containing heterocycle.

In some embodiments, ring D is monocyclic N-containing heteroaryl.

In some embodiments, ring D is monocyclic N-containing heteroaryl selected from pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, and pyridazinyl.

In some embodiments,

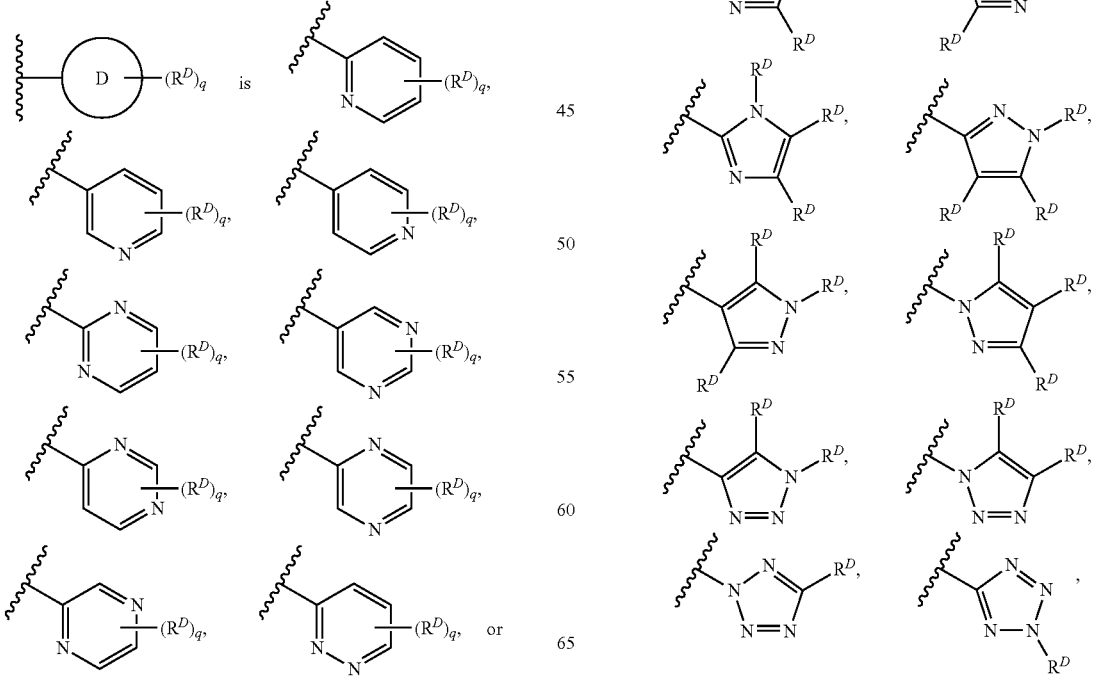

In some embodiments,

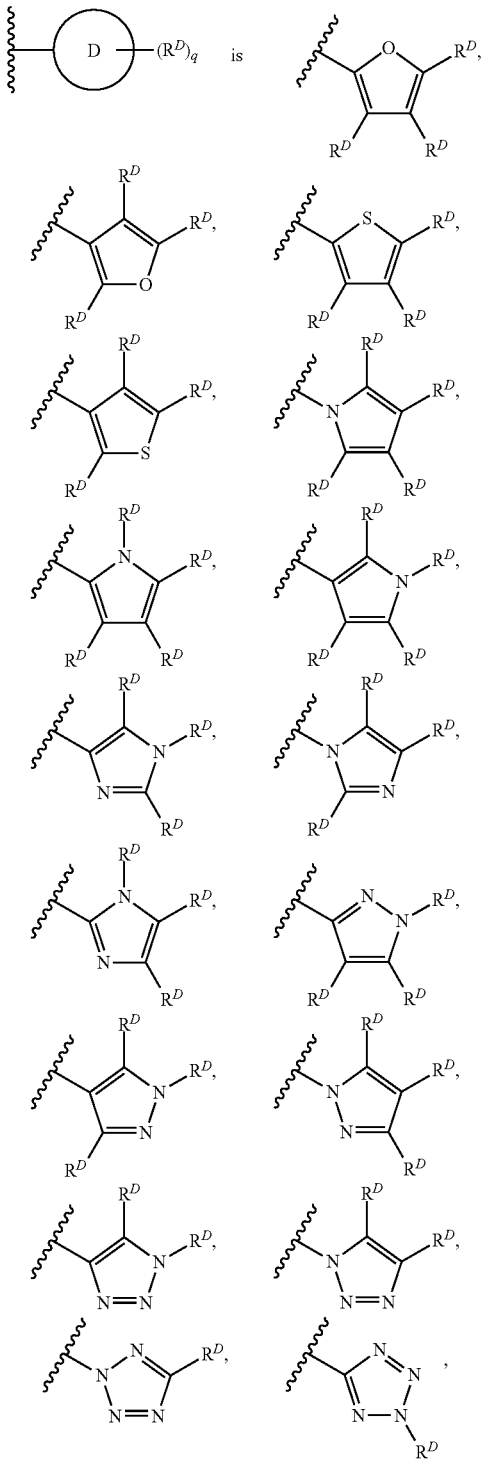

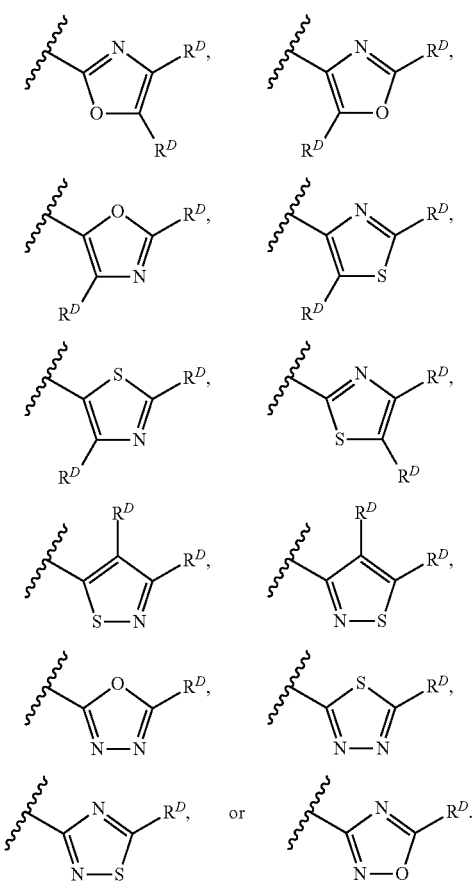

In some embodiments,

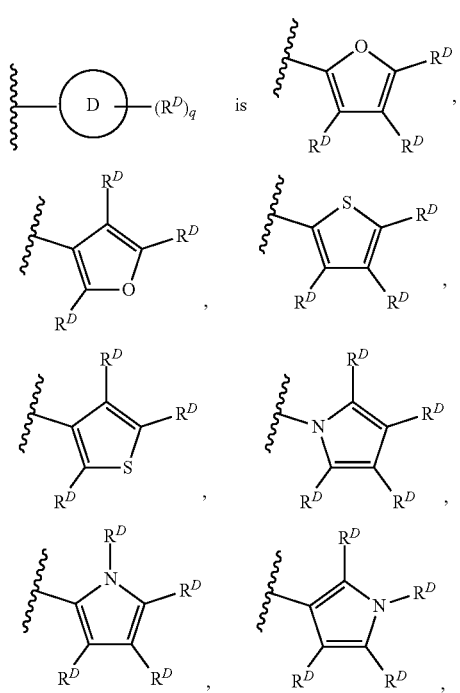

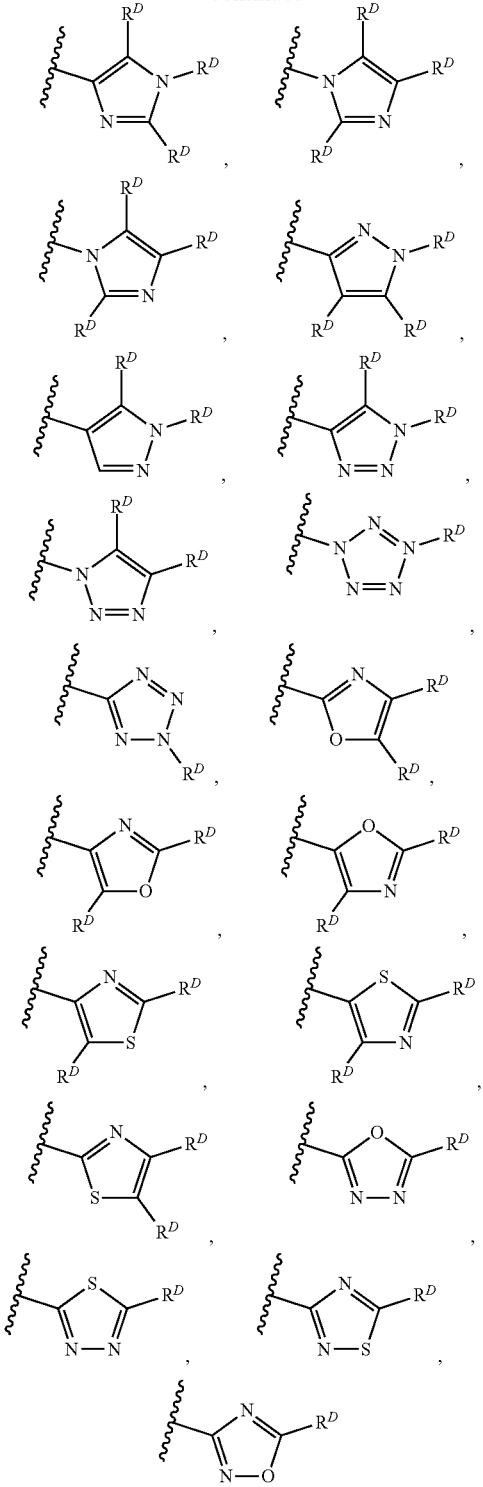

In some embodiments, each $R^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, unsubstituted or substituted $C_3$-$C_{10}$cycloalkyl, and substituted or unsubstituted $C_2$-$C_{10}$heterocycloalkyl.

In some embodiments, each $R^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, and substituted or unsubstituted $C_1$-$C_6$heteroalkyl.

In some embodiments, each $R^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —C(=O)N(R$^{10}$)$_2$, —NR$^{10}$C(=O)R$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, unsubstituted or substituted $C_3$-$C_6$cycloalkyl, and substituted or unsubstituted $C_2$-$C_6$heterocycloalkyl.

In some embodiments, each $R^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —C(=O)N(R$^{10}$)$_2$, —NR$^{10}$C(=O)R$^{11}$, $C_1$-$C_6$alkyl, $C_2$-$C_6$alkenyl, $C_2$-$C_6$alkynyl, $C_1$-$C_6$fluoroalkyl, substituted or unsubstituted $C_1$-$C_6$heteroalkyl, and unsubstituted or substituted $C_3$-$C_6$cycloalkyl. In some embodiments, each $R^D$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —C(=O)N(R$^{10}$)$_2$, —NR$^{10}$C(=O)R$^{11}$, $C_1$-$C_6$alkyl, $C_2$-$C_6$alkenyl, $C_2$-$C_6$alkynyl, $C_1$-$C_6$fluoroalkyl, and substituted or unsubstituted $C_1$-$C_6$heteroalkyl.

In some embodiments, $L^3$ is —$X^2$-$L^4$- or -$L^4$-$X^2$—; $X^2$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —C(=O)NR$^{10}$—, —NR$^{10}$C(=O)—, —NR$^{10}$S(=O)$_2$—, or —NR$^{10}$—; $L^4$ is absent or —CH$_2$—.

In some embodiments, $L^3$ is —$X^2$—.

In some embodiments, $L^3$ is absent, —O—, —S—, —S—CH$_2$—, —CH$_2$—S—, —CH$_2$—, —CH=CH—, —C≡C—, —C(=O)—, —C(=O)O—, —OC(=O)—, —C(=O)NR$^{10}$—, —NR$^{10}$C(=O)—, —NR$^{10}$S(=O)$_2$—, —NR$^{10}$—, —NR$^{10}$—CH$_2$—, or —CH$_2$—NR$^{10}$—.

In some embodiments, $L^3$ is absent, —O—, —S—, —CH=CH—, —C≡C—, or —NR$^{10}$—.

In some embodiments, ring A is a monocyclic carbocycle.

In some embodiments, ring A is monocyclic carbocycle that is phenyl or a $C_3$-$C_8$cycloalkyl.

In some embodiments, ring A is phenyl.

In some embodiments,

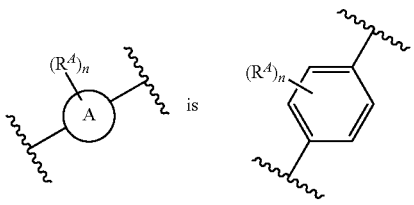 is

In some embodiments, the compound has the following structure:

Formula (II)

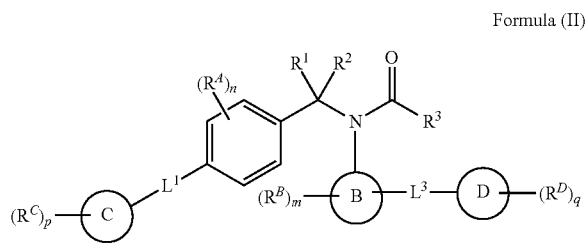

In some embodiments, ring A is monocyclic $C_3$-$C_8$cycloalkyl that is selected from cyclopropyl, cyclobutyl, cyclopentyl, cyclohexyl, cycloheptyl, and cyclooctyl.

In some embodiments, ring A is a monocyclic heterocycle.

In some embodiments, ring A is a monocyclic heterocycle that is a monocyclic $C_1$-$C_5$heteroarylene containing 1-4 N atoms, and 0 or 1 O or S atom.

In some embodiments, ring A is a monocyclic heterocycle that is a monocyclic $C_1$-$C_5$heteroarylene containing 0-4 N atoms, and 1 O or S atom.

In some embodiments, ring A is a monocyclic heterocycle that is a monocyclic 6-membered heteroarylene selected from pyridinylene, pyrimidinylene, pyrazinylene, and pyridazinylene.

In some embodiments,

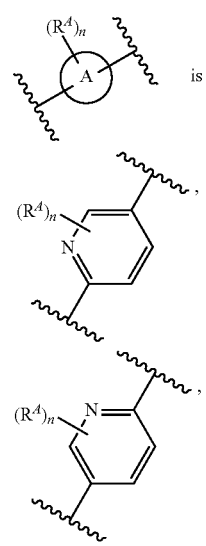

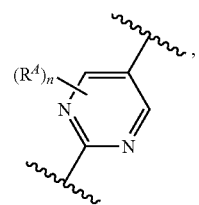,
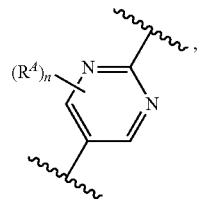,
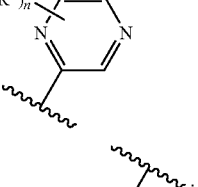 or
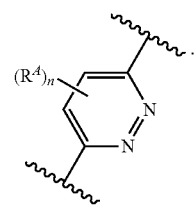.
In some embodiments, ring A is a monocyclic heterocycle that is a monocyclic 5-membered heteroarylene selected from furanylene, thienylene, pyrrolylene, oxazolylene, thiazolylene, imidazolylene, pyrazolylene, triazolylene, tetrazolylene, isoxazolylene, isothiazolylene, oxadiazolylene, and thiadiazolylene.
In some embodiments,
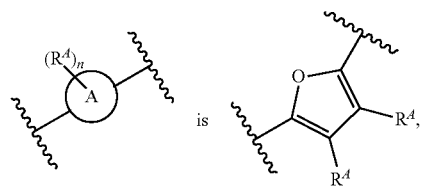
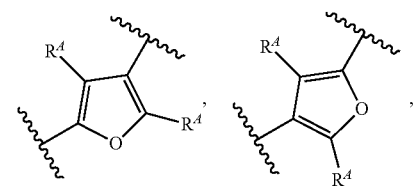
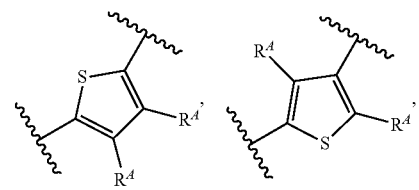
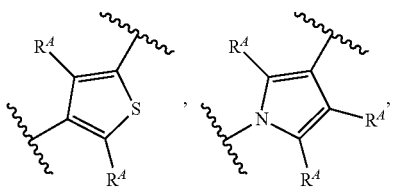
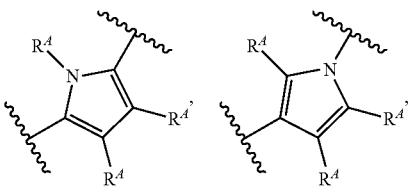
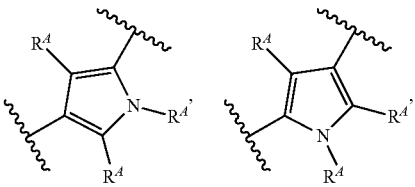
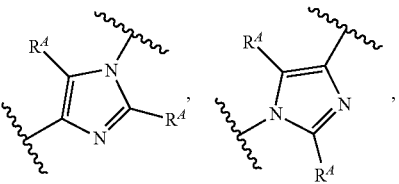
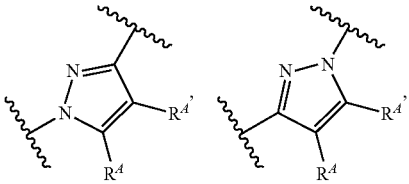
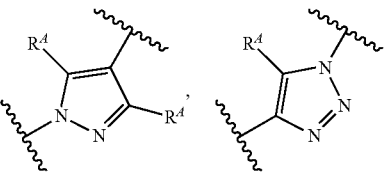
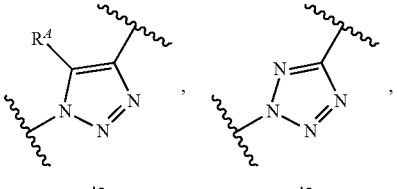
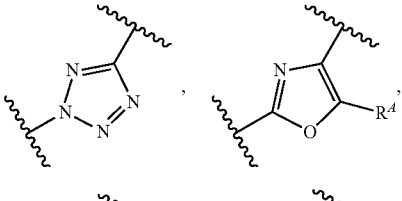
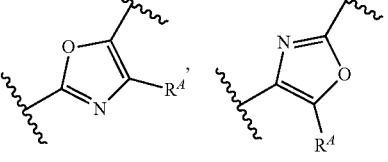

-continued

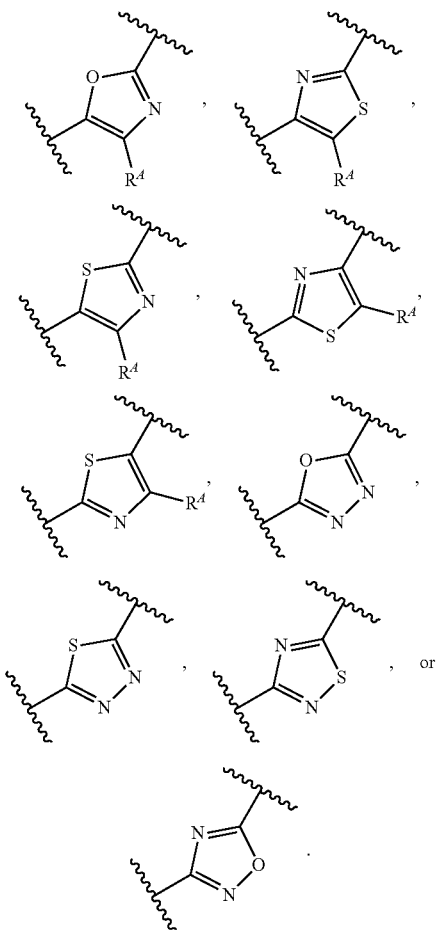

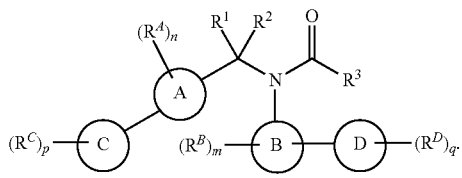

In some embodiments, ring A is a monocyclic carbocycle, monocyclic heteroaryl; ring C is monocyclic carbocycle, or monocyclic heterocycle; ring B is a monocyclic carbocycle, or monocyclic heterocycle; ring D is phenyl, monocyclic N-containing heterocycloalkyl, or monocyclic heteroaryl.

In some embodiments, ring A is a phenyl, $C_3$-$C_6$cycloalkyl, or monocyclic heteroaryl; ring C is phenyl, $C_3$-$C_6$cycloalkyl, or monocyclic heteroaryl; ring B is phenyl, or monocyclic heteroaryl; ring D is phenyl, monocyclic N-containing heterocycloalkyl, or monocyclic heteroaryl. In some embodiments, ring A is a phenyl, $C_3$-$C_6$cycloalkyl, or monocyclic heteroaryl; ring C is phenyl, or monocyclic heteroaryl; ring B is phenyl, or monocyclic heteroaryl; ring D is phenyl, monocyclic N-containing heterocycloalkyl, or monocyclic heteroaryl.

In some embodiments, ring A is a monocyclic heterocycle that is a monocyclic $C_2$-$C_8$heterocycloalkyl containing at least 1 N atom in the ring.

In some embodiments, ring A is a monocyclic heterocycle that is a monocyclic $C_2$-$C_8$heterocycloalkyl containing at least 1 N atom in the ring that is selected from aziridinyl, azetidinyl, pyrrolidinyl, piperidinyl, piperazinyl, and azepanyl.

In some embodiments,

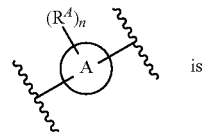 is

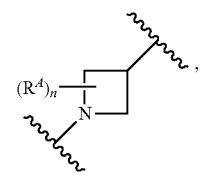,

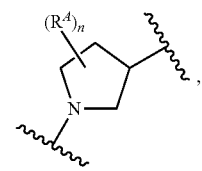,

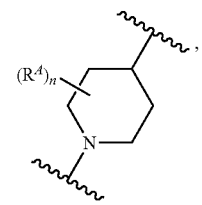,

In some embodiments, $L^1$ is —$X^1$-$L^2$- or -$L^2$-$X^1$—; $X^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —C(=O)NR$^{10}$—, —NR$^{10}$C(=O)—, —NR$^{10}$S(=O)$_2$—, or —NR$^{10}$—; $L^2$ is absent or —CH$_2$—.

In some embodiments, $L^1$ is absent, —O—, —S—, —S—CH$_2$—, —CH$_2$—S—, —CH$_2$—, —CH=CH—, —C≡C—, —C(=O)—, —C(=O)O—, —OC(=O)—, —C(=O)NR$^{10}$—, —NR$^{11}$C(=O)—, —NR$^{10}$S(=O)$_2$—, —N$^{10}$—, —NR$^{10}$—CH$_2$—, or —CH$_2$—NR$^{10}$—.

In some embodiments, $L^1$ is absent.

In some embodiments, the compound of Formula (I) has the following structure:

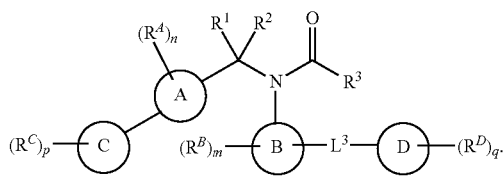

In some embodiments, the compound of Formula (I) has the following structure:

-continued

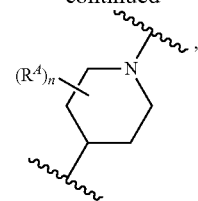

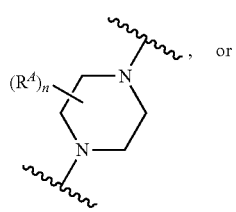, or

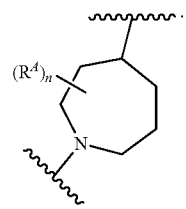

In some embodiments, the compound of Formula (I) has the structure of Formula (III), or a pharmaceutically acceptable salt or solvate thereof:

Formula (III)

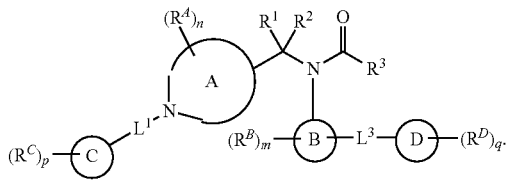

wherein, ring A is a monocyclic heterocycle containing 1-4 N atoms or a bicyclic heterocycle containing 1-4 N atoms.

In some embodiments, ring A is a monocyclic heterocycle that is a monocyclic 5-membered $C_1$-$C_4$heteroarylene containing 1-4 N atoms.

In some embodiments,

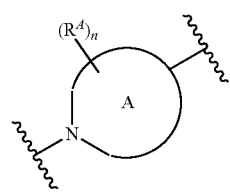

is a monocyclic 5-membered $C_1$-$C_4$heteroarylene containing 1-4 N atoms that has the structure

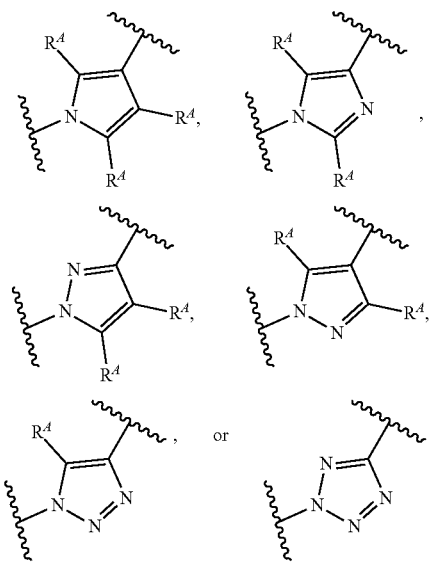

In some embodiments, ring A is a monocyclic heterocycle that is a monocyclic $C_2$-$C_8$heterocycloalkyl containing at least 1 N atom in the ring that is selected from aziridinyl, azetidinyl, pyrrolidinyl, piperidinyl, piperazinyl, and azepanyl.

In some embodiments,

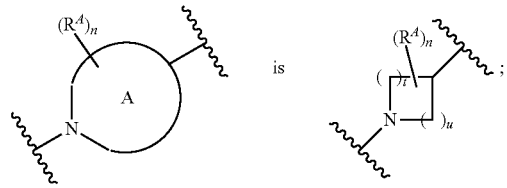

wherein, t is 1, 2, or 3; u is 1, 2, or 3.

In some embodiments,

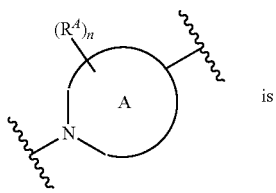

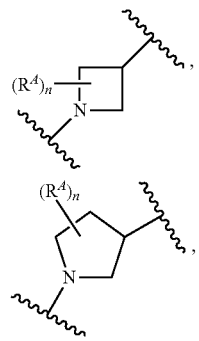

-continued

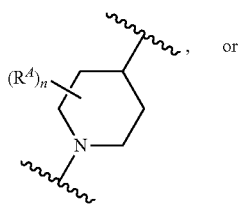, or

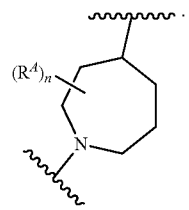

In some embodiments,

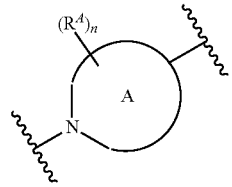 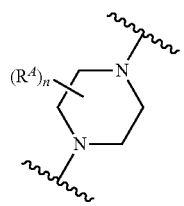

is

In some embodiments, ring A is a monocyclic heterocycle containing 1-4 N atoms or a bicyclic heterocycle containing 1-4 N atoms that is selected from a β-lactam, γ-lactam, δ-lactam or ε-lactam.

In some embodiments, ring A is a bicyclic $C_5$-$C_8$heterocycloalkyl that is a fused bicyclic $C_5$-$C_8$heterocycloalkyl, bridged bicyclic $C_5$-$C_8$heterocycloalkyl, or spiro bicyclic $C_5$-$C_8$heterocycloalkyl.

In some embodiments,

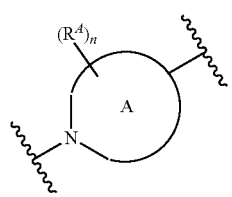

is a bridged bicyclic $C_5$-$C_8$heterocycloalkyl that is

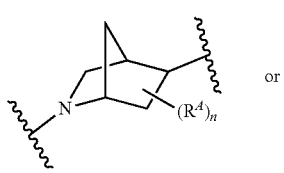 or

-continued

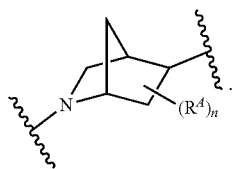.

In some embodiments,

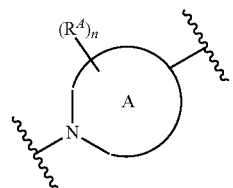

is spiro bicyclic $C_5$-$C_8$heterocycloalkyl that is

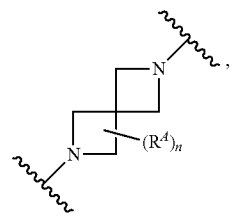,

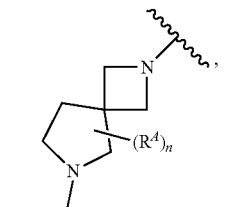,

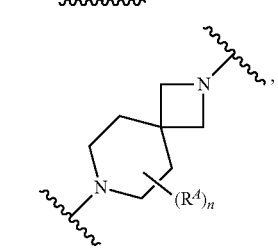,

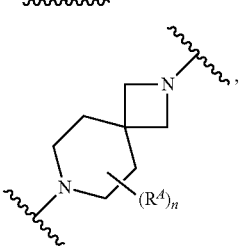,

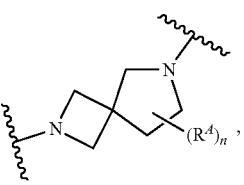, or

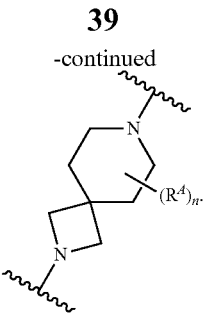

In some embodiments, $L^1$ is —$X^1$-$L^2$- or -$L^2$-$X^1$—; $X^1$ is absent, —S(=O)—, —S(=O)$_2$—, —CH$_2$—, —C(=O)—, —OC(=O)—, —NR$^{10}$C(=O)—, or —NR$^{10}$S(=O)$_2$—; $L^2$ is absent or substituted or unsubstituted $C_1$-$C_4$alkylene.

In some embodiments, $L^1$ is —$X^1$-$L^2$- or -$L^2$-$X^1$—; $X^1$ is absent, —S(=O)$_2$—, —CH$_2$—, or —C(=O)—; $L^2$ is absent or —CH$_2$—.

In some embodiments, ring C is monocyclic carbocycle, or bicyclic carbocycle.

In some embodiments, ring C is monocyclic carbocycle selected from cyclopropyl, cyclobutyl, cyclopentyl, cyclohexyl, and phenyl.

In some embodiments, ring C is phenyl.

In some embodiments, ring C is bicyclic carbocycle selected from indanyl, indenyl, and naphthyl.

In some embodiments, ring C is monocyclic heterocycle, or bicyclic heterocycle.

In some embodiments, ring C is a monocyclic heteroaryl selected from furanyl, thienyl, pyrrolyl, oxazolyl, thiazolyl, imidazolyl, pyrazolyl, triazolylene, tetrazolyl, isoxazolyl, isothiazolyl, oxadiazolyl, thiadiazolyl, pyridinyl, pyrimidinyl, pyrazinyl, pyridazinyl, and triazinyl.

In some embodiments,

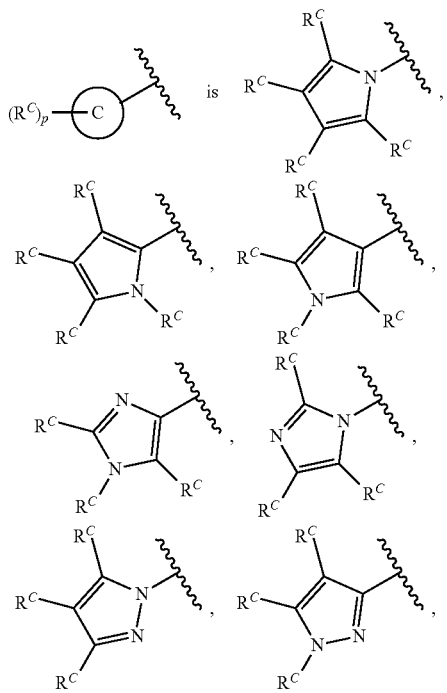

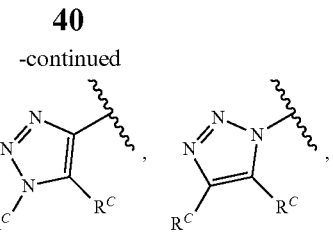

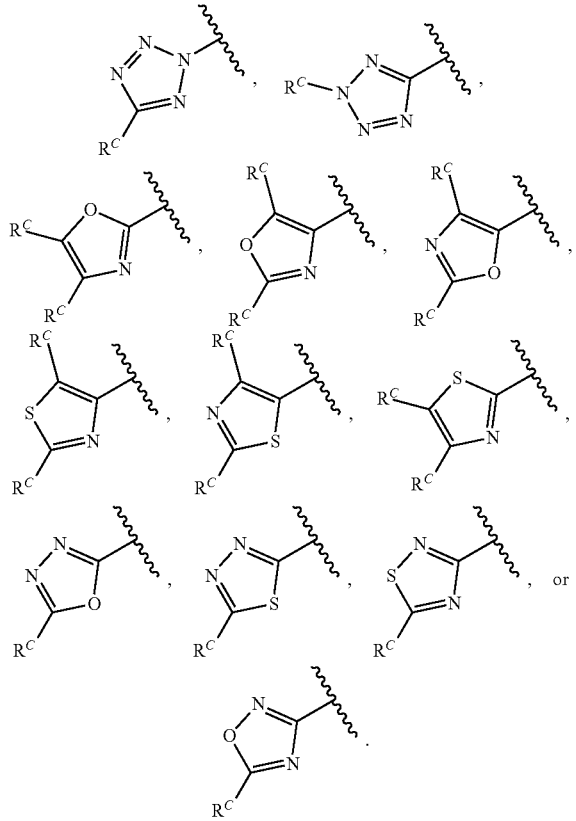

In some embodiments, ring C is a bicyclic heteroaryl selected from quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, and purinyl.

In some embodiments

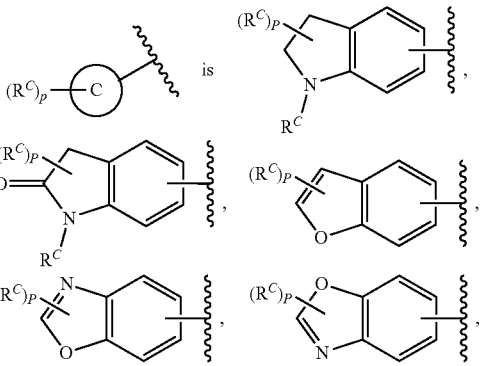

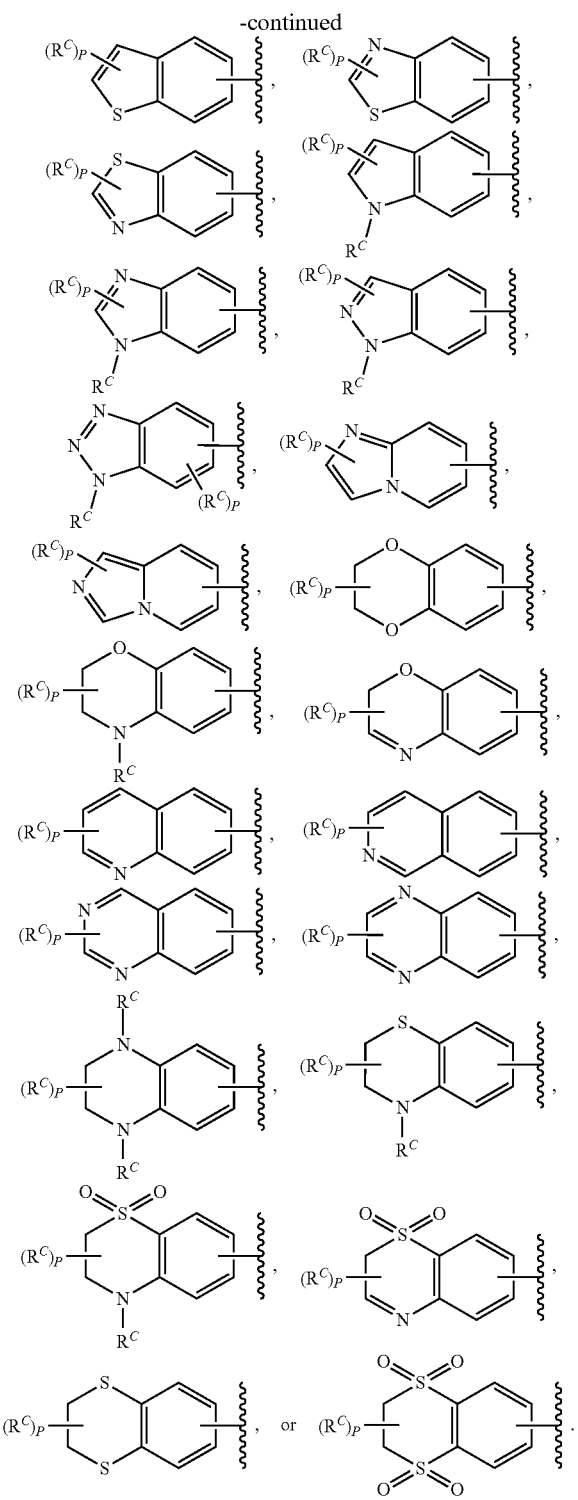
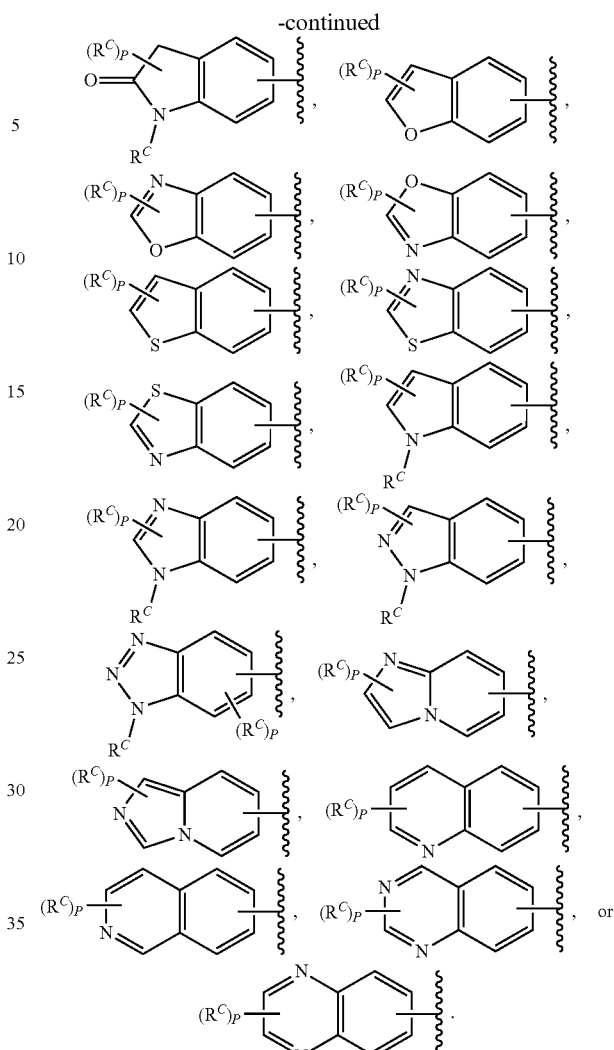

In some embodiments, ring C is monocyclic heterocycloalkyl selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, and 1,2,3,6-tetrahydropyridinyl.

In some embodiments, ring C is a monocyclic $C_2$-$C_8$heterocycloalkyl containing at least 1 N atom in the ring.

In some embodiments, ring C is a monocyclic $C_2$-$C_8$heterocycloalkyl containing at least 1 N atom in the ring that is selected from aziridinyl, azetidinyl, pyrrolidinyl, morpholinyl, thiomorpholinyl, piperidinyl, piperazinyl, and azepanyl.

In some embodiments, 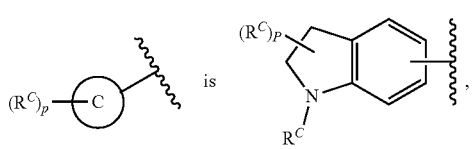 is

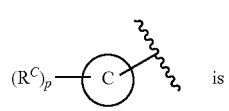 is

-continued

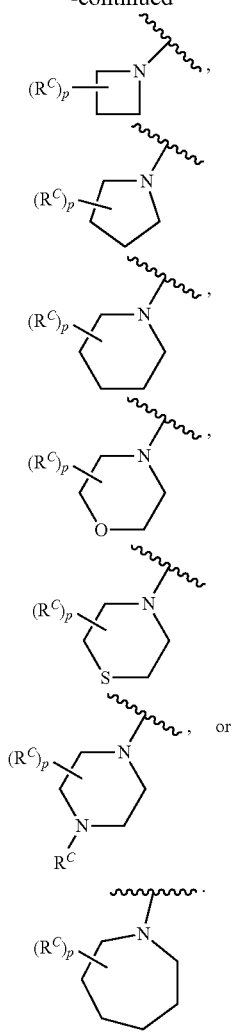

In some embodiments,

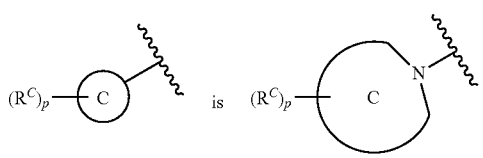

wherein, ring C is a 5-membered N-containing heteroaryl, or a N-containing C$_2$-C$_8$heterocycloalkyl.

In some embodiments, ring C is a 5-membered N-containing heteroaryl containing 1-4 N atoms.

In some embodiments,

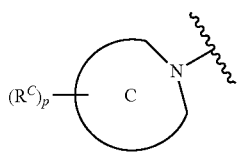

is a monocyclic 5-membered C$_1$-C$_4$heteroarylene containing 1-4 N atoms that has the structure

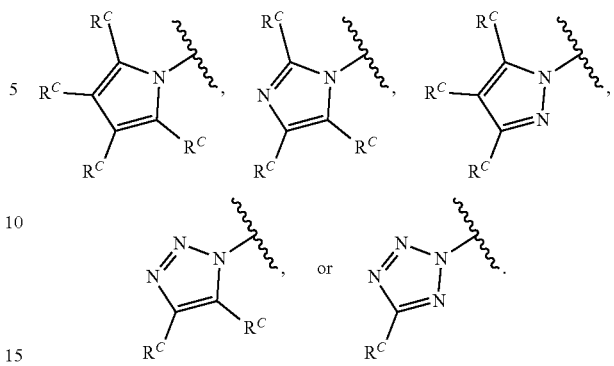

In some embodiments, ring C is a monocyclic C$_2$-C$_8$heterocycloalkyl containing at least 1 N atom in the ring that is selected from aziridinyl, azetidinyl, pyrrolidinyl, morpholinyl, thiomorpholinyl, piperidinyl, piperazinyl, and azepanyl.

In some embodiments,

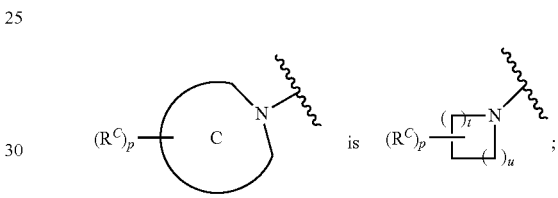

wherein, t is 1, 2, or 3; u is 1, 2, or 3.

In some embodiments,

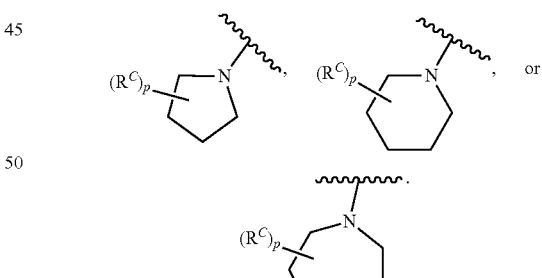

In some embodiments, ring C is a monocyclic C$_2$-C$_8$heterocycloalkyl containing 1 N atom in the ring that is selected from a β-lactam, γ-lactam, δ-lactam or ε-lactam.

In some embodiments, ring C is a bicyclic C$_5$-C$_8$heterocycloalkyl that is a fused bicyclic C$_5$-C$_8$heterocycloalkyl, bridged bicyclic C$_5$-C$_8$heterocycloalkyl, or spiro bicyclic C$_5$-C$_8$heterocycloalkyl.

In some embodiments,

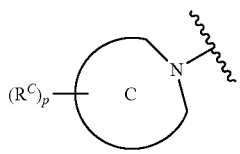

is a bridged bicyclic $C_5$-$C_8$heterocycloalkyl that is

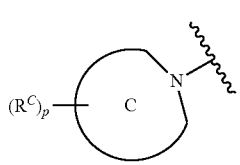

In some embodiments,

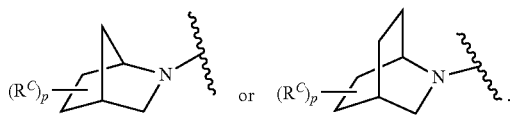

is spiro bicyclic $C_5$-$C_8$heterocycloalkyl that

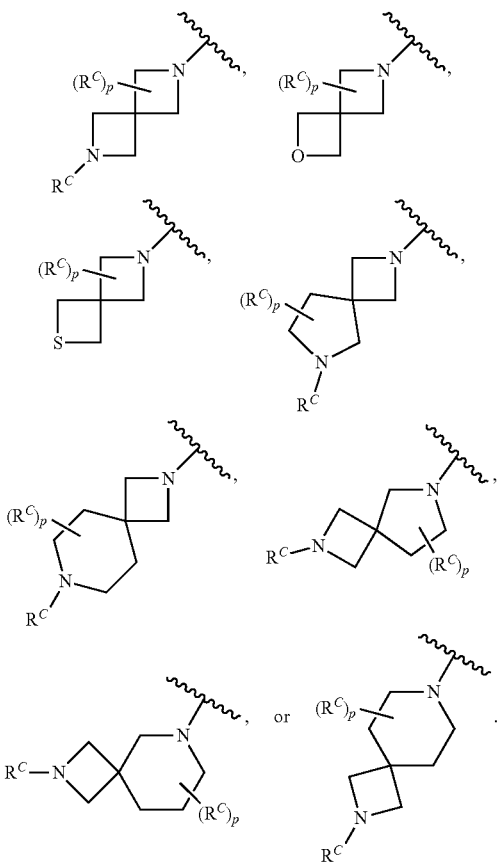

In some embodiments, $R^3$ is selected from substituted or unsubstituted $C_1$-$C_{10}$alkyl, substituted or unsubstituted $C_3$-$C_{10}$cycloalkyl, or substituted or unsubstituted aryl, wherein if $R^3$ is substituted then $R^3$ is substituted with one or more $R^{12}$ groups.

In some embodiments, $R^3$ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

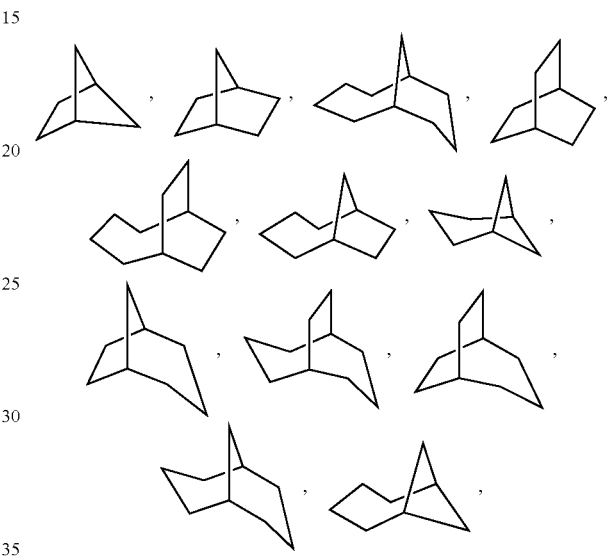

and adamantyl.

In some embodiments, $R^3$ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl. In some embodiments, $R^3$ is selected from iso-propyl, iso-butyl, tert-butyl, tert-pentyl, neopentyl, isopentyl, sec-pentyl, 3-pentyl, isohexyl, 3-methylpentyl, 2,3-dimethylbutyl, neohexyl, substituted or unsubstituted cyclopentyl, substituted or unsubstituted cyclohexyl, and substituted or unsubstituted phenyl. In some embodiments, $R^3$ is substituted or unsubstituted cyclohexyl.

In another aspect, described herein is a compound that has the structure of Formula (IV), or a pharmaceutically acceptable salt or solvate thereof:

Formula (IV)

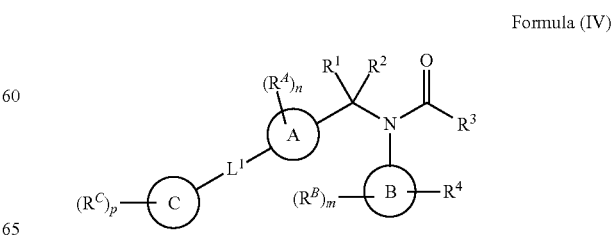

wherein
R$^1$ and R$^2$ are each independently selected from H, D, F, C$_1$-C$_4$alkyl, or C$_1$-C$_4$fluoroalkyl;
or R$^1$ and R$^2$ are taken together with the carbon atom to which they are attached to form a substituted or unsubstituted C$_3$-C$_{10}$cycloalkyl, or substituted or unsubstituted C$_2$-C$_{10}$heterocycloalkyl;
or R$^1$ and R$^2$ are taken together with the carbon atom to which they are attached to form a carbonyl (C=O);
R$^3$ is selected from substituted or unsubstituted C$_1$-C$_{10}$alkyl, substituted or unsubstituted C$_2$-C$_{10}$alkenyl, substituted or unsubstituted C$_2$-C$_{10}$alkynyl, substituted or unsubstituted C$_3$-C$_{10}$cycloalkyl, substituted or unsubstituted C$_2$-C$_{10}$heterocycloalkyl, substituted or unsubstituted aryl, or substituted or unsubstituted heteroaryl, wherein if R$^3$ is substituted then R$^3$ is substituted with one or more R$^{12}$ groups;
each R$^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NHC(=O)R$^{11}$, —NHC(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^5$-L$^6$-R$^{13}$;
L$^5$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;
L$^6$ is absent, unsubstituted or substituted C$_1$-C$_{10}$alkylene, unsubstituted or substituted C$_1$-C$_{10}$heteroalkylene, unsubstituted or substituted C$_2$-C$_{10}$alkenylene, unsubstituted or substituted C$_2$-C$_{10}$alkynylene, unsubstituted or substituted C$_3$-C$_{10}$cycloalkylene, unsubstituted or substituted C$_2$-C$_{10}$heterocycloalkylene, unsubstituted or substituted arylene, or unsubstituted or substituted heteroarylene;
R$^{13}$ is H, halogen, unsubstituted or substituted C$_1$-C$_{10}$alkyl, unsubstituted or substituted C$_2$-C$_{10}$alkenyl, unsubstituted or substituted C$_2$-C$_{10}$alkynyl, unsubstituted or substituted C$_1$-C$_{10}$cycloalkyl, unsubstituted or substituted C$_1$-C$_{10}$heterocycloalkyl, unsubstituted or substituted aryl, or substituted or unsubstituted heteroaryl;
ring A is a monocyclic carbocycle, monocyclic heterocycle, or bicyclic heterocycle;
each R$^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl;

L$^1$ is —X$^1$-L$^2$- or -L$^2$-X$^1$—;
X$^1$ is absent, —O—, —S—, —S(=O)—, —S(=O)$_2$—, —S(=O)$_2$NR$^{10}$—, —CH$_2$—, —CH=CH—, —C≡C—, —C(=O)—, —C(=O)O—, —OC(=O)—, —OC(=O)O—, —C(=O)NR$^{10}$—, —NR$^{10}$C(=O)—, —OC(=O)NR$^{10}$—, —NR$^{10}$C(=O)O—, —NR$^{10}$C(=O)NR$^{10}$—, —NR$^{10}$S(=O)$_2$—, or —NR$^{10}$—;
L$^2$ is absent or substituted or unsubstituted C$_1$-C$_4$alkylene;
ring C is monocyclic carbocycle, bicyclic carbocycle, monocyclic heterocycle, or bicyclic heterocycle;
each R$^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, substituted or unsubstituted C$_1$-C$_6$heteroalkyl, substituted or unsubstituted phenyl and substituted or unsubstituted monocyclic heteroaryl;
ring B is a monocyclic carbocycle, bicyclic carbocycle, monocyclic heterocycle, or bicyclic heterocycle;
each R$^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted C$_1$-C$_6$alkyl, substituted or unsubstituted C$_2$-C$_6$alkenyl, substituted or unsubstituted C$_2$-C$_6$alkynyl, substituted or unsubstituted C$_1$-C$_6$fluoroalkyl, and substituted or unsubstituted C$_1$-C$_6$heteroalkyl;
R$^4$ is C$_2$-C$_{10}$alkenyl; or
R$^4$ is —N(R$^9$)$_2$, -(substituted or unsubstituted C$_1$-C$_6$alkylene)-N(R$^9$)$_2$, —NR$^9$—C(R$^7$)(R$^8$)—CO$_2$R$^{10}$, —NR$^9$-(Substituted or unsubstituted C$_1$-C$_6$alkylene)-N(R$^9$)$_2$—, or -L$^3$-Y;
L$^3$ is —C(R$^5$)(R$^6$)—, or —C(R$^5$)(R$^6$)—C(R$^7$)(R$^8$)—;
R$^5$ and R$^7$ are each independently selected from H, D, C$_1$-C$_4$alkyl and C$_3$-C$_6$cycloalkyl;
or R$^5$ and R$^7$ are taken together with the intervening atoms to form a double bond;
or R$^5$ and R$^7$ are taken together with the intervening atoms to form an epoxide or a substituted or unsubstituted C$_3$-C$_6$cycloalkyl;
R$^6$ and R$^8$ are each independently selected from H, D, C$_1$-C$_4$alkyl or C$_3$-C$_6$cycloalkyl;
Y is —CH$_2$N(R$^9$)$_2$, —C(=O)N(R$^9$)$_2$,

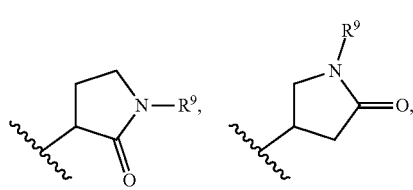

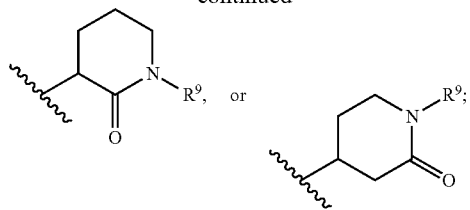

each $R^9$ is independently selected from H, substituted or unsubstituted $C_1$-$C_6$alkyl, substituted or unsubstituted $C_1$-$C_6$heteroalkyl, substituted or unsubstituted $C_2$-$C_6$alkenyl, substituted or unsubstituted $C_3$-$C_6$cycloalkyl, substituted or unsubstituted heterocycle, —S(=O)$_2$R$^{11}$, —S(=O)$_2$N(R$^{10}$)$_2$, —C(=O)R$^{11}$, —CO$_2$R$^{10}$, or —C(=O)N(R$^{10}$)$_2$;

or two $R^9$ on the same N atom are taken together with the N atom to which they are attached to form a N-containing heterocycle;

each $R^{10}$ is independently selected from H, substituted or unsubstituted $C_1$-$C_6$alkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

or two $R^{10}$ on the same N atom are taken together with the N atom to which they are attached to form a N-containing heterocycle;

each $R^{11}$ is independently selected from substituted or unsubstituted $C_1$-$C_6$alkyl, substituted or unsubstituted $C_1$-$C_6$heteroalkyl, substituted or unsubstituted $C_1$-$C_6$fluoroalkyl, substituted or unsubstituted $C_3$-$C_6$cycloalkyl, substituted or unsubstituted phenyl, substituted or unsubstituted monocyclic heteroaryl, and substituted or unsubstituted benzyl;

m is 0, 1, or 2;
n is 0, 1, or 2;
p is 0, 1, 2, 3, or 4.

In some embodiments, ring B is a monocyclic carbocycle or monocyclic heterocycle wherein the groups

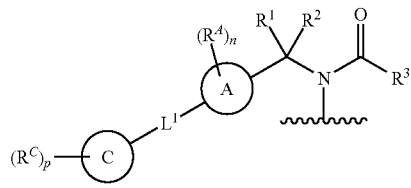

and $R^4$ are in a 1,3-relationship on ring B.

In some embodiments, ring B is a monocyclic carbocycle or monocyclic heterocycle wherein the groups

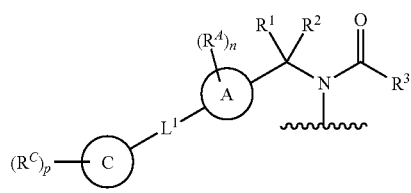

and $R^4$ are in a 1,4-relationship on ring B.

In some embodiments, ring B is phenyl.
In some embodiments, ring B is monocyclic heteroaryl.
In some embodiments, ring B is monocyclic 6-membered heteroaryl selected from pyridinyl, pyrimidinyl, pyrazinyl, and pyridazinyl.

In some embodiments, is

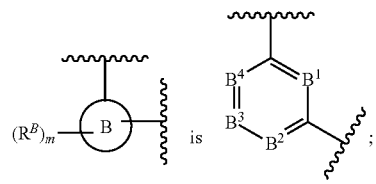

$B^1$ is $CR^B$ or N; $B^2$ is $CR^B$ or N; $B^3$ is $CR^B$ or N; $B^4$ is $CR^B$ or N.

In some embodiments, $B^1$ is $CR^B$; $B^2$ is $CR^B$; $B^3$ is $CR^B$; $B^4$ is $CR^B$.

In some embodiments, $B^1$ is N; $B^2$ is $CR^B$ or N; $B^3$ is $CR^B$; $B^4$ is $CR^B$.

In some embodiments, $B^1$ is $CR^B$ or N; $B^2$ is $CR^B$; $B^3$ is $CR^B$ or N; $B^4$ is $CR^B$.

In some embodiments, $B^1$ is $CR^B$ or N; $B^2$ is $CR^B$; $B^3$ is $CR^B$; $B^4$ is $CR^B$ or N.

In some embodiments, $B^1$ is $CR^B$ or N; $B^2$ is N; $B^3$ is $CR^B$; $B^4$ is $CR^B$ or N.

In some embodiments,

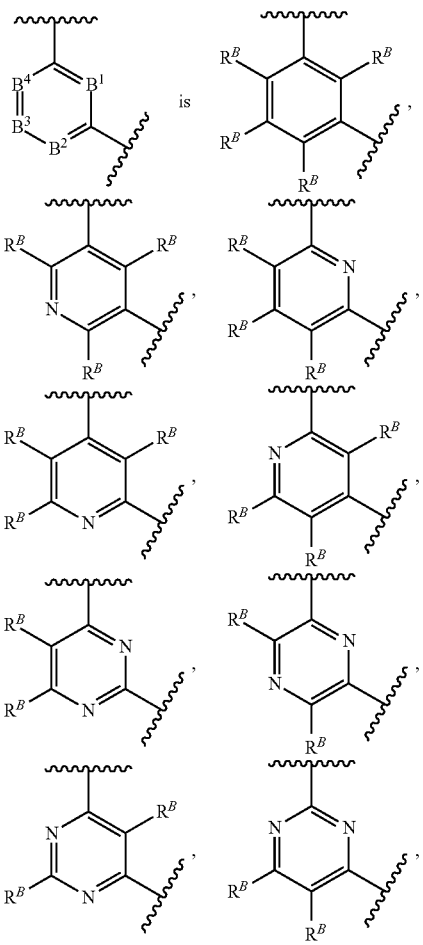

-continued

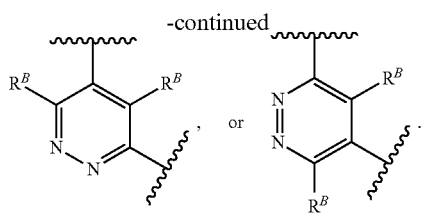

In some embodiments, ring A is a monocyclic carbocycle.
In some embodiments, ring A is monocyclic carbocycle that is phenyl or a $C_3$-$C_8$cycloalkyl.
In some embodiments, ring A is phenyl.
In some embodiments,

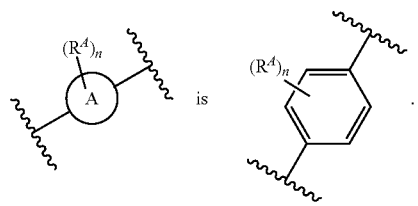

In some embodiments, the compound has the following structure:

Formula (V)

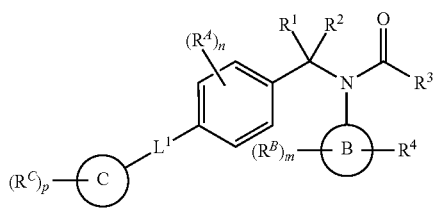

In some embodiments, ring A is $C_3$-$C_8$cycloalkyl that is selected from cyclopropyl, cyclobutyl, cyclopentyl, cyclohexyl, cycloheptyl, and cyclooctyl.
In some embodiments, ring A is

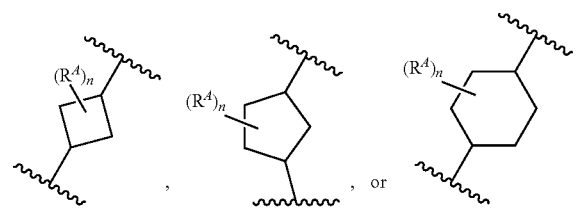

In some embodiments, ring A is a monocyclic heterocycle.
In some embodiments, ring A is a monocyclic heterocycle that is a monocyclic $C_1$-$C_5$heteroarylene containing 1-4 N atoms, and 0 or 1 O or S atom.
In some embodiments, ring A is a monocyclic heterocycle that is a monocyclic $C_1$-$C_5$heteroarylene containing 0-4 N atoms, and 1 O or S atom.
In some embodiments, ring A is a monocyclic heterocycle that is a monocyclic 6-membered heteroarylene selected from pyridinylene, pyrimidinylene, pyrazinylene, or pyridazinylene.

In some embodiments,

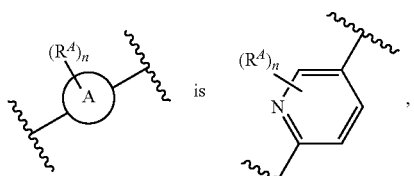

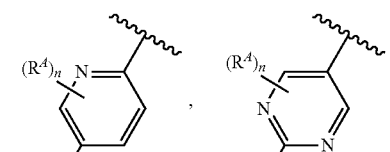

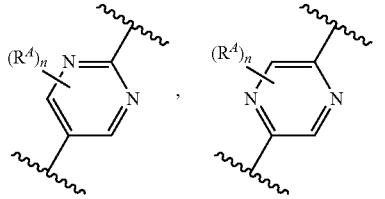

In some embodiments, ring A is a monocyclic heterocycle that is a monocyclic 5-membered heteroarylene selected from furanylene, thienylene, pyrrolylene, oxazolylene, thiazolylene, imidazolylene, pyrazolylene, triazolylene, tetrazolylene, isoxazolylene, isothiazolylene, oxadiazolylene, and thiadiazolylene.
In some embodiments,

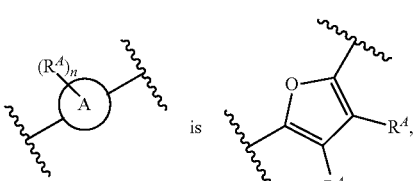

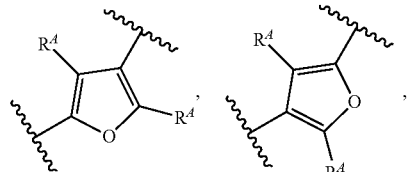

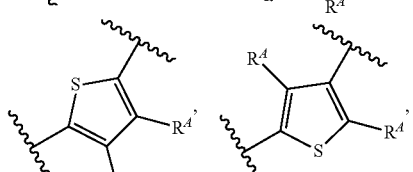

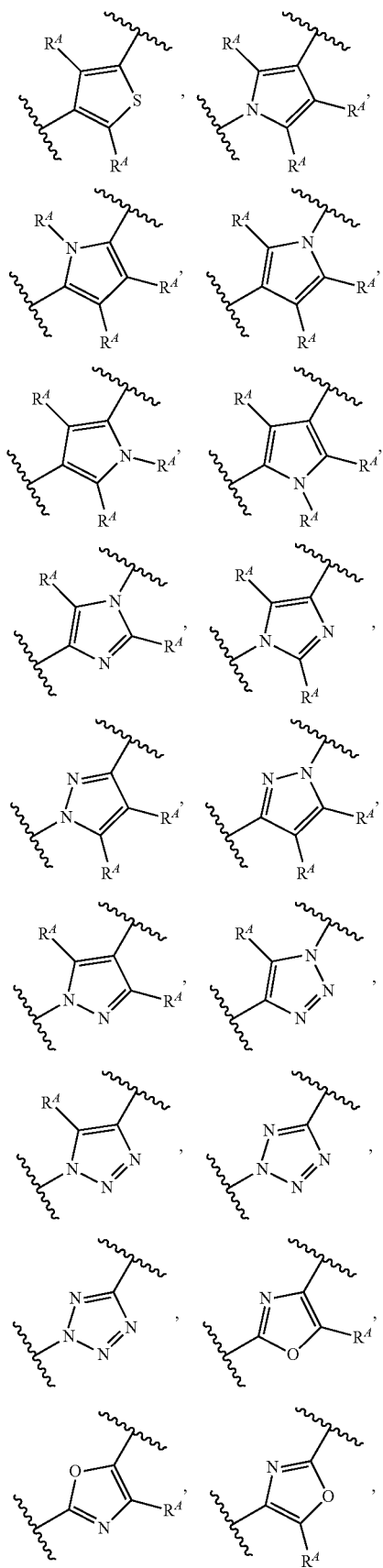

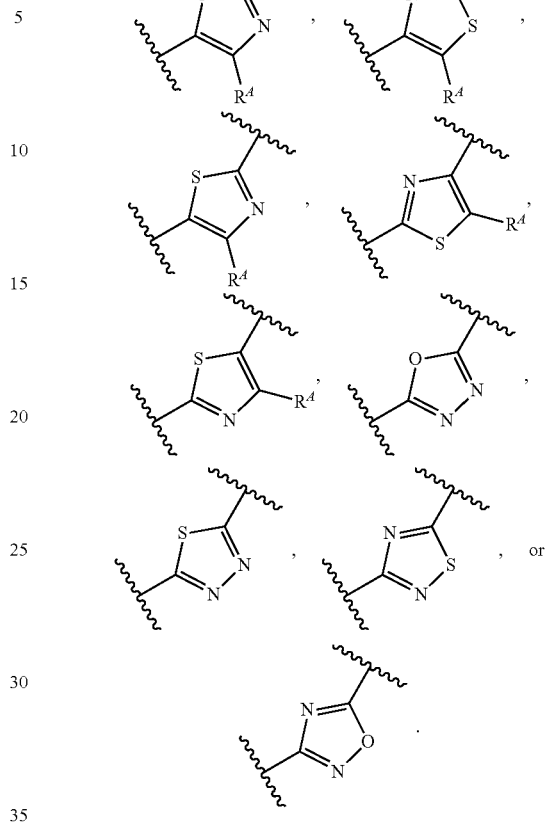

In some embodiments, $L^1$ is $-X^1-L^2-$ or $-L^2-X^1-$; $X^1$ is absent, $-O-$, $-S-$, $-S(=O)-$, $-S(=O)_2-$, $-S(=O)_2NR^{10}-$, $-CH_2-$, $-CH=CH-$, $-C\equiv C-$, $-C(=O)-$, $-C(=O)O-$, $-OC(=O)-$, $-C(=O)NR^{10}-$, $-NR^{10}C(=O)-$, $-NR^{10}S(=O)_2-$, or $-NR^{10}-$; $L^2$ is absent or $-CH_2-$.

In some embodiments, $L^1$ is absent, $-O-$, $-S-$, $-S-CH_2-$, $-CH_2-S-$, $-CH_2-$, $-CH=CH-$, $-C\equiv C-$, $-C(=O)-$, $-C(=O)O-$, $-OC(=O)-$, $-C(=O)NR^{10}-$, $-NR^{10}C(=O)-$, $-NR^{10}S(=O)_2-$, $-NR^{10}-$, $-NR^{10}-CH_2-$, or $-CH_2-NR^{10}-$.

In some embodiments, $L^1$ is absent.

In some embodiments, ring A is a monocyclic heterocycle that is a monocyclic $C_2$-$C_8$heterocycloalkyl containing at least 1 N atom in the ring.

In some embodiments, ring A is a monocyclic heterocycle that is a monocyclic $C_2$-$C_8$heterocycloalkyl containing at least 1 N atom in the ring that is selected from aziridinyl, azetidinyl, pyrrolidinyl, piperidinyl, piperazinyl, and azepanyl.

In some embodiments,

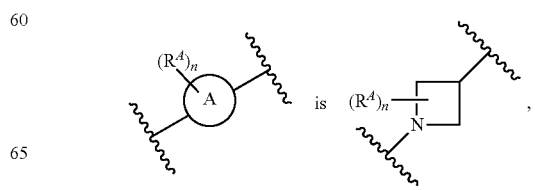

-continued

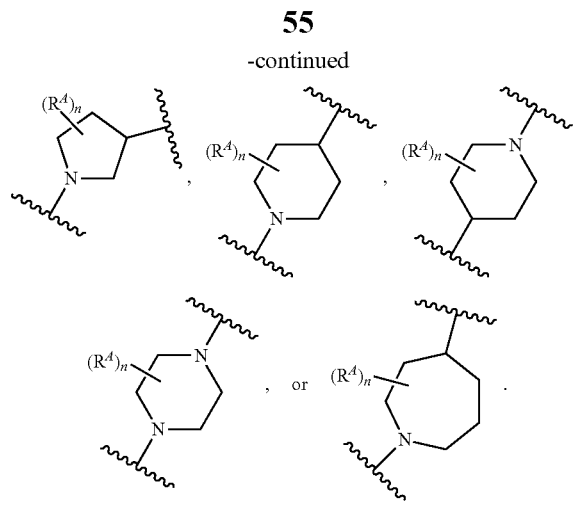

In some embodiments, the compound of Formula (IV) has the structure of Formula (II), or a pharmaceutically acceptable salt or solvate thereof:

Formula (VI)

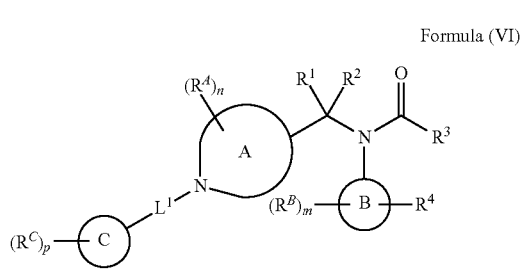

wherein, ring A is a monocyclic heterocycle containing 1-4 N atoms or a bicyclic heterocycle containing 1-4 N atoms.

In some embodiments, ring A is a monocyclic heterocycle that is a monocyclic 5-membered $C_1$-$C_4$heteroarylene containing 1-4 N atoms.

In some embodiments,

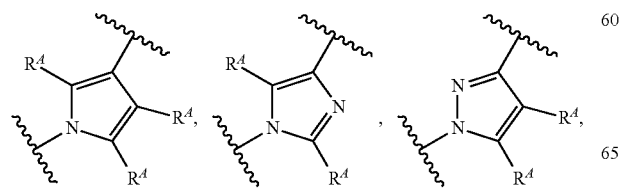

is a monocyclic 5-membered $C_1$-$C_4$heteroarylene containing 1-4 N atoms that has the structure -continued

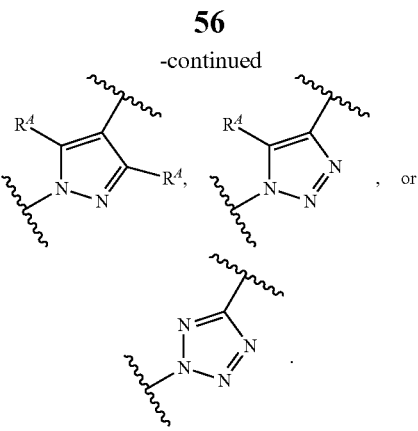

In some embodiments, ring A is a monocyclic heterocycle that is a monocyclic $C_2$-$C_8$heterocycloalkyl containing at least 1 N atom in the ring that is selected from aziridinyl, azetidinyl, pyrrolidinyl, piperidinyl, piperazinyl, and azepanyl.

In some embodiments,

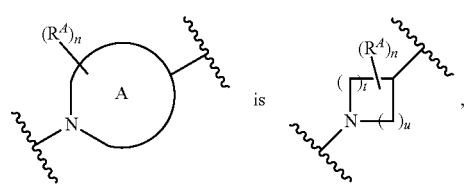

wherein, t is 1, 2, or 3; u is 1, 2, or 3.

In some embodiments,

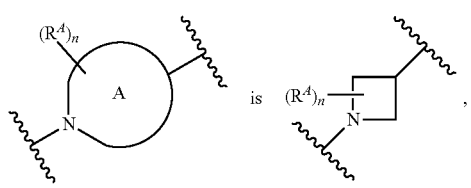

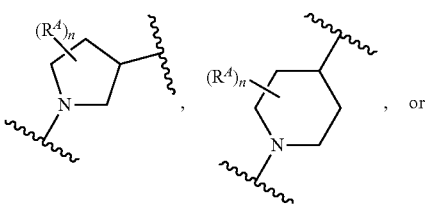

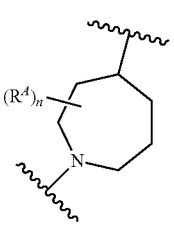

In some embodiments,

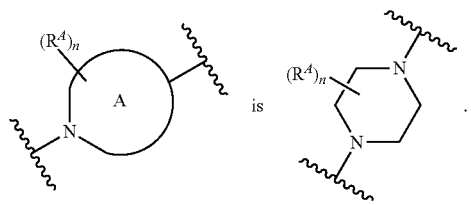 is

In some embodiments, ring A is a monocyclic heterocycle containing 1-4 N atoms or a bicyclic heterocycle containing 1-4 N atoms that is selected from a β-lactam, γ-lactam, δ-lactam or ε-lactam.

In some embodiments, ring A is a bicyclic C$_5$-C$_8$heterocycloalkyl that is a fused bicyclic C$_5$-C$_8$heterocycloalkyl, bridged bicyclic C$_5$-C$_8$heterocycloalkyl, or spiro bicyclic C$_5$-C$_8$heterocycloalkyl.

In some embodiments,

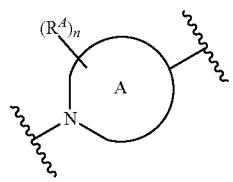

is a bridged bicyclic C$_5$-C$_8$heterocycloalkyl that is

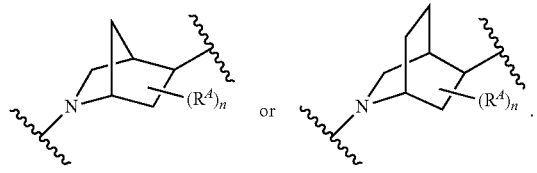

In some embodiments,

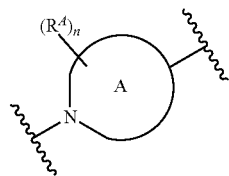

is spiro bicyclic C$_5$-C$_8$heterocycloalkyl that is

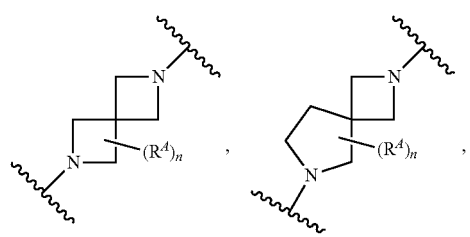

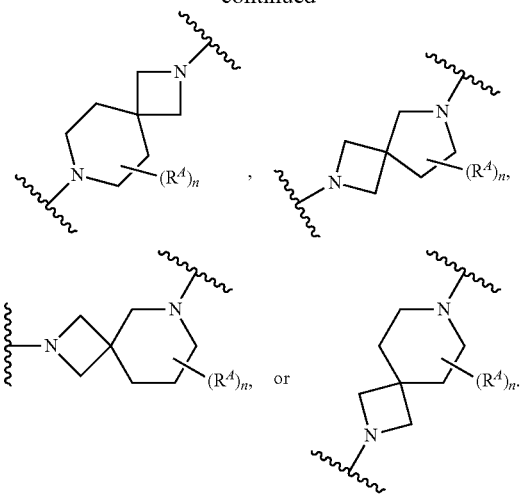

In some embodiments, L$^1$ is —X$^1$-L$^2$- or -L$^2$-X$^1$—; X$^1$ is absent, —S(=O)—, —S(=O)$_2$—, —CH$_2$—, —C(=O)—, —OC(=O)—, —NR$^{10}$C(=O)—, or —NR$^{10}$S(=O)$_2$—; L$^2$ is absent or substituted or unsubstituted C$_1$-C$_4$alkylene.

In some embodiments, L$^1$ is —X$^1$-L$^2$- or -L$^2$-X$^1$—; X$^1$ is absent, —S(=O)$_2$—, —CH$_2$—, or —C(=O)—; L$^2$ is absent or —CH$_2$—.

In some embodiments, ring C is monocyclic carbocycle, or bicyclic carbocycle.

In some embodiments, ring C is monocyclic carbocycle selected from cyclopropyl, cyclobutyl, cyclopentyl, cyclohexyl, and phenyl.

In some embodiments, ring C is phenyl.

In some embodiments, ring C is bicyclic carbocycle selected from indanyl, indenyl, and naphthyl.

In some embodiments, ring C is monocyclic heterocycle, or bicyclic heterocycle.

In some embodiments, ring C is a monocyclic heteroaryl selected from furanyl, thienyl, pyrrolyl, oxazolyl, thiazolyl, imidazolyl, pyrazolyl, triazolylene, tetrazolyl, isoxazolyl, isothiazolyl, oxadiazolyl, thiadiazolyl, pyridinyl, pyrimidinyl, pyrazinyl, pyridazinyl, and triazinyl.

In some embodiments,

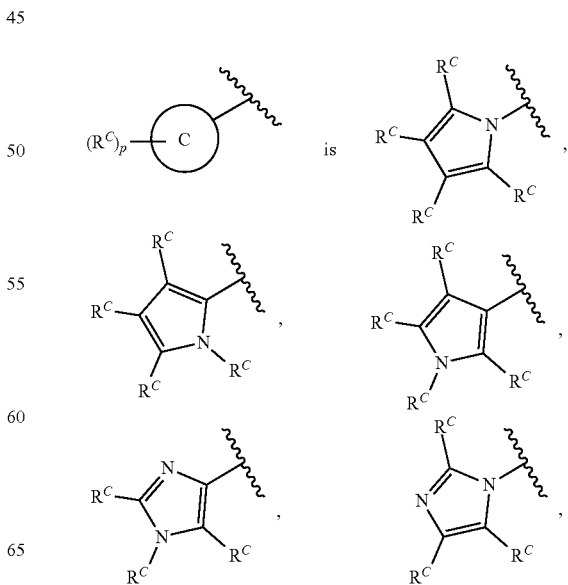

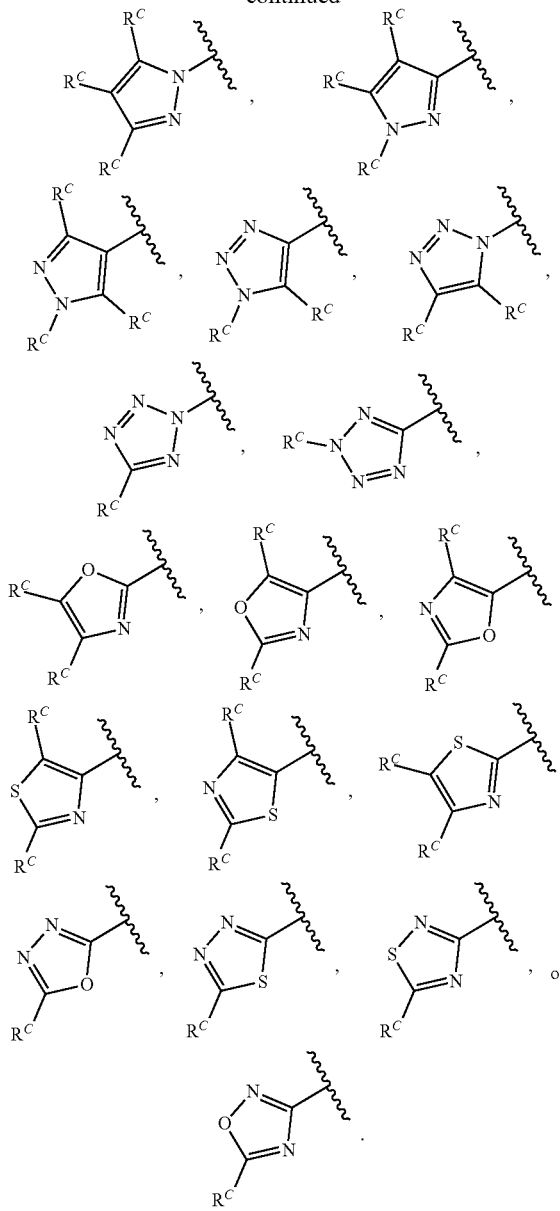

In some embodiments, ring C is a bicyclic heteroaryl selected from quinolinyl, isoquinolinyl, cinnolinyl, phthalazinyl, quinazolinyl, quinoxalinyl, naphthyridinyl, pteridinyl, indolizinyl, azaindolizinyl, indolyl, azaindolyl, indazolyl, azaindazolyl, benzimidazolyl, azabenzimidazolyl, benzotriazolyl, azabenzotriazolyl, benzoxazolyl, azabenzoxazolyl, benzisoxazolyl, azabenzisoxazolyl, benzofuranyl, azabenzofuranyl, benzothienyl, azabenzothienyl, benzothiazolyl, azabenzothiazolyl, and purinyl.

In some embodiments,

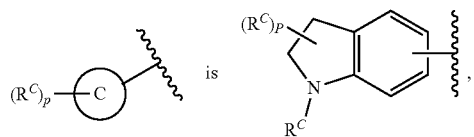

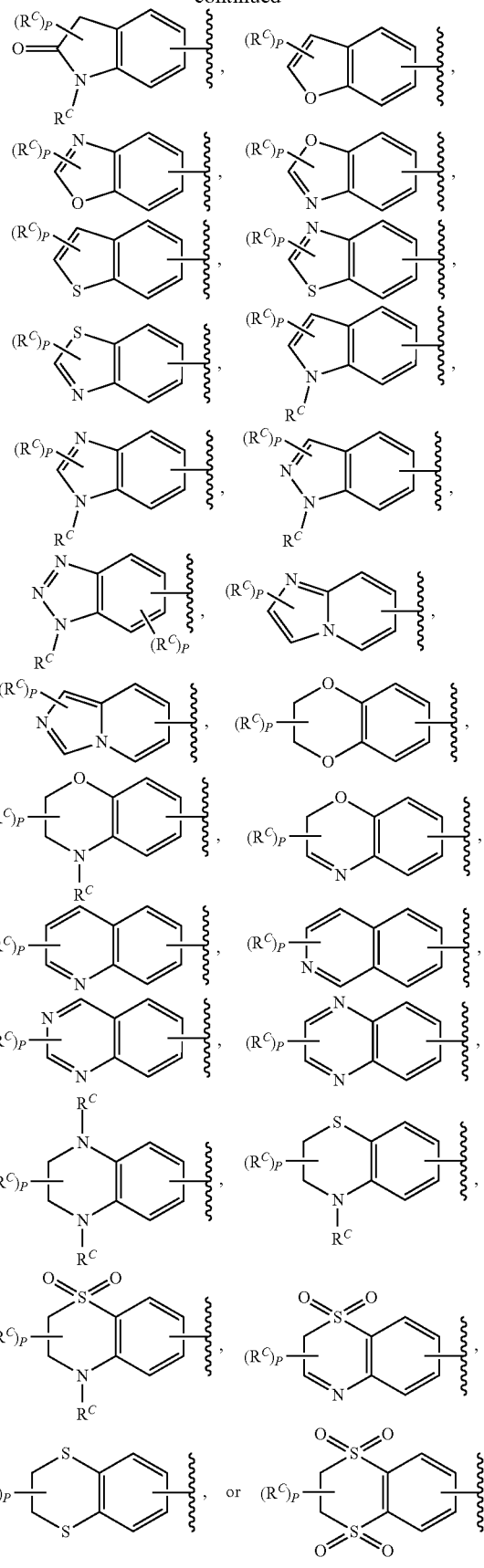

In some embodiments, ring C is monocyclic heteroaryl selected from furanyl, thienyl, pyridinyl, pyrazolyl, pyrrolyl, imidazolyl, oxazolyl, isoxazolyl, thiazolyl, isothiazolyl, triazolyl, pyrimidinyl, pyrazinyl, and triazinyl.

In some embodiments, ring C is a monocyclic 6-membered heteroaryl containing 1-3 N atoms.

In some embodiments,

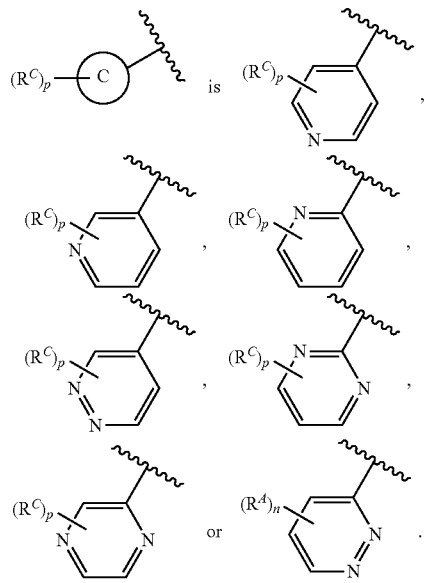

In some embodiments, ring C is a monocyclic 5-membered $C_1$-$C_4$heteroaryl.

In some embodiments, ring C is pyrrolyl, oxazolyl, thiazolyl, imidazolyl, pyrazolyl, triazolyl, tetrazolyl, isoxazolyl, isothiazolyl, oxadiazolyl, or thiadiazolyl.

In some embodiments,

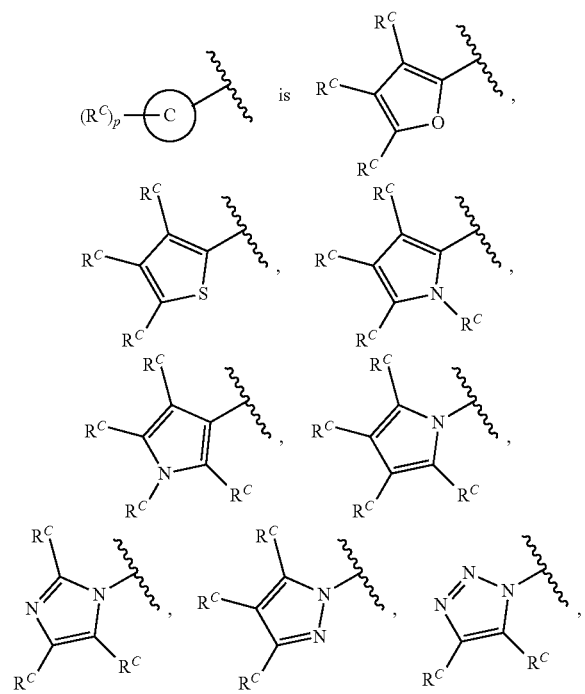

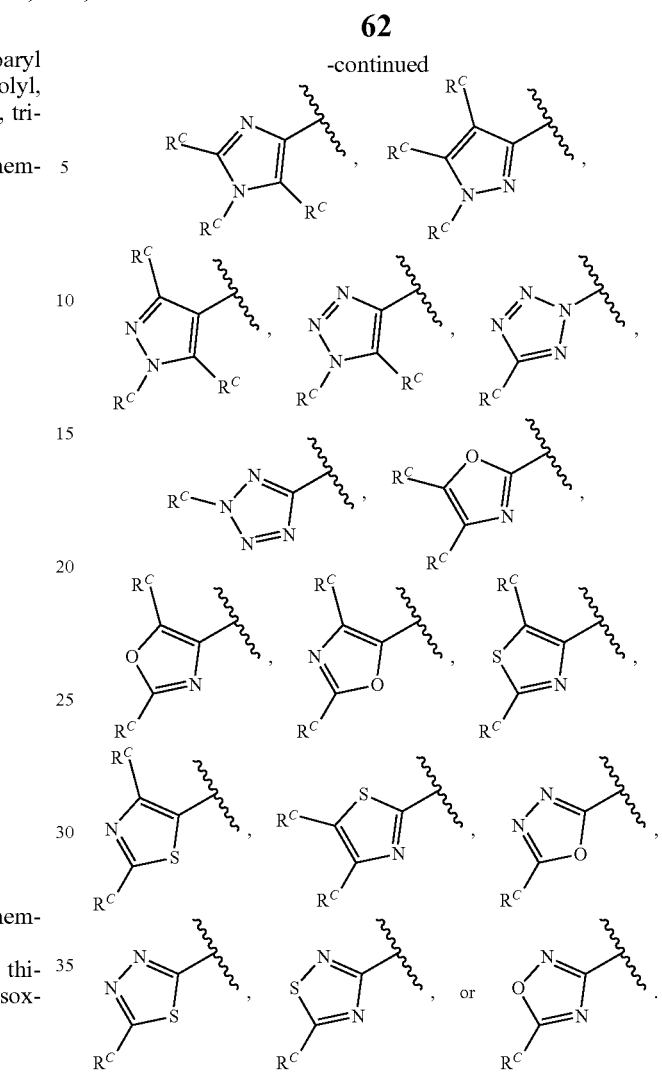

In some embodiments, ring C is monocyclic heterocycle selected from pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, and 1,2,3,6-tetrahydropyridinyl.

In some embodiments, ring C is a monocyclic $C_2$-$C_8$heterocycloalkyl containing at least 1 N atom in the ring.

In some embodiments, ring C is a monocyclic $C_2$-$C_8$heterocycloalkyl containing at least 1 N atom in the ring that is selected from aziridinyl, azetidinyl, pyrrolidinyl, morpholinyl, thiomorpholinyl, piperidinyl, piperazinyl, and azepanyl.

In some embodiments,

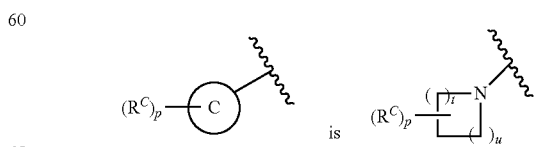

wherein, t is 1, 2, or 3; u is 1, 2, or 3.

In some embodiments

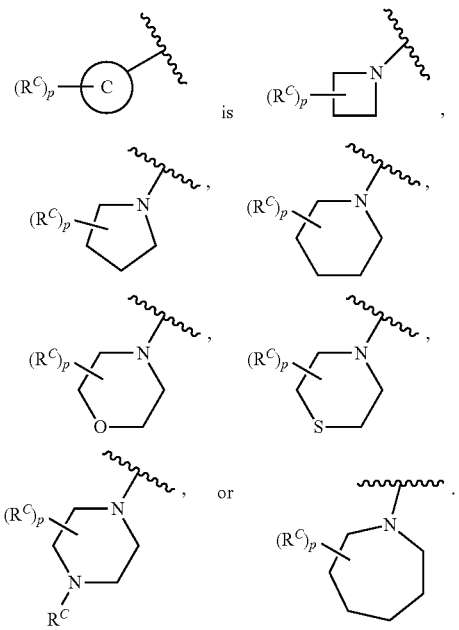

In some embodiments, ring C is a $C_2$-$C_8$heterocycloalkyl containing 1 N atom in the ring that is selected from a β-lactam, γ-lactam, δ-lactam or ε-lactam.

In some embodiments, ring C is a bicyclic $C_5$-$C_8$heterocycloalkyl that is a fused bicyclic $C_5$-$C_8$heterocycloalkyl, bridged bicyclic $C_5$-$C_8$heterocycloalkyl, or spiro bicyclic $C_5$-$C_8$heterocycloalkyl.

In some embodiments,

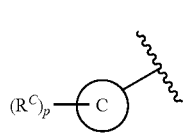

is a bridged bicyclic $C_5$-$C_8$heterocycloalkyl that is

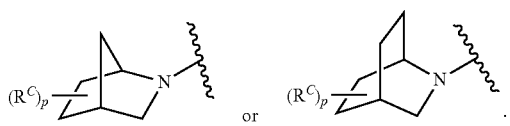

In some embodiments,

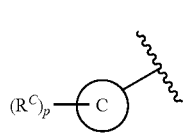

is spiro bicyclic $C_5$-$C_8$heterocycloalkyl that is

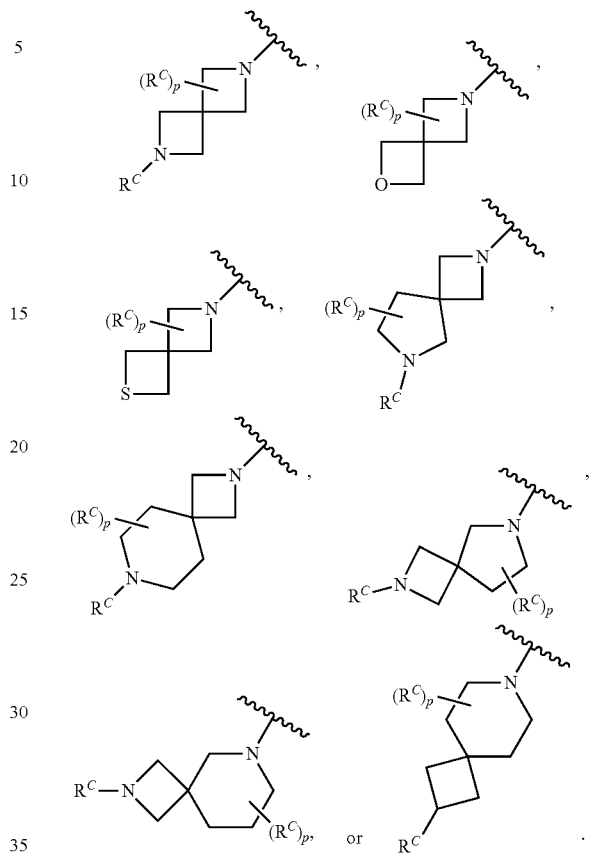

In some embodiments, $R^3$ is selected from substituted or unsubstituted $C_1$-$C_{10}$alkyl, substituted or unsubstituted $C_3$-$C_{10}$cycloalkyl, or substituted or unsubstituted aryl, wherein if $R^3$ is substituted then $R^3$ is substituted with one or more $R^{12}$ groups.

In some embodiments, $R^3$ is selected from substituted or unsubstituted $C_3$-$C_{10}$cycloalkyl, or substituted or unsubstituted phenyl, wherein if $R^3$ is substituted then $R^3$ is substituted with one or more $R^{12}$ groups.

In some embodiments, $R^3$ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl,

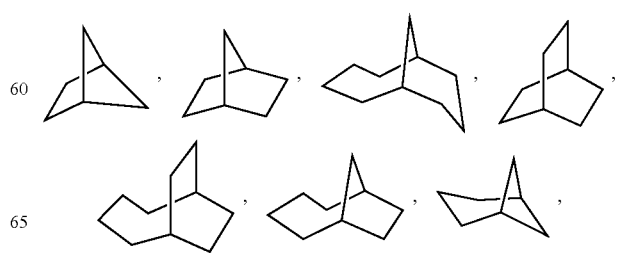

-continued

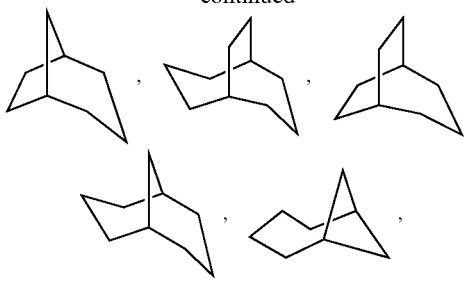

and adamantyl.

In some embodiments, $R^3$ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, neohexyl, substituted or unsubstituted cyclopropyl, substituted or unsubstituted cyclobutyl, substituted or unsubstituted cyclopentyl, substituted or unsubstituted cyclohexyl, substituted or unsubstituted phenyl.

In some embodiments, $R^3$ is selected from methyl, ethyl, propyl, iso-propyl, n-butyl, iso-butyl, tert-butyl, n-pentyl, tert-pentyl, neopentyl, isopentyl, sec-pentyl, 3-pentyl, n-hexyl, isohexyl, 3-methylpentyl, 2,3-dimethylbutyl, or neohexyl. In some embodiments, $R^3$ is selected from methyl, ethyl, propyl, iso-propyl, n-butyl, iso-butyl, or tert-butyl.

In some embodiments, $R^3$ is selected from substituted or unsubstituted cyclopropyl, substituted or unsubstituted cyclobutyl, substituted or unsubstituted cyclopentyl, substituted or unsubstituted cyclohexyl, or unsubstituted phenyl. In some embodiments, $R^3$ is substituted or unsubstituted cyclopropyl. In some embodiments, $R^3$ is substituted or unsubstituted cyclobutyl. In some embodiments, $R^3$ is substituted or unsubstituted cyclopentyl. In some embodiments, $R^3$ is substituted or unsubstituted cyclohexyl. In some embodiments, $R^3$ is substituted or unsubstituted phenyl.

In some embodiments, each $R^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted C$_1$-C$_{10}$alkyl, unsubstituted or substituted C$_1$-C$_{10}$fluoroalkyl, unsubstituted or substituted C$_2$-C$_{10}$alkenyl, unsubstituted or substituted C$_2$-C$_{10}$alkynyl, unsubstituted or substituted C$_1$-C$_{10}$heteroalkyl, unsubstituted or substituted C$_3$-C$_{10}$cycloalkyl, unsubstituted or substituted aryl, unsubstituted or substituted heteroaryl, and -L$^5$-L$^6$-R$^{13}$.

In some embodiments, each $R^{12}$ is independently selected from D, halogen, —CN, —OR$^{10}$, —SR$^{10}$, —S(=O)R$^{11}$, —S(=O)$_2$R$^{10}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, C$_1$-C$_6$alkyl, C$_1$-C$_6$fluoroalkyl, C$_2$-C$_6$alkenyl, C$_2$-C$_6$alkynyl, unsubstituted or substituted C$_1$-C$_6$heteroalkyl, unsubstituted or substituted C$_3$-C$_6$cycloalkyl, unsubstituted or substituted phenyl, unsubstituted or substituted monocyclic heteroaryl, and -L$^5$-L$^6$-R$^{13}$.

In some embodiments, each $R^{12}$ is independently selected from D, halogen, —CN, —OR$^{10}$, —C(=O)R$^{11}$, —OC(=O)R$^{11}$, —CO$_2$R$^{10}$, —N(R$^{10}$)$_2$, —C(=O)N(R$^{10}$)$_2$, —NR$^{10}$C(=O)R$^{11}$, C$_1$-C$_6$alkyl, C$_1$-C$_6$fluoroalkyl, C$_2$-C$_6$alkenyl, C$_2$-C$_6$alkynyl, unsubstituted or substituted C$_1$-C$_6$heteroalkyl, unsubstituted or substituted C$_3$-C$_6$cycloalkyl, unsubstituted or substituted phenyl, unsubstituted or substituted monocyclic heteroaryl, and -L$^5$-L$^6$-R$^{13}$.

In some embodiments, $R^{13}$ is H, —N(R$^{10}$)$_2$, halogen, unsubstituted or substituted C$_1$-C$_{10}$alkyl, unsubstituted or substituted C$_2$-C$_{10}$alkenyl, unsubstituted or substituted C$_2$-C$_{10}$alkynyl, unsubstituted or substituted C$_1$-C$_{10}$cycloalkyl, unsubstituted or substituted C$_1$-C$_{10}$heterocycloalkyl, unsubstituted or substituted aryl, or unsubstituted or substituted heteroaryl.

In some embodiments, $R^4$ is

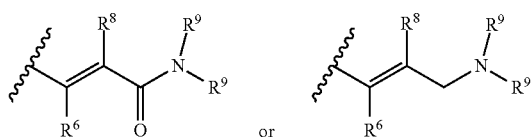

In some embodiments, $R^4$ is

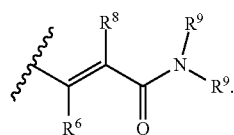

In some embodiments, $R^4$ is

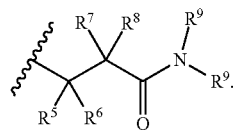

In some embodiments, $R^4$ is

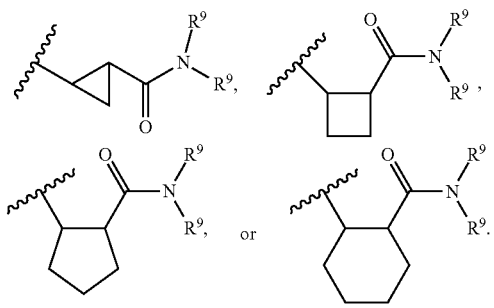

In some embodiments, $R^4$ is -L$^3$-Y; L$^3$ is —CH$_2$—; Y is

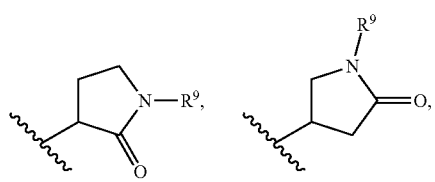

-continued

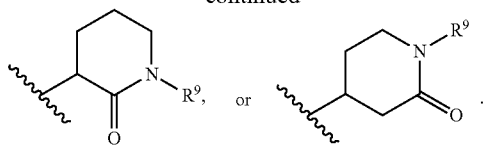

Any combination of the groups described above for the various variables is contemplated herein. Throughout the specification, groups and substituents thereof are chosen by one skilled in the field to provide stable moieties and compounds.

In some embodiments, compounds described herein include, but are not limited to, those described in Table 1 and Table 2.

TABLE 1

| Compound No. | Structure | Chemical Name |
| --- | --- | --- |
| 1 | 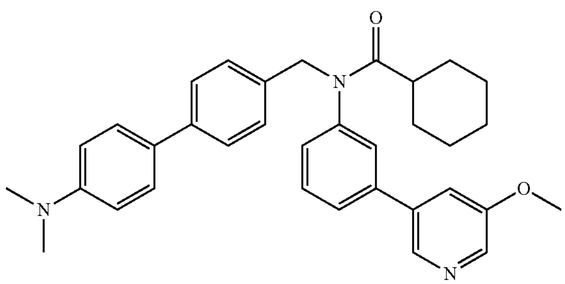 | N-((4'-(Dimethylamino)-[1,1'-biphenyl]-4-yl)methyl)-N-(3-(5-methoxypyridin-3-yl)phenyl)cyclohexanecarboxamide |
| 2 | 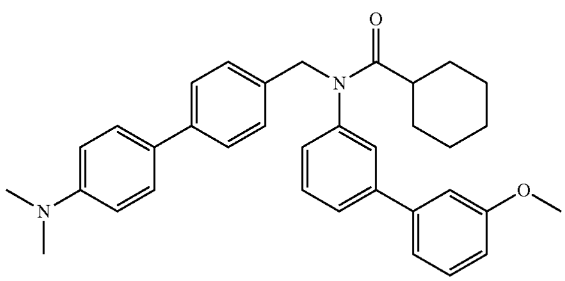 | N-((4'-(Dimethylamino)-[1,1'-biphenyl]-4-yl)methyl)-N-(3'-methoxy-[1,1'-biphenyl]-3-yl)cyclohexanecarboxamide |
| 3 | 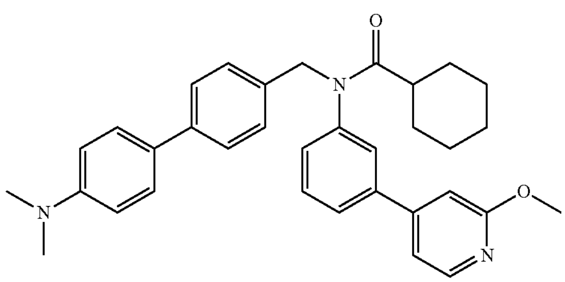 | N-((4'-(Dimethylamino)-[1,1'-biphenyl]-4-yl)methyl)-N-(3-(2-methoxypyridin-4-yl)phenyl)cyclohexanecarboxamide |
| 3.1 | 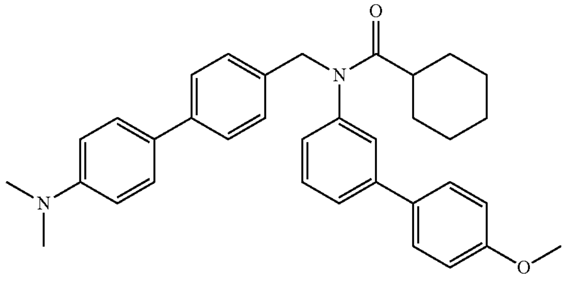 | N-((4'-(Dimethylamino)-[1,1'-biphenyl]-4-yl)methyl)-N-(4'-methoxy-[1,1'-biphenyl]-3-yl)cyclohexanecarboxamide |

TABLE 1-continued

| Compound No. | Structure | Chemical Name |
|---|---|---|
| 4 | 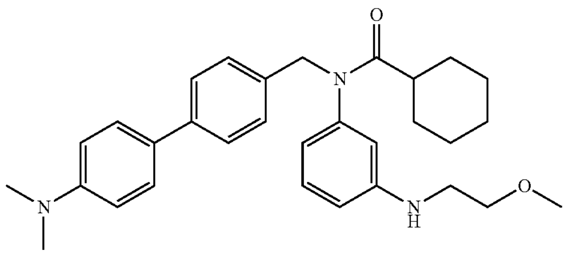 | N-((4'-(dimethylamino)[1,1'-biphenyl]-4-yl)methyl)-N-(3-((2-methoxyethyl)amino)phenyl)cyclohexanecarboxamide |
| 5 | 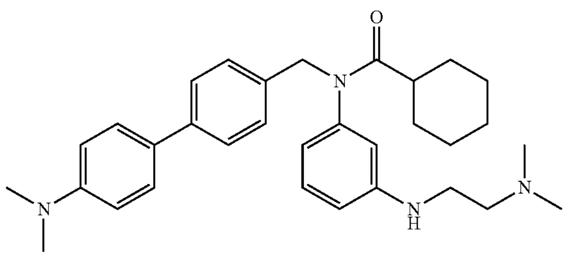 | N-((4'-(dimethylamno)-[1,1'-biphenyl]-4-yl)methyl)-N-(3-((2-(dimethylamino)ethyl)amino)phenyl)cyclohexanecarboxamide |
| 6 | 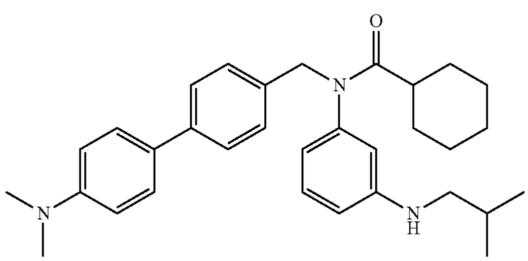 [SMILES: CC(C)CNc1cccc(N(Cc2ccc(-c3ccc(N(C)C)cc3)cc2)C(=O)C2CCCCC2)c1] | N-((4'-(dimethylamino)-[1,1'-biphenyl]-4-yl)methyl)-N-(3-(isobutylamino)phenyl)cyclohexanecarboxamide |
| 7 | 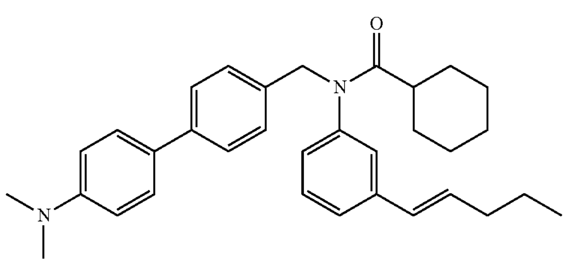 [SMILES: CCC/C=C/c1cccc(N(Cc2ccc(-c3ccc(N(C)C)cc3)cc2)C(=O)C2CCCCC2)c1] | N-(3-Bromophenyl)-N-((4'-(dimethylamino)-[1,1'-biphenyl]-4-yl)methyl)cyclohexanecarboxamide |
| 8 | 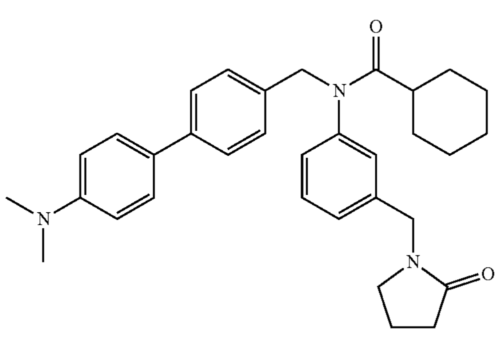 [SMILES: CN(C)c1ccc(-c2ccc(CN(C(=O)C3CCCCC3)c3cccc(CN4CCCC4=O)c3)cc2)cc1] | N-((4'-(Dimethylamino)-[1,1'-biphenyl]-4-yl)methyl)-N-(3-((2-oxopyrrolidin-1-yl)methyl)phenyl)cyclohexanecarboxamide |

TABLE 1-continued

| Compound No. | Structure | Chemical Name |
| --- | --- | --- |
| 9 | 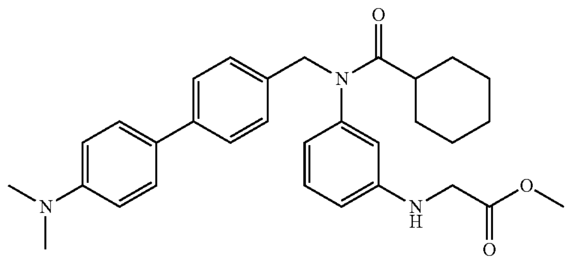 | Methyl 2-((3-(N-((4'-(dimethylamino)-[1,1'-biphenyl]-4-yl)methyl)cyclohexane carboxamido)phenyl)amino)acetate |
| 10 | 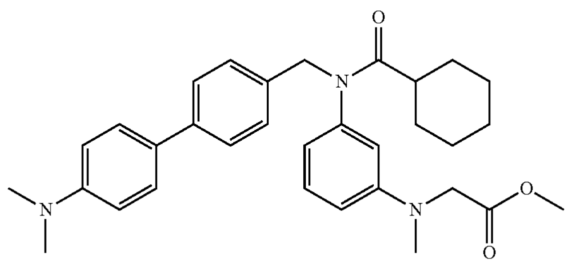 | Methyl 2-((3-(N-((4'-(dimethylamino)-[1,1'-biphenyl]-4-yl)methyl)cyclohexanecarboxamido)phenyl)(methyl)amino)acetate |
| 11 | 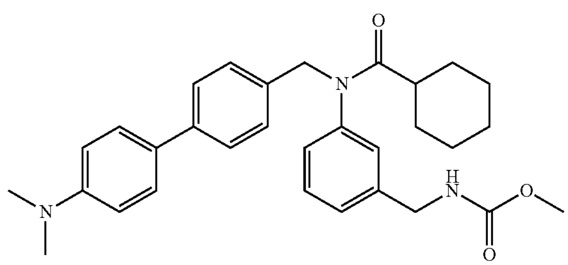 | Methyl 3-(N-((4'-(dimethylamino)-[1,1'-biphenyl]-4-yl)methyl)cyclohexanecarboxamido)benzylcarbamate |
| 12 | 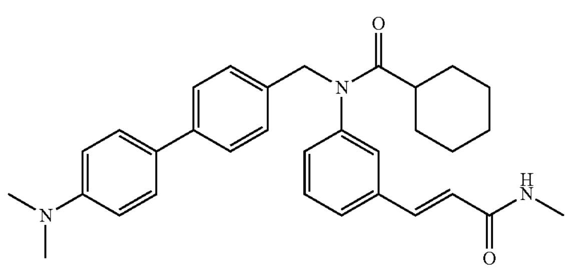 | (E)-N-((4'-(Dimethylamino)-[1,1'-biphenyl]-4-yl)methyl)-N-(3-(3-(methylamino)-3-oxoprop-1-en-1-yl)phenyl)cyclohexanecarboxamide |
| 13 | 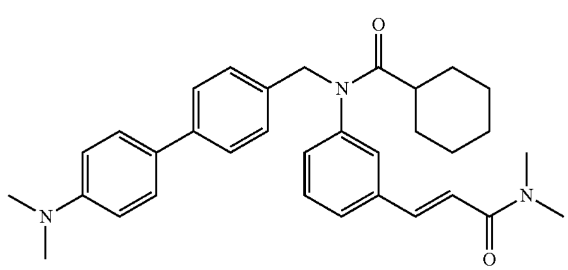 | (E)-N-(3-(3-(Dimethylamino)-3-oxoprop-1-en-1-yl)phenyl)-N-((4'-(dimethylamino)-[1,1'-biphenyl]-4-yl)methyl)cyclohexanecarboxamide |
| 14 | 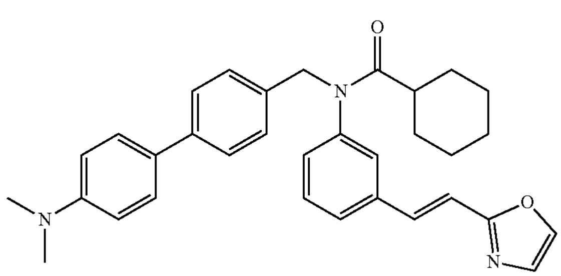 [SMILES: CN(C)c1ccc(-c2ccc(CN(C(=O)C3CCCCC3)c3cccc(/C=C/c4ncco4)c3)cc2)cc1] | (E)-N-((4'-(Dimethylamino)-[1,1'-biphenyl]-4-yl)methyl)-N-(3-(2-(oxazol-2-yl)vinyl)phenyl)cyclohexanecarboxamide |

TABLE 1-continued

| Compound No. | Structure | Chemical Name |
|---|---|---|
| 15 | 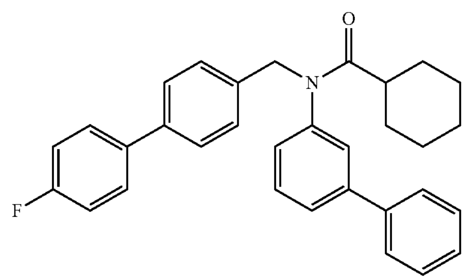 [SMILES: O=C(C1CCCCC1)N(Cc1ccc(-c2ccc(F)cc2)cc1)c1cccc(-c2ccccc2)c1] | N-([1,1'-Biphenyl]-3-yl)-N-((4'-fluoro-[1,1'-biphenyl]-4-yl)methyl)cyclohexanecarboxamide |
| 16 | 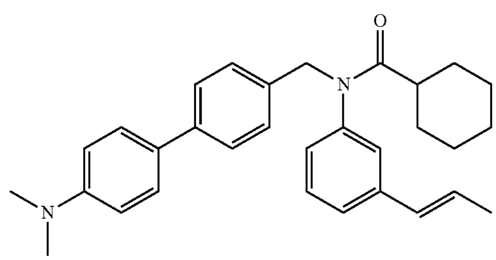 [SMILES: C/C=C/c1cccc(N(Cc2ccc(-c3ccc(N(C)C)cc3)cc2)C(=O)C2CCCCC2)c1] | (E)-N-((4'-(Dimethylamino)-[1,1'-biphenyl]-4-yl)methyl)-N-(3-(prop-1-en-1-yl)phenyl)cyclohexanecarboxamide |
| 17 | 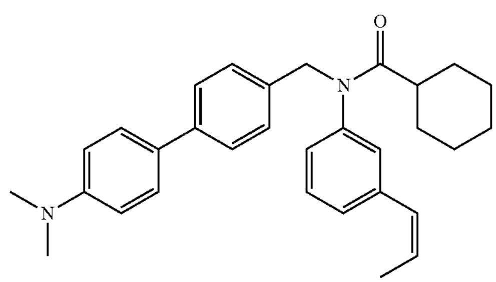 [SMILES: C/C=C\c1cccc(N(Cc2ccc(-c3ccc(N(C)C)cc3)cc2)C(=O)C2CCCCC2)c1] | (Z)-N-((4'-(Dimethylamino)-[1,1'-biphenyl]-4-yl)methyl)-N-(3-(prop-1-en-1-yl)phenyl)cyclohexanecarboxamide |
| 18 | 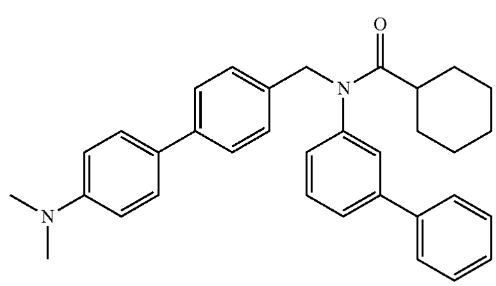 [SMILES: CN(C)c1ccc(-c2ccc(CN(C(=O)C3CCCCC3)c3cccc(-c4ccccc4)c3)cc2)cc1] | N-([1,1'-Biphenyl]-3-yl)-N-((4'-(dimethylamino)-[1,1'-biphenyl]-4-yl)methyl)cyclohexanecarboxamide |
| 19 | 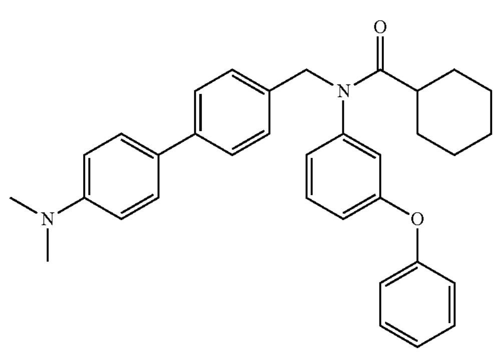 [SMILES: CN(C)c1ccc(-c2ccc(CN(C(=O)C3CCCCC3)c3cccc(Oc4ccccc4)c3)cc2)cc1] | N-((4'-(Dimethylamino)-[1,1'-biphenyl]-4-yl)methyl)-N-(3-phenoxyphenyl)cyclohexanecarboxamide |

TABLE 1-continued

| Compound No. | Structure | Chemical Name |
| --- | --- | --- |
| 20 | 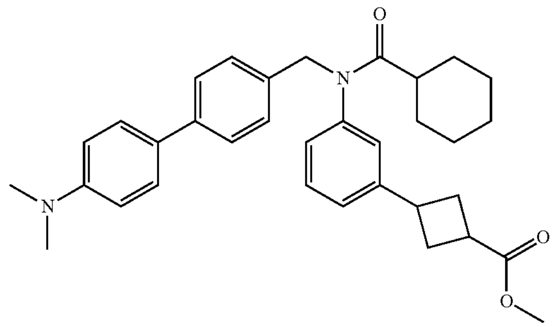 | Methyl 3-(3-(N-((4'-(dimethylamino)-[1,1'-biphenyl]-4-yl)methyl)cyclohexanecarboxamido)phenyl)cyclobutanecarboxylate |
| 21 | 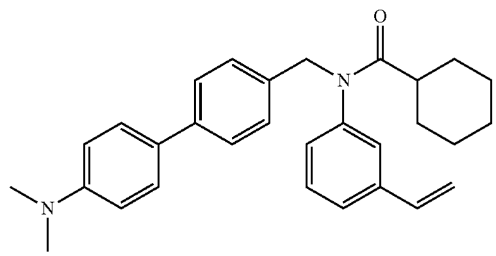 [SMILES: C=Cc1cccc(N(Cc2ccc(-c3ccc(N(C)C)cc3)cc2)C(=O)C2CCCCC2)c1] | N-((4'-(Dimethylamino)-[1,1'-biphenyl]-4-yl)methyl)-N-(3-vinylphenyl)cyclohexanecarboxamide |
| 22 | 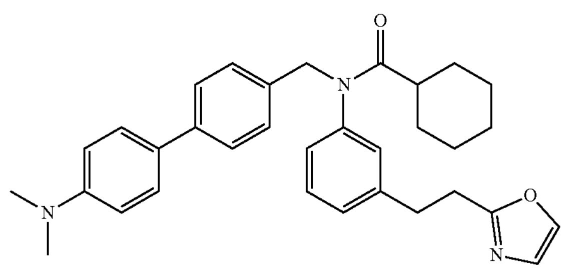 [SMILES: CN(C)c1ccc(-c2ccc(CN(C(=O)C3CCCCC3)c3cccc(CCc4ncco4)c3)cc2)cc1] | N-((4'-(Dimethylamino)-[1,1'-biphenyl]-4-yl)methyl)-N-(3-(2-(oxazol-2-yl)ethyl)phenyl)cyclohexanecarboxamide |
| 23 | 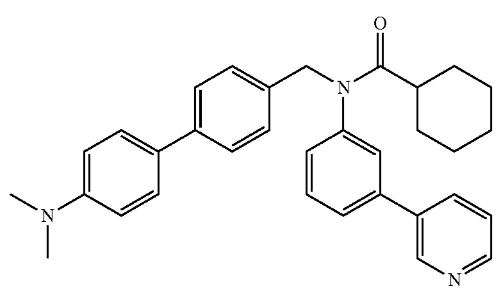 [SMILES: CN(C)c1ccc(-c2ccc(CN(C(=O)C3CCCCC3)c3cccc(-c4cccnc4)c3)cc2)cc1] | N-((4'-(Dimethylamino)-[1,1'-biphenyl]-4-yl)methyl)-N-(3-(pyridin-3-yl)phenyl)cyclohexanecarboxamide |
| 24 | 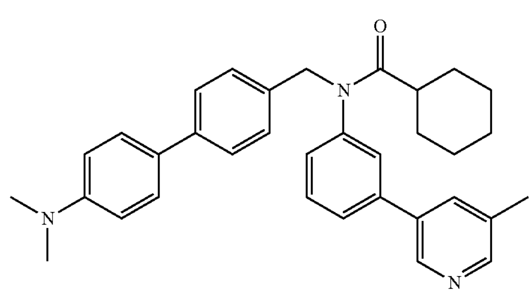 | N-((4'-(Dimethylamino)-[1,1'-biphenyl]-4-yl)methyl)-N-(3-(5-methylpyridin-3-yl)phenyl)cyclohexanecarboxamide |

TABLE 1-continued

| Compound No. | Structure | Chemical Name |
|---|---|---|
| 25 | 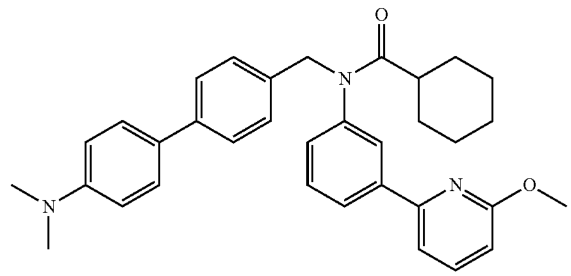 | N-((4'-(dimethylamino)-[1,1'-biphenyl]-4-yl)methyl)-N-(3-(6-methoxypyridin-2-yl)phenyl)cyclohexanecarboxamide |
| 26 | 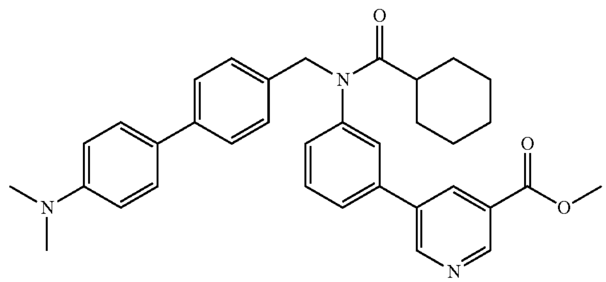 | Methyl 5-(3-(N-((4'-(dimethylamino)-[1,1'-biphenyl]-4-yl)methyl)cyclohexanecarboxamido)phenyl)nicotinate |
| 27 | 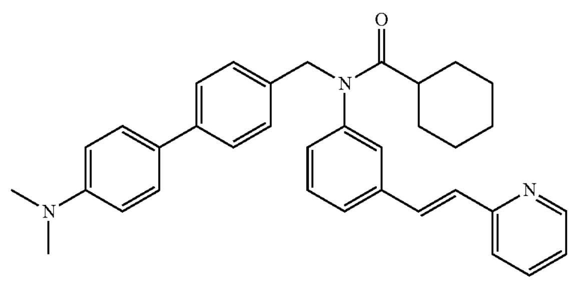 [SMILES: CN(C)c1ccc(-c2ccc(CN(C(=O)C3CCCCC3)c3cccc(/C=C/c4ccccn4)c3)cc2)cc1] | (E)-N-((4'-(Dimethylamino)-[1,1'-biphenyl]-4-yl)methyl)-N-(3-(2-(pyridin-2-yl)vinyl)phenyl)cyclohexanecarboxamide |
| 28 | 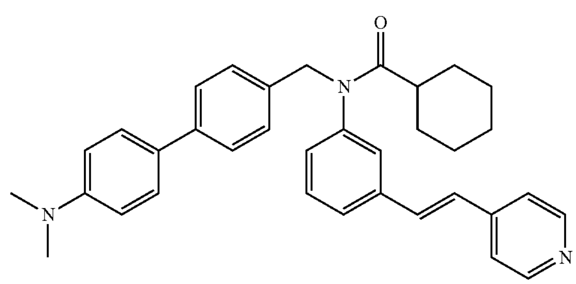 [SMILES: CN(C)c1ccc(-c2ccc(CN(C(=O)C3CCCCC3)c3cccc(/C=C/c4ccncc4)c3)cc2)cc1] | (E)-N-((4'-(Dimethylamino)-[1,1'-biphenyl]-4-yl)methyl)-N-(3-(2-(pyridin-4-yl)vinyl)phenyl)cyclohexanecarboxamide |
| 29 | 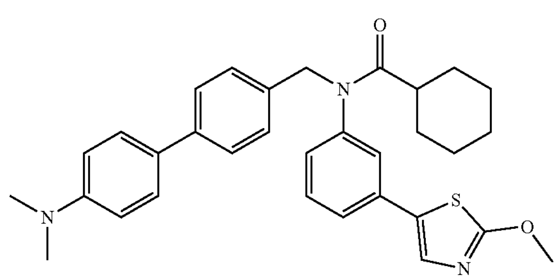 | N-((4'-(Dimethylamino)-[1,1'-biphenyl]-4-yl)methyl)-N-(3-(2-methoxythiazol-5-yl)phenyl)cyclohexanecarboxamide |

TABLE 1-continued

| Compound No. | Structure | Chemical Name |
|---|---|---|
| 30 | 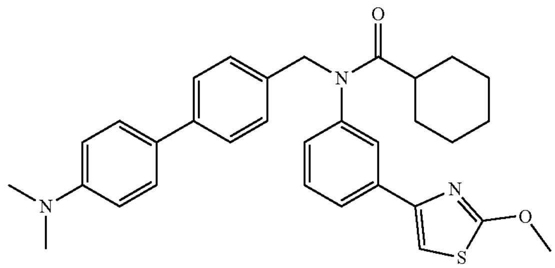 | N-((4'-(Dimethylamino)-[1,1'-biphenyl]-4-yl)methyl)-N-(3-(2-methoxythiazol-4-yl)phenyl)cyclohexanecarboxamide |
| 31 | 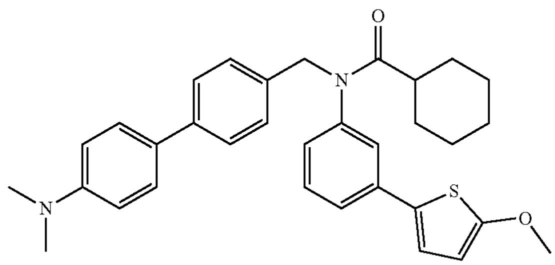 | N-((4'-(Dimethylamino)-[1,1'-biphenyl]-4-yl)methyl)-N-(3-(5-methoxythiophen-2-yl)phenyl)cyclohexanecarboxamide |
| 32 | 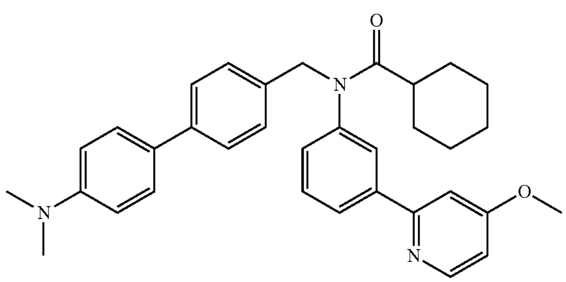 | N-((4'-(Dimethylamino)-[1,1'-biphenyl]-4-yl)methyl)-N-(3-(4-methoxypyridin-2-yl)phenyl)cyclohexanecarboxamide |
| 33 | 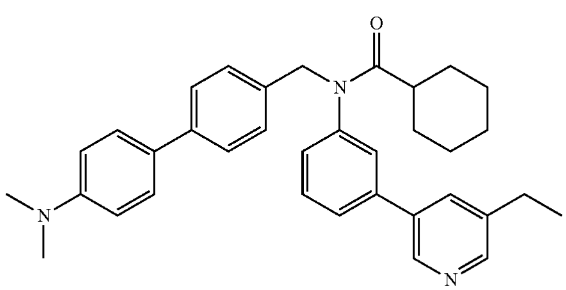 [SMILES: CCc1cncc(-c2cccc(N(Cc3ccc(-c4ccc(N(C)C)cc4)cc3)C(=O)C3CCCCC3)c2)c1] | N-((4'-(Dimethylamino)-[1,1'-biphenyl]-4-yl)methyl)-N-(3-(5-ethylpyridin-3-yl)phenyl)cyclohexanecarboxamide |
| 34 | 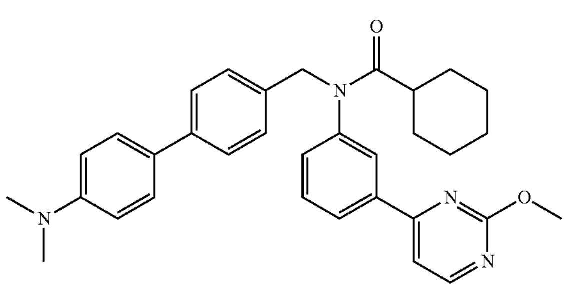 | N-((4'-(Dimethylamino)-[1,1'-biphenyl]-4-yl)methyl)-N-(3-(2-methoxypyrimidin-4-yl)phenyl)cyclohexanecarboxamide |

TABLE 1-continued

| Compound No. | Structure | Chemical Name |
|---|---|---|
| 35 | 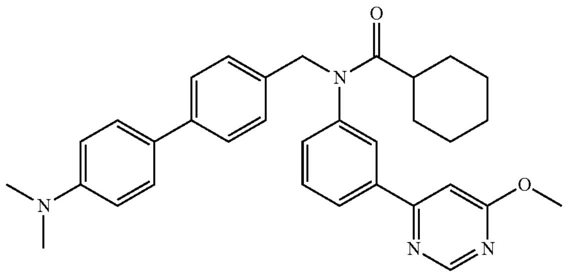 | N-((4'-(Dimethylamino)-[1,1'-biphenyl]-4-yl)methyl)-N-(3-(6-methoxypyrimidin-4-yl)phenyl)cyclohexanecarboxamide |
| 36 | 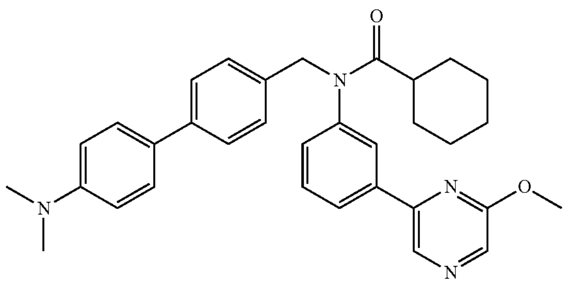 | N-((4'-(Dimethylamino)-[1,1'-biphenyl]-4-yl)methyl)-N-(3-(6-methoxypyrazin-2-yl)phenyl)cyclohexanecarboxamide |
| 37 | 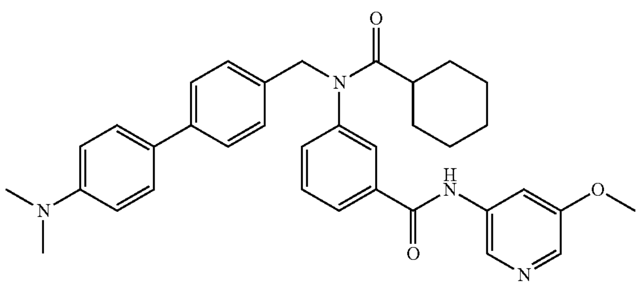 | 3-(N-((4'-(Dimethylamino)-[1,1'-biphenyl]-4-yl)methyl)cyclohexanecarboxamido)-N-(5-methoxypyridin-3-yl)benzamide |
| 38 | 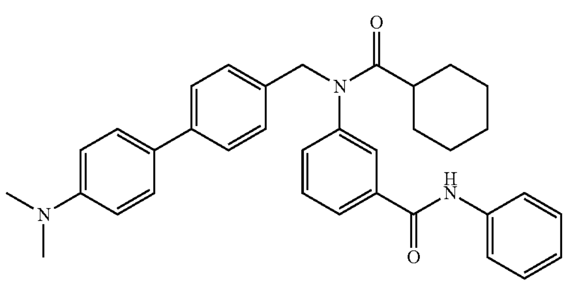 [SMILES: CN(C)c1ccc(-c2ccc(CN(C(=O)C3CCCCC3)c3cccc(C(=O)Nc4ccccc4)c3)cc2)cc1] | 3-(N-((4'-(Dimethylamino)-[1,1'-biphenyl]-4-yl)methyl)cyclohexanecarboxamido)-N-phenylbenzamide |
| 39 | 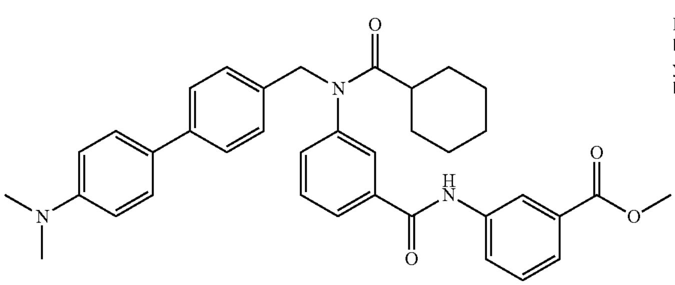 | Methyl 3-(3-(N-((4'-(dimethylamino)-[1,1'-biphenyl]-4-yl)methyl)cyclohexanecarboxamido)benzamido)benzoate |

TABLE 1-continued

| Compound No. | Structure | Chemical Name |
|---|---|---|
| 40 | 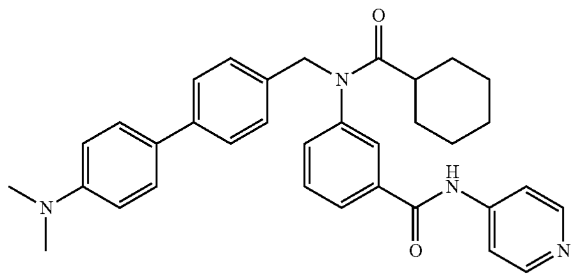 [SMILES: CN(C)c1ccc(-c2ccc(CN(C(=O)C3CCCCC3)c3cccc(C(=O)Nc4ccncc4)c3)cc2)cc1] | 3-(N-((4'-(Dimethylamino)-[1,1'-biphenyl]-4-yl)methyl)cyclohexanecarboxamido)-N-(pyridin-4-yl)benzamide |
| 41 | 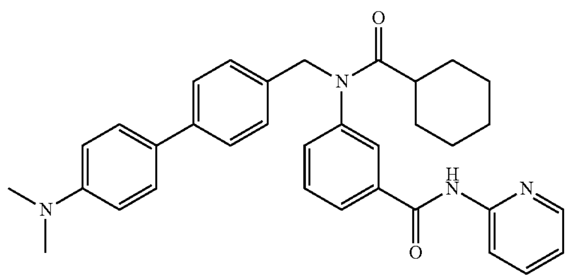 | 3-(N-((4'-(Dimethylamino)-[1,1'-biphenyl]-4-yl)methyl)cyclohexanecarboxamido)-N-(pyridin-2-yl)benzamide |
| 42 | 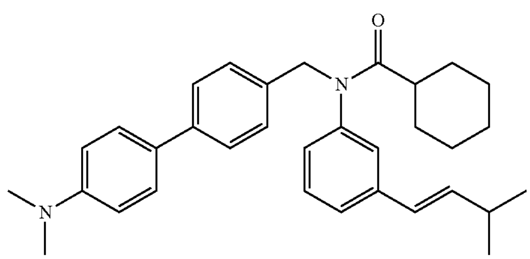 [SMILES: CC(C)/C=C/c1cccc(N(Cc2ccc(-c3ccc(N(C)C)cc3)cc2)C(=O)C2CCCCC2)c1] | (E)-N-((4'-(Dimethylamino)-[1,1'-biphenyl]-4-yl)methyl)-N-(3-(3-methylbut-1-en-1-yl)phenyl)cyclohexanecarboxamide |
| 43 | 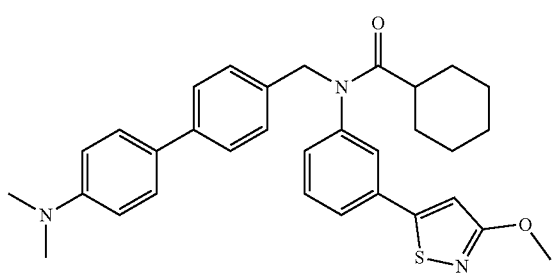 | N-((4'-(Dimethylamino)-[1,1'-biphenyl]-4-yl)methyl)-N-(3-(3-methoxyisothiazol-5-yl)phenyl)cyclohexanecarboxamide |
| 44 | 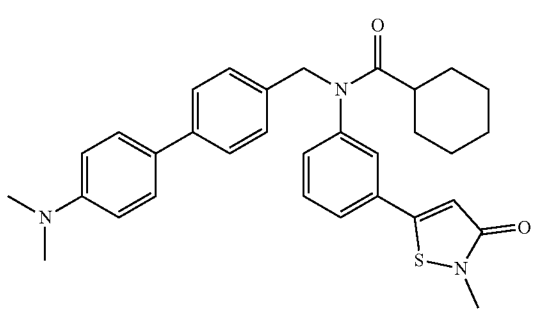 [SMILES: CN(C)c1ccc(-c2ccc(CN(C(=O)C3CCCCC3)c3cccc(-c4cc(=O)n(C)s4)c3)cc2)cc1] | N-((4'-(Dimethylamino)-[1,1'-biphenyl]-4-yl)methyl)-N-(3-(2-methyl-3-oxo-2,3-dihydroisothiazol-5-yl)phenyl)cyclohexanecarboxamide |

TABLE 1-continued

| Compound No. | Structure | Chemical Name |
| --- | --- | --- |
| 45 | 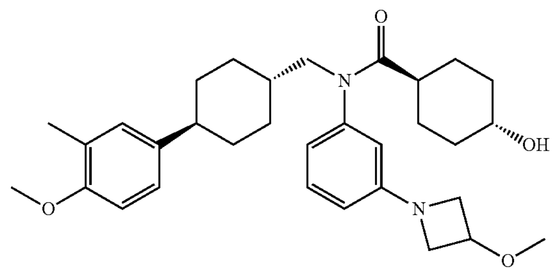 | trans-4-Hydroxy-N-((trans-4-(4-methoxy-3-methylphenyl)cyclohexyl)methyl)-N-(3-(3-methoxyazetidin-1-yl)phenyl)cyclohexanecarboxamide |
| 46 | 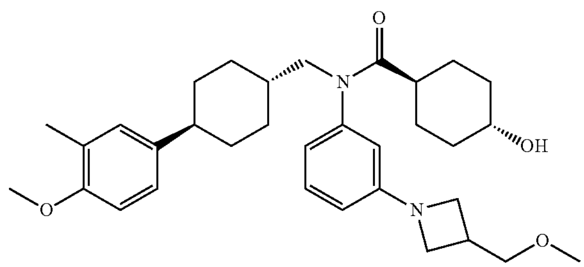 | trans-4-Hydroxy-N-((trans-4-(4-methoxy-3-methylphenyl)cyclohexyl)methyl)-N-(3-(3-(methoxymethyl)azetidin-1-yl)phenyl)cyclohexanecarboxamide |
| 47 | 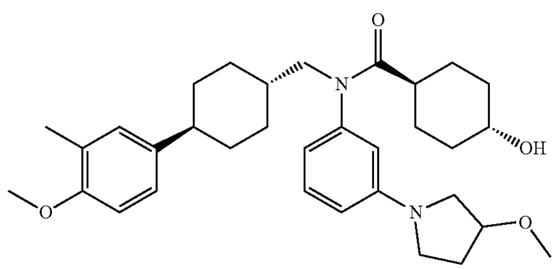 | trans-4-Hydroxy-N-((trans-4-(4-methoxy-3-methylphenyl)cyclohexyl)methyl)-N-(3-(3-methoxypyrrolidin-1-yl)phenyl)cyclohexanecarboxamide |
| 48 | 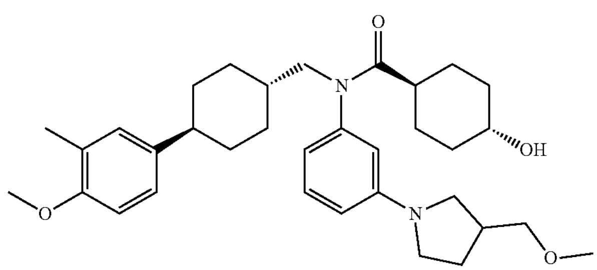 | trans-4-Hydroxy-N-((trans-4-(4-methoxy-3-methylphenyl)cyclohexyl)methyl)-N-(3-(3-(methoxymethyl)pyrrolidin-1-yl)phenyl)cyclohexanecarboxamide |
| 49 | 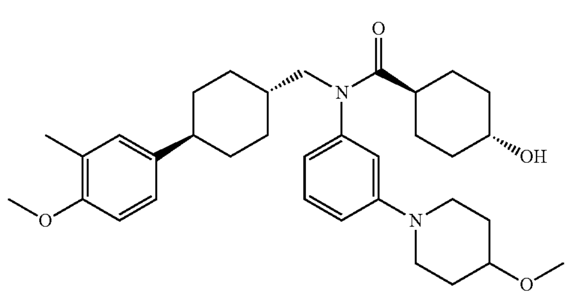 | trans-4-Hydroxy-N-((trans-4-(4-methoxy-3-methylphenyl)cyclohexyl)methyl)-N-(3-(4-methoxypiperidin-1-yl)phenyl)cyclohexanecarboxamide |

TABLE 1-continued

| Compound No. | Structure | Chemical Name |
|---|---|---|
| 50 | 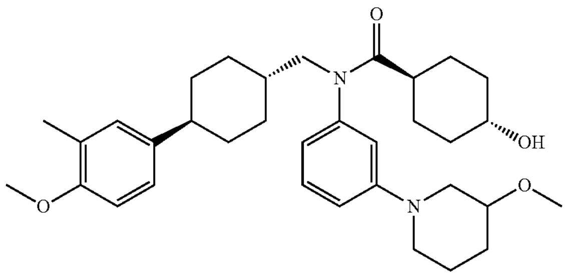 | trans-4-Hydroxy-N-((trans-4-(4-methoxy-3-methylphenyl)cyclohexyl)methyl)-N-(3-(3-methoxypiperidin-1-yl)phenyl)cyclohexanecarboxamide |

TABLE 2

| Structure | Name |
|---|---|
| 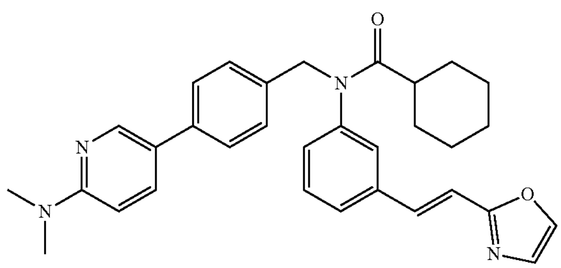 | (E)-N-(4-(6-(Dimethylamino)pyridin-3-yl)benzyl)-N-(3-(2-(oxazol-2-yl)vinyl)phenyl)cyclohexanecarboxamide |
| 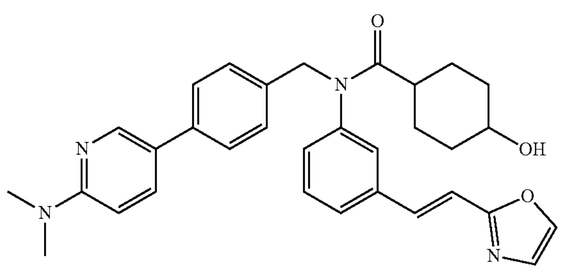 [SMILES: CN(C)c1ccc(-c2ccc(CN(C(=O)C3CCC(O)CC3)c3cccc(/C=C/c4ncco4)c3)cc2)cn1] | (E)-N-(4-(6-(Dimethylamino)pyridin-3-yl)benzyl)-4-hydroxy-N-(3-(2-(oxazol-2-yl)vinyl)phenyl)cyclohexanecarboxamide |
| 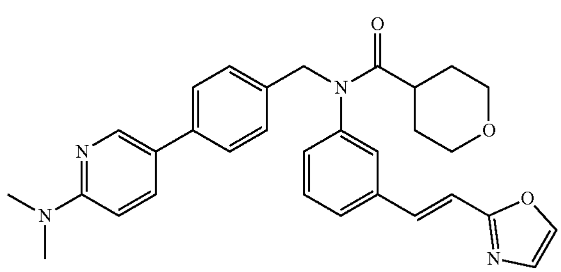 [SMILES: CN(C)c1ccc(-c2ccc(CN(C(=O)C3CCOCC3)c3cccc(/C=C/c4ncco4)c3)cc2)cn1] | (E)-N-(4-(6-(Dimethylamino)pyridin-3-yl)benzyl)-N-(3-(2-(oxazol-2-yl)vinyl)phenyl)tetrahydro-2H-pyran-4-carboxamide |
| 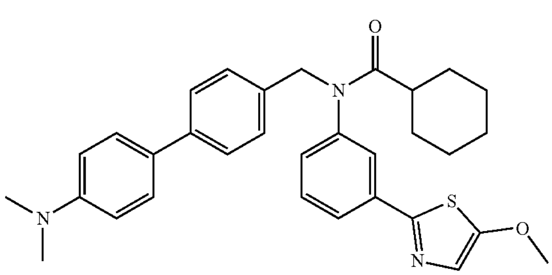 | N-((4'-(Dimethylamino)-[1,1'-biphenyl]-4-yl)methyl-N-(3-(5-methoxythiazol-2-yl)phenyl)cyclohexanecarboxamide |

TABLE 2-continued

| Structure | Name |
|---|---|
| 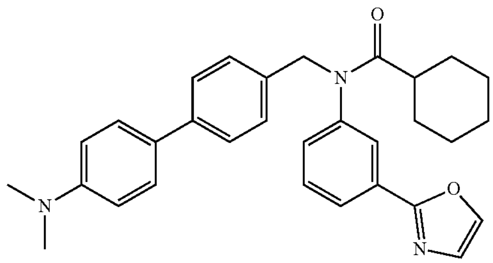 [SMILES: CN(C)c1ccc(-c2ccc(CN(C(=O)C3CCCCC3)c3cccc(-c4ncco4)c3)cc2)cc1] | N-((4'-(Dimethylamino)-[1,1'-biphenyl]-4-yl)methyl)-N-(3-(oxazol-2-yl)phenyl)cyclohexanecarboxamide |
| 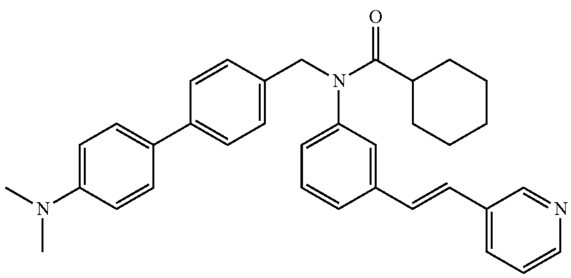 [SMILES: CN(C)c1ccc(-c2ccc(CN(C(=O)C3CCCCC3)c3cccc(/C=C/c4cccnc4)c3)cc2)cc1] | (E)-N-((4'-(Dimethylamino)-[1,1'-biphenyl]-4-yl)methyl)-N-(3-(2-(pyridin-3-yl)vinyl)phenyl)cyclohexanecarboxamide |
| 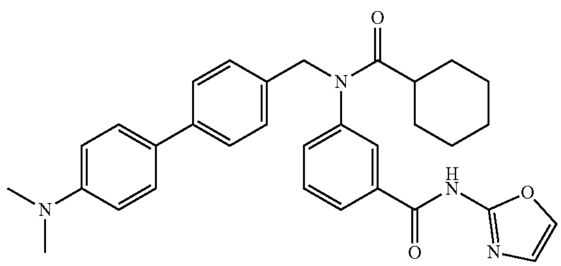 [SMILES: CN(C)c1ccc(-c2ccc(CN(C(=O)C3CCCCC3)c3cccc(C(=O)Nc4ncco4)c3)cc2)cc1] | 3-(N-((4'-(Dimethylamino)-[1,1'-biphenyl]-4-yl)methyl)cyclohexanecarboxamido)-N-(oxazol-2-yl)benzamide |
| 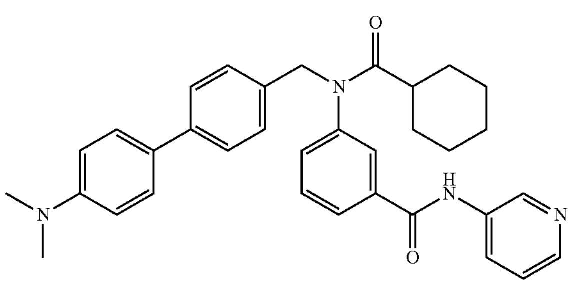 [SMILES: CN(C)c1ccc(-c2ccc(CN(C(=O)C3CCCCC3)c3cccc(C(=O)Nc4cccnc4)c3)cc2)cc1] | 3-(N-((4'-(Dimethylamino)-[1,1'-biphenyl]-4-yl)methyl)cyclohexanecarboxamido)-N-(pyridin-3-yl)benzamide |
| 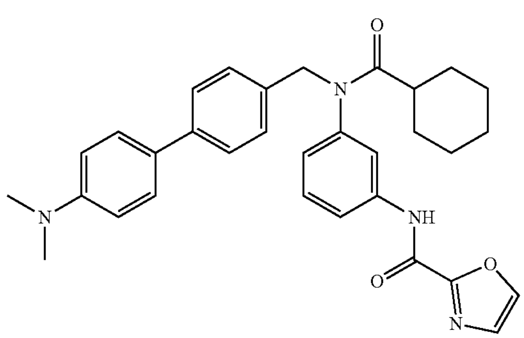 [SMILES: CN(C)c1ccc(-c2ccc(CN(C(=O)C3CCCCC3)c3cccc(NC(=O)c4ncco4)c3)cc2)cc1] | N-(3-(N-((4'-(Dimethylamino)-[1,1'-biphenyl]-4-yl)methyl)cyclohexanecarboxamido)phenyl)oxazole-2-carboxamide |

TABLE 2-continued

| Structure | Name |
|---|---|
| 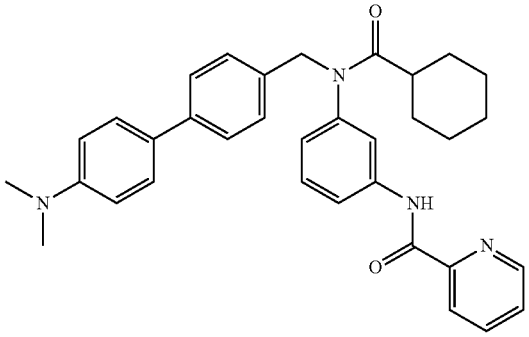 [SMILES: CN(C)c1ccc(-c2ccc(CN(C(=O)C3CCCCC3)c3cccc(NC(=O)c4ccccn4)c3)cc2)cc1] | N-(3-(N-((4'-(dimethylamino)-[1,1'-biphenyl]-4-yl)methyl)cyclohexanecarboxamido)phenyl)picolinamide |
| 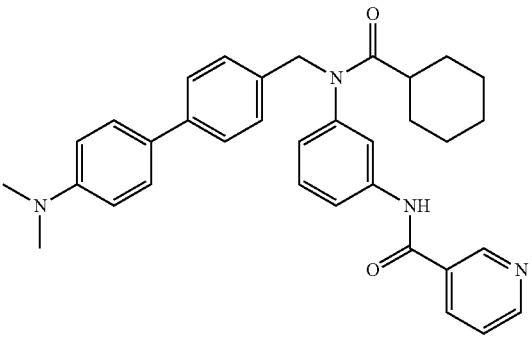 [SMILES: CN(C)c1ccc(-c2ccc(CN(C(=O)C3CCCCC3)c3cccc(NC(=O)c4cccnc4)c3)cc2)cc1] | N-(3-(N-((4'-(Dimethylamino)-[1,1'-biphenyl]-4-yl)methyl)cyclohexanecarboxamido)phenyl)nicotinamide |
| 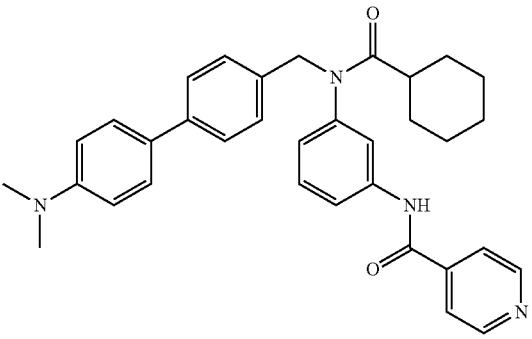 [SMILES: CN(C)c1ccc(-c2ccc(CN(C(=O)C3CCCCC3)c3cccc(NC(=O)c4ccncc4)c3)cc2)cc1] | N-(3-N-((4'-(Dimethylamino)-[1,1'-biphenyl]-4-yl)methyl)cyclohexanecarboxamido)phenyl)iso-nicotinamide |
| 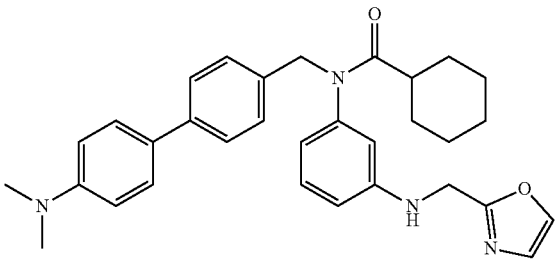 [SMILES: CN(C)c1ccc(-c2ccc(CN(C(=O)C3CCCCC3)c3cccc(NCc4ncco4)c3)cc2)cc1] | N-((4'-(Dimethylamino)-[1,1'-biphenyl]-4-yl)methyl)-N-(3-((oxazol-2-ylmethyl)amino)phenyl)cyclohexanecarboxamide |
| 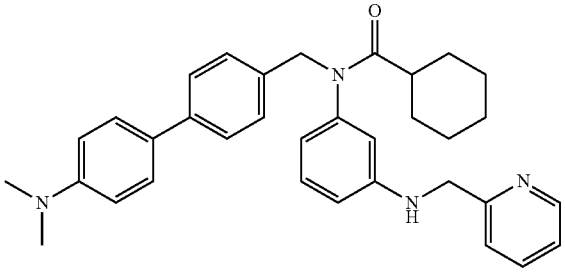 [SMILES: CN(C)c1ccc(-c2ccc(CN(C(=O)C3CCCCC3)c3cccc(NCc4ccccn4)c3)cc2)cc1] | N-((4'-(Dimethylamino)-[1,1'-biphenyl]-4-yl)methyl)-N-(3-((pyridin-2-ylmethyl)amino)phenyl)cyclohexanecarboxamide |

TABLE 2-continued

| Structure | Name |
|---|---|
| 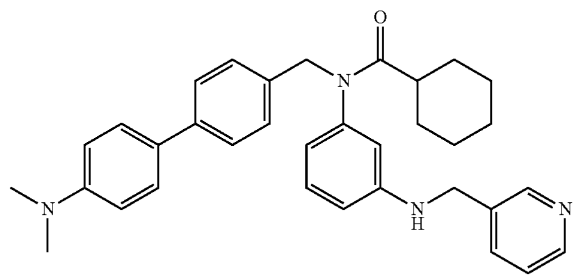 [SMILES: CN(C)c1ccc(-c2ccc(CN(C(=O)C3CCCCC3)c3cccc(NCc4cccnc4)c3)cc2)cc1] | N-((4'-(Dimethylamino)-[1,1'-biphenyl]-4-yl)methyl)-N-(3-((pyridin-3-ylmethyl)amino)phenyl)cyclohexanecarboxamide |
| 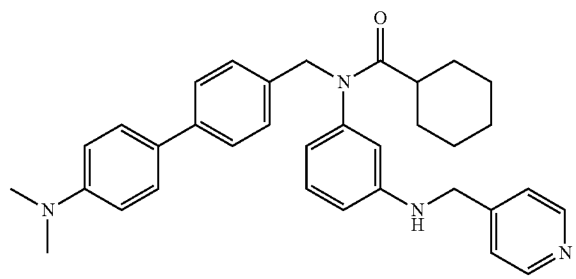 [SMILES: CN(C)c1ccc(-c2ccc(CN(C(=O)C3CCCCC3)c3cccc(NCc4ccncc4)c3)cc2)cc1] | N-((4'-(Dimethylamino)-[1,1'-biphenyl]-4-yl)methyl)-N-(3-((pyridin-4-ylmethyl)amino)phenyl)cyclohexanecarboxamide |
| 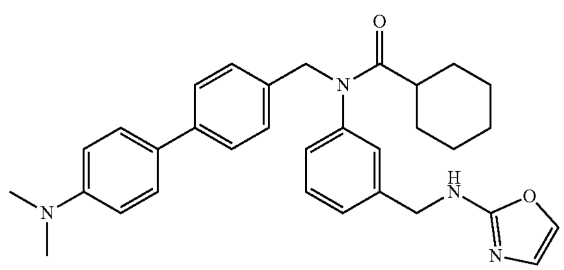 [SMILES: CN(C)c1ccc(-c2ccc(CN(C(=O)C3CCCCC3)c3cccc(CNc4ncco4)c3)cc2)cc1] | N-((4'-(Dimethylamino)-[1,1'-biphenyl]-4-yl)methyl)-N-(3-((oxazol-2-ylamino)methyl)phenyl)cyclohexanecarboxamide |
| 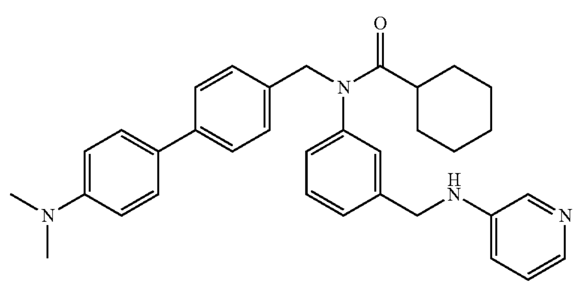 [SMILES: CN(C)c1ccc(-c2ccc(CN(C(=O)C3CCCCC3)c3cccc(CNc4cccnc4)c3)cc2)cc1] | N-((4'-(Dimethylamino)-[1,1'-biphenyl]-4-yl)methyl)-N-(3-((pyridin-3-ylamino)methyl)phenyl)cyclohexanecarboxamide |
| 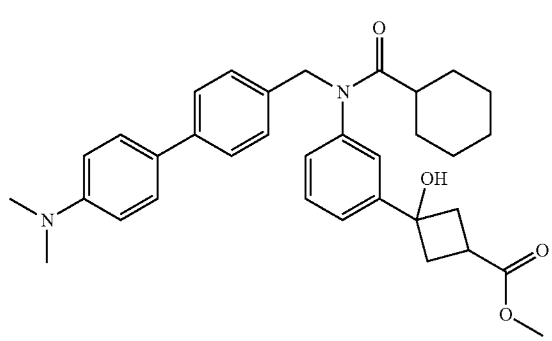 | Methyl 3-(3-(N-((4'-(dimethylamino)-[1,1'-biphenyl]-4-yl)methyl)cyclohexanecarboxamido)phenyl)-3-hydroxycyclobutanecarboxylate |

TABLE 2-continued

| Structure | Name |
|---|---|
| 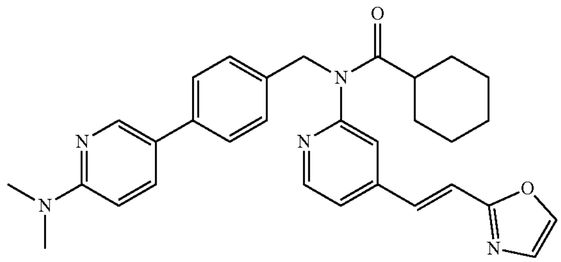 [SMILES: CN(C)c1ccc(-c2ccc(CN(C(=O)C3CCCCC3)c3cc(/C=C/c4ncco4)ccn3)cc2)cn1] | (E)-N-(4-(6-(Dimethylamino)pyridin-3-yl)benzyl)-4-hydroxy-N-(4-(2-(oxazol-2-yl)vinyl)pyridin-2-yl)cyclohexanecarboxamide |
| 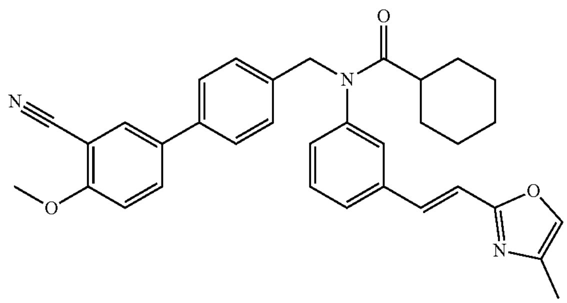 [SMILES: COc1ccc(-c2ccc(CN(C(=O)C3CCCCC3)c3cccc(/C=C/c4nc(C)co4)c3)cc2)cc1C#N] | (E)-N-((3'-Cyano-4'-methoxy-[1,1'-biphenyl]-4-yl)methyl)-N-(3-(2-(4-methyloxazol-2-yl)vinyl)phenyl)cyclohexanecarboxamide |
| 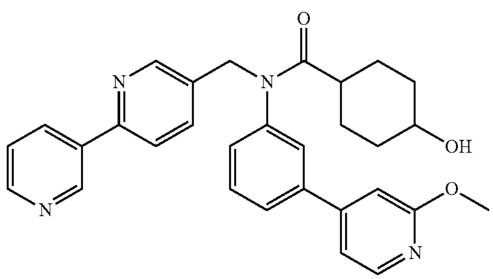 [SMILES: COc1cc(-c2cccc(N(Cc3ccc(-c4cccnc4)nc3)C(=O)C3CCC(O)CC3)c2)ccn1] | N-([2,3'-Bipyridin]-5-ylmethyl)-4-hydroxy-N-(3-(2-methoxypyridin-4-yl)phenyl)cyclohexanecarboxamide |
| 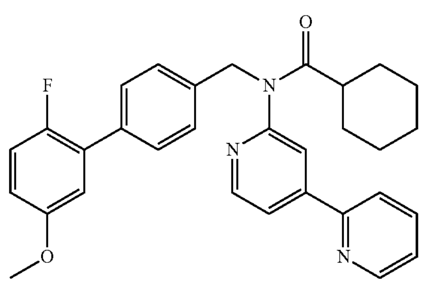 [SMILES: COc1ccc(F)c(-c2ccc(CN(C(=O)C3CCCCC3)c3cc(-c4ccccn4)ccn3)cc2)c1] | N-([2,4'-Bipyridin]-2'-yl)-N-((2'-fluoro-5'-methoxy-[1,1'-biphenyl]-4-yl)methyl)cyclohexanecarboxamide |
| 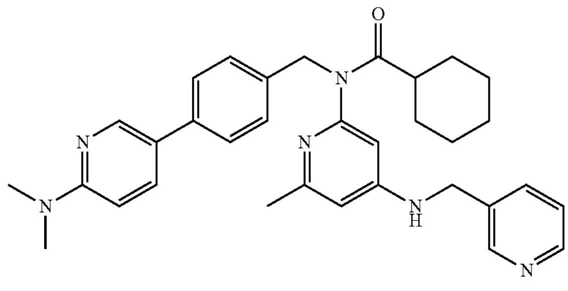 [SMILES: Cc1cc(NCc2cccnc2)cc(N(Cc2ccc(-c3ccc(N(C)C)nc3)cc2)C(=O)C2CCCCC2)n1] | N-(4-(6-(Dimethylamino)pyridin-3-yl)benzyl)-N-(6-methyl-4-((pyridin-3-ylmethyl)amino)pyridin-2-yl)cyclohexanecarboxamide |

TABLE 2-continued

| Structure | Name |
|---|---|
| 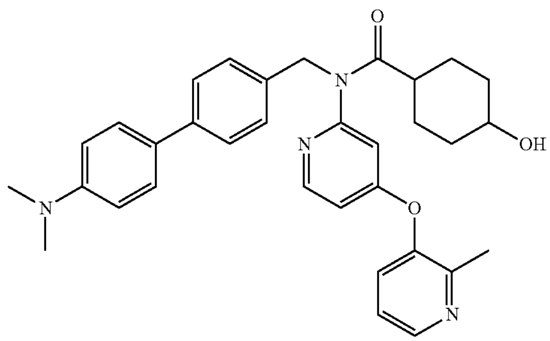 [SMILES: Cc1ncccc1Oc1ccnc(N(Cc2ccc(-c3ccc(N(C)C)cc3)cc2)C(=O)C2CCC(O)CC2)c1] | N-((4'-(Dimethylamino)-[1,1'-biphenyl]-4-yl)methyl)-4-hydroxy-N-(4-((2-methylpyridin-3-yl)oxy)pyridin-2-yl)cyclohexanecarboxamide |
| 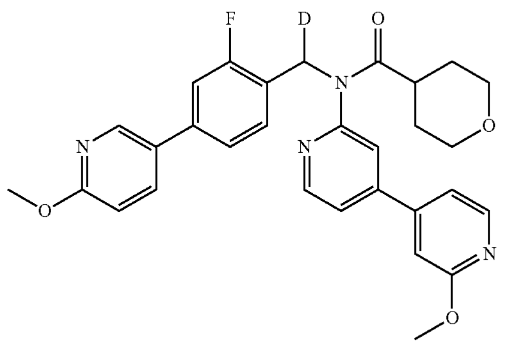 [SMILES: [2H]C(c1ccc(-c2ccc(OC)nc2)cc1F)N(C(=O)C1CCOCC1)c1cc(-c2ccnc(OC)c2)ccn1] | N-(Deutero(2-fluoro-4-(6-methoxypyridin-3-yl)phenyl)methyl)-N-(2'-methoxy-[4,4'-bipyridin]-2-yl)tetrahydro-2H-pyran-4-carboxamide |
| 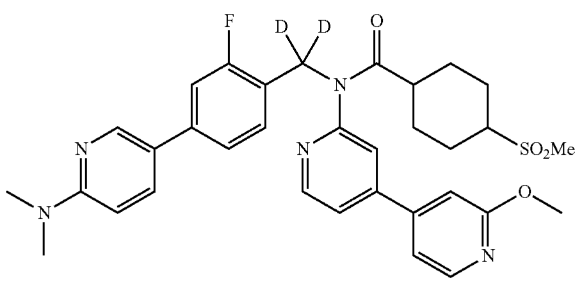 | N-((4-(6-(Dimethylamino)pyridin-3-yl)-2-fluorophenyl)dideuteromethyl)-N-(2'-methoxy-[4,4'-bipyridin]-2-yl)-4-(methylsulfonyl)cyclohexanecarboxamide |
| 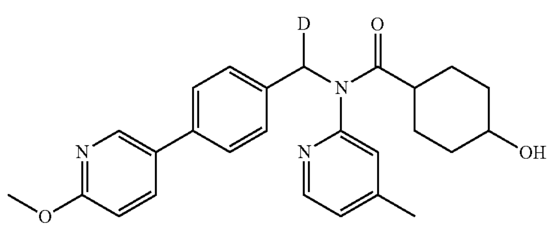 [SMILES: [2H]C(c1ccc(-c2ccc(OC)nc2)cc1)N(C(=O)C1CCC(O)CC1)c1cc(C)ccn1] | N-(Deutero(4-(6-methoxypyridin-3-yl)phenyl)methyl)-4-hydroxy-N-(4-methylpyridin-2-yl)cyclohexanecarboxamide |
| 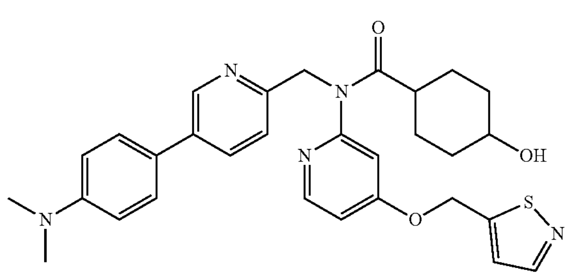 [SMILES: CN(C)c1ccc(-c2ccc(CN(C(=O)C3CCC(O)CC3)c3cc(OCc4ccns4)ccn3)nc2)cc1] | N-((5-(4-(Dimethylamino)phenyl)pyridin-2-yl)methyl)-4-hydroxy-N-(4-(isothiazol-5-ylmethoxy)pyridin-2-yl)cyclohexanecarboxamide |

TABLE 2-continued

| Structure | Name |
|---|---|
| 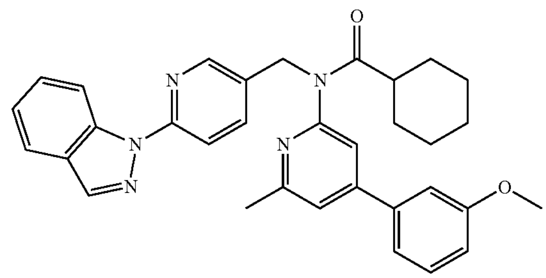 [SMILES: COc1cccc(-c2cc(C)nc(N(Cc3ccc(-n4ncc5ccccc54)nc3)C(=O)C3CCCCC3)c2)c1] | N-((6-(1H-Indazol-1-yl)pyridin-3-yl)methyl)-N-(4-(3-methoxyphenyl)-6-methylpyridin-2-yl)cyclohexanecarboxamide |
| 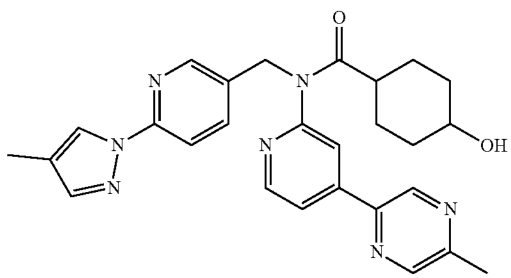 | 4-Hydroxy-N-((6-(4-methyl-1H-pyrazol-1-yl)pyridin-3-yl)methyl)-N-(4-(5-methylpyrazin-2-yl)pyridin-2-yl)cyclohexanecarboxamide |
| 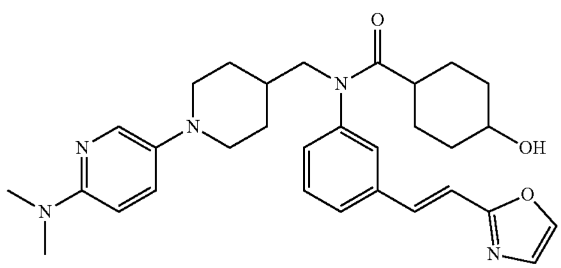 [SMILES: CN(C)c1ccc(N2CCC(CN(C(=O)C3CCC(O)CC3)c3cccc(/C=C/c4ncco4)c3)CC2)cn1] | (E)-N-((1-(6-(Dimethylamino)pyridin-3-yl)piperidin-4-yl)methyl)-4-hydroxy-N-(3-(2-(oxazol-2-yl)vinyl)phenyl)cyclohexanecarboxamide |
| 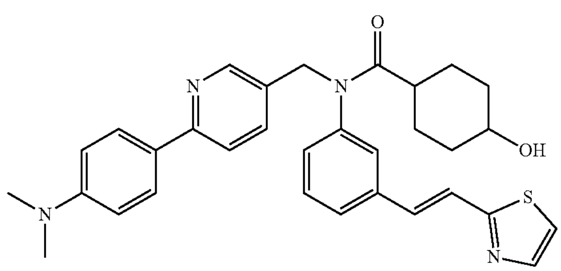 [SMILES: CN(C)c1ccc(-c2ccc(CN(C(=O)C3CCC(O)CC3)c3cccc(/C=C/c4nccs4)c3)cn2)cc1] | (E)-N-((6-(4-(Dimethylamino)phenyl)pyridin-3-yl)methyl)-4-hydroxy-N-(3-(2-(thiazol-2-yl)vinyl)phenyl)cyclohexanecarboxamide |
| 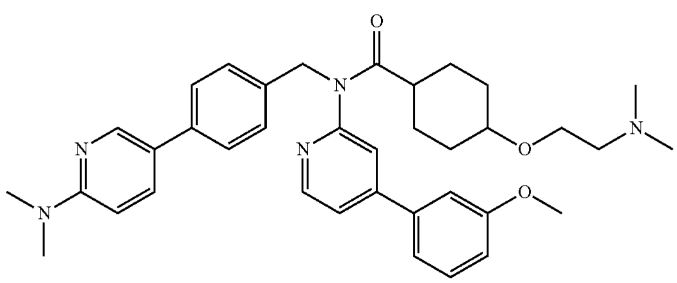 | 4-(2-(Dimethylamino)ethoxy)-N-(4-(6-(dimethylamino)pyridin-3-yl)benzyl)-N-(4-(3-methoxyphenyl)pyridin-2-yl)cyclohexanecarboxamide |

TABLE 2-continued

| Structure | Name |
|---|---|
| 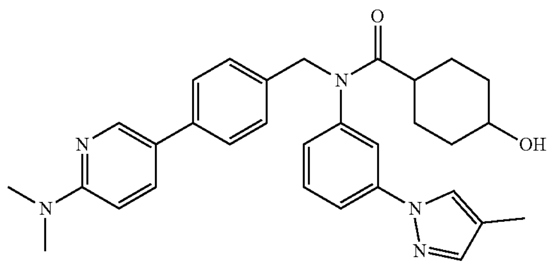 [SMILES: Cc1cnn(-c2cccc(N(Cc3ccc(-c4ccc(N(C)C)nc4)cc3)C(=O)C3CCC(O)CC3)c2)c1] | N-(4-(6-(Dimethylamino)pyridin-3-yl)benzyl)-4-hydroxy-N-(3-(4-methyl-1H-pyrazol-1-yl)phenyl)cyclohexanecarboxamide |
| 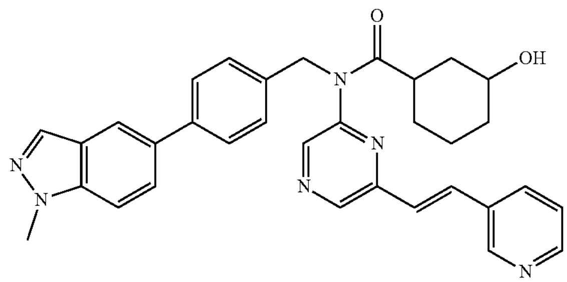 [SMILES: Cn1ncc2cc(-c3ccc(CN(C(=O)C4CCCC(O)C4)c4cncc(/C=C/c5cccnc5)n4)cc3)ccc21] | (E)-3-Hydroxy-N-(4-(1-methyl-1H-indazol-5-yl)benzyl)-N-(6-(2-(pyridin-3-yl)vinyl)pyrazin-2-yl)cyclohexanecarboxamide |
| 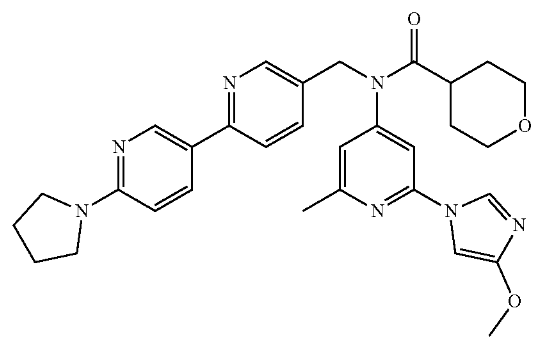 [SMILES: COc1cn(-c2cc(N(Cc3ccc(-c4ccc(N5CCCC5)nc4)nc3)C(=O)C3CCOCC3)cc(C)n2)cn1] | N-(2-(4-Methoxy-1H-imidazol-1-yl)-6-methylpyridin-4-yl)-N-((6'-(pyrrolidin-1-yl)-[2,3'-bipyridin]-5-yl)methyl)tetrahydro-2H-pyran-4-carboxamide |
| 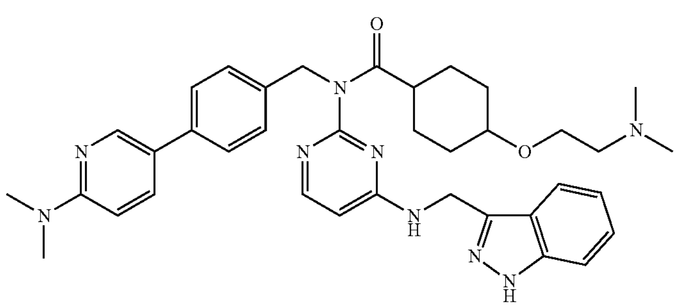 | N-(4-(((1H-Indazol-3-yl)methyl)amino)pyrimidin-2-yl)-4-(2-(dimethylamino)ethoxy)-N-(4-(6-(dimethylamino)pyridin-3-yl)benzyl)cyclohexanecarboxamide |
| 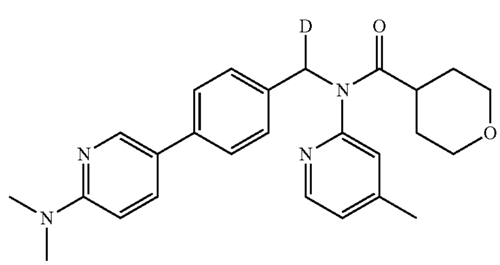 [SMILES: [2H]C(c1ccc(-c2ccc(N(C)C)nc2)cc1)N(C(=O)C1CCOCC1)c1cc(C)ccn1] | N-(Deutero(4-(6-(dimethylamino)pyridin-3-yl)phenyl)methyl)-N-(4-methylpyridin-2-yl)tetrahydro-2H-pyran-4-carboxamide |

TABLE 2-continued

| Structure | Name |
|---|---|
| 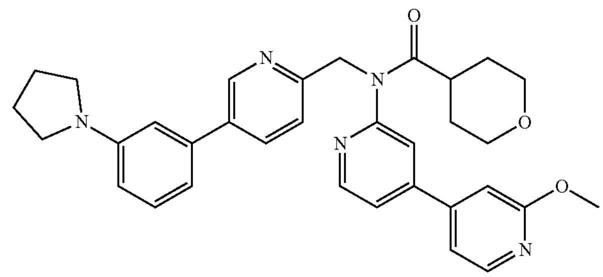 [SMILES: COc1cc(-c2ccnc(N(Cc3ccc(-c4cccc(N5CCCC5)c4)cn3)C(=O)C3CCOCC3)c2)ccn1] | N-(2'-Methoxy-[4,4'-bipyridin]-2-yl)-N-((5-(3-(pyrrolidin-1-yl)phenyl)pyridin-2-yl)methyl)tetrahydro-2H-pyran-4-carboxamide |
| | N-((6-((4-(Dimethylamino)phenoxy)methyl)pyridin-3-yl)methyl)-N-(2-((((2-methoxypyridin-4-yl)methyl)amino)-6-methylpyrimidin-4-yl)cyclohexanecarboxamide |
| 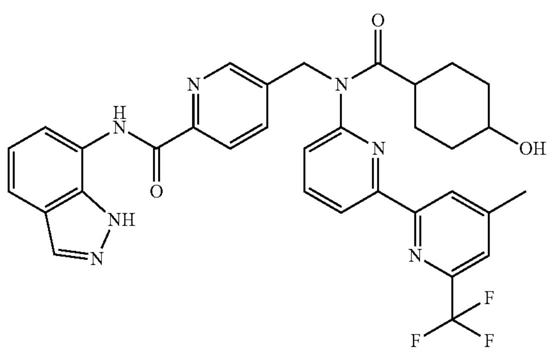 [SMILES: Cc1cc(-c2cccc(N(Cc3ccc(C(=O)Nc4cccc5cn[nH]c45)nc3)C(=O)C3CCC(O)CC3)n2)nc(C(F)(F)F)c1] | 5-((4-Hydroxy-N-(4'-methyl-6'-(trifluoromethyl)-[2,2'-bipyridin]-6-yl)cyclohexanecarboxamido)methyl)-N-(1H-indazol-7-yl)picolinamide |
| 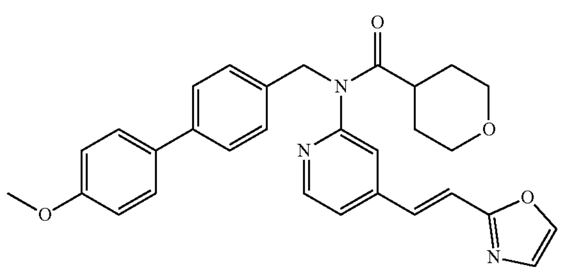 [SMILES: COc1ccc(-c2ccc(CN(C(=O)C3CCOCC3)c3cc(/C=C/c4ncco4)ccn3)cc2)cc1] | (E)-N-((4'-Methoxy-[1,1'-biphenyl]-4-yl)methyl)-N-(4-(2-(oxazol-2-yl)vinyl)pyridin-2-yl)tetrahydro-2H-pyran-4-carboxamide |
| 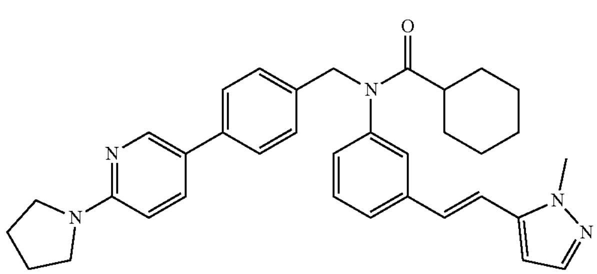 [SMILES: Cn1nccc1/C=C/c1cccc(N(Cc2ccc(-c3ccc(N4CCCC4)nc3)cc2)C(=O)C2CCCCC2)c1] | (E)-N-(3-(2-(1-Methyl-1H-pyrazol-5-yl)vinyl)phenyl)-N-(4-(6-(pyrrolidin-1-yl)pyridin-3-yl)benzyl)cyclohexanecarboxamide |

TABLE 2-continued

| Structure | Name |
| --- | --- |
| 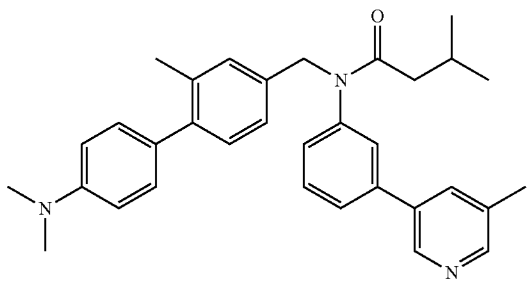 | N-((4'-(Dimethylamino)-2-methyl-[1,1'-biphenyl]-4-yl)methyl)-3-methyl-N-(3-(5-methylpyridin-3-yl)phenyl)butanamide |
| 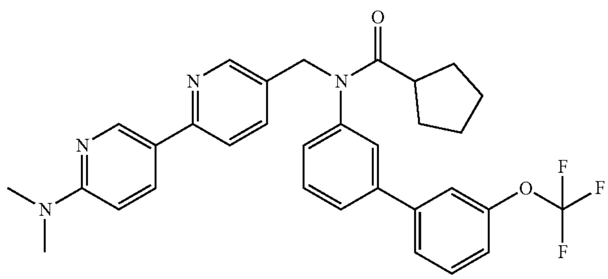 [SMILES: CN(C)c1ccc(-c2ccc(CN(C(=O)C3CCCC3)c3cccc(-c4cccc(OC(F)(F)F)c4)c3)cn2)cn1] | N-((6'-(Dimethylamino)-[2,3'-bipyridin]-5-yl)methyl)-N-(3'-(trifluoromethoxy)-[1,1'-biphenyl]-3-yl)cyclopentanecarboxamide |
| 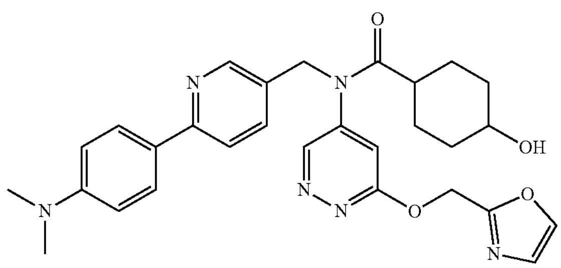 [SMILES: CN(C)c1ccc(-c2ccc(CN(C(=O)C3CCC(O)CC3)c3cnnc(OCc4ncco4)c3)cn2)cc1] | N-((6-(4-(Dimethylamino)phenyl)pyridin-3-yl)methyl)-4-hydroxy-N-(6-(oxazol-2-ylmethoxy)pyridazin-4-yl)cyclohexanecarboxamide |
| 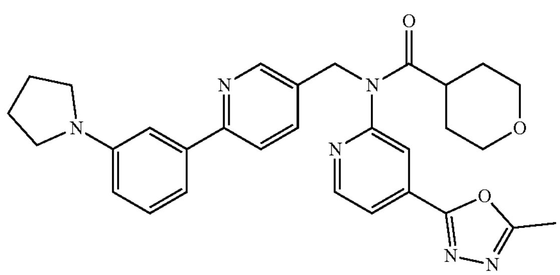 [SMILES: Cc1nnc(-c2ccnc(N(Cc3ccc(-c4cccc(N5CCCC5)c4)nc3)C(=O)C3CCOCC3)c2)o1] | N-(4-(5-Methyl-1,3,4-oxadiazol-2-yl)pyridin-2-yl)-N-((6-(3-(pyrrolidin-1-yl)phenyl)pyridin-3-yl)methyl)tetrahydro-2H-pyran-4-carboxamide |
| 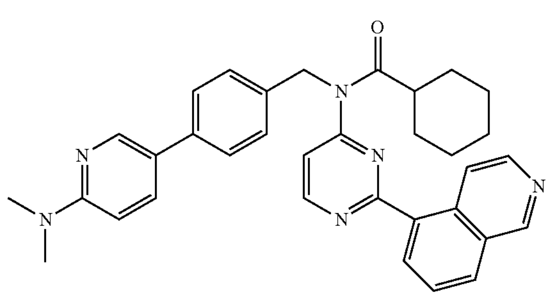 [SMILES: CN(C)c1ccc(-c2ccc(CN(C(=O)C3CCCCC3)c3ccnc(-c4cccc5cnccc45)n3)cc2)cn1] | N-(4-(6-(Dimethylamino)pyridin-3-yl)benzyl)-N-(2-(isoquinolin-5-yl)pyrimidin-4-yl)cyclohexanecarboxamide |

TABLE 2-continued

| Structure | Name |
|---|---|
| 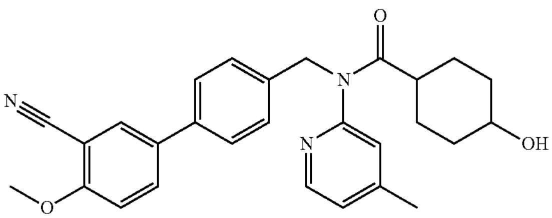 [SMILES: COc1ccc(-c2ccc(CN(C(=O)C3CCC(O)CC3)c3cc(C)ccn3)cc2)cc1C#N] | N-((3'-Cyano-4'-methoxy-[1,1'-biphenyl]-4-yl)metehyl)-4-hydroxy-N-(4-methylpyridin-2-yl)cyclohexanecarboxamide |
| 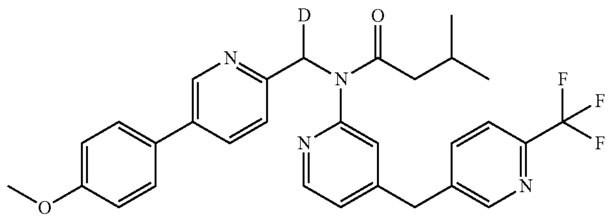 [SMILES: [2H]C(c1ccc(-c2ccc(OC)cc2)cn1)N(C(=O)CC(C)C)c1cc(Cc2ccc(C(F)(F)F)nc2)ccn1] | N-(Deutero(5-(4-methoxyphenyl)pyridin-2-yl)methyl)-3-methyl-N-(4-((6-(trifluoromethyl)pyridin-3-yl)methyl)pyridin-2-yl)butanamide |
| 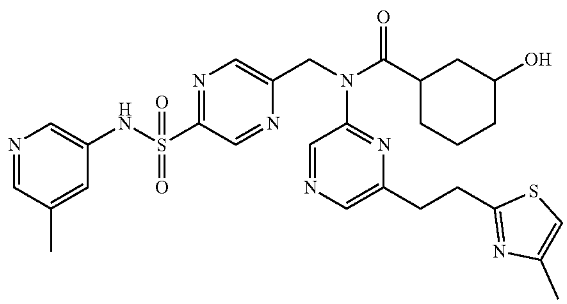 [SMILES: Cc1cncc(NS(=O)(=O)c2cnc(CN(C(=O)C3CCCC(O)C3)c3cncc(CCc4nc(C)cs4)n3)cn2)c1] | 3-Hydroxy-N-((5-(N-(5-methylpyridin-3-yl)sulfamoyl)pyrazin-2-yl)methyl)-N-(6-(2-(4-methylthiazol-2-yl)ethyl)pyrazin-2-yl)cyclohexanecarboxamide |
| 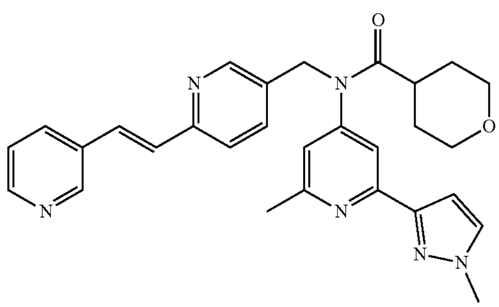 [SMILES: Cc1cc(N(Cc2ccc(/C=C/c3cccnc3)nc2)C(=O)C2CCOCC2)cc(-c2ccn(C)n2)n1] | (E)-N-(2-Methyl-6-(1-methyl-1H-pyrazol-3-yl)pyridin-4-yl)-N-((6-(2-(pyridin-3-yl)vinyl)pyridin-3-yl)methyl)tetrahydro-2H-pyran-4-carboxamide |
| 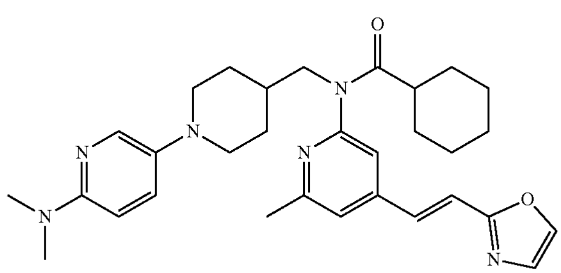 [SMILES: Cc1cc(/C=C/c2ncco2)cc(N(CC2CCN(c3ccc(N(C)C)nc3)CC2)C(=O)C2CCCCC2)n1] | (E)-N-((1-(5-(Dimethylamino)pyridin-3-yl)piperidin-4-yl)methyl)-N-(6-methyl-4-(2-(oxazol-2-yl)vinyl)pyridin-2-yl)cyclohexanecarboxamide |
| 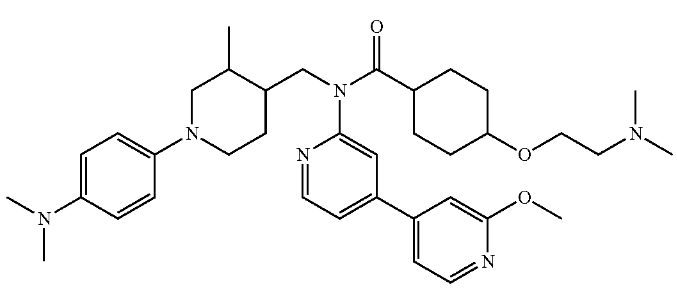 | 4-(2-(Dimethylamino)ethoxy)-N-((1-(4-(dimethylamino)phenyl)-3-methylpiperidin-4-yl)methyl)-N-(2'-methoxy-[4,4'-bipyridin]-2-yl)cyclohexanecarboxamide |

TABLE 2-continued

| Structure | Name |
|---|---|
| 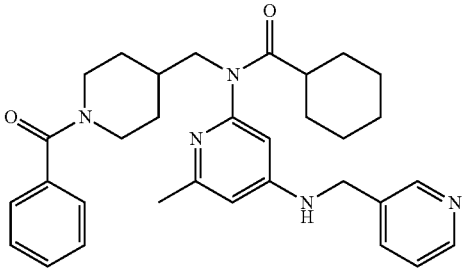 [SMILES: Cc1cc(NCc2cccnc2)cc(N(CC2CCN(C(=O)c3ccccc3)CC2)C(=O)C2CCCCC2)n1] | N-((1-Benzoylpiperidin-4-yl)methyl)-N-(6-methyl-4-((pyridin-3-ylmethyl)amino)pyridin-2-yl)cyclohexanecarboxamide |
| 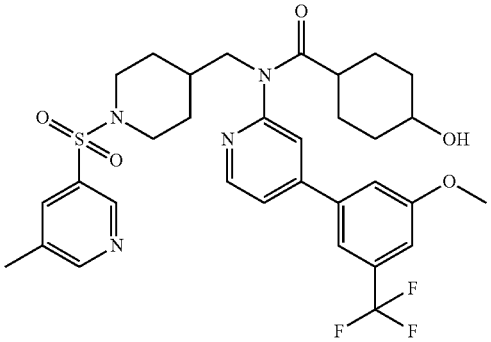 | 4-Hydroxy-N-(4-(3-methoxy-5-(trifluoromethyl)phenyl)pyridin-2-yl)-N-((1-((5-methylpyridin-3-yl)sulfonyl)piperidin-4-yl)methyl)cyclohexanecarboxamide |
| 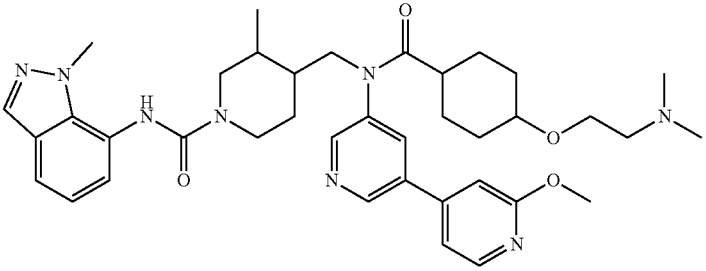 [SMILES: COc1cc(-c2cncc(N(CC3CCN(C(=O)Nc4cccc5cnn(C)c45)CC3C)C(=O)C3CCC(OCCN(C)C)CC3)c2)ccn1] | 4-((4-(2-(Dimethylamino)ethoxy)-N-(2'-methoxy-[3,4'-bipyridin]-5-yl)cyclohexanecarboxamido)methyl)-3-methyl-N-(1-methyl-1H-indazol-7-yl)piperidine-1-carboxamide |
| 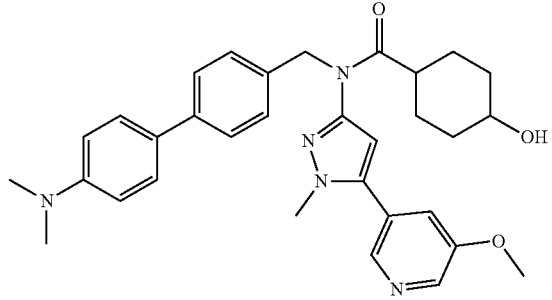 [SMILES: COc1cncc(-c2cc(N(Cc3ccc(-c4ccc(N(C)C)cc4)cc3)C(=O)C3CCC(O)CC3)nn2C)c1] | N-((4'-(Dimethylamino)-[1,1'-biphenyl]-4-yl)methyl)-4-hydroxy-N-(5-(5-methoxypyridin-3-yl)-1-methyl-1H-pyrazol-3-yl)cyclohexanecarboxamide |
| 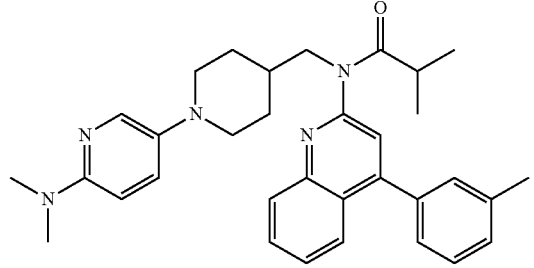 | N-((1-(6-(Dimethylamino)pyridin-3-yl)piperidin-4-yl)methyl)-N-(4-(m-tolyl)quinolin-2-yl)isobutyramide |

TABLE 2-continued

| Structure | Name |
|---|---|
| 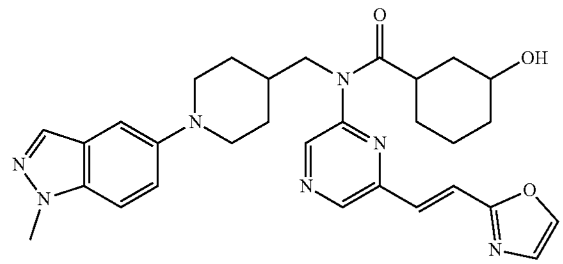 [SMILES: Cn1ncc2cc(N3CCC(CN(C(=O)C4CCCC(O)C4)c4cncc(/C=C/c5ncco5)n4)CC3)ccc21] | (E)-3-Hydroxy-N-((1-(1-methyl-1H-indazol-5-yl)piperidin-4-yl)methyl)-N-(6-(2-(oxazol-2-yl)vinyl)pyrazin-2-yl)cyclohexanecarboxamide |
| 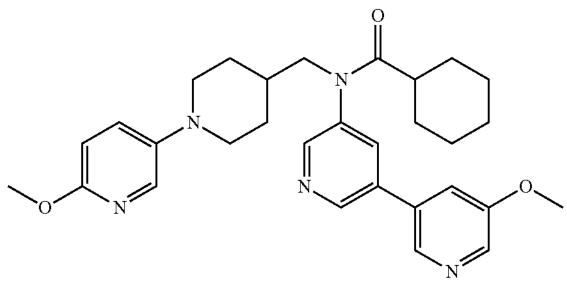 | N-(5'-Methoxy-[3,3'-bipyridin]-5-yl)-N-((1-(6-methoxypyridin-3-yl)piperidin-4-yl)methyl)cyclohexanecarboxamide |
| 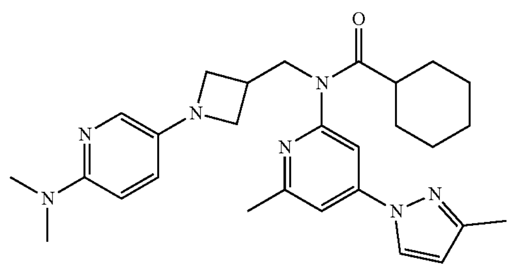 | N-((1-(6-(Dimethylamino)pyridin-3-yl)azetidin-3-yl)methyl)-N-(6-methyl-4-(3-methyl-1H-pyrazol-1-yl)pyridin-2-yl)cyclohexanecarboxamide |
| 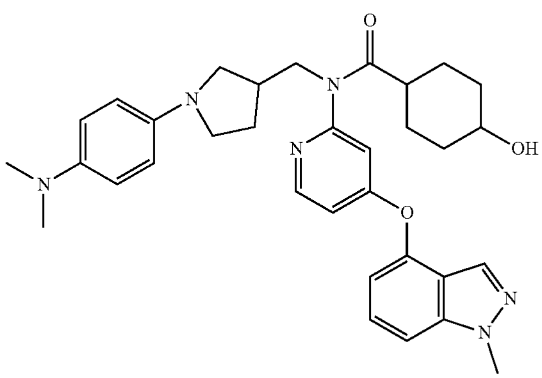 [SMILES: CN(C)c1ccc(N2CCC(CN(C(=O)C3CCC(O)CC3)c3cc(Oc4cccc5c4cnn5C)ccn3)C2)cc1] | N-((1-(4-(Dimethylamino)phenyl)pyrrolidin-3-yl)methyl)-4-hydroxy-N-(4-((1-methyl-1H-indazol-4-yl)oxy)pyridin-2-yl)cyclohexanecarboxamide |
| 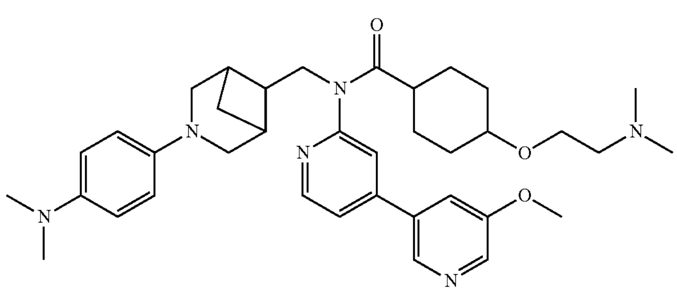 | 4-(2-(Dimethylamino)ethoxy)-N-((3-(4-(dimethylamino)phenyl)-3-azabicyclo[3.1.1]heptan-6-yl)methyl)-N-(5-methoxy-[3,4'-bipyridin]-2'-yl)cyclohexanecarboxamide |

TABLE 2-continued

| Structure | Name |
|---|---|
| | N-(5-(((3-(Methylsulfonyl)benzyl)oxy)isothiazol-3-yl)-N-((6'-(pyrrolidin-1-yl)-[2,3'-bipyridin]-5-yl)methyl)tetrahydro-2H-pyran-4-carboxamide |
| 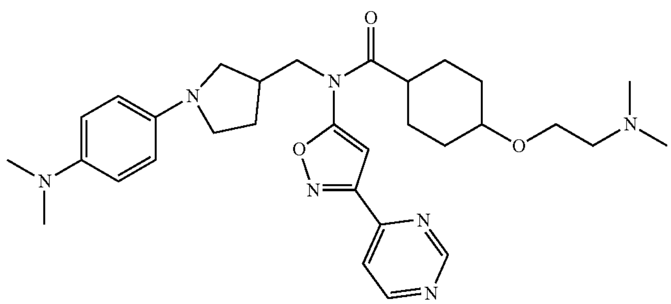 | 4-(2-(Dimethylamino)ethoxy)-N-((1-(4-(dimethylamino)phenyl)pyrrolidin-3-yl)methyl)-N-(3-(pyrimidin-4-yl)isoxazol-5-yl)cyclohexanecarboxamide |
| 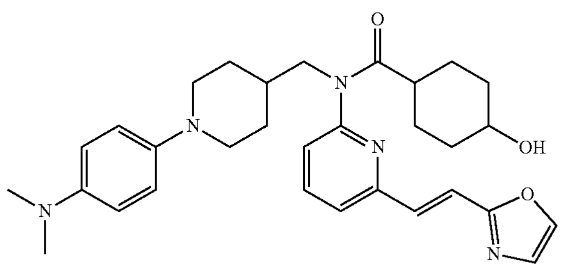 [SMILES: CN(C)c1ccc(N2CCC(CN(C(=O)C3CCC(O)CC3)c3cccc(/C=C/c4ncco4)n3)CC2)cc1] | (E)-N-((1-(4-(Dimethylamino)phenyl)piperidin-4-yl)methyl)-4-hydroxy-N-(6-(2-(oxazol-2-yl)vinyl)pyridin-2-yl)cyclohexanecarboxamide |
| 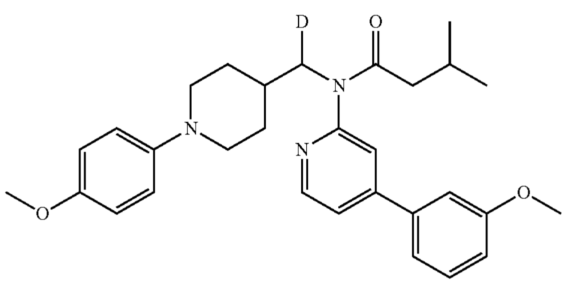 | N-(Deutero(1-(4-methoxyphenyl)piperidin-4-yl)methyl)-N-(4-(3-methoxyphenyl)pyridin-2-yl)-3-methylbutanamide |
| 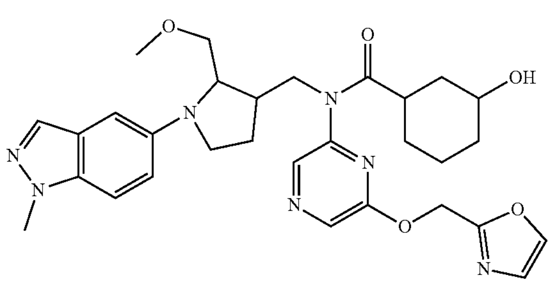 [SMILES: COCC1C(CN(C(=O)C2CCCC(O)C2)c2cncc(OCc3ncco3)n2)CCN1c1ccc2c(cnn2C)c1] | 3-Hydroxy-N-((2-(methoxymethyl)-1-(1-methyl-1H-indazol-5-yl)pyrrolidin-3-yl)methyl)-N-(6-(oxazol-2-ylmethoxy)pyrazin-2-yl)cyclohexanecarboxamide |

TABLE 2-continued

| Structure | Name |
|---|---|
| 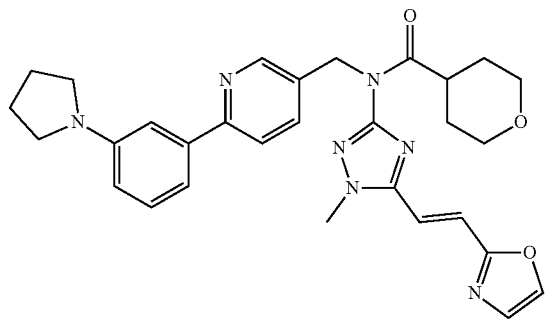 [SMILES: Cn1nc(N(Cc2ccc(-c3cccc(N4CCCC4)c3)nc2)C(=O)C2CCOCC2)nc1/C=C/c1ncco1] | (E)-N-(1-Methyl-5-(2-(oxazol-2-yl)vinyl)-1H-1,2,4-triazol-3-yl)-N-((6-(3-(pyrrolidin-1-yl)phenyl)pyridin-3-yl)methyl)tetrahydro-2H-pyran-4-carboxamide |
| 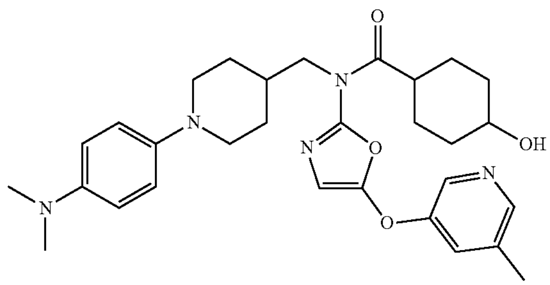 [SMILES: Cc1cncc(Oc2cnc(N(CC3CCN(c4ccc(N(C)C)cc4)CC3)C(=O)C3CCC(O)CC3)o2)c1] | N-((1-(4-(Dimethylamino)phenyl)piperidin-4-yl)methyl)-4-hydroxy-N-(5-((5-methylpyridin-3-yl)oxy)oxazol-2-yl)cyclohexanecarboxamide |
| 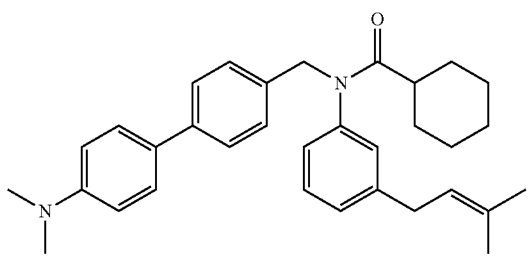 [SMILES: CC(C)=CCc1cccc(N(Cc2ccc(-c3ccc(N(C)C)cc3)cc2)C(=O)C2CCCCC2)c1] | N-((4'-(Dimethylamino)-[1,1'-biphenyl]-4-yl)methyl)-N-(3-(3-methylbut-2-en-1-yl)phenyl)cyclohexanecarboxamide |

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers to a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, Handbook of Pharmaceutical Salts: Properties, Selection and Use, Weinheim/Zürich:Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound described herein with an acid to provide a "pharmaceutically acceptable acid addition salt." In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt.

In some embodiments, pharmaceutically acceptable salts are obtained by reacting a compound described herein with a base to provide a "pharmaceutically acceptable base addition salt."

In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methyl amine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of isolating or purifying the compound with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements. In some embodiments, one or more hydrogen atoms of the compounds described herein is replaced with deuterium.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elsevier, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

In some embodiments, the compounds described herein are rapidly metabolized following absorption from the gastro-intestinal tract to metabolites that have greatly reduced FXR agonist activity.

In additional or further embodiments, the compounds are rapidly metabolized in plasma.

In additional or further embodiments, the compounds are rapidly metabolized by the intestines.

In additional or further embodiments, the compounds are rapidly metabolized by the liver.

Synthesis of Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, $6^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. The starting materials are available from commercial sources or are readily prepared.

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

The compounds described herein are prepared by the general synthetic routes described below in Schemes 1-12.

In some embodiments, compounds described herein are prepared as outlined in Scheme 1.

acyl chloride I-4 affords compound I-5. Suitable acylation conditions include but are not limited to TEA or pyridine in a suitable solvent, such as DCM, at an appropriate time and temperature, such as about 0° C. for about 15 min to about 2 h. In some embodiments, the appropriate time and temperature is about 0° C. to rt for about 2 h to about 10 h.

In some embodiments, compounds described herein are prepared as outlined in Scheme 2.

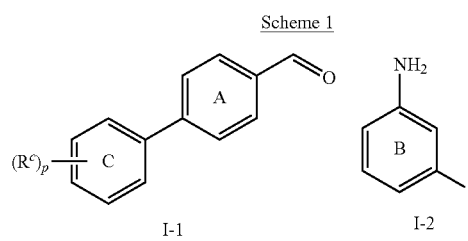

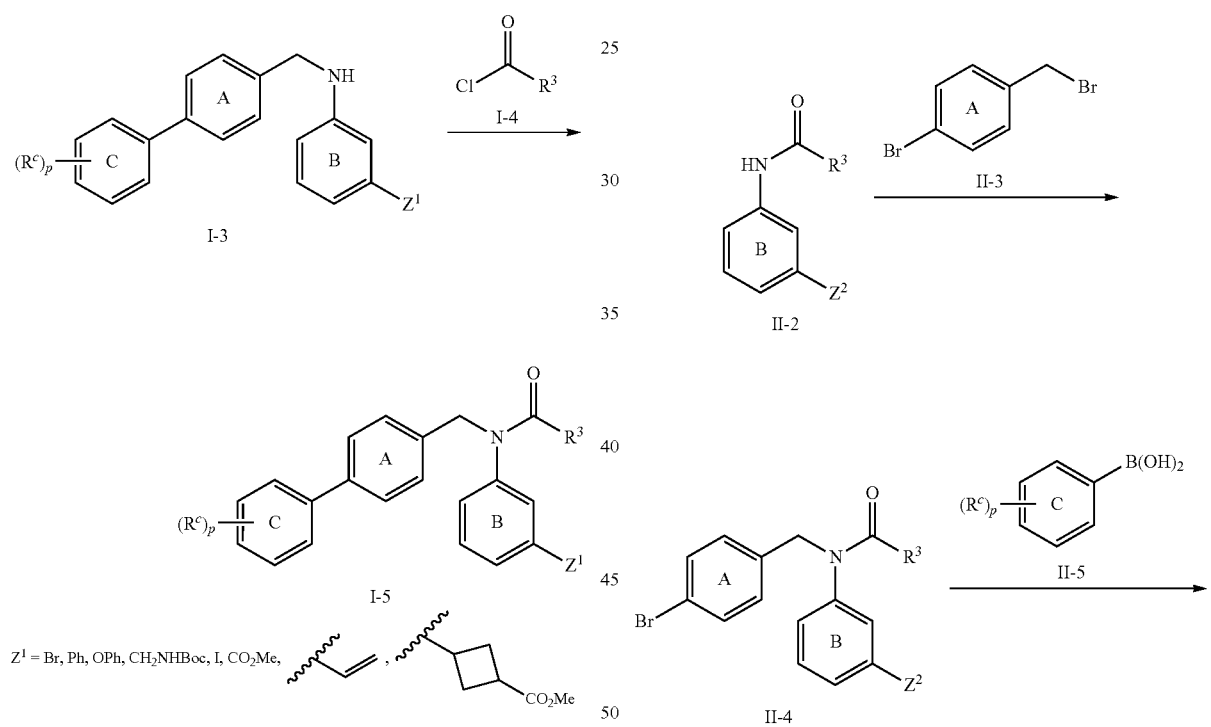

In Scheme 1, rings A, B, and C are as described herein. In some embodiments, $R^3$ is cyclohexyl. In some embodiments, $R^C$ is —$N(R^{10})_2$ and p is 1. In some embodiments, $R^{10}$ is methyl. In some embodiments, $Z^1$ are the substituents as shown in Scheme 1. In some embodiments, $Z^1$ is halo, aryl, —O-aryl, —$CH_2(NH)(R)$, $CO_2R$, alkenyl, or cycloalkyl; and R is alkyl, such as Me, or Boc.

As shown in Scheme 1, compound I-3 is obtained from subjecting aldehyde I-1 and amine I-2 under reductive amination conditions. In some embodiments, aldehyde I-1 and amine I-2 are first treated under acidic conditions, such as AcOH in DCE at rt for about 5 min to about 1 h, which is then followed by the addition of an appropriate reducing agent, such as $NaBH(OAc)_3$, for a suitable amount of time at an appropriate temperature, such as rt for about 15 min to about 1 h. In some embodiments, acylation of amino I-3 with In Scheme 2, rings A, B, and C are as described herein. In some embodiments, $R^3$ is cyclohexyl. In some embodiments, $R^C$ is —$N(R^{10})_2$ and p is 1. In some embodiments, $R^{10}$ is methyl.

As shown in Scheme 2, compound II-2 may be prepared from amino II-1 in some embodiments. In some embodiments, acylation of amino II-1 with acyl chloride I-4 affords compound II-2. Suitable acylation conditions include but are not limited to TEA or pyridine in a suitable solvent, such as DCM or ACN, for an appropriate amount of time at an appropriate temperature. In some embodiments, the appropriate time and temperature is about 1 h at about 0° C. and then about 11 h at rt. In some embodiments, the appropriate temperature is about 0° C. to rt. In some embodiments, compound II-4 is prepared from the N-alkylation of II-2 with benzyl bromide II-3 with a suitable base and suitable solvent, such as ACN, THF, or DMF, at a suitable temperature for a suitable amount of time. Suitable bases include but are not limited to $Cs_2CO_3$ and NaH. In some embodiments, the compound II-2 is pretreated with the suitable base for an appropriate amount of time at an appropriate temperature, such as about 0.5 h at about 0° C., before the addition of benzyl bromide II-3. In some embodiments, the appropriate time and temperature is about 3 h to about 12 h and about 90° C. In some embodiments, the appropriate time and temperature is about 2.5 h and about 0° C. to rt. In some embodiments, the appropriate time and temperature is about 24 h and about 80° C. In some embodiments, compound II-6 is prepared from the palladium-catalyzed cross-coupling of bromide II-4 with boronic acid II-5. In some embodiments, if $R^C$ is —$N(R^{10})_2$, p is 1, and $R^{10}$ is methyl, the II-5 is in the form of the free amine or respective salt. Suitable palladium catalysts for cross-coupling include but are not limited to $Pd(PPh_3)_4$, $PdCl_2(PPh_3)_2$, $Pd(dppf)Cl_2$ in a suitable solvent, such as DMF, dioxane/$H_2O$, THF, and EtOH/$H_2O$, with an appropriate base at the suitable temperature for an appropriate amount of time. In some embodiments, the appropriate base is $Na_2CO_3$, $Cs_2CO_3$, CsF, or $NaHCO_3$. In some embodiments, the suitable temperature is about 75° C., about 80° C., about 90° C., or about 100° C. In some embodiments, the appropriate amount of time is about 5 h, about 12 h, or about 24 h.

In some embodiments, compounds described herein are prepared as outlined in Scheme 3.

Scheme 3

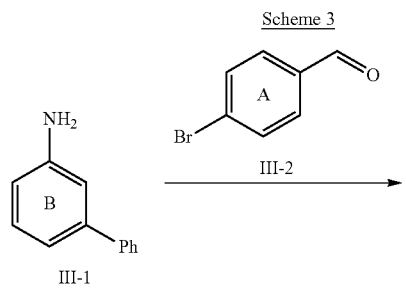

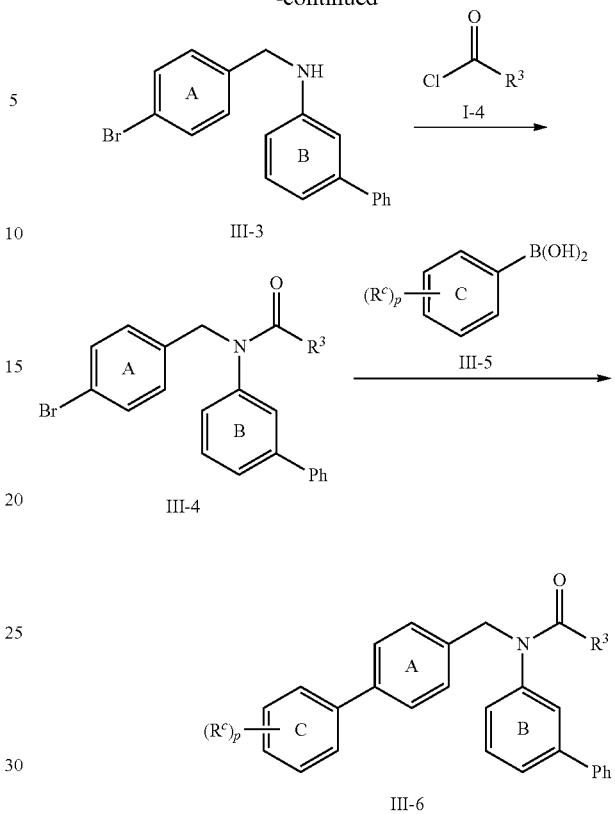

In Scheme 3, rings A, B, and C are as described herein. In some embodiments, $R^3$ is cyclohexyl. In some embodiments, $R^C$ is —F and p is 1.

As shown in Scheme 3, compound III-3 is obtained from subjecting aldehyde III-2 and amine III-1 under reductive amination conditions. In some embodiments, aldehyde III-2 and amine III-1 are first subjected under acidic conditions, such as AcOH in DCE, followed by the addition of an appropriate reducing agent, such as $NaBH(OAc)_3$, for a suitable amount of time at an appropriate temperature, such as rt for about 1 h. In some embodiments, acylation of amino III-3 with acyl chloride I-4 affords compound III-4. Suitable acylation conditions include but are not limited to TEA or pyridine in a suitable solvent, such as DCM, for an appropriate amount of time at an appropriate temperature, such as at about 0° C. for about 1 h. In some embodiments, compound III-6 is prepared from the palladium-catalyzed cross-coupling of bromide III-4 with boronic acid III-5. Suitable palladium catalysts for cross-coupling include but are not limited to $Pd(dppf)Cl_2$ in a suitable solvent, such as DMF, with an appropriate base at the suitable temperature for an appropriate amount of time. In some embodiments, the appropriate base is $Cs_2CO_3$. In some embodiments, the suitable temperature is about 80° C. In some embodiments, the appropriate amount of time is about 1 h.

In some embodiments, compounds described herein are prepared as outlined in Scheme 4.

Scheme 4

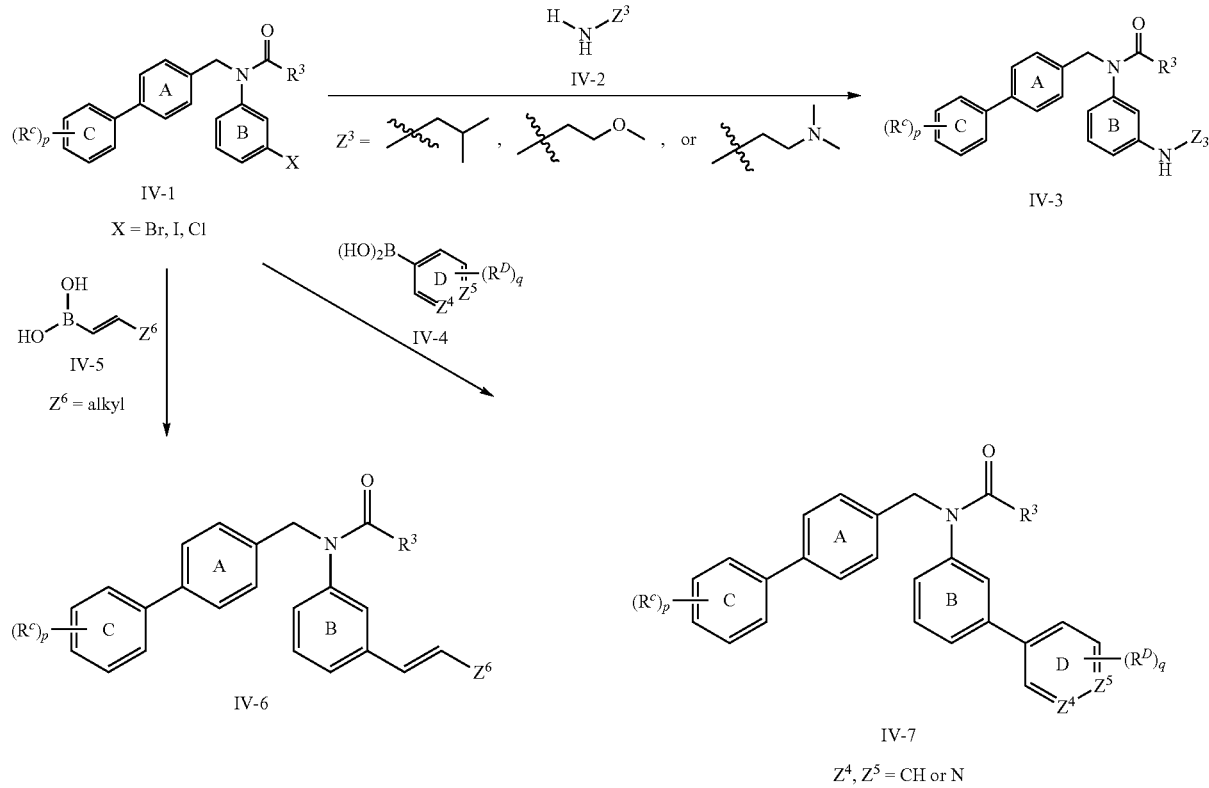

In Scheme 4, rings A, B, and C are as described herein. In some embodiments, $R^3$ is cyclohexyl. In some embodiments, $R^C$ is —$N(R^{10})_2$ and p is 1. In some embodiments, $R^{10}$ is methyl. In some embodiments, $R^D$ is —OMe and q is 1. In some embodiments, $Z^6$ is n-propyl. In some embodiments, X is bromo. In some embodiments, X is iodo. In some embodiments, X is chloro.

In some embodiments, halide IV-1 is further functionalized via palladium-catalyzed cross-coupling chemistry with the appropriate cross coupling partner. In some embodiments, halide IV-I is reacted with amine IV-2 to provide IV-3 with the appropriate palladium-catalyzed cross-coupling reaction conditions. In some embodiments, the hydrochloride salt of amine IV-2 is used instead of the amine IV-2. In some embodiments, a suitable palladium catalyst is $Pd(OAc)_2$ or $Pd_2(dba)_3$. Examples of suitable ligands for cross-coupling include but are not limited to SPhos, Trixie-Phos, and XantPhos. In some embodiments, a suitable solvent is PhMe. In some embodiments, a suitable solvent is dioxane. In some embodiments, the appropriate base is $K_3PO_4$. In some embodiments, the appropriate base is $Cs_2CO_3$. In some embodiments, the suitable temperature is about 100° C. In some embodiments, the appropriate amount of time is about 3 h. In some embodiments, the appropriate amount of time is about 18 h to about 26 h.

In some embodiments, halide IV-I is reacted with boronic acid IV-4 to provide IV-7 with the appropriate palladium-catalyzed cross-coupling reaction conditions. In some embodiments, a suitable palladium catalyst is $Pd(dppf)Cl_2$. In some embodiments, a suitable solvent is DMF. In some embodiments, the appropriate base is $Cs_2CO_3$. In some embodiments, the suitable temperature is about 80° C. In some embodiments, the appropriate amount of time is about 2 h to about 22 h.

In some embodiments, halide IV-I is reacted with boronic acid IV-5 to provide IV-6 with the appropriate palladium-catalyzed cross-coupling reaction conditions. In some embodiments, a suitable palladium catalyst is $Pd(dppf)Cl_2$. In some embodiments, a suitable solvent is dioxane. In some embodiments, the appropriate base is $K_2CO_3$. In some embodiments, the suitable temperature is about 80° C. In some embodiments, the appropriate amount of time is about 5 h.

In some embodiments, compounds described herein are prepared as outlined in Scheme 5.

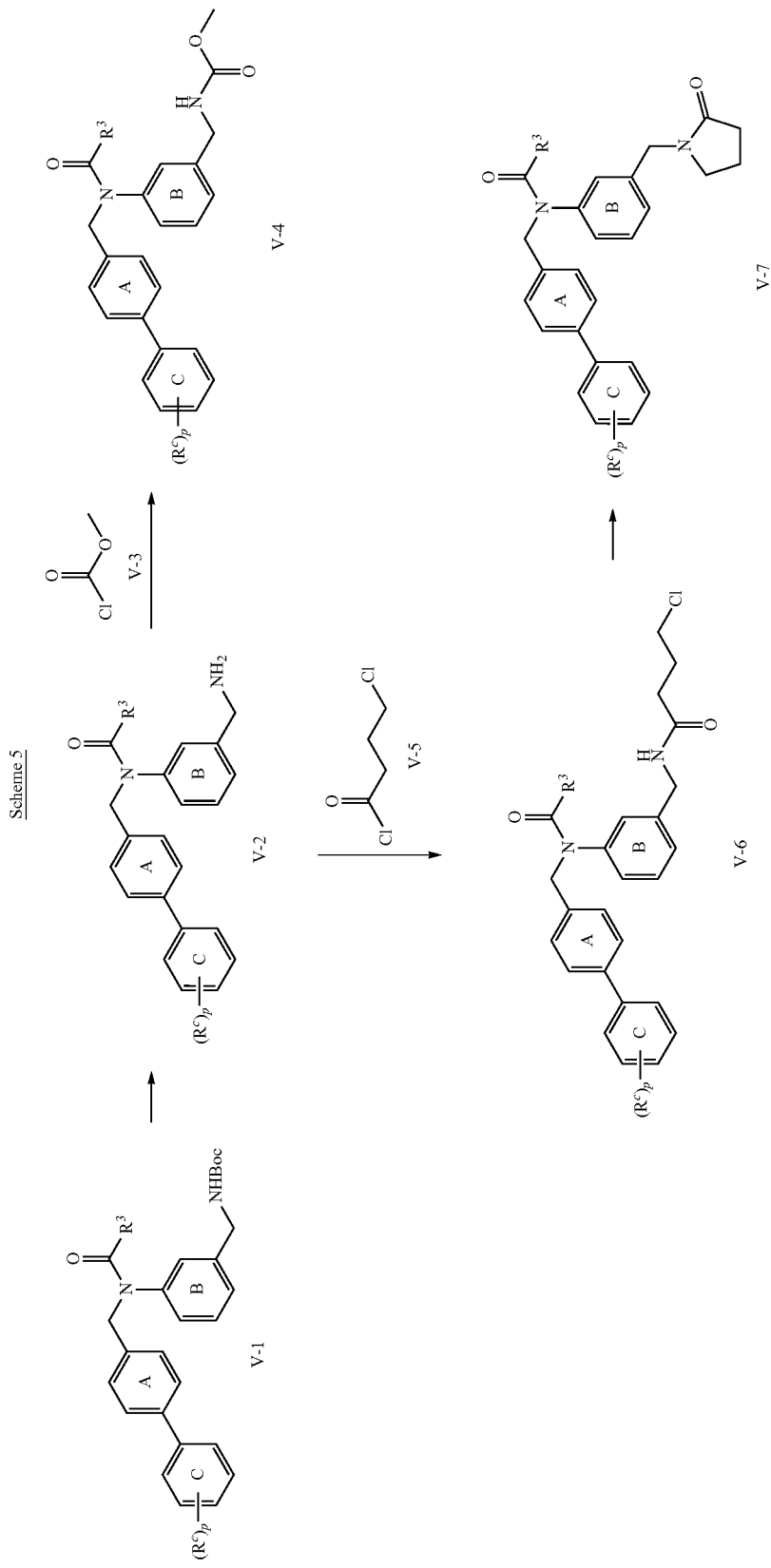

In Scheme 5, rings A, B, and C are as described herein. In some embodiments, R$^3$ cyclohexyl. In some embodiments, R$^C$ is —N(R$^{10}$)$_2$ and p is 1. In some embodiments, R$^{10}$ is methyl.

In some embodiments, V-1 is subjected under appropriate acidic conditions to provide V-2. In some embodiments, the appropriate acidic conditions are TFA in a suitable solvent, such as DCM, at an appropriate temperature for an appropriate amount of time, such as rt for about 0.5 h. In some embodiments, V-2 is reacted with methyl chloroformate V-3 to provide V-4 in the presence of a suitable base and solvent at an appropriate temperature for an appropriate amount of time. In some embodiments, the suitable base is TEA. In some embodiments, the suitable solvent is DCM. In some embodiments, the appropriate temperature for an appropriate amount of time is about 0° C. for about 0.25 h.

Alternatively, V-2 is reacted with acyl chloride V-5 to provide V-6 in the presence of a suitable base and solvent at an appropriate temperature for an appropriate amount of time. In some embodiments, the suitable base is TEA. In some embodiments, the suitable solvent is DCM. In some embodiments, the appropriate temperature for an appropriate amount of time is about 0° C. for about 0.25 h. In some embodiments, V-6 is further treated under basic conditions to provide cyclized V-7. In some embodiments, the suitable base is NaH. In some embodiments, the suitable solvent is DMF. In some embodiments, the appropriate temperature for an appropriate amount of time is about 0° C. for about 0.25 h.

In some embodiments, compounds described herein are prepared as outlined in Scheme 6.

In Scheme 6, rings A, B, and C are as described herein. In some embodiments, R$^3$ is cyclohexyl. In some embodiments, R$^C$ is —N(R$^{10}$)$_2$ and p is 1. In some embodiments, R$^{10}$ is methyl.

In some embodiments, as shown in Scheme 6, VI-2 is prepared from the reduction of VI-1. Suitable reaction conditions for reduction include H$_2$ (50 psi) with 10% Pd/C in a suitable solvent at an appropriate temperature for an appropriate amount of time. In some embodiments, the suitable solvent is MeOH. In some embodiments, the appropriate temperature is rt and the appropriate time is about 24 h. In some embodiments, VI-2 is further reacted with VI-3 under basic conditions to provide VI-4. Suitable basic conditions include NaHCO$_3$ in a suitable solvent at an appropriate temperature for an appropriate amount of time. In some embodiments, the suitable solvent is DMF. In some embodiments, the appropriate temperature is about 75° C. and the appropriate time is about 6 h. In some embodiments, VI-4 is further N-alkylated to provide VI-5 via a two-step treatment that employs CH$_2$O with AcOH in a suitable solvent, such as MeOH, for a suitable amount of time at an appropriate temperature, such as for about 2 h at rt, for the first step and a reducing agent, such as NaBH$_3$CN, for a suitable amount of time at an appropriate temperature, such as for about 16 h at rt, for the second step.

In some embodiments, compounds described herein are prepared as outlined in Scheme 7.

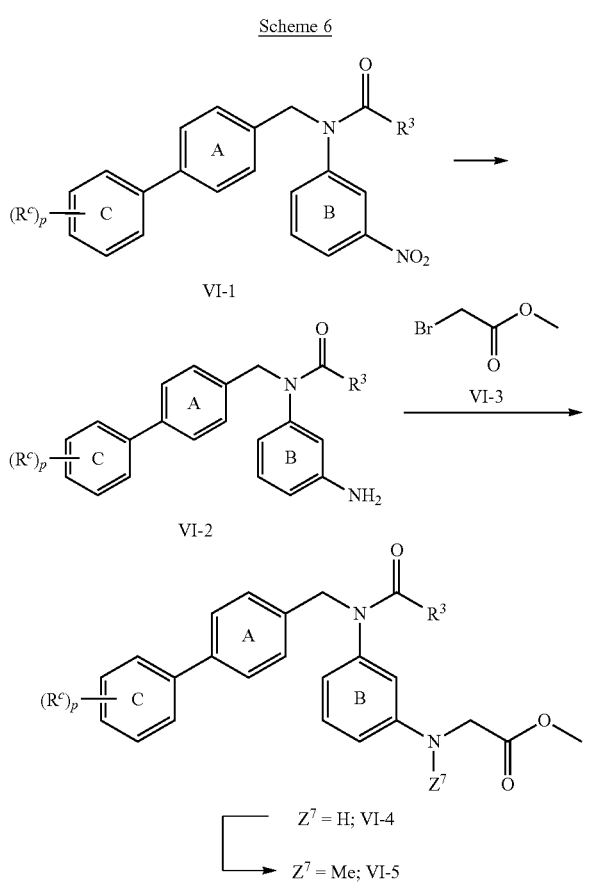

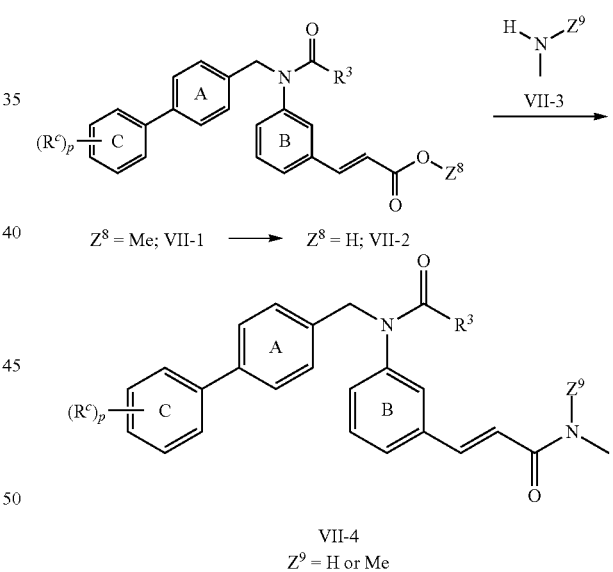

In Scheme 7, rings A, B, and C are as described herein. In some embodiments, R$^3$ is cyclohexyl. In some embodiments, R$^C$ is —N(R$^{10}$)$_2$ and p is 1. In some embodiments, R$^{10}$ is methyl.

Alternatively, VII-1 may be subjected under basic conditions to provide VII-2. Suitable basic conditions include the use of NaOH (1M) in a suitable solvent for a suitable amount of time at an appropriate temperature, such as for about 2 h at rt. In some embodiments, the suitable solvent is THF/MeOH. In some embodiments, VII-4 is obtained from treating VII-2 with amine VII-3 and a coupling agent in the presence of a suitable amine in a suitable solvent for a suitable amount of time at an appropriate temperature. In some embodiments, compound VII-2 is pretreated with coupling agent for a suitable amount of time at a suitable temperature, such as for 1 h at rt, prior to the addition of VII-3. In some embodiments, the coupling agent is HATU. In some embodiments, the amine base is iPr$_2$NEt. In some embodiments, the suitable solvent is DMF. In some embodiments, reaction is allowed to proceed for about 0.5 h at rt after the addition of amine VII-3.

In some embodiments, intermediates used in the preparation of compounds described herein are prepared as outlined in Scheme 8.

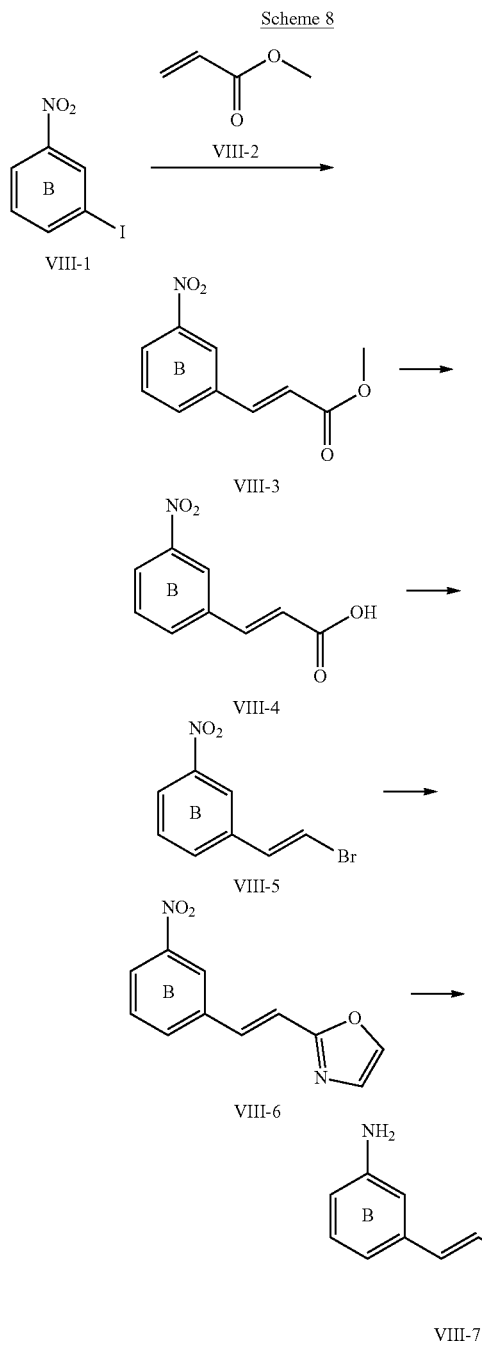

dium-catalyzed Heck cross-coupling of iodide VIII-1 with acrylate VIII-2. Suitable conditions for palladium-catalyzed cross-coupling include an appropriate palladium source, such as Pd$_2$dba$_3$, with a suitable ligand and base and solvent at an appropriate temperature for an appropriate amount of time. In some instances, the suitable ligand is P(o-tolyl)$_3$. In some instances, the suitable base is TEA. In some instances, the suitable solvent is DMF. In some instances, the appropriate temperature is about 80° C. or about 90° C. In some instances, the appropriate reaction time is about 5 h to about 12 h. In some embodiments, compound VIII-3 is subjected under basic conditions to provide acid VIII-4. Examples of suitable basic conditions include are not limited to the use of LiOH in a suitable solvent, such as THF, at a suitable temperature for a suitable amount of time, such as rt for about 12 h. In some embodiments, VIII-5 is prepared from treating VIII-4 with PhI(OAc)$_2$ and Et$_4$NBr in a suitable solvent, such as DCM, for an appropriate amount of time at a suitable temperature, such as about 16 h at rt. In some embodiments, VIII-6 is obtained from reacting VIII-5 with oxazole in the presence Pd(OAc)$_2$, CuI, and phenanthroline with a suitable base and solvent at a suitable temperature for a suitable amount of time, such as about 120° C. for about 12 h. In some embodiments, the suitable base is LiOtBu. In some embodiments, the suitable solvent is dioxane. In some embodiments, more oxazole is added to the reaction after about 12 h and reaction is allowed for proceed for another about 12 h at about 120° C. In some instances, VIII-6 is subjected under transition-metal reduction conditions to provide amine VIII-7. Suitable reaction conditions for transition-metal mediated reduction include but are not limited to Fe, NH$_4$Cl in a suitable solvent mixture at an appropriate temperature for an appropriate amount of time. In some embodiments, the suitable solvent is EtOH and H$_2$O. In other instances, the appropriate temperature is about 90° C. and the appropriate time is about 12 h.

In some embodiments, intermediates used in the preparation of compounds described herein are prepared as outlined in Scheme 9.

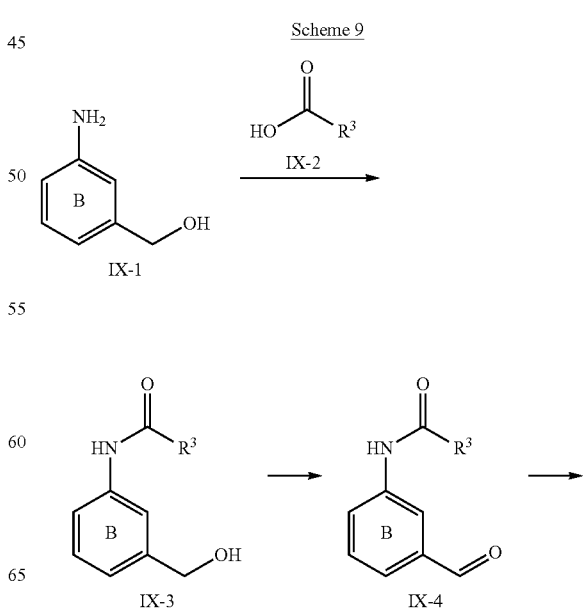

In Scheme 8, the B ring is as described herein. In some embodiments, compound VIII-3 is prepared from the palla- 133
-continued

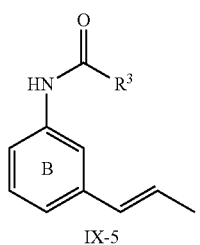

IX-5

In Scheme 9, the B ring is as described herein. In some embodiments, amide IX-3 is obtained from treating amine IX-1 with acid IX-2 and coupling agent in the presence of a suitable base in a suitable solvent for a suitable amount of time at an appropriate temperature. In some embodiments, the coupling agent is HATU. In some embodiments, the base is TEA. In some embodiments, the suitable solvent is DCM. In some embodiments, the suitable time at an appropriate temperature is for about 14 h at rt. In some embodiments, IX-4 is obtained from oxidizing IX-3 with $MnO_2$ in the presence of a suitable solvent for a suitable amount of time at an appropriate temperature. In some embodiments, the suitable solvent is DCM. In some embodiments, the suitable time at an appropriate temperature is about 12 h at about 80° C. In some embodiments, IX-5 is obtained from a one-carbon homologation reaction of IX-4, such as a Wittig reaction. In some embodiments, the Wittig reaction is performed with $EtPPh_3^+Br^-$ with an appropriate base in a suitable solvent. In some embodiments, the appropriate base is tBuOK. In some embodiments, the suitable solvent is THF. In some embodiments, the $EtPPh_3^+Br^-$ is pre-stirred with the base for a suitable time at an appropriate temperature, such as for 0.5 h at rt, before the addition of aldehyde IX-4. In some embodiments, after the aldehyde IX-4 is added, the reaction is run at rt for about 12 h.

In some embodiments, compounds described herein are prepared as outlined in Scheme 10.

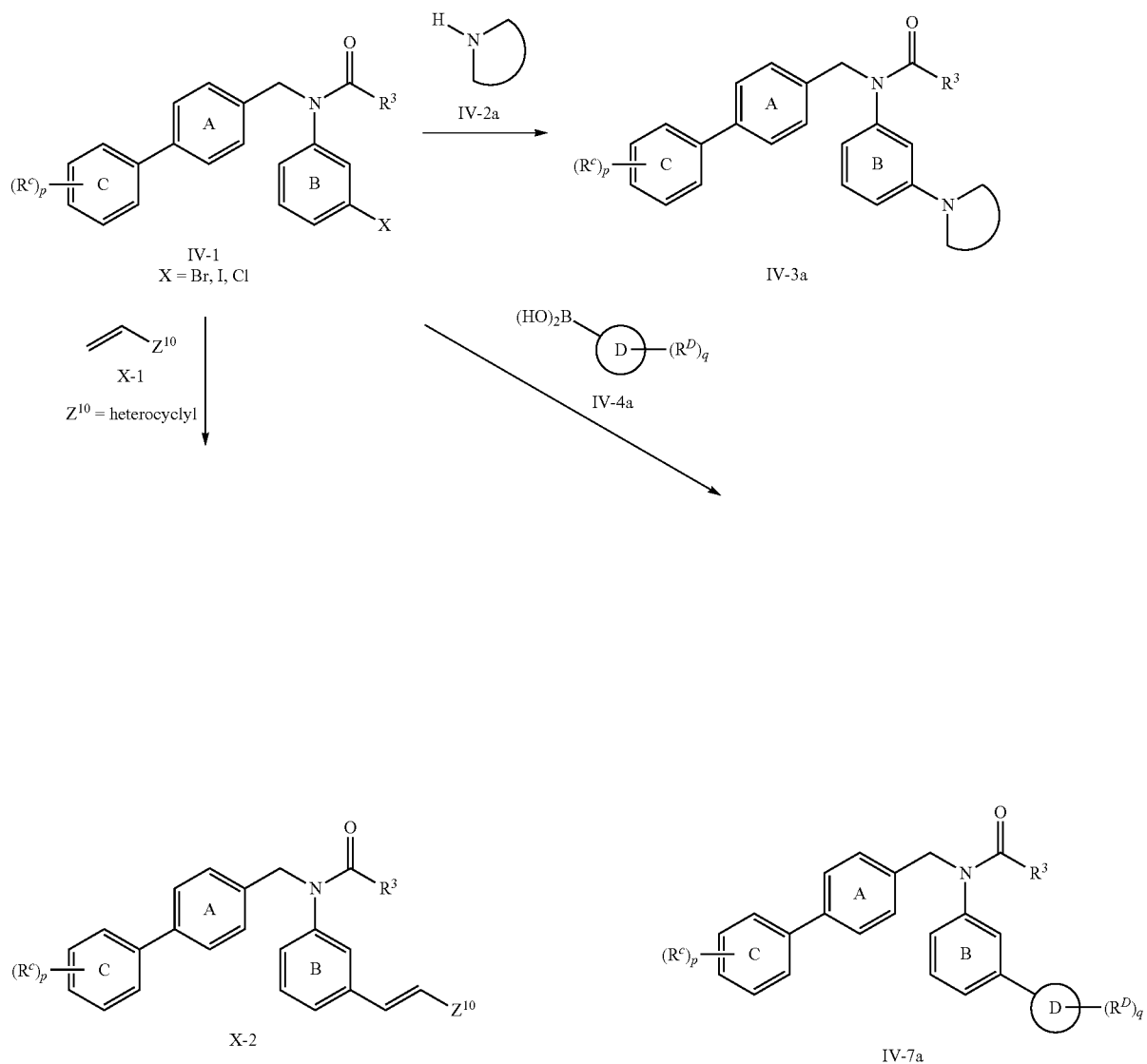

In Scheme 10, rings A, B, and C are as described herein. In some embodiments, $R^3$ is cyclohexyl. In some embodiments, $R^C$ is —$N(R^{10})_2$ and p is 1. In some embodiments, X is bromo. In some embodiments, X is iodo. In some embodiments, X is chloro. In some embodiments, IV-2a is a substituted or unsubstituted azetidine, substituted or unsubstituted pyrrolidine, or substituted or unsubstituted piperidine. In some embodiments, the D ring of IV-4a is a 6-membered heterocycle or 5-membered heterocycle. In some embodiments, $Z^{10}$ is a 6-membered heterocycle or 5-membered heterocycle. In some embodiments, $Z^{10}$ is 2-pyridyl or 4-pyridyl.

In some embodiments, halide IV-1 is further functionalized via palladium-catalyzed cross-coupling chemistry with the appropriate cross coupling partner. In some embodiments, halide IV-I is reacted with amine IV-2a to provide IV-3a with the appropriate palladium-catalyzed cross-coupling reaction conditions. In some embodiments, the hydrochloride salt of amine IV-2a is used instead of the amine IV-2a. In some embodiments, a suitable palladium catalyst is $Pd(OAc)_2$ or $Pd_2(dba)_3$. Examples of suitable ligands for cross-coupling include but are not limited to SPhos, TrixiePhos, and XantPhos. In some embodiments, a suitable solvent is PhMe. In some embodiments, a suitable solvent is dioxane. In some embodiments, the appropriate base is $K_3PO_4$. In some embodiments, the appropriate base is $Cs_2CO_3$. In some embodiments, the suitable temperature is about 100° C. In some embodiments, the appropriate amount of time is about 3 h. In some embodiments, the appropriate amount of time is about 18 h to about 26 h.

In some embodiments, halide IV-I is reacted with boronic acid IV-4a to provide IV-7a with the appropriate palladium-catalyzed cross-coupling reaction conditions. In some embodiments, a suitable palladium catalyst is $Pd(dppf)Cl_2$. In some embodiments, a suitable solvent is DMF. In some embodiments, the appropriate base is $Cs_2CO_3$. In some embodiments, the suitable temperature is about 80° C.

In some embodiments, halide IV-I is reacted with X-1 to provide X-2 with the appropriate palladium-catalyzed cross-coupling reaction conditions. In some embodiments, a suitable palladium catalyst is $Pd(OAc)_2$. In some embodiments, a suitable ligand is $P(o-tolyl)_3$. In some embodiments, a suitable solvent is DMF. In some embodiments, the appropriate base is $Et_3N$. In some embodiments, the suitable temperature is about 80° C. In some embodiments, the appropriate amount of time is about 1 h.

In some embodiments, intermediates used in the preparation of compounds described herein are prepared as outlined in Scheme 11.

Scheme 11

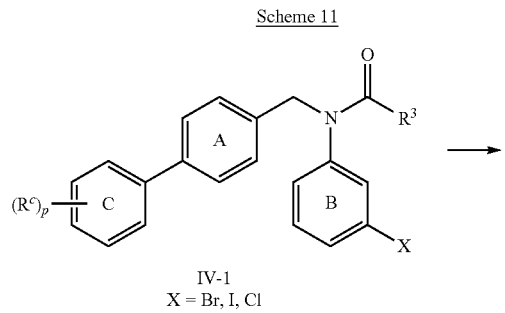

IV-1
X = Br, I, Cl

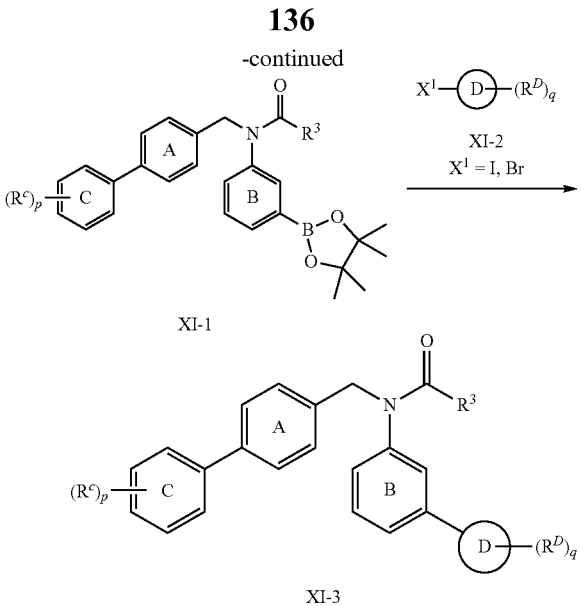

XI-1

XI-3

In Scheme 11, rings A, B, and C are as described herein. In some embodiments, $R^3$ is cyclohexyl. In some embodiments, $R^C$ is —$N(R^{10})_2$ and p is 1. In some embodiments, X is bromo. In some embodiments, X is iodo. In some embodiments, X is chloro. In some embodiments, the D ring of $X^1$-2 is a 6-membered heterocycle or 5-membered heterocycle. In some embodiments, $X^1$ is bromo or iodo.

In some embodiments, halide IV-1 is further functionalized via palladium-catalyzed cross-coupling chemistry with the appropriate cross coupling partner. In some embodiments, halide IV-I is reacted with $(Bpin)_2$ to provide $X^1$-1 with the appropriate palladium-catalyzed cross-coupling reaction conditions. In some embodiments, a suitable palladium catalyst is $Pd(dppf)Cl_2$. In some embodiments, a suitable solvent is dioxane. In some embodiments, the appropriate base is KOAc. In some embodiments, the suitable temperature is about 80° C. In some embodiments, the appropriate amount of time is overnight.

In some embodiments, XI-1 is reacted with halide $X^1$-2 to provide $X^1$-3 with the appropriate palladium-catalyzed cross-coupling reaction conditions. In some embodiments, a suitable palladium catalyst is $Pd(dppf)Cl_2$. In some embodiments, a suitable solvent is dioxane or DMF. In some embodiments, the appropriate base is $Cs_2CO_3$. In some embodiments, the suitable temperature is about 80° C.

In some embodiments, intermediates used in the preparation of compounds described herein are prepared as outlined in Scheme 12.

Scheme 12

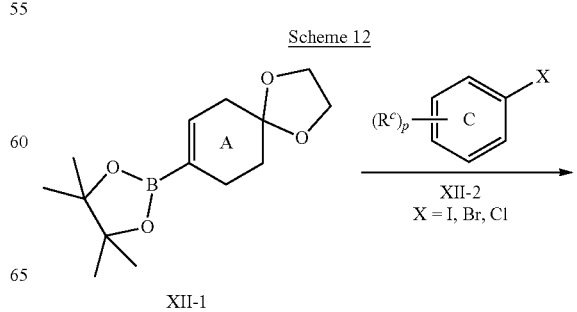

XII-1

XII-2
X = I, Br, Cl

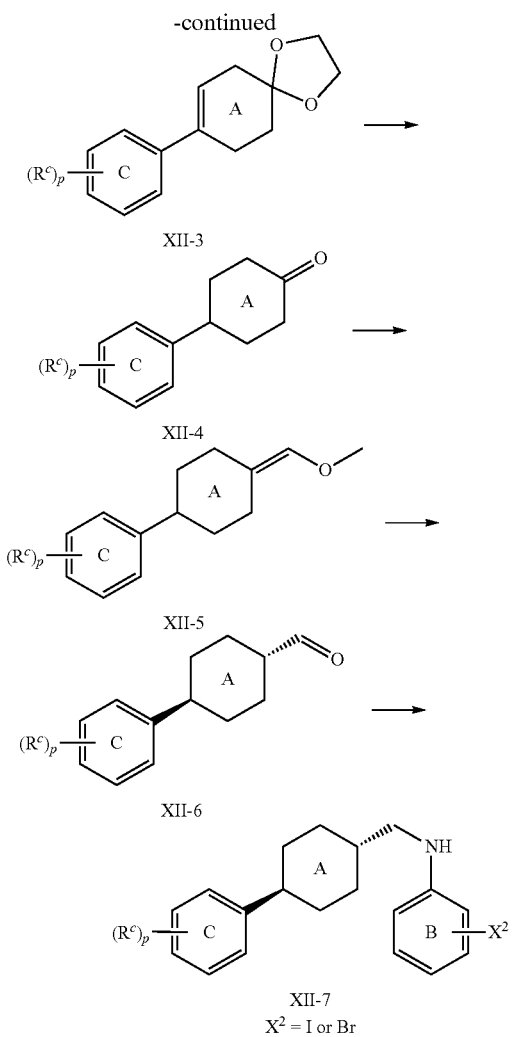

In Scheme 12, rings A, B, and C are as described herein. In some embodiments, p is 2 and each $R^c$ is independently selected from —$OR^{10}$ and substituted or unsubstituted $C_1$-$C_6$alkyl, such as methyl. In some embodiments, $R^{10}$ is methyl. In some embodiments, X is bromo. In some embodiments, X is iodo. In some embodiments, X is chloro. In some embodiments, $X^2$ is bromo. In some embodiments, $X^2$ is iodo.

In some embodiments, boronic ester XII-1 is reacted with halide XII-2 under suitable palladium-catalyzed cross-coupling reaction conditions to provide XII-3. In some embodiments, suitable palladium-catalyzed cross-coupling reaction conditions include Pd(dppf)Cl$_2$ with an appropriate base, such as 1M Na$_2$CO$_3$, with an appropriate solvent for an appropriate time and at an appropriate temperature. In some embodiments, the appropriate solvent is dioxane. In some embodiments, the appropriate time and appropriate temperature is about 2.5 hours at about 50° C. In some embodiments, XII-3 is subjected under suitable palladium-catalyzed hydrogenation conditions followed by treatment under appropriate acidic conditions to provide cyclohexanone XII-4. In some embodiments, suitable palladium-catalyzed hydrogenation conditions include 10% Pd/C with hydrogen (1 atm) in a suitable solvent, such as EtOAc, for an appropriate amount of time at an appropriate temperature. In some embodiments, the appropriate amount of time is about 4.5 hours at room temperature. In some embodiments, appropriate acidic conditions include formic acid in water and toluene for a suitable amount of time at an appropriate temperature. In some embodiments, the suitable amount of time at an appropriate temperature is about 4 hours at about 120° C. In some embodiments, XII-4 is reacted with under suitable one carbon-homologation conditions to provide XII-5. In some embodiments, suitable one-carbon-homologation conditions, includes pre-treating the (methoxymethyl)triphenyl phosphonium chloride [Ph$_3$P$^+$CH$_2$OCH$_3$ Cl$^-$] with an appropriate base, such as NaHMDS, with an appropriate solvent for an appropriate amount of time at an appropriate temperature before the addition of cyclohexanone XII-4. In some embodiments, the appropriate solvent is THF. In some embodiments, the appropriate amount of time at an appropriate temperature is about 30 mins at about 0° C. In some embodiments, after XII-4 is added the reaction is continued for an additional about 30 mins at about 0° C. In some embodiments, XII-5 is then subjected under suitable acidic conditions to provide a mixture of cis and trans aldehydes XII-6. In some embodiments, suitable acidic conditions include formic acid in water/toluene at about 120° C. for about 2 hours. In some embodiments, further subjection of aldehyde XII-6 under appropriate basic conditions provides a mostly trans aldehyde XII-6. In some embodiments, appropriate basic conditions include NaOH in a suitable solvent mixture, such as EtOH and PhMe, for an appropriate amount of time at an appropriate temperature. In some embodiments, the appropriate amount of time at an appropriate temperature is about 5.5 hours at room temperature. In some embodiments, further purification via crystallization or chromatography provides pure trans aldehyde XII-6. In some embodiments, trans aldehyde XII-6 is further reacted with an appropriate aniline compound to provide XII-7. In some embodiments, trans aldehyde XII-6 is reacted with the appropriate aniline compound under suitable reaction conditions. In some embodiments, suitable reaction conditions include acetic acid in an appropriate solvent, such as DCM, at an appropriate temperature for a suitable amount of time. In some embodiments, the appropriate temperature is about room temperature. In some embodiments, the suitable amount of time is about 5 min to about 1 hour. In some embodiments, the reaction is then further subjected to suitable conditions to afford XII-7. In some embodiments, suitable conditions include NaBH(OAc)$_3$ for an appropriate amount of time at a suitable temperature. In some embodiments, the appropriate amount of time is about 1 to about 16 hours. In some embodiments, the appropriate temperature is room temperature.

In some embodiments, XII-7 is then subjected under appropriate conditions to provide a compound wherein $X^2$ is $R^B$ as described herein. In some embodiments, XII-7 is then subjected under appropriate conditions to provide a compound wherein the B ring is as substituted as shown in any one of Schemes 1-11, such as Schemes 1, 2, 4, 10 and 11 for instance. In some embodiments, XII-7 is then subjected under appropriate conditions to provide a compound wherein $X^2$ is $Z^1$ as described in Scheme 1. In some embodiments, XII-7 is then subjected under appropriate conditions to provide a compound wherein $X^2$ is $Z^2$ as described in Scheme 2.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, 4 carbon atoms, 5 carbon atoms, 6 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$alkylene. In other embodiments, an alkylene is a $C_1$-$C_4$alkylene. In certain embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises two carbon atoms (e.g., $C_2$ alkylene). In other embodiments, an alkylene comprises two to four carbon atoms (e.g., $C_2$-$C_4$ alkylene). Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=$CR_2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$, —C≡$CCH_2CH_3$, —$CH_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycle includes cycloalkyl and aryl.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicyclo[1.1.1] pentyl. In some embodiments, a cycloalkyl is a $C_3$-$C_6$cycloalkyl. In some embodiments, a cycloalkyl is a monocyclic cycloalkyl. Monocyclic cycloalkyls include, but are not limited to, cyclopropyl, cyclobutyl, cyclopentyl, cyclohexyl, cycloheptyl, and cyclooctyl. Polycyclic cycloalkyls include, for example, adamantyl, norbornyl (i.e., bicyclo[2.2.1]heptanyl), norbornenyl, decalinyl, 7,7-dimethyl-bicyclo[2.2.1]heptanyl, and the like The term "halo" or, alternatively, "halogen" or "halide" means fluoro, chloro, bromo or iodo. In some embodiments, halo is fluoro, chloro, or bromo.

The term "haloalkyl" refers to an alkyl in which one or more hydrogen atoms are replaced by a halogen atom. In one aspect, a fluoroalkyl is a $C_1$-$C_6$fluoroalkyl.

The term "fluoroalkyl" refers to an alkyl in which one or more hydrogen atoms are replaced by a fluorine atom. In one aspect, a fluoroalkyl is a $C_1$-$C_6$fluoroalkyl. In some embodiments, a fluoroalkyl is selected from trifluoromethyl, difluoromethyl, fluoromethyl, 2,2,2-trifluoroethyl, 1-fluoromethyl-2-fluoroethyl, and the like.

The term "heteroalkyl" refers to an alkyl group in which one or more skeletal atoms of the alkyl are selected from an atom other than carbon, e.g., oxygen, nitrogen (e.g.

—NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. In some embodiments, heterocycles are monocyclic, bicyclic, polycyclic, spirocyclic or bridged compounds. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an agonist.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from administration of a FXR agonist. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

Disclosed herein, are methods of administering a FXR agonist in combination with an additional therapeutic agent. In some embodiments, the additional therapeutic agent comprises a therapeutic agent for treatment of diabetes or diabetes related disorder or conditions, alcoholic or non-alcoholic liver disease, inflammation related intestinal conditions, or cell proliferative disorders.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion, the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d)

administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a FXR agonist is administered in combination with an additional therapeutic agent for the treatment of diabetes or diabetes related disorder or conditions.

In some instances, the additional therapeutic agent comprises a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anagliptin, teneligliptin, alogliptin, gemigliptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or a combination thereof. In some cases, the statin is a HMG-CoA reductase inhibitor. In other instances, additional therapeutic agents include fish oil, fibrate, vitamins such as niacin, retinoic acid (e.g., 9 cis-retinoic acid), nicotinamide ribonucleoside or its analogs thereof, or combinations thereof. In some instances, nicotinamide ribonucleoside or its analogs thereof, which promote $NAD^+$ production, a substrate for many enzymatic reactions including p450s which is a target for FXR (e.g., see Yang et al., *J. Med. Chem.* 50:6458-61, 2007).

In some embodiments, a FXR agonist is administered in combination with an additional therapeutic agent such as a statin, an insulin sensitizing drug, an insulin secretagogue, an alpha-glucosidase inhibitor, a GLP agonist, a DPP-4 inhibitor (such as sitagliptin, vildagliptin, saxagliptin, linagliptin, anaglptin, teneligliptin, alogliptin, gemiglptin, or dutoglpitin), a catecholamine (such as epinephrine, norepinephrine, or dopamine), peroxisome proliferator-activated receptor (PPAR)-gamma agonist (e.g., a thiazolidinedione (TZD) [such as pioglitazone, rosiglitazone, rivoglitazone, or troglitazone], aleglitazar, farglitazar, muraglitazar, or tesaglitazar), or combinations thereof, for the treatment of diabetes or diabetes related disorder or conditions. In some embodiments, a FXR agonist is administered in combination with an additional therapeutic agent such as fish oil, fibrate, vitamins such as niacin, retinoic acid (e.g., 9 cis-retinoic acid), nicotinamide ribonucleoside or its analogs thereof, or combinations thereof, for the treatment of diabetes or diabetes related disorder or conditions.

In some embodiments, a FXR agonist is administered in combination with a statin such as a HMG-CoA reductase inhibitor, fish oil, fibrate, niacin or a combination thereof, for the treatment of dyslipidemia.

In additional embodiments, a FXR agonist is administered in combination with a vitamin such as retinoic acid for the treatment of diabetes and diabetes related disorder or condition such as lowering elevated body weight and/or lowering elevated blood glucose from food intake.

In some embodiments, the farnesoid X receptor agonist is administered with at least one additional therapy. In some embodiments, the at least one additional therapy is a glucose-lowering agent. In some embodiments, the at least one additional therapy is an anti-obesity agent. In some embodiments, the at least one additional therapy is selected from among a peroxisome proliferator activated receptor (PPAR) agonist (gamma, dual, or pan), a dipeptidyl peptidase (IV) inhibitor, a glucagon-like peptide-1 (GLP-I) analog, insulin or an insulin analog, an insulin secretagogue, a sodium glucose co-transporter 2 (SGLT2) inhibitor, a glucophage, a human amylin analog, a biguanide, an alpha-glucosidase inhibitor, a meglitinide, a thiazolidinedione, and sulfonylurea. In some embodiments, the at least one additional therapy is metformin, sitagliptin, saxaglitpin, repaglinide, nateglinide, exenatide, liraglutide, insulin lispro, insulin aspart, insulin glargine, insulin detemir, insulin isophane, and glucagon-like peptide 1, or any combination thereof. In some embodiments, the at least one additional therapy is a lipid-lowering agent. In certain embodiments, the at least one additional therapy is administered at the same time as the farnesoid X receptor agonist. In certain embodiments, the at least one additional therapy is administered less frequently than the farnesoid X receptor agonist. In certain embodiments, the at least one additional therapy is administered more frequently than the farnesoid X receptor agonist. In certain embodiments, the at least one additional therapy is administered prior to administration of the farnesoid X receptor agonist. In certain embodiments, the at least one additional therapy is administered after administration of the farnesoid X receptor agonist.

In some embodiments, a compound described herein, or a pharmaceutically acceptable salt thereof, is administered in combination with chemotherapy, anti-inflammatory agents, radiation therapy, monoclonal antibodies, or combinations thereof.

In some embodiments, a FXR agonist is administered in combination with an additional therapeutic agent for the treatment of alcoholic or non-alcoholic liver disease. In some embodiments, the additional therapeutic agent includes antioxidant, corticosteroid, anti-tumor necrosis factor (TNF) or a combination thereof.

In some embodiments, a FXR agonist is administered in combination with an additional therapeutic agent such as antioxidant, corticosteroid, anti-tumor necrosis factor (TNF), or a combination thereof, for the treatment of alcoholic or non-alcoholic liver disease. In some embodiments, a FXR agonist is administered in combination with an antioxidant, a vitamin precursor, a corticosteroid, an anti-tumor necrosis factor (TNF), or a combination thereof, for the treatment of alcoholic or non-alcoholic liver disease.

In some embodiments, a FXR agonist is administered in combination with an additional therapeutic agent for the treatment of inflammation related intestinal conditions. In some instances, the additional therapeutic agent comprises an antibiotic (such as metronidazole, vancomycin, and/or fidaxomicin), a corticosteroid, or an additional anti-inflammatory or immuno-modulatory therapy.

In some instances, a FXR agonist is administered in combination with an additional therapeutic agent such as an antibiotic, a corticosteroid, or an additional anti-inflammatory or immuno-modulatory therapy, for the treatment of inflammation related intestinal conditions. In some cases, a FXR agonist is administered in combination with metronidazole, vancomycin, fidaxomicin, corticosteroid, or combinations thereof, for the treatment of inflammation related intestinal conditions.

As discussed above, inflammation is sometimes associated with pseudomembranous colitis. In some instances, pseudomembranous colitis is associated with bacterial overgrowth (such as *C. dificile* overgrowth). In some embodiments, a FXR agonist is administered in combination with an antibiotic such as metronidazole, vancomycin, fidaxomicin, or a combination thereof, for the treatment of inflammation associated with bacterial overgrowth (e.g., pseudomembranous colitis).

In some embodiments, the FXR agonist is administered in combination with an additional therapeutic agent for the treatment of cell proliferative disorders. In some embodiments, the additional therapeutic agent includes a chemotherapeutic, a biologic (e.g., antibody, for example bevacizumab, cetuximab, or panitumumab), a radiotherapeutic (e.g., FOLFOX, FOLFIRI, CapeOX, 5-FU, leucovorin, regorafenib, irinotecan, or oxaliplatin), or combinations thereof.

In some embodiments, the FXR agonist is administered in combination with an additional therapeutic agent for the treatment of primary biliary cirrhosis. In some embodiments, the additional therapeutic agent includes ursodeoxycholic acid (UDCA).

In some embodiments, a FXR agonist is administered in combination with an additional therapeutic agent such as a chemotherapeutic, a biologic, a radiotherapeutic, or combinations thereof, for the treatment of a cell proliferative disorder. In some instances, a FXR agonist is administered in combination with an antibody (e.g., bevacizumab, cetuximab, or panitumumab), chemotherapeutic, FOLFOX, FOLFIRI, CapeOX, 5-FU, leucovorin, regorafenib, irinotecan, oxaliplatin, or combinations thereof, for the treatment of a cell proliferative disorder.

EXAMPLES

The following examples are provided for illustrative purposes only and not to limit the scope of the claims provided herein.

As used above, and throughout the description of the invention, the following abbreviations, unless otherwise indicated, shall be understood to have the following meanings:

ACN or MeCN acetonitrile
Ac acetyl
AcOH acetic acid
BINAP 2,2'-bis(diphenylphosphino)-1,1'-binaphthalene
Bn benzyl
BOC or Boc tert-butyl carbamate
t-Bu tert-butyl
Cy cyclohexyl
DBA or dba dibenzylideneacetone
DBU 1,8-diazabicyclo[5.4.0]undec-7-ene
DCE dichloroethane (ClCH$_2$CH$_2$Cl)
DCM dichloromethane (CH$_2$Cl$_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
Dppf or dppf 1,1'-bis(diphenylphosphino)ferrocene
EEDQ 2-Ethoxy-1-ethoxycarbonyl-1,2-dihydroquinoline
eq equivalent(s)
Et ethyl
Et$_2$O diethyl ether
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum anhydride
LCMS liquid chromatography mass spectrometry
Me methyl
MeOH methanol
MS mass spectroscopy
NMM N-methyl-morpholine
NMP N-methyl-pyrrolidin-2-one
NMR nuclear magnetic resonance
PCC pyridinium chlorochromate
Ph phenyl
pin pinacolato
i-Pr iso-propyl
RP-HPLC reverse phase-high pressure liquid chromatography
TBS tert-butyldimethylsilyl
TFA trifluoroacetic acid
TEA triethylamine
TrixiePhos rac-2-(di-tert-butylphosphino)-1,1'-binaphthyl
THF tetrahydrofuran
TLC thin layer chromatography
XantPhos 4,5-bis(diphenylphosphino)-9,9-dimethylxanthene Intermediate 1

4'-(Dimethylamino)-[1,1'-biphenyl]-4-carbaldehyde

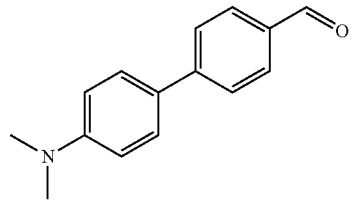 [SMILES: CN(C)c1ccc(-c2ccc(C=O)cc2)cc1]

A mixture of 4-bromo-N,N-dimethylaniline (21.28 g, 106.4 mmol), (4-formylphenyl)boronic acid (19.09 g, 127.4 mmol), potassium phosphate tribasic (67.77 g, 319.4 mmol), 2-dicyclohexylphosphino-2',6'-dimethoxybiphenyl (4.38 g, 10.7 mmol), toluene (100 mL), iso-propanol (100 mL), and water (100 mL) was degassed with vacuum/nitrogen cycles (3×). Palladium acetate (1.22 g, 5.42 mmol) was added, and the mixture was stirred at room temperature for 3 h. The reaction mixture was diluted with DCM (800 mL) and water (500 mL), filtered through Celite, and the Celite was washed with DCM (200 mL). The layers were separated, and the organic layer was washed (500 mL water). The combined aqueous layer was extracted with DCM (200 mL). The organic extracts were combined, dried (Na$_2$SO$_4$), and concentrated under reduced pressure. The resulting solid was stirred in 1:1 hexanes/ethyl acetate (400 mL) for 15 min and filtered to give 4'-(dimethylamino)-[1,1'-biphenyl]-4-carbaldehyde (21.17 g, 88%) as a yellow solid. The filtrate was concentrated, stirred in 1:1 hexanes/ethyl acetate (200 mL) for 15 min and filtered to afford additional material (2.30 g, ~90% pure, 8%). $^1$H NMR (400 MHz, DMSO-d$_6$): δ 9.98 (s, 1H), 7.93 (d, J=8.5 Hz, 2H), 7.83 (d, J=8.5 Hz, 2H), 7.66 (d, J=8.9 Hz, 2H), 6.82 (d, J=8.9 Hz, 2H), 2.96 (s, 6H).

Intermediate 2

N-(3-bromophenyl)-N-((4'-(dimethylamino)-[1,1'-biphenyl]-4-yl)methyl)cyclohexanecarboxamide

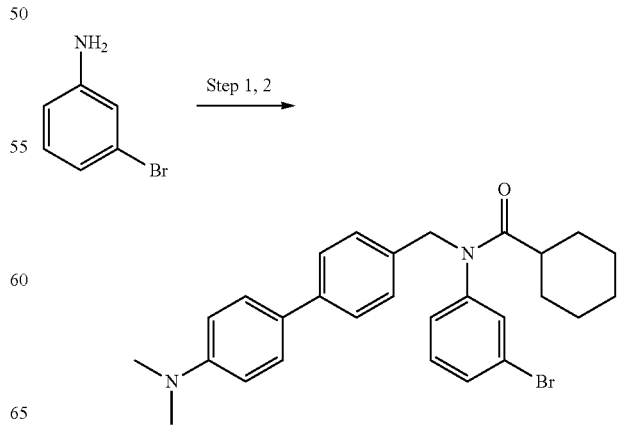

Step 1: 4'-(((3-Bromophenyl)amino)methyl)-N,N-dimethyl-[1,1'-biphenyl]-4-amine A solution of Intermediate 1 (3.30 g, 14.7 mmol), 3-bromoaniline (2.4 mL, 22 mmol), and acetic acid (1.7 mL, 29.3 mmol) in DCM (50 mL) was stirred at 25° C. for 1 h, and then sodium triacetoxyborohydride (15.5 g, 73.3 mmol) was added. The reaction mixture was stirred at 25° C. for 11 h, washed with saturated NaHCO$_3$ (2×30 mL), dried over Na$_2$SO$_4$, filtered, and concentrated. The residue was purified by column chromatography (petroleum ether/ethyl acetate; 50:1) to give 4'-(((3-bromophenyl)amino)methyl)-N,N-dimethyl-[1,1'-biphenyl]-4-amine (4.0 g, 64%) as a yellow oil. $^1$H NMR (CDCl$_3$): δ 7.51-7.60 (m, 4H), 7.40 (d, 2H), 7.01-7.09 (m, 1H), 6.80-6.90 (m, 4H), 6.56-6.62 (m, 1H), 4.34 (br s, 2H), 4.12 (br s, 1H), 3.00-3.08 (m, 6H); MS: 381.0 [M+H]$^+$.

Step 2: N-(3-bromophenyl)-N-((4'-(dimethylamino)-[1,1'-biphenyl]-4-yl)methyl) cyclohexane carboxamide Cyclohexanecarbonyl chloride (2.10 mL, 15.8 mmol) was added to a solution of 4'-(((3-bromophenyl)amino)methyl)-N,N-dimethyl-[1,1'-biphenyl]-4-amine (4 g, 10.5 mmol) and TEA (4.36 mL, 31.5 mmol) in DCM (100 mL) over 2 h at 0° C. The mixture was stirred at 25° C. for 10 h and then washed (50 mL water and then 50 mL brine). The organic layer was dried over Na$_2$SO$_4$, filtered, and concentrated. The residue was purified by column chromatography (petroleum ether/ethyl acetate; 50/1) to give N-(3-bromophenyl)-N-((4'-(dimethylamino)-[1,1'-biphenyl]-4-yl)methyl)cyclohexanecarboxamide (4.5 g, 84%) as a yellow solid. $^1$H NMR (CDCl$_3$): δ 7.38-7.52 (m, 5H), 7.10-7.22 (m, 4H), 6.88 (d, 1H), 6.73-6.81 (m, 2H), 4.70-4.86 (m, 2H), 2.97 (s, 6H), 2.12 (br s, 1H), 1.55-1.76 (m, 7H), 1.13-1.23 (m, 1H), 0.90-1.06 (m, 2H); MS: 491.0 [M+H]$^+$.

The Intermediates below were synthesized from appropriate starting materials following the procedures described for Intermediate 2.

| Int | structure | Name | [M + H]$^+$ |
|---|---|---|---|
| 2.1 | 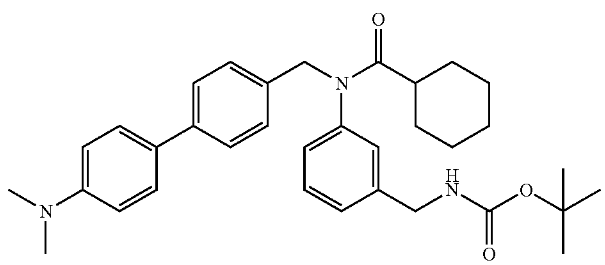 [SMILES: CN(C)c1ccc(-c2ccc(CN(C(=O)C3CCCCC3)c3cccc(CNC(=O)OC(C)(C)C)c3)cc2)cc1] | N-(3-(Aminomethyl)phenyl)-N-((4'-(dimethylamino)-[1,1'-biphenyl]-4-yl)methyl)cyclohexanecarboxamide | 542.3 |
| 2.2* | 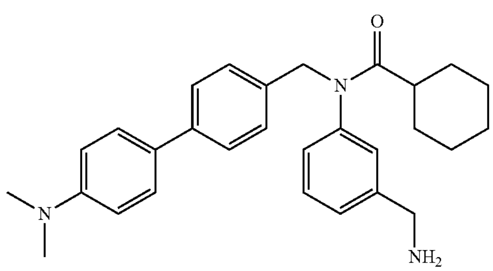 [SMILES: CN(C)c1ccc(-c2ccc(CN(C(=O)C3CCCCC3)c3cccc(CN)c3)cc2)cc1] | N-((4'-(dimethylamino)-[1,1'-biphenyl]-4-yl)methyl)-N-(3-((2-(dimethylamino)ethyl)amino)phenyl)cyclohexanecarboxamide | 442.3 |
| 2.3 | 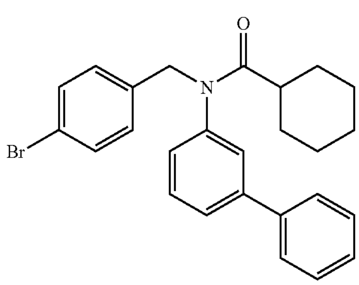 [SMILES: O=C(C1CCCCC1)N(Cc1ccc(Br)cc1)c1cccc(-c2ccccc2)c1] | N-([1,1'-Biphenyl]-3-yl)-N-(4-bromobenzyl)cyclohexanecarboxamide | |

-continued

| Int | structure | Name | [M + H]+ |
|---|---|---|---|
| 2.4 | 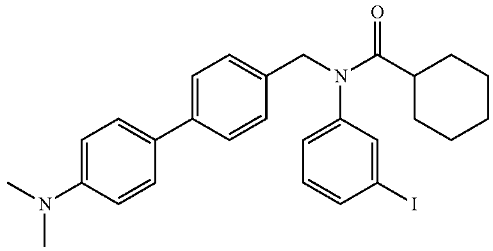 [SMILES: CN(C)c1ccc(-c2ccc(CN(C(=O)C3CCCCC3)c3cccc(I)c3)cc2)cc1] | N-((4'-(Dimethylamino)-[1,1'-biphenyl]-4-yl)methyl)-N-(3-iodophenyl)cyclohexanecarboxamide | 539.6 |
| 2.5 | 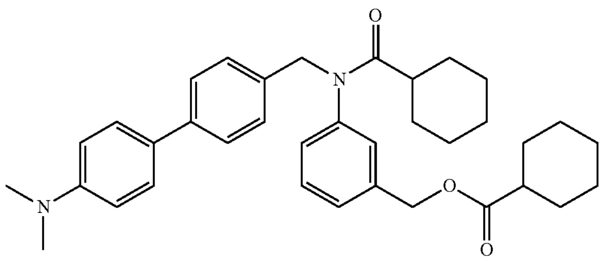 [SMILES: CN(C)c1ccc(-c2ccc(CN(C(=O)C3CCCCC3)c3cccc(COC(=O)C4CCCCC4)c3)cc2)cc1] | 3-(N-((4'-(Dimethylamino)-[1,1'-biphenyl]-4-yl)methyl)cyclohexanecarboxamido) benzyl cyclohexanecarboxylate | 553.3 |
| 2.6 | 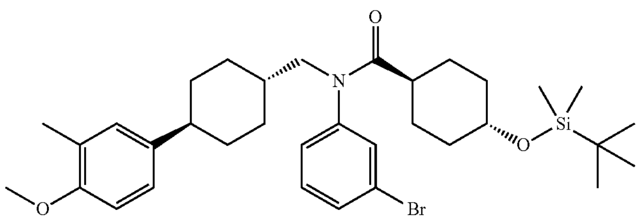 [SMILES: COc1ccc([C@H]2CC[C@H](CN(c3cccc(Br)c3)C(=O)[C@H]3CC[C@H](O[Si](C)(C)C(C)(C)C)CC3)CC2)cc1C] | trans-N-(3-Bromophenyl)-4-((tert-butyldimethylsilyl)oxy)-N-((trans-4-(4-methoxy-3-methylphenyl)cyclohexyl)methyl)cyclohexanecarboxamide | 628.5 |
| 2.7 | 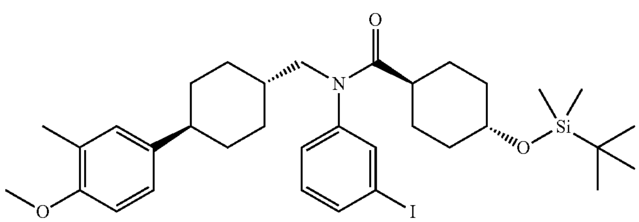 [SMILES: COc1ccc([C@H]2CC[C@H](CN(c3cccc(I)c3)C(=O)[C@H]3CC[C@H](O[Si](C)(C)C(C)(C)C)CC3)CC2)cc1C] | trans-4-((tert-Butyldimethylsilyl)oxy)-N-(3-iodophenyl)-N-((trans-4-(4-methoxy-3-methylphenyl)cyclohexyl)methyl)cyclohexanecarboxamide | 676.7 |
| 2.8 | 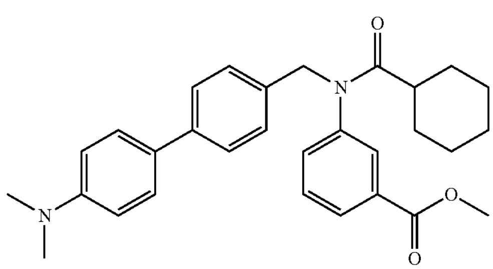 | Methyl 3-(N-((4'-(dimethylamino)-[1,1'-biphenyl]-4-yl)methyl)cyclohexanecarboxamido) benzoate | 471.3 |

Reductive amination conditions varied: 1.0-1.5 eq. aniline; 1.5-5 eq. sodium triacetoxyborohydride; DCM or DCE; 0.5-2 h. Acylation conditions varied: 1.3-2 eq. acid chloride; 2-4 eq. TEA or pyridine; acid chloride added at 0° C. or rt; 0.5-10 h. * Synthesized from Intermediate 2.1 by Boc removal (TFA/DCM).

Intermediate 3

N-(3-aminophenyl)-N-((4'-(dimethylamino)-[1,1'-biphenyl]-4-yl)methyl)cyclohexanecarboxamide

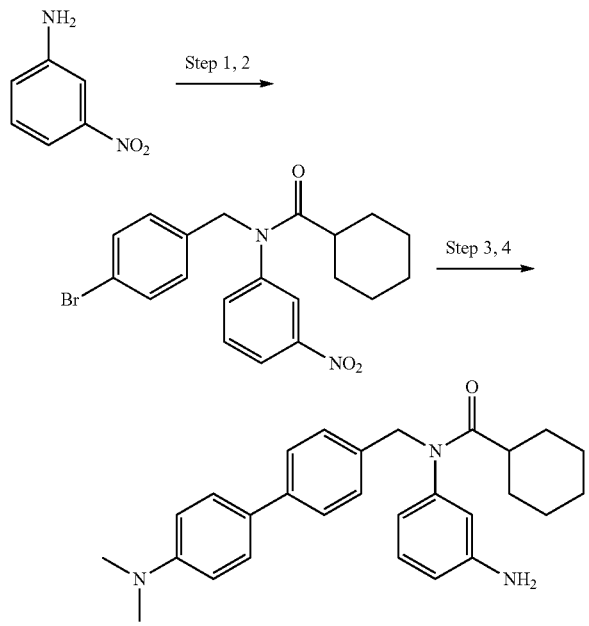

Step 1: N-(3-nitrophenyl)cyclohexanecarboxamide

Triethylamine (22 g, 217 mmol) was slowly added to a solution of 3-nitroaniline (15 g, 109 mmol) in acetonitrile (200 mL) at 0° C. After stirring the mixture for 30 min, cyclohexanecarbonyl chloride (23.9 g, 163 mmol) was added slowly. The resulting mixture was allowed to warm to 16° C. Water (300 mL) was added, and the mixture was extracted with ethyl acetate (2×300 mL). The combined organic layers were washed with brine (600 mL), dried over Na$_2$SO$_4$, filtrated, and concentrated. The residue was purified by column chromatography (SiO$_2$, petroleum ether/ethyl acetate; 50/1 to 5/1) to give N-(3-nitrophenyl)cyclohexanecarboxamide (15 g, 43%) as white solid. MS: 249.2 [M+H]$^+$.

Step 2: N-(4-Bromobenzyl)-N-(3-nitrophenyl)cyclohexanecarboxamide

The mixture of N-(3-nitrophenyl)cyclohexanecarboxamide (10 g, 40.3 mmol) and 1-bromo-4-(bromomethyl)benzene (10.1 g, 40.3 mmol), and Cs$_2$CO$_3$ (39.4 g, 121 mmol) in acetonitrile (100 mL) was heated at reflux (oil bath 90° C.) for 3 h. Water (300 mL) was added at 25° C., and the mixture was extracted with ethyl acetate (2×400 mL). The combined organic layers were dried over Na$_2$SO$_4$, filtered, and concentrated. The residue was purified by re-crystallization from petroleum ether (20 mL) to give N-(4-bromobenzyl)-N-(3-nitrophenyl)cyclohexanecarboxamide (8.0 g, 24%) as yellow solid. MS: 417.1 [M+H]$^+$.

Step 3: N-((4'-(Dimethylamino)-[1,1'-biphenyl]-4-yl)methyl)-N-(3-nitrophenyl)cyclohexanecarboxamide A mixture of (4-(dimethylamino)phenyl)boronic acid (3.56 g, 21.6 mmol), N-(4-bromobenzyl)-N-(3-nitrophenyl)cyclohexanecarboxamide (6.0 g, 14.4 mmol), Pd(PPh$_3$)$_4$ (2.5 g, 2.16 mmol), and Cs$_2$CO$_3$ (14.1 g, 43.1 mmol) in DMF (50 mL) was degassed with vacuum/nitrogen cycles (3×), stirred at 75° C. for 24 h, and then cooled to 15° C. Water (200 mL) and DCM (200 mL) were added, and the mixture was extracted with DCM (3×100 mL). The combined organic layers were washed with brine (2×500 mL), dried over Na$_2$SO$_4$, filtered and concentrated. The residue was purified by column chromatography (SiO$_2$, DCM/methanol; 10/1) to yield N-((4'-(dimethylamino)-[1,1'-biphenyl]-4-yl)methyl)-N-(3-nitrophenyl)cyclohexanecarboxamide (2.8 g, 40%) as a red solid. MS: 458.3 [M+H]$^+$ Step 4: N-(3-Aminophenyl)-N-((4'-(dimethylamino)-[1,1'-biphenyl]-4-yl)methyl)cyclohexane carboxamide Palladium on carbon (700 mg, 10%) was added to a solution of N-((4'-(dimethylamino)-[1,1'-biphenyl]-4-yl)methyl)-N-(3-nitrophenyl)cyclohexanecarboxamide (2.8 g, 6.12 mmol) in methanol (160 mL). The suspension was degassed and purged with H$_2$ (3×) and then stirred under H$_2$ (50 Psi) at 15° C. for 24 h. The reaction mixture was passed through a pad of Celite, and the filtrate was concentrated to give N-(3-aminophenyl)-N-((4'-(dimethylamino)-[1,1'-biphenyl]-4-yl)methyl)cyclohexanecarboxamide (2.5 g, 86%) as a yellow solid. $^1$H NMR (400 MHz, CDCl$_3$): δ 7.50 (dd, 4H), 7.19-7.28 (m, 2H), 7.11 (t, J=7.8 Hz, 1H), 6.75-6.86 (m, 2H), 6.57-6.66 (m, 1H), 6.42 (d, 1H), 6.33 (br s, 1H), 4.81-4.90 (m, 2H), 3.71 (br s, 2H), 3.01 (s, 6H), 2.21-2.38 (m, 1H), 1.54-1.76 (m, 7H), 1.14-1.30 (m, 1H), 0.94-1.11 (m, 2H); MS: 428.3 [M+H]$^+$.

Intermediate 4

(E)-Methyl 3-(3-nitrophenyl)acrylate

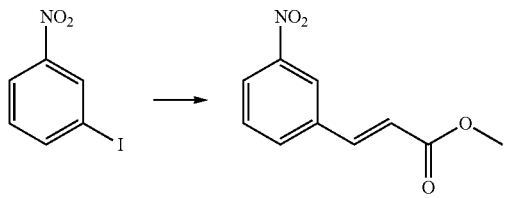

A mixture of 1-iodo-3-nitro-benzene (30 g, 120 mmol), methyl prop-2-enoate (43 mL, 482 mmol), Pd$_2$(dba)$_3$ (5.52 g, 6.02 mmol), P(o-tolyl)$_3$ (9.17 g, 30.1 mmol) and TEA (83 mL, 602 mmol) in DMF (300 mL) was degassed by vacuum/nitrogen cycles (3×) and stirred at 90° C. for 12 h. The reaction mixture was filtered, diluted with water (800 mL), and extracted with ethyl acetate (3×400 mL). The combined organic layers were washed with water (3×800 mL), dried over anhydrous Na$_2$SO$_4$, filtered, and concentrated. Methyl tert-butyl ether (50 mL) was added to the residue, and the mixture was stirred for 2 h. The resulting solid was filtered and dried in vacuo to give (E)-methyl 3-(3-nitrophenyl)acrylate (20 g, 74%) as a light yellow solid. $^1$H NMR (CDCl$_3$): δ 8.39 (s, 1H), 8.25 (dd, 1H), 7.84 (d, 1H), 7.74 (d, 1H), 7.61 (t, 1H), 6.58 (d, 1H), 3.85 (s, 3H); MS: 208.0 [M+H]$^+$.

Intermediate 5

(E)-1-(2-Bromovinyl)-3-nitrobenzene

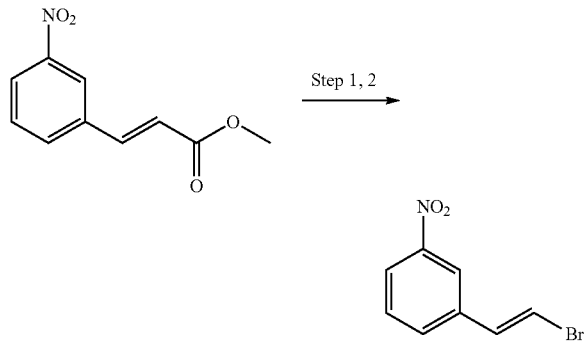

Step 1: (E)-3-(3-Nitrophenyl)acrylic acid

Lithium hydroxide monohydrate (2.73 g, 910 mmol) was added to a solution of Intermediate 4 (13.5 g, 65.2 mmol) in THF (200 mL) and water (200 mL). The mixture was stirred at 25° C. for 12 h, acidified with 1 N HCl to pH=1, and then extracted with ethyl acetate (3×100 mL). The combined organic layers were washed with water (100 mL), dried over $Na_2SO_4$, filtered, and concentrated to give (E)-3-(3-nitrophenyl)acrylic acid (12 g, crude) as a white solid. MS: 192.1 [M–H]$^-$.

Step 2: (E)-1-(2-Bromovinyl)-3-nitrobenzene (E)-3-(3-Nitrophenyl)acrylic acid (12.0 g, 62.1 mmol) was added to a solution of diacetoxyiodobenzene (29 mL, 93.2 mmol) and tetraethylammonium bromide (17.5 mL, 93.2 mmol) in DCM (240 mL). The reaction mixture was stirred at 25° C. for 16 h. Water (100 mL) was added, and the mixture was extracted with DCM (2×200 mL). The combined organic layers were dried over $Na_2SO_4$, filtered, and concentrated. The residue was purified by MPLC (petroleum ether/ethyl acetate; 50/1 to 10/1) to give (E)-1-(2-bromovinyl)-3-nitrobenzene (2.6 g, 17%) as a yellow oil. $^1$H NMR (CDCl$_3$): δ 8.15-8.19 (m, 2H), 7.62-7.64 (m, 1H), 7.52-7.56 (m, 1H), 7.17-7.21 (d, 1H), 7.02-6.98 (d, 1H).

Intermediate 6

(E)-3-(2-(Oxazol-2-yl)vinyl)aniline

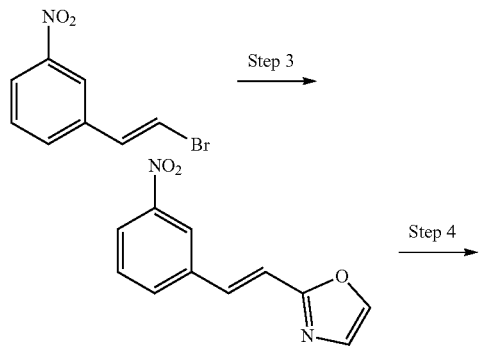

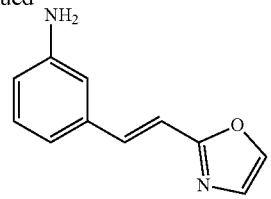

Step 1: (E)-2-(3-Nitrostyryl)oxazole

Lithium tert-butoxide (2.29 g, 28.5 mmol), CuI (434 mg, 2.28 mmol), phenanthroline (616 mg, 3.42 mmol) and Pd(OAc)$_2$ (512 mg, 2.28 mmol) were added to a solution Intermediate 5 (2.6 g, 11.4 mmol) and oxazole (3.54 g, 51.3 mmol) in dioxane (50 mL). The mixture was stirred at 120° C. for 12 h, recharged with more oxazole (3.54 g, 51.3 mmol), and stirred at 120° C. for additional 12 h. Water (50 mL) and ethyl acetate (100 mL) were added, and the reaction mixture was filtered. The layers was separated, and the aqueous layer was extracted with ethyl acetate (100 mL). The combined organic layers were dried over $Na_2SO_4$, filtered and, concentrated. The residue was purified by column chromatography (petroleum ether/ethyl acetate; 10/1) to give (E)-2-(3-nitrostyryl)oxazole (1.3 g, 24%) as a yellow oil. $^1$H NMR (CDCl$_3$): δ 8.30 (s, 1H), 8.10-8.12 (d, 1H), 7.75-7.78 (m, 1H), 7.61 (s, 1H), 7.46-7.54 (m, 2H), 7.17-7.19 (m, 1H), 7.00-7.04 (d, 1H); MS: 217.1 [M+H]$^+$.

Step 2: (E)-3-(2-(Oxazol-2-yl)vinyl)aniline

Ammonium chloride (1.48 g, 27.8 mmol) and Fe (1.55 g, 27.8 mmol) were added to a solution of (E)-2-(3-nitrostyryl)oxazole (1.20 g, 5.55 mmol) in ethanol (200 mL) and water (50 mL). The mixture was heated at 90° C. for 12 h, filtered, and concentrated to give (E)-3-(2-(oxazol-2-yl)vinyl)aniline (1.0 g, crude) as yellow oil.

Intermediate 7

(E)-N-(4-Bromobenzyl)-N-(3-(prop-1-en-1-yl)phenyl)cyclohexanecarboxamide

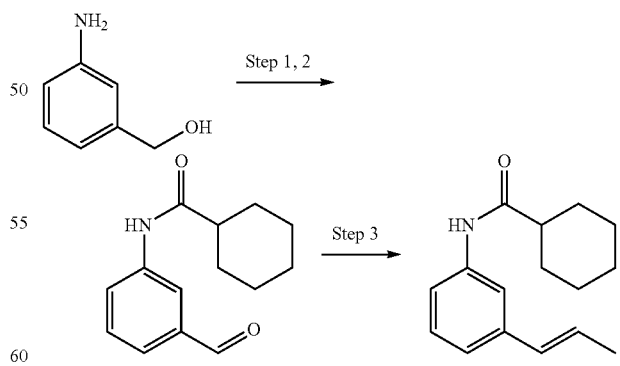

Step 1: N-(3-(Hydroxymethyl)phenyl)cyclohexanecarboxamide

HATU (3.09 g, 8.12 mmol) was added to a mixture of (3-aminophenyl)methanol (1.0 g, 8.12 mmol), cyclohexanecarboxylic acid (1.14 g, 8.93 mmol), and TEA (1.64 g, 16.2 mmol) in DMF (10 mL) at 25° C. The reaction mixture was stirred for 10 h, diluted with water (30 mL) and then extracted with ethyl acetate (3×20 mL). The combined organic layers were dried over Na$_2$SO$_4$, filtered and concentrated. The residue was purified by column chromatography (SiO$_2$, petroleum ether/ethyl acetate; 5/1 to 1/1) to give N-(3-(hydroxymethyl)phenyl)cyclohexanecarboxamide (1.5 g, 71%) as a white solid.

Step 2:
N-(3-Formylphenyl)cyclohexanecarboxamide

Manganese (IV) oxide (9.32 g, 107.15 mmol) was added to a solution of N-(3-(hydroxymethyl)phenyl)cyclohexanecarboxamide (2.5 g, 10.7 mmol) in THF (15 mL) and DCM (15 mL). The mixture was stirred at 80° C. for 12 h, filtered, and concentrated to give N-(3-formylphenyl)cyclohexanecarboxamide (1.5 g, crude) as a yellow solid. MS: 232.1 [M+H]$^+$.

Step 3: (E)-N-(4-Bromobenzyl)-N-(3-(prop-1-en-1-yl)phenyl)cyclohexanecarboxamide Potassium tert-butoxide (1.82 g, 16.2 mmol) was added in portions to a solution of (methyltriphenylphosphoranyl)methylium bromide (6.02 g, 16.2 mmol) in THF (20 mL) at 25° C. After stirring the mixture for 30 min, N-(3-formylphenyl)cyclohexanecarboxamide (1.5 g, crude) was added in portions. The resulting mixture was stirred for 12 h, filtered, and concentrated. The residue was purified by column chromatography (SiO$_2$, petroleum ether/ethyl acetate; 15/1) to give (E)-N-(3-(prop-1-en-1-yl)phenyl)cyclohexanecarboxamide (1.5 g, 92%) as a colorless oil. MS: 244.2 [M+H]$^+$.

Intermediate 8

(E)-3-(3-(N-((4'-(dimethylamino)-[1,1'-biphenyl]-4-yl)methyl)cyclohexane carboxamido)phenyl)acrylic Acid

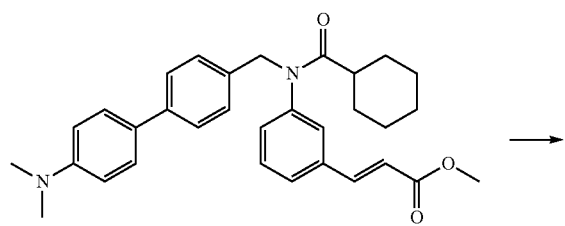

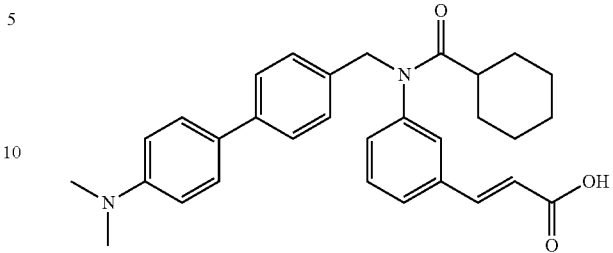

Aqueous sodium hydroxide (1N, 23 mL, 23 mmol) was added to a mixture of (E)-methyl 3-(3-(N-((4'-(dimethylamino)-[1,1'-biphenyl]-4-yl)methyl)cyclohexanecarboxamido)phenyl)acrylate (2.31 g, 4.64 mmol), THF (46 mL), and methanol (23 mL) at room temperature. The reaction mixture was stirred for 2 h, concentrated, and diluted with water (100 mL). The mixture was acidified (1N HCl, pH=4), stirred for 15 min, and filtered. The filter cake was washed (50 mL water) and dried to give (E)-3-(3-(N-((4'-(dimethylamino)-[1,1'-biphenyl]-4-yl)methyl)cyclohexane carboxamido)phenyl)acrylic acid (2.22 g, 99%) as a yellow solid. $^1$H NMR (400 MHz, DMSO-d$_6$): δ 12.46 (br, 1H), 7.65 (d, 1H), 7.61-7.59 (m, 1H), 7.56 (d, 1H), 7.52-7.45 (m, 4H), 7.40 (t, 1H), 7.19-7.00 (m, 3H), 6.78 (d, 2H), 6.54 (d, 1H), 4.85 (s, 2H), 2.92 (s, 6H), 2.22-2.10 (m, 1H), 1.75-1.55 (m, 4H), 1.54-1.47 (m, 1H), 1.46-1.30 (m, 2H), 1.26-1.11 (m, 1H), 0.95-0.80 (m, 2H); LCMS: 483.7 [M+H]$^+$.

The Intermediate below was synthesized from Intermediate 2.8 following the procedure described for Intermediate 8.

| Int | structure | Name | [M + H]$^+$ |
|---|---|---|---|
| 8.1 | 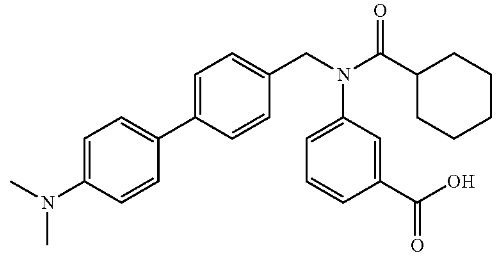 [SMILES: CN(C)c1ccc(-c2ccc(CN(C(=O)C3CCCCC3)c3cccc(C(=O)O)c3)cc2)cc1] | 3-(N-((4'-(Dimethylamino)-[1,1'-biphenyl]-4-yl)methyl)cyclohexanecarboxamido)benzoic Acid | 457.5 |

Intermediate 9

N-((4'-(Dimethylamino)-[1,1'-biphenyl]-4-yl)methyl)-N-(3-(4,4,5,5-tetramethyl-1,3,2-dioxaborolan-2-yl)phenyl)cyclohexanecarboxamide

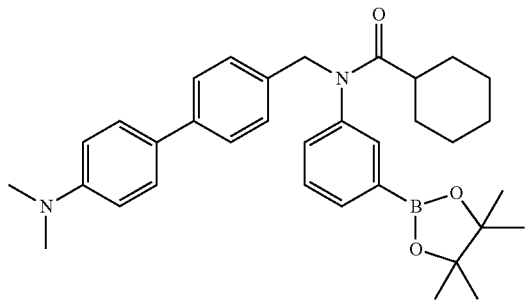

To a solution of Intermediate 2 (7.00 g, 14.24 mmol) and 4,4,4',4',5,5,5',5'-octamethyl-2,2'-bi(1,3,2-dioxaborolane) (7.23 g, 28.48 mmol) in dioxane (200 mL) under $N_2$ was added AcOK (3.48 g, 35.46 mmol) and Pd(dppf)$Cl_2$ (1.04 g, 1.42 mmol). The reaction was heated to 80° C. overnight, filtered and concentrated. The residue was dissolved in EtOAc (300 mL) and washed with water (100 mL×2). The organic layer was dried over $Na_2SO_4$, filtered, concentrated, and then purified by chromatography on silica gel (petroleum ether/EtOAc=20/1) to give N-((4'-(dimethylamino)-[1,1'-biphenyl]-4-yl)methyl)-N-(3-(4,4,5,5-tetramethyl-1,3,2-dioxaborolan-2-yl)phenyl)cyclohexanecarboxamide (5.21 g, 8.44 mmol, 59.30% yield, 87.28% purity) as yellow solid. $^1$H NMR (400 MHz, CDCl$_3$): δ 7.66 (d, 1H), 7.51-7.29 (m, 5H), 7.25-7.19 (m, 1H), 7.11 (d, 2H), 6.90 (d, 1H), 6.71 (d, 2H), 4.80 (br s, 2H), 2.91 (s, 6H), 2.12-2.00 (m, 1H), 1.69-1.42 (m, 7H), 1.27 (s, 12H), 1.17-1.03 (m, 1H), 0.97-0.85 (m, 2H); MS: 539.5 [M+H]$^+$.

Intermediate 10

Methyl 3-(3-aminophenyl)cyclobutanecarboxylate

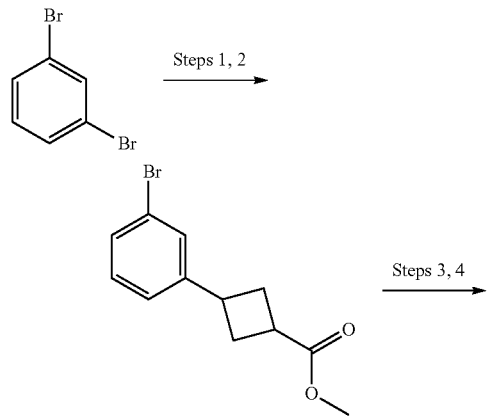

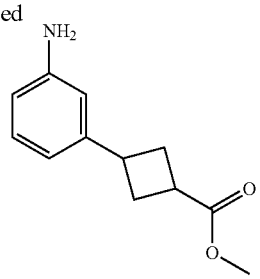

Step 1: Methyl 3-(3-bromophenyl)-3-hydroxycyclobutanecarboxylate

To a solution of 1,3-dibromobenzene (30.06 g, 127.17 mmol) in THF (300 mL) at −78° C., n-BuLi (2.5 M, 50 mL, 127.17 mmol) was added slowly. The reaction was stirred at −78° C. for 1 h and then added dropwise to a solution of methyl 3-oxocyclobutanecarboxylate (15.82 g, 123.47 mmol) in THF (300 mL) at −78° C. The mixture was stirred at −78° C. for 2 h, added to sat. aq. NH$_4$Cl (500 mL), and then concentrated. The remaining aqueous was extracted with EtOAc (1000 mL×2). The organic layer was dried over Na$_2$SO$_4$, filtered, and concentrated. The residue was purified by column chromatography on silica gel (Petroleum ether/Ethyl acetate; 10:1) to give methyl 3-(3-bromophenyl)-3-hydroxycyclobutanecarboxylate (15.20 g, 47.98 mmol, 38.86% yield, 90% purity) as yellow oil. $^1$H NMR (400 MHz, CDCl$_3$): δ 7.68 (s, 1H), 7.52-7.39 (m, 2H), 7.30-7.24 (m, 1H), 3.78 (s, 3H), 3.26 (br s, 1H), 2.98-2.81 (m, 3H), 2.72-2.56 (m, 2H); MS: 267.1 [M−OH]$^+$.

Step 2: Methyl 3-(3-bromophenyl)cyclobutanecarboxylate

To a solution of methyl 3-(3-bromophenyl)-3-hydroxycyclobutanecarboxylate (10.05 g, 35.25 mmol) in TFA (300 mL) at 0° C. was added Et$_3$SiH (20.44 g, 175.78 mmol). The reaction was stirred at 0° C. for 0.5 h, warmed to rt, and stirred for an additional 2.5 h. The mixture was concentrated, dissolved in EtOAc (1000 mL), and then washed with sat. aq. NaHCO$_3$ (200 mL×2). The organic layer was dried over Na$_2$SO$_4$, filtered, and concentrated. The residue was purified by column chromatography on silica gel (Petroleum ether/Ethyl acetate; 100:1) to give methyl 3-(3-bromophenyl)cyclobutanecarboxylate (5.08 g, 18.87 mmol, 71.5% yield) as yellow oil. $^1$H NMR (400 MHz, CDCl$_3$; cis & trans mixture): δ 7.40-7.30 (m, 2H), 7.23-7.09 (m, 2H), 3.75 (s, 1H), 3.70 (s, 2H), 3.44-3.35 (m, 1H), 3.20-3.04 (m, 1H), 2.74-2.54 (m, 2H), 2.46-2.34 (m, 2H); MS: 269.1 [M+H]$^+$.

Step 3: Methyl 3-(3-((diphenylmethylene)amino)phenyl)cyclobutanecarboxylate

To a solution of methyl 3-(3-bromophenyl)cyclobutanecarboxylate (2.66 g, 9.88 mmol) and diphenylmethanimine (2.15 g, 11.86 mmol) in toluene (120 mL) at rt was added BINAP (1.19 g, 1.91 mmol), Cs$_2$CO$_3$ (8.07 g, 24.77 mmol) and Pd$_2$(dba)$_3$ (905.7 mg, 989.06 umol). The reaction was stirred at 100° C. overnight under N$_2$, filtered, and concentrated to give methyl 3-(3-((diphenylmethylene)amino)phenyl)cyclobutanecarboxylate (5.22 g, crude) as yellow oil. MS: 370.1 [M+H]$^+$.

Step 4: Methyl 3-(3-aminophenyl)cyclobutanecarboxylate

To a solution of methyl 3-(3-((diphenylmethylene)amino) phenyl)cyclobutanecarboxylate (7.13 g, 19.30 mmol) in THF (400 mL) at rt was added TFA (110.88 g, 972.46 mmol). The reaction was stirred at rt overnight, concentrated, dissolved in EtOAc (1000 mL), and then washed with sat. aq. NaHCO₃ (300 mL×2). The organic layer was dried over Na₂SO₄, filtered, and concentrated. The residue was purified by column chromatography on silica gel (Petroleum ether/Ethyl acetate; 5:1) to give methyl 3-(3-aminophenyl) cyclobutanecarboxylate (2.26 g, 10.22 mmol, 52.95% yield, 92.84% purity) as yellow oil. ¹H NMR (400 MHz, CDCl₃, cis & trans mixture): δ 7.16-7.05 (m, 1H), 6.69-6.47 (m, 3H), 3.74 (s, 1H), 3.69 (s, 2H), 3.64 (br s, 2H), 3.43-3.28 (m, 1H), 3.17-3.01 (m, 1H), 2.66-2.52 (m, 2H), 2.45-2.36 (m, 2H); MS: 206.1 [M+H]⁺.

Intermediate 11

(Isobutylsulfonyl)benzene

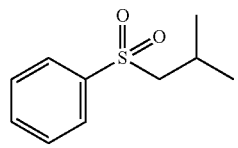

A stirred mixture of benzenesulfonyl chloride (1.62 g, 9.17 mmol), NaHCO₃ (1.53 g, 18.16 mmol) and Na₂SO₃ (2.34 g, 18.53 mmol) in water (7 mL) was heated to 95-100° C. for 1 h under nitrogen. The reaction was cooled to 50° C., and n-Bu₄NBr (105.2 mg, 326.33 umol) and 1-bromo-2-methyl-propane (1.41 g, 10.29 mmol) were added. The reaction was heated at 70° C. overnight, cooled, treated with water (10 mL), and then extracted with DCM (15 mL×3). The combined organic layers were dried with MgSO₄, filtered, concentrated, and then purified by chromatography on silica gel (Petroleum ether/Ethyl acetate; 3:1) to give (isobutylsulfonyl)benzene (389.6 mg, 1.96 mmol, 21.43% yield) as colorless oil. ¹H NMR (400 MHz, CDCl₃): δ 7.91 (d, 2H), 7.67-7.61 (m, 1H), 7.59-7.52 (m, 2H), 2.98 (d, 2H), 2.29-2.14 (m, 1H), 1.05 (d, 6H); MS: 199.2 [M+H]⁺.

Intermediate 12

5-Chloro-3-(methoxymethoxy)isothiazole

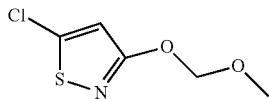

To a solution of 5-chloroisothiazol-3-ol (4.03 g, 29.73 mmol) and DBU (7.07 g, 46.44 mmol) in THF (80 mL) at 0° C., a solution of chloro(methoxy)methane (5.74 g, 71.3 mmol) in THF (40 mL) was added dropwise. The mixture was warmed to rt and stirred for 16 h. EtOAc (300 mL) was added, and the solution was washed with water (100 mL). The organic layer was dried over Na₂SO₄, filtered, concentrated, and purified by chromatography on silica gel (petroleum ether/EtOAc=100/1) to give 5-chloro-3-(methoxymethoxy)isothiazole (701.5 mg, 3.91 mmol, 52.92% yield) as yellow oil. ¹H NMR (400 MHz, CDCl₃): δ 6.59 (s, 1H), 5.43 (s, 2H), 3.52 (s, 3H); MS: 180.1 [M+H]⁺.

Intermediate 13 trans-4-(4-Methoxy-3-methylphenyl)cyclohexanecarbaldehyde

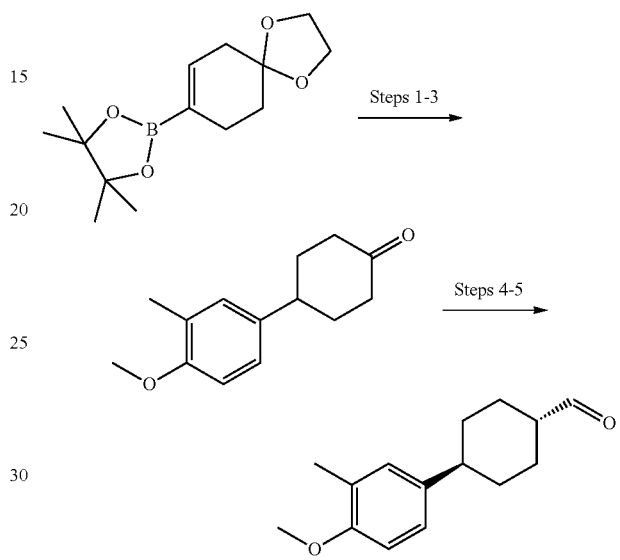

Step 1: 8-(4-methoxy-3-methylphenyl)-1,4-dioxaspiro[4.5]dec-7-ene

A mixture of 1,4-dioxa-spiro[4,5]dec-7-en-8-boronic acid pinacol ester (25.0 g, 93.9 mmol), 4-iodo-2-methylanisole (28.0 g, 113 mmol), 1,1'-bis(diphenylphosphino)ferrocene dichloropalladium(II) (1.38 g, 1.89 mmol), dioxane (470 mL) and 1M Na₂CO₃ (282 mL, 282 mmol) was degassed with 3 vacuum/N₂ cycles, stirred at 50° C. for 2.5 h, and then allowed to cool to it. The mixture was diluted with ethyl acetate (500 mL) and washed with saturated NaHCO₃ (500 mL×2). The aqueous layers were back extracted with ethyl acetate (200 mL). The combined ethyl acetate extracts were dried (Na₂SO₄), filtered, concentrated and purified by silica gel chromatography (0-5% ethyl acetate in hexanes) to give 8-(4-methoxy-3-methylphenyl)-1,4-dioxaspiro[4.5]dec-7-ene (19.9 g, 81%). ¹H NMR (400 MHz, DMSO-d₆): δ 7.21-7.16 (m, 2H), 6.85 (d, 1H), 5.89-5.84 (m, 1H), 3.90 (s, 4H), 3.76 (s, 3H), 2.52-2.47 (m, 2H), 2.32 (br s, 2H), 2.13 (s, 3H), 1.77 (t, 2H); MS: 261.1 [M+H]⁺.

Step 2: 8-(4-Methoxy-3-methylphenyl)-1,4-dioxaspiro[4.5]decane

Palladium on carbon (10 wt %, 8.08 g, 7.59 mmol) was added to a solution of 8-(4-methoxy-3-methylphenyl)-1,4-dioxaspiro[4.5]dec-7-ene (19.8 g, 76.1 mmol) in ethyl acetate (300 mL) at rt under N₂. The N₂ inlet was replaced with a balloon of H₂. The reaction was stirred for 4.5 h, filtered through Celite with ethyl acetate, and then concentrated to give 8-(4-methoxy-3-methylphenyl)-1,4-dioxaspiro[4.5]decane (18.2 g; contains 13% ketone) as a white solid. $^1$H NMR (400 MHz, DMSO-d$_6$): δ 7.00-6.95 (m, 2H), 6.81 (d, 1H), 3.91-3.84 (m, 4H), 3.73 (s, 3H), 2.49-2.42 (m, 1H), 2.11 (s, 3H), 1.76-1.68 (m, 4H), 1.67-1.55 (m, 4H); MS: 263.1 [M+H]$^+$.

Step 3: 4-(4-Methoxy-3-methylphenyl)cyclohexanone

Formic acid (96%, 14 mL, 356 mmol) and then water (2.20 mL, 122 mmol) were added to a solution of 8-(4-methoxy-3-methylphenyl)-1,4-dioxaspiro[4.5]decane (18.2 g) in toluene (60 mL) at rt under N$_2$. The reaction was heated at 120° C. for 4 hours, allowed to cool to rt, and then poured into 200 mL H$_2$O and 200 mL toluene. The toluene layer was washed with 200 mL H$_2$O and then 200 mL saturated NaHCO$_3$. The aqueous layers were back extracted with 100 mL toluene. The combined toluene extracts were dried (Na$_2$SO$_4$), filtered and concentrated to give 4-(4-methoxy-3-methylphenyl)cyclohexanone (15.5 g, 88% over 2 steps) as a white solid. $^1$H NMR (400 MHz, DMSO-d$_6$): δ 7.08-7.03 (m, 2H), 6.84 (d, 1H), 3.74 (s, 3H), 3.00-2.91 (m, 1H), 2.61-2.51 (m, 2H), 2.28-2.20 (m, 2H), 2.12 (s, 3H), 2.06-1.98 (m, 2H), 1.88-1.76 (m, 2H); MS: 219.0 [M+H]$^+$.

Step 4: 1-Methoxy-4-(4-(methoxymethylene)cyclohexyl)-2-methylbenzene

A mixture of (methoxymethyl)triphenyl phosphonium chloride (35.74 g, 104.3 mmol) and THF (260 mL) under N$_2$ was cooled to −2.2° C. in an ice/brine bath. Sodium bis(trimethylsilyl)amide solution (2M in THF, 50 mL, 100 mmol) was added dropwise via addition funnel over 12 min (internal temp ≤0.6° C.) with THF rinsing (5 mL). The reaction was stirred for 30 min, and then 4-(4-methoxy-3-methylphenyl)cyclohexanone (14.5 g, 66.6 mmol) was added portionwise over 5 min (exotherm to 7.3° C.). Residual cyclohexanone was rinsed into the reaction with THF (20 mL). The reaction was stirred at 0° C. for 25 min, and then poured into 400 mL H$_2$O and 400 mL toluene. The toluene layer was washed with 400 mL H$_2$O, dried (Na$_2$SO$_4$), filtered, concentrated and purified by silica gel chromatography (0-5% ethyl acetate in hexanes) to give 1-methoxy-4-(4-(methoxymethylene)cyclohexyl)-2-methylbenzene (15.6 g, 95%) as a pale gold oil. $^1$H NMR (400 MHz, DMSO-d$_6$): δ 6.99-6.94 (m, 2H), 6.80 (d, 1H), 5.87 (s, 1H), 3.73 (s, 3H), 3.48 (s, 3H), 2.78-2.71 (m, 1H), 2.56-2.44 (m, 1H), 2.10 (s, 3H), 2.17-2.09 (m, 1H), 2.01-1.91 (m, 1H), 1.83-1.73 (m, 2H), 1.72-1.63 (m, 1H), 1.38-1.23 (m, 2H); MS: 247.1 [M+H]$^+$.

Step 5: trans-4-(4-Methoxy-3-methylphenyl)cyclohexanecarbaldehyde

Formic acid (96%, 12.5 mL, 331 mmol) and then water (2.5 mL, 139 mmol) were added to a solution of 1-methoxy-4-(4-(methoxymethylene)cyclohexyl)-2-methylbenzene (16.05 g, 65.15 mmol) in toluene (130 mL) under N$_2$. The reaction was heated at 120° C. for 2 hours, allowed to cool to rt, and then poured into 350 mL ethyl acetate and 350 mL H$_2$O. The organic layer was washed with 350 mL H$_2$O, dried (Na$_2$SO$_4$), filtered and concentrated to give 4-(4-methoxy-3-methylphenyl)cyclohexanecarbaldehyde (15.05 g) as a 1:1 mixture of stereoisomers. Aqueous sodium hydroxide (3.2 M, 31 mL, 99 mmol) was added to a solution of this mixture (14.68 g, 63.19 mmol), toluene (60 mL) and ethanol (250 mL) at rt. The reaction was stirred for 5.5 hours (equilibration monitored by NMR) and then poured into 350 mL H$_2$O and 350 mL ethyl acetate. The organic layer was washed with 350 mL H$_2$O, and the aqueous layers were back extracted with 150 mL ethyl acetate. The combined extracts were dried (Na$_2$SO$_4$), filtered, concentrated and purified by silica gel chromatography (0-5% ethyl acetate in hexanes) to give trans-4-(4-methoxy-3-methylphenyl)cyclohexanecarbaldehyde (10.17 g, 69%) as a white solid. $^1$H NMR (400 MHz, DMSO-d$_6$): δ 9.60 (s, 1H), 7.01-6.97 (m, 2H), 6.82 (d, 1H), 3.74 (s, 3H), 2.41-2.27 (m, 2H), 2.12 (s, 3H), 2.03-1.96 (m, 2H), 1.87-1.80 (m, 2H), 1.51-1.39 (m, 2H), 1.35-1.23 (m, 2H); MS: 233.0 [M+H]$^+$.

Intermediate 14 trans-4-((tert-Butyldimethylsilyl)oxy)cyclohexanecarbonyl chloride

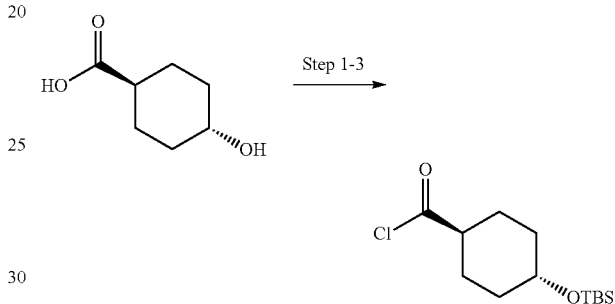

Step 1: trans-tert-Butyldimethylsilyl 4-((tert-butyldimethylsilyl)oxy)cyclohexanecarboxylate tert-Butyldimethylsilyl chloride (31.47 g, 208.8 mmol) was added to a mixture of trans-4-hydroxy-cyclohexanecarboxylic acid (10.03 g, 69.57 mmol), imidazole (18.96 g, 278.5 mmol), and DMF (140 mL) at rt under N$_2$ (reaction exothermed to 32° C.). The reaction was stirred at rt for 2 hours and then diluted with 300 mL diethyl ether. The organic layer was washed with 1 N HCl (2×300 mL), washed with 300 mL brine, dried (Na$_2$SO$_4$), filtered and concentrated to give trans-tert-butyldimethylsilyl 4-((tert-butyldimethylsilyl)oxy)cyclohexanecarboxylate (31.5 g) as a clear oil. $^1$H NMR (400 MHz, DMSO-d$_6$): δ 3.61-3.53 (m, 1H), 2.26-2.18 (m, 1H), 2.04-1.96 (m, 2H), 1.92-1.85 (m, 2H), 1.51-1.39 (m, 2H), 1.39-1.27 (m, 2H), 0.94 (s, 9H), 0.89 (s, 9H), 0.26 (s, 6H), 0.06 (s, 6H).

Step 2: trans-4-((tert-Butyldimethylsilyl)oxy)cyclohexanecarboxylic Acid

Potassium carbonate (58.01 g, 419.7 mmol) in water (300 mL) was added to a mixture of trans-tert-butyldimethyl silyl 4-((tert-butyldimethylsilyl)oxy)cyclohexanecarboxylate (31.5 g crude, 69.6 mmol), ethanol (1000 mL) and THF (300 mL) at rt under N$_2$. The reaction was stirred at rt for 3 hours, concentrated until 300 mL remained, diluted with 600 mL brine, and then acidified to pH 2-3 with 20% NaHSO$_4$ (550 mL). The aqueous layer was extracted with 800 mL diethyl ether. The organic layer was washed with 800 mL brine, dried (Na$_2$SO$_4$), filtered and concentrated to give trans-4-((tert-butyldimethylsilyl)oxy)cyclohexanecarboxylic acid (17.3 g, 96% over 2 steps) as a white solid. $^1$H NMR (400 MHz, DMSO-d$_6$): δ 12.30 (br s, 1H), 3.59-3.51 (m, 1H), 2.15-2.05 (m, 1H), 1.88-1.74 (m, 4H), 1.41-1.29 (m, 2H), 1.28-1.16 (m, 2H), 0.84 (s, 9H), 0.02 (s, 6H).

Step 3: trans-4-((tert-Butyldimethylsilyl)oxy)cyclohexanecarbonyl Chloride

Potassium carbonate (17.69 g, 128 mmol) in a round bottom flask under high vacuum was heated via heat gun for 5 min and then allowed to cool to rt. (Chloromethylene)dimethyl iminium chloride (6.47 g, 50.5 mmol) was added, the reaction was placed under $N_2$, and then toluene (100 mL) was added. After stirring for 10 min, trans-4-((tert-butyldimethylsilyl)oxy)cyclohexanecarboxylic acid (6.51 g, 25.2 mmol) was added. The reaction was stirred for 30 min, Celite was added to the reaction, and then the reaction was filtered through Celite with toluene washing (3×25 mL). The filtrate was partially concentrated to give a solution of trans-4-((tert-butyldimethylsilyl)oxy)cyclohexanecarbonyl chloride in toluene (18.55 g, 32.8 wt %). This solution was used immediately. $^1$H NMR (400 MHz, DMSO-$d_6$): δ 3.66-3.58 (m, 1H), 2.76-2.67 (m, 1H), 2.23-2.14 (m, 2H), 1.98-1.89 (m, 2H), 1.67-1.56 (m, 2H), 1.44-1.32 (m, 2H), 0.91 (s, 9H), 0.08 (s, 6H).

Compound 1

N-((4'-(Dimethylamino)-[1,1'-biphenyl]-4-yl)methyl)-N-(3-(5-methoxypyridin-3-yl)phenyl)cyclohexanecarboxamide

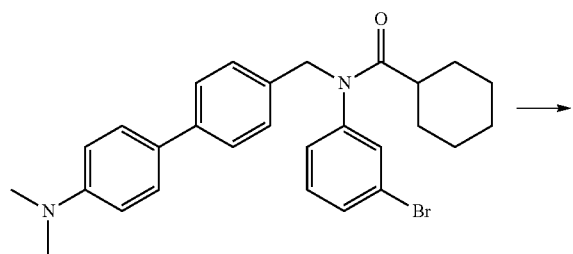

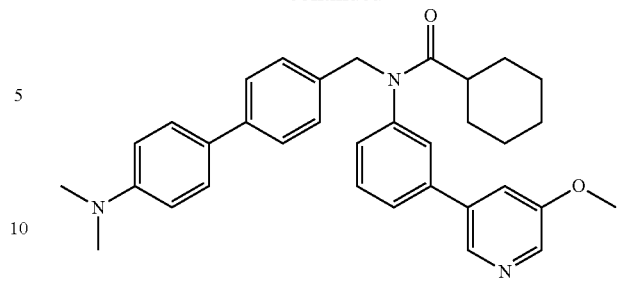

A mixture of Intermediate 2 (100 mg, 0.20 mmol), (5-methoxypyridin-3-yl)boronic acid (50 mg, 0.33 mmol), cesium carbonate (199 mg, 0.61 mmol), [1,1'-bis(diphenylphosphino)ferrocene]dichloropalladium(II) (16 mg, 0.022 mmol), and DMF (2 mL) was degassed by bubbling nitrogen for 10 min. The reaction mixture was heated at 80° C. overnight, cooled to room temperature, and diluted with ethyl acetate (50 mL). The organic phase was washed (50 mL saturated $NaHCO_3$), dried ($Na_2SO_4$), and concentrated. The residue was purified by silica gel chromatography to give N-((4'-(dimethylamino)-[1,1'-biphenyl]-4-yl)methyl)-N-(3-(5-methoxypyridin-3-yl)phenyl)cyclohexanecarboxamide (45 mg, 43%) as a white solid. $^1$H NMR (400 MHz, DMSO-$d_6$): δ 8.41 (d, 1H), 8.27 (d, 1H), 7.72 (d, 1H), 7.57 (t, 1H), 7.54-7.49 (m, 5H), 7.48 (d, 1H), 7.23-7.16 (m, 3H), 6.77 (d, 2H), 4.91 (s, 2H), 3.85 (s, 3H), 2.92 (s, 6H), 2.30-2.18 (m, 1H), 1.78-1.57 (m, 4H), 1.55-1.50 (m, 1H), 1.50-1.38 (m, 2H), 1.18-1.05 (m, 1H), 0.95-0.80 (m, 2H); LCMS: 520.8 [M+H]$^+$.

The Compounds below were synthesized from appropriate starting materials following the procedure described for Compound 1.

| Cmpd | Structure | Name | [M + H]$^+$ |
| --- | --- | --- | --- |
| 2 | 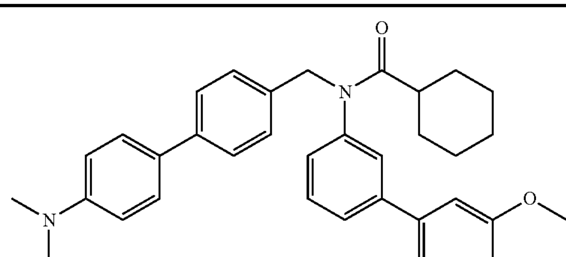 | N-((4'-(Dimethylamino-[1,1'-biphenyl]-4-yl)methyl)-N-(3'-methoxy-[1,1'-biphenyl]-3-yl)cyclohexanecarboxamide | 519.3 |
| 3 | 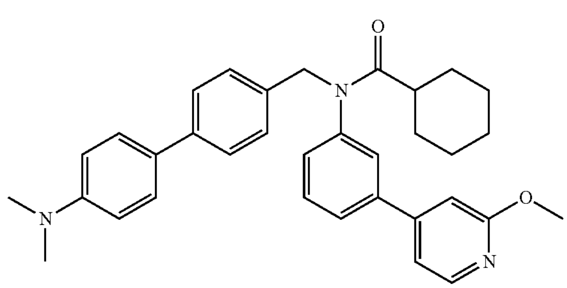 | N-((4'-(Dimethylamino)-[1,1'-biphenyl]-4-yl)methyl)-N-(3-(2-methoxypyridin-4-yl)phenyl)cyclohexanecarboxamide | 520.2 |

| Cmpd | Structure | Name | [M + H]+ |
|---|---|---|---|
| 3.1 | 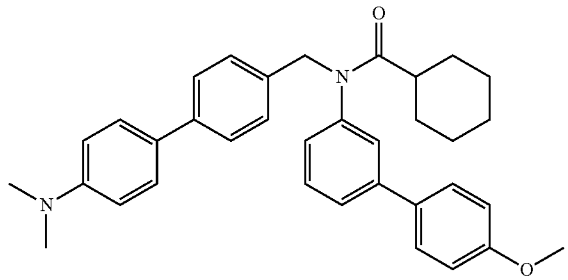 | N-((4'-(Dimethylamino)-[1,1'-biphenyl]-4-yl)methyl)-N-(4'-methoxy-[1,1'-biphenyl]-3-yl)cyclohexanecarboxamide | 519.4 |

Reaction conditions varied: 1.5-2 eq boronic acid; 3-4 eq Cs$_2$CO$_3$; 0.03-0.01M DMF; 70-80 OC.

Compound 4

N-((4'-(dimethylamino)-[1,1'-biphenyl]-4-yl) methyl)-N-(3-((2-methoxyethyl)amino)phenyl)cyclohexanecarboxamide

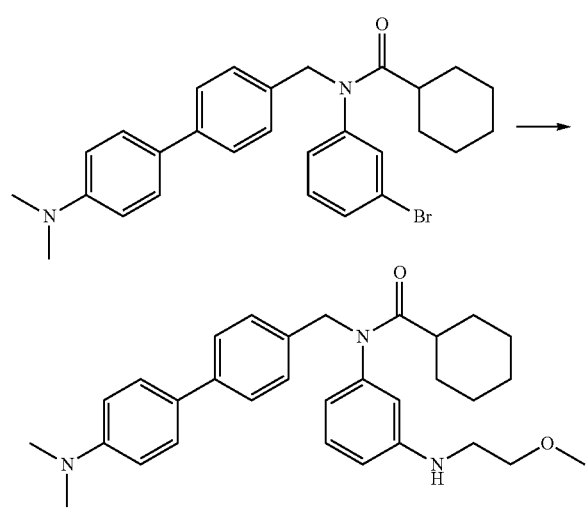

A mixture of Intermediate 2 (101 mg, 0.21 mmol), K$_3$PO$_4$ (87 mg, 0.41 mmol), Pd(OAc)$_2$ (10 mg, 0.045 mmol), Trixiephos (34 mg, 0.085 mmol) and toluene (2 mL) was degassed with three vacuum/N$_2$ cycles. 2-Methoxyethylamine (35 µL, 0.40 mmol) was added, and the reaction was stirred at 100° C. for 18 hours. The reaction was allowed to cool to room temperature, diluted with ethyl acetate (20 mL) and water (20 mL). The aqueous layer was back extracted with additional ethyl acetate (20 mL). The combined organics were washed with water (30 mL), washed with brine (30 mL), dried (Na$_2$SO$_4$), filtered, concentrated and purified by silica gel chromatography (10-40% ethyl acetate in hexanes). The compound was re-purified by reverse-phase HPLC (30-51% acetonitrile/water w/0.1% TFA). The fractions were concentrated to dryness, diluted with ethyl acetate (20 mL), and then washed with saturated NaHCO$_3$ (2×20 mL), washed with brine (20 mL), dried (Na$_2$SO$_4$), filtered and concentrated to give N-((4'-(dimethylamino)-[1,1'-biphenyl]-4-yl)methyl)-N-(3-((2-methoxyethyl)amino) phenyl)cyclohexanecarboxamide (38 mg, 37%) as a white solid. $^1$H NMR (400 MHz, DMSO-d$_6$): δ 7.53-7.46 (m, 4H), 7.17 (d, 2H), 7.05 (t, 1H), 6.78 (d, 2H), 6.53 (d, 1H), 6.31 (s, 1H), 6.27 (d, 1H), 5.82 (t, 1H), 4.76 (s, 2H), 3.38 (t, 2H), 3.21 (s, 3H), 3.12-3.06 (m, 2H), 2.96 (s, 6H), 2.34-2.26 (m, 1H), 1.70-1.59 (m, 4H), 1.58-1.50 (m, 1H), 1.49-1.37 (m, 2H), 1.16-1.06 (m, 1H), 1.01-0.87 (m, 2H); LCMS: 486.8 [M+H]+.

The Compounds below were synthesized following the procedure described for Compound 4.

| Cmpd | Structure | Name | [M + H]+ |
|---|---|---|---|
| 5 | 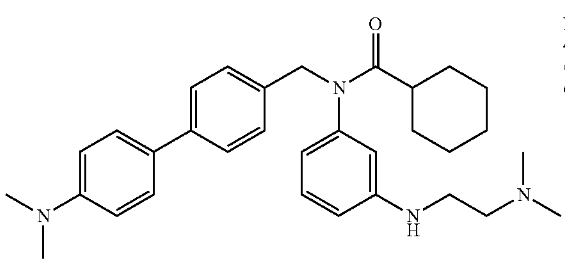 | N-((4'-(Dimethylamino-[1,1'-biphenyl]-4-yl)methyl)-N-(3-((2-(dimethylamino)ethyl)amino)phenyl)cyclohexanecarboxamide | 499.8 |

| Cmpd | Structure | Name | [M + H]⁺ |
|---|---|---|---|
| 6* | 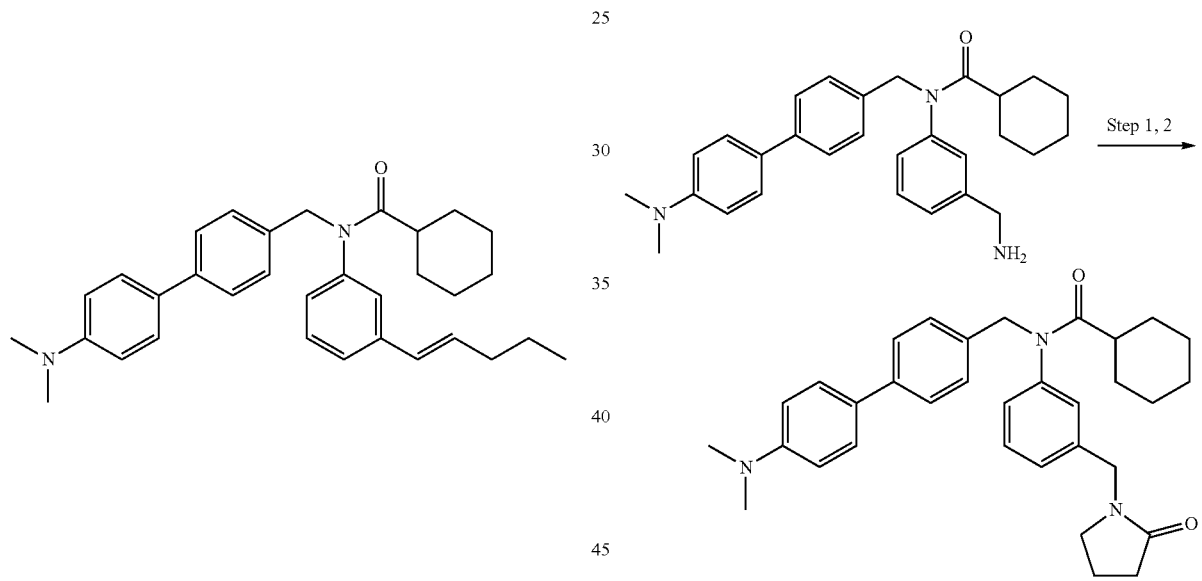 | N-((4'-(Dimethylamino)-[1,1'-biphenyl]-4-yl)methyl)-N-(3-(isobutylamino)phenyl) cyclohexanecarboxamide | 484.8 |

*XantPhos and Pd₂(dba)₃ were used instead of Trixiephos and Pd(OAc)₂.

Compound 7

N-(3-Bromophenyl)-N-((4'-(dimethylamino)-[1,1'-biphenyl]-4-yl)methyl) cyclohexanecarboxamide Compound 8

N-((4'-(Dimethylamino)-[1,1'-biphenyl]-4-yl) methyl)-N-(3-((2-oxopyrrolidin-1-yl)methyl)phenyl) cyclohexanecarboxamide A mixture of Intermediate 2 (500 mg, 1.02 mmol), (E)-pent-1-en-1-ylboronic acid (128 mg, 1.12 mmol) K₂CO₃ (281 mg, 2.03 mmol), and Pd(dppf)Cl₂ (74 mg, 0.10 mmol) in dioxane (20 mL) was degassed with vacuum/nitrogen cycles (3×), and stirred at 80° C. for 5 h. The reaction mixture was quenched with water (30 mL) and then extracted with ethyl acetate (3×30 mL). The combined organic phases were washed with brine (2×30 mL), dried over anhydrous Na₂SO₄, filtered and concentrated. The residue was purified by reverse-phase HPLC to give (E)-N-((4'-(dimethylamino)-[1,1'-biphenyl]-4-yl)methyl)-N-(3-(pent-1-en-1-yl)phenyl)cyclohexanecarboxamide (45 mg, 9%) as a light yellow solid. ¹H NMR (DMSO-d₆): δ 7.47-7.54 (m, 4H), 7.27-7.38 (m, 2H), 7.18 (d, 3H), 6.96 (d, 1H), 6.79 (d, 2H), 6.34-6.41 (m, 1H), 6.21-6.30 (m, 1H), 4.83 (br s, 2H), 2.94 (s, 6H), 2.14 (q, 3H), 1.65 (t, 4H), 1.38-1.55 (m, 5H), 1.06-1.25 (m, 1H), 0.90 (t, 5H); MS: 481.4 [M+H]⁺.

Step 1: N-(3-((4-Chlorobutanamido)methyl)phenyl)-N-((4'-(dimethylamino)-[1,1'-biphenyl]-4-yl)methyl) cyclohexanecarboxamide 4-Chlorobutanoyl chloride (40 μL, 0.36 mmol) was added to a mixture of Intermediate 2.2 (105 mg, 0.24 mmol), trimethylamine (50 μL, 0.36 mmol), and DCM (2.4 mL) at 0° C. The reaction mixture was stirred for 15 min, diluted with DCM (20 mL), washed (2×20 mL saturated NaHCO₃), dried (Na₂SO₄), and concentrated under reduced pressure. The residue was purified by silica gel chromatography to give N-(3-((4-chlorobutanamido)methyl)phenyl)-N-((4'-(dimethylamino)-[1,1'-biphenyl]-4-yl)methyl)cyclohexanecarboxamide (84 mg, 65%) as a white solid. ¹H NMR (400 MHz, DMSO-d₆): δ 8.41 (t, 1H), 7.53-7.43 (m, 4H), 7.33 (t, 1H), 7.18 (m, 1H), 7.14 (d, 2H), 7.05 (s, 1H), 7.00 (d, 1H), 6.77 (d, 2H), 4.80 (s, 2H), 4.23 (d, 2H), 3.57 (t, 2H), 2.92 (s, 6H), 2.24 (t, 2H), 2.20-2.10 (m, 1H), 1.95-1.85 (m, 2H), 1.70-1.55 (m, 4H), 1.54-1.47 (m, 1H), 1.46-1.35 (m, 2H), 1.18-1.05 (m, 1H), 0.95-0.80 (m, 2H); LCMS: 546.8 [M+H]+.

Step 2: N-((4'-(Dimethylamino)-[1,1'-biphenyl]-4-yl)methyl)-N-(3-((2-oxopyrrolidin-1-yl)methyl)phenyl)cyclohexanecarboxamide Sodium hydride (60% in dispersion in mineral oil, 4 mg, 0.10 mmol) was added to a solution of N-(3-((4-chlorobutanamido)methyl)phenyl)-N-((4'-(dimethylamino)-[1,1'-biphenyl]-4-yl)methyl)cyclohexanecarboxamide (38 mg, 0.070 mmol) and DMF (1 mL) at 0° C. The reaction mixture was stirred for 15 min at room temperature, diluted with water (10 mL), and extracted with ethyl acetate (20 mL). The organic phase was dried (Na₂SO₄), concentrated, and then purified by silica gel chromatography to give N-((4'-(dimethylamino)-[1,1'-biphenyl]-4-yl)methyl)-N-(3-((2-oxopyrrolidin-1-yl)methyl)phenyl)cyclohexanecarboxamide (20 mg, 57%) as a white solid. ¹H NMR (DMSO-d₆): δ 7.53-7.45 (m, 4H), 7.38 (t, 1H), 7.19 (d, 1H), 7.16-7.10 (m, 3H), 6.83 (s, 1H), 6.77 (d, 2H), 4.80 (s, 2H), 4.30 (s, 2H), 2.99 (t, 2H), 2.92 (s, 6H), 2.19-2.05 (m, 3H), 1.80-1.68 (m, 2H), 1.68-1.55 (m, 4H), 1.54-1.47 (m, 1H), 1.46-1.35 (m, 2H), 1.18-1.05 (m, 1H), 0.95-0.80 (m, 2H); LCMS: 510.8 [M+H]+.

Compound 9

Methyl 2-((3-(N-((4'-(dimethylamino)-[1,1'-biphenyl]-4-yl)methyl)cyclohexanecarboxamido)phenyl)amino)acetate

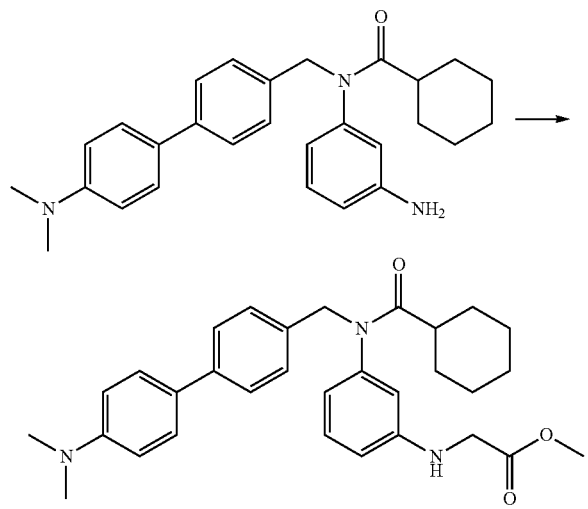

A mixture of Intermediate 3 (1.0 g, 2.1 mmol), methyl 2-bromoacetate (220 uL, 2.31 mmol), NaHCO₃ (388 mg, 4.62 mmol), and DMF (10 mL) was degassed with vacuum/nitrogen cycles (3×), stirred at 75° C. for 6 h, diluted with water (100 mL) and then extracted with ethyl acetate (3×100 mL). The combined organic layers were dried over Na₂SO₄, filtered and concentrated. The residue was purified by reverse-phase HPLC to yield methyl 2-((3-(N-((4'-(dimethylamino)-[1,1'-biphenyl]-4-yl)methyl)cyclohexanecarboxamido)phenyl)amino)acetate (230 mg, 21%) as a white solid. ¹H NMR (400 MHz, DMSO-d₆): δ 7.51 (d, 4H), 7.17 (d, 2H), 7.08 (t, 1H), 6.80 (d, 2H), 6.53 (d, 1H), 6.27-6.36 (m, 2H), 6.22 (t, 1H), 4.76 (s, 2H), 3.85 (d, 2H), 3.61 (s, 3H), 2.94 (s, 6H), 2.20-2.37 (m, 1H), 1.65 (d, 4H), 1.55 (d, 1H), 1.34-1.49 (m, 2H), 1.14 (q, 1H), 0.95 (d, 2H); MS: 500.3 [M+H]+.

Compound 10

Methyl 2-((3-(N-((4'-(dimethylamino)-[1,1'-biphenyl]-4-yl)methyl)cyclohexanecarboxamido)phenyl)(methyl)amino)acetate

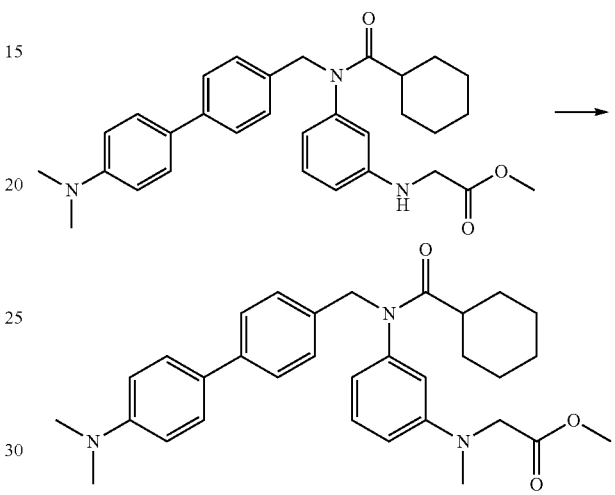

A solution of Compound 9 (340 mg, 0.68 mmol), formaldehyde (250 uL, 3.40 mmol) and acetic acid (19 uL, 0.34 mmol) in methanol (3 mL) was stirred for 2 h. Sodium cyanoborohydride (128 mg, 2.04 mmol) was added, and the solution was stirred for 16 h at 25° C. The reaction was quenched with water (50 mL), and then extracted with DCM (3×50 mL). The combined organic layers were washed with brine (200 mL), concentrated, and purified by reverse-phase HPLC to yield methyl 2-((3-(N-((4'-(dimethylamino)-[1,1'-biphenyl]-4-yl)methyl)cyclohexanecarboxamido)phenyl)(methyl)amino)acetate (75 mg, 21%) as a white solid. ¹H NMR (400 MHz, CDCl₃): δ 7.47 (dd, 4H), 7.15-7.27 (m, 3H), 6.80 (d, 2H), 6.62 (dd, 1H), 6.41 (d, 1H), 6.18 (s, 1H), 4.84 (s, 2H), 3.95 (s, 2H), 3.66 (s, 3H), 2.92-3.03 (m, 9H), 2.26 (t, 1H), 1.58-1.75 (m, 7H), 1.13-1.28 (m, 1H), 0.93-1.09 (m, 2H); MS: 514.4 [M+H]+.

Compound 11

Methyl 3-(N-((4'-(dimethylamino)-[1,1'-biphenyl]-4-yl)methyl)cyclohexanecarboxamido)benzylcarbamate

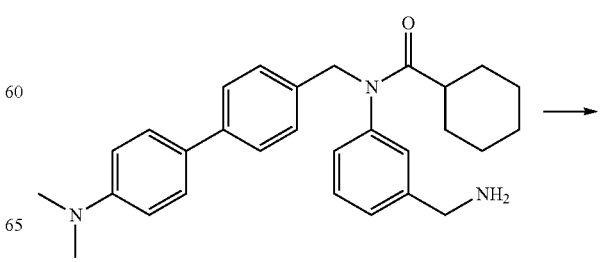

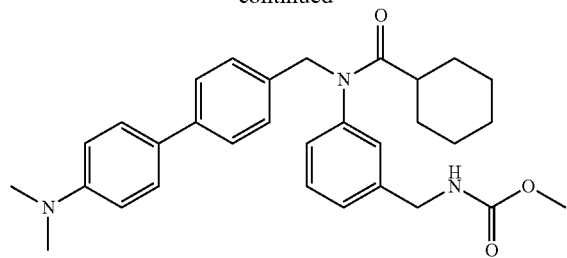

Methyl chloroformate (16 µL, 0.21 mmol) was added to a mixture of Intermediate 2.2 (58 mg, 0.13 mmol), trimethylamine (35 µL, 0.25 mmol), and DCM (1.3 mL) at 0° C. The reaction mixture was stirred for 15 min, diluted with DCM (20 mL), washed (2×20 mL saturated NaHCO$_3$), dried (Na$_2$SO$_4$), and concentrated. The residue was purified by silica gel chromatography to give methyl 3-(N-((4'-(dimethylamino)-[1,1'-biphenyl]-4-yl)methyl)cyclohexanecarboxamido)benzylcarbamate (45 mg, 68%) as a white solid. $^1$H NMR (DMSO-d$_6$): δ 7.69 (t, 1H), 7.51-7.47 (m, 4H), 7.33 (t, 1H), 7.19 (d, 1H), 7.15 (d, 2H), 7.08 (s, 1H), 7.01 (d, 1H), 6.77 (d, 2H), 4.80 (s, 2H), 4.15 (d, 2H), 3.50 (s, 3H), 2.92 (s, 6H), 2.20-2.10 (m, 1H), 1.69-1.57 (m, 4H), 1.55-1.47 (m, 1H), 1.46-1.36 (m, 2H), 1.14-1.08 (m, 1H), 0.97-0.82 (m, 2H); LCMS: 500.8 [M+H]$^+$.

Compound 12

(E)-N-((4'-(Dimethylamino)-[1,1'-biphenyl]-4-yl)methyl)-N-(3-(3-(methylamino)-3-oxoprop-1-en-1-yl)phenyl)cyclohexanecarboxamide

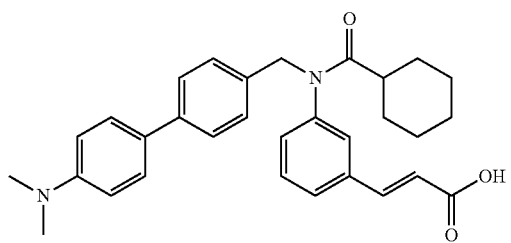

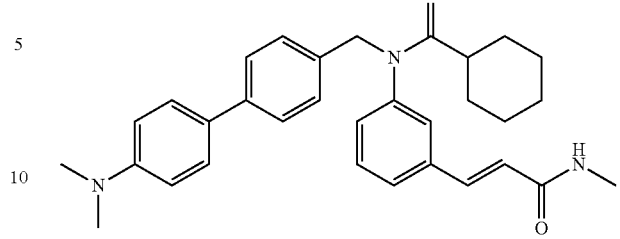

HATU (83 mg, 0.22 mmol) was added to a mixture of Intermediate 8 (95 mg, 0.20 mmol), DIEA (0.07 mL, 0.41 mmol), and DMF (4 mL) at room temperature. After stirring the mixture for 1 h, DIEA (0.17 mL, 0.98 mmol) and methylamine hydrochloride (67 mg, 0.99 mmol) were added. The mixture was stirred for 30 min, diluted with water (10 mL), and extracted with ethyl acetate (2×20 mL). The combined organic extracts were washed (10 mL water and then 10 mL brine), dried (Na$_2$SO$_4$), and concentrated. The residue was purified by silica gel chromatography to give (E)-N-((4'-(Dimethylamino)-[1,1'-biphenyl]-4-yl)methyl)-N-(3-(3-(methylamino)-3-oxoprop-1-en-1-yl)phenyl)cyclohexanecarboxamide (48 mg, 49%). $^1$H NMR (DMSO-d$_6$): δ 8.06-8.00 (m, 1H), 7.55-7.46 (m, 5H), 7.43-7.34 (m, 3H), 7.16 (d, 2H), 7.12 (d, 1H), 6.77 (d, 2H), 6.58 (d, 1H), 4.84 (s, 2H), 2.92 (s, 6H), 2.68 (d, 3H), 2.23-2.08 (m, 1H), 1.72-1.67 (m, 4H), 1.66-1.47 (m, 1H), 1.47-1.34 (m, 2H), 1.15-1.04 (m, 1H), 0.97-0.82 (m, 2H); LCMS: 496.3 [M+H]$^+$.

The Compound below was synthesized following the procedure described for Compound 12.

| Cmpd | Structure | Name | [M + H]$^+$ |
|---|---|---|---|
| 13 | (structure shown) | (E)-N-(3-(3-(Dimethylamino)-3-oxoprop-1-en-1-yl)phenyl)-N-((4'-(dimethylamino)-[1,1'-biphenyl]-4-yl)methyl)cyclohexanecarboxamide | 510.2 |

Compound 14

(E)-N-((4'-(Dimethylamino)-[1,1'-biphenyl]-4-yl)methyl)-N-(3-(2-(oxazol-2-yl)vinyl)phenyl)cyclohexanecarboxamide

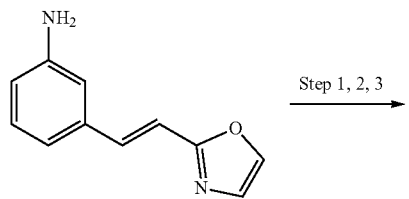

Step 1, 2, 3

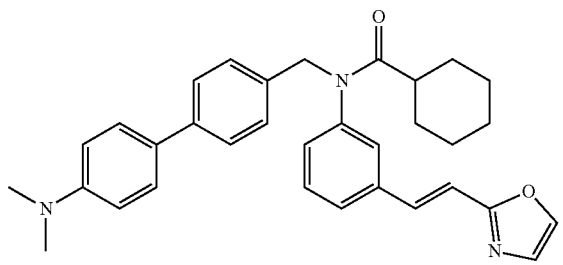

Step 1: (E)-N-(3-(2-(Oxazol-2-yl)vinyl)phenyl)cyclohexanecarboxamide

Cyclohexanecarbonyl chloride (790 uL. 5.91 mmol) was added over 1 h to a solution of Intermediate 6 (1.0 g, 5.37 mmol) and TEA (2.2 mL, 16.1 mmol) in DCM (30 mL) at 0° C. The mixture was stirred at 25° C. for 11 h and then washed with water (2×20 mL). The organic layer was dried over $Na_2SO_4$, filtered, and concentrated. The residue was purified by column chromatography (petroleum ether/ethyl acetate; 1/1) to give (E)-N-(3-(2-(oxazol-2-yl)vinyl)phenyl)cyclohexanecarboxamide (1.3 g 74%) as a yellow oil. $^1$H NMR (CDCl$_3$): δ 7.78 (s, 1H), 7.65 (m, 1H), 7.48-7.52 (m, 2H), 7.28-7.36 (m, 2H), 7.21 (s, 1H), 6.96-7.00 (d, 1H), 2.01-2.27 (m, 1H), 1.97 (m, 2H), 1.88-1.89 (m, 2H), 1.85 (m, 1H), 1.56-1.59 (m, 2H), 1.29-1.32 (m, 3H); MS: 297.2 [M+H]$^+$.

Step 2: (E)-N-(4-Bromobenzyl)-N-(3-(2-(oxazol-2-yl)vinyl)phenyl)cyclohexanecarboxamide Cesium carbonate (5.72 g, 17.6 mmol) was added to a solution of (E)-N-(3-(2-(oxazol-2-yl)vinyl)phenyl)cyclohexanecarboxamide (1.3 g, 4.4 mmol) and 1-bromo-4-(bromomethyl)benzene (2.74 g, 10.97 mmol) in acetonitrile (50 mL). The mixture was heated at reflux for 12 h and then concentrated. Water (50 mL) was added, and the mixture was extracted with DCM (100 mL). The organic layer was dried over $Na_2SO_4$, filtered, and concentrated. The residue was purified by column chromatography (petroleum ether/ethyl acetate; 1/1) to give (E)-N-(4-bromobenzyl)-N-(3-(2-(oxazol-2-yl)vinyl)phenyl)cyclohexanecarboxamide (1.8 g, 79%) as a yellow oil. $^1$H NMR (CDCl$_3$): δ 7.65 (s, 1H), 7.40-7.51 (m, 1H), 7.33-7.37 (m, 4H), 7.20-7.26 (d, 1H), 7.05-7.07 (m, 3H), 6.88-6.92 (m, 2H), 4.80 (s, 2H), 2.14-2.17 (m, 1H), 1.52-1.68 (m, 6H), 1.25-1.27 (m, 1H), 0.91-0.96 (m, 3H); MS: 465.0 [M+H]$^+$.

Step 3: (E)-N-((4'-(Dimethylamino)-[1,1'-biphenyl]-4-yl)methyl)-N-(3-(2-(oxazol-2-yl)vinyl)phenyl)cyclohexanecarboxamide Sodium carbonate (454 mg, 4.28 mmol) and Pd(dppf)Cl$_2$ (157 mg, 0.21 mmol) were added to a solution of (E)-N-(4-bromobenzyl)-N-(3-(2-(oxazol-2-yl)vinyl)phenyl)cyclohexanecarboxamide (500 mg, 1.07 mmol) and [4-(dimethylamino)phenyl]boronic acid hydrochloride (431 mg, 2.14 mmol) in dioxane (40 mL) and H$_2$O (5 mL). The mixture was heated at 100° C. for 12 h, filtered, and extracted with ethyl acetate (100 mL). The organic layer was washed with water (40 mL), dried over $Na_2SO_4$, filtered, and concentrated. The residue was purified by column chromatography (petroleum ether/ethyl acetate; 3/1) to give (E)-N-((4'-(dimethylamino)-[1,1'-biphenyl]-4-yl)methyl)-N-(3-(2-(oxazol-2-yl)vinyl)phenyl)cyclohexanecarboxamide (150 mg, 27%). $^1$H NMR (DMSO-d$_6$): δ 8.13 (s, 1H), 7.60-7.74 (m, 2H), 7.45-7.54 (m, 5H), 7.40 (t, 1H), 7.34 (s, 1H), 7.14-7.28 (m, 3H), 7.10 (d, 1H), 6.76-6.79 (d, 2H), 4.88 (br s, 2H), 2.93 (s, 6H), 2.23 (m, 1H), 1.58-1.73 (m, 4H), 1.41-1.55 (m, 3H), 1.11-1.19 (m, 1H), 0.93 (d, 2H); MS: 506.3 [M+H]$^+$.

The Compound below was synthesized from Intermediate 2.3 and (4-fluorophenyl)boronic acid following procedure described for Compound 14 (Step 3).

| Cmpd | Structure | Name | [M + H]$^+$ |
| --- | --- | --- | --- |
| 15 | ![structure] | N-([1,1'-Biphenyl]-3-yl)-N-((4'-fluoro-[1,1'-biphenyl]-4-yl)methyl)cyclohexanecarboxamide | 464.7 |

The Compounds below were synthesized from Intermediate 7 following procedure described for Compound 14 (Steps 2 and 3).

| Cmpd | Structure | Name | [M + H]+ |
|---|---|---|---|
| 16* | 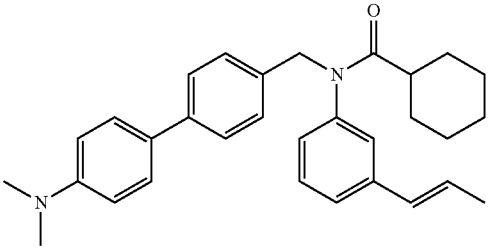 [SMILES: C/C=C/c1cccc(N(Cc2ccc(-c3ccc(N(C)C)cc3)cc2)C(=O)C2CCCCC2)c1] | (E)-N-((4'-(Dimethylamino)-[1,1'-biphenyl]-4-yl)methyl)-N-(3-(prop-1-en-1-yl)phenyl)cyclohexanecarboxamide | 453.3 |
| 17** | 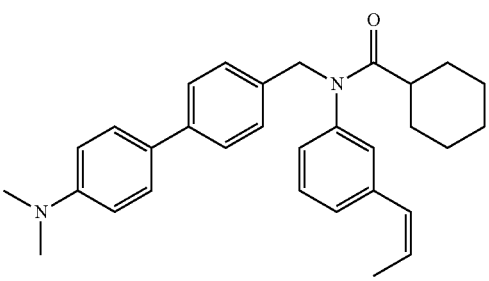 [SMILES: C/C=C\c1cccc(N(Cc2ccc(-c3ccc(N(C)C)cc3)cc2)C(=O)C2CCCCC2)c1] | (Z)-N-((4'-(Dimethylamino-[1,1'-biphenyl]-4-yl)methyl)-N-(3-(prop-1-en-1-yl)phenyl)cyclohexanecarboxamide | 453.3 |

*Pd(PPh$_3$)$_4$ was used instead of Pd(dppf)Cl$_2$.
**Isolated during the purification of Compound 16.

30

The Compounds below were synthesized from the appropriate amines following the procedures described for Intermediate 2.

| Cmpd | Structure | Name | [M + H]+ |
|---|---|---|---|
| 18 | 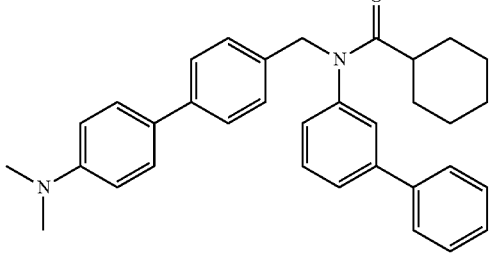 | N-([1,1'-Biphenyl]-3-yl)-N-((4'-(dimethylamino)-[1,1'-biphenyl]-4-yl)methyl)cyclohexanecarboxamide | 489.7 |
| 19 | 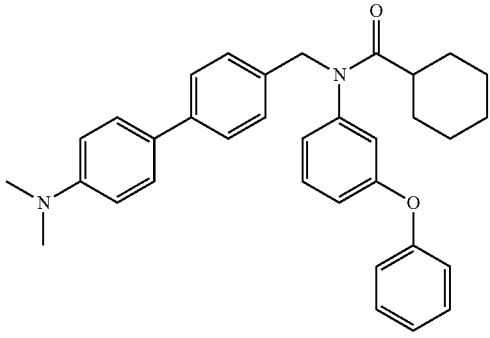 [SMILES: CN(C)c1ccc(-c2ccc(CN(C(=O)C3CCCCC3)c3cccc(Oc4ccccc4)c3)cc2)cc1] | N-((4'-(Dimethylamino)-[1,1'-biphenyl]-4-yl)methyl)-N-(3-phenoxyphenyl)cyclohexanecarboxamide | 505.7 |

-continued

| Cmpd | Structure | Name | [M + H]⁺ |
|---|---|---|---|
| 20 | 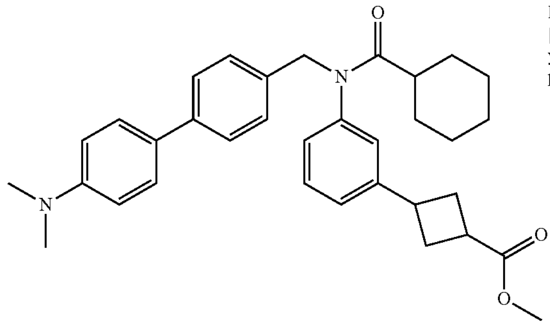 | Methyl 3-(3-(N-((4'-(dimethylamino)-[1,1'-biphenyl]-4-yl)methyl)cyclohexanecarboxamido)phenyl)cyclobutanecarboxylate | 525.6 |
| 21 | 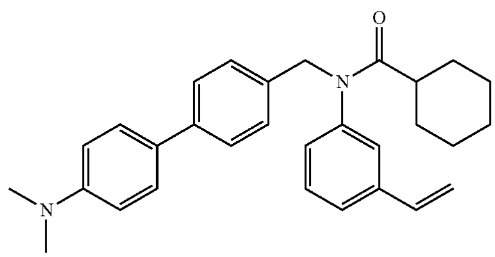 [SMILES: C=Cc1cccc(N(Cc2ccc(-c3ccc(N(C)C)cc3)cc2)C(=O)C2CCCCC2)c1] | N-((4'-(Dimethylamino)-[1,1'-biphenyl]-4-yl)methyl)-N-(3-vinylphenyl)cyclohexanecarboxamide | 439.6 |

Reductive amination conditions varied: 1-2 eq. acetic acid; NaBH₃CN, MeOH or NaBH(OAc)₃, DCM. Acylation conditions varied: 1.2-1.5 eq. acid chloride; 2-3 eq. TEA; 0.03-0.1M DCM; acid chloride addition at 0° C. or rt.

The compound below was synthesized from Compound 14 using standard hydrogenation conditions (1 atm H₂, 10% Pd/C, EtOAc, rt).

| Cmpd | Structure | Name | [M + H]⁺ |
|---|---|---|---|
| 22 | 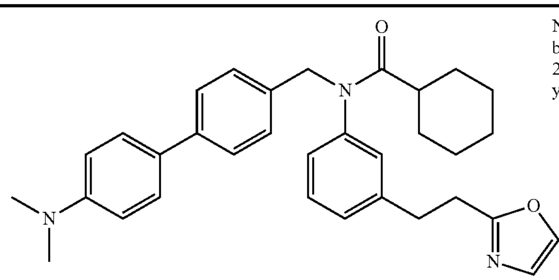 | N-((4'-(Dimethylamino)-[1,1'-biphenyl]-4-yl)methyl)-N-(3-(2-(oxazol-2-yl)ethyl)phenyl)cyclohexanecarboxamide | 508.4 |

The Compounds below were synthesized from Intermediate 2.4 and the appropriate boronic acid using standard Suzuki conditions [Pd(dppf)Cl₂, Cs₂CO₃, DMF, 80° C.].

| Cmpd | Structure | Name | [M + H]+ |
|---|---|---|---|
| 23 | 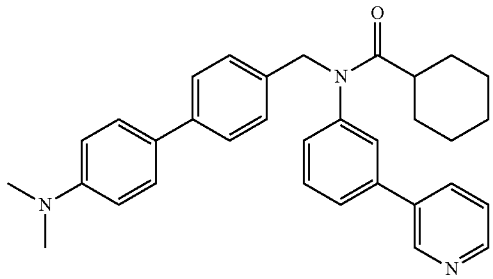 [SMILES: CN(C)c1ccc(-c2ccc(CN(C(=O)C3CCCCC3)c3cccc(-c4cccnc4)c3)cc2)cc1] | N-((4'-(Dimethylamino)-[1,1'-biphenyl]-4-yl)methyl)-N-(3-(pyridin-3-yl)phenyl)cyclohexanecarboxamide | 490.8 |
| 24 | 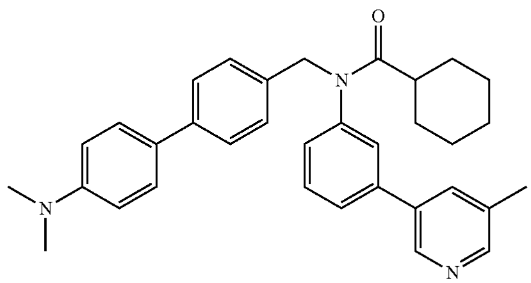 | N-((4'-(Dimethylamino)-[1,1'-biphenyl]-4-yl)methyl)-N-(3-(5-methylpyridin-3-yl)phenyl)cyclohexanecarboxamide | 504.8 |
| 25 | 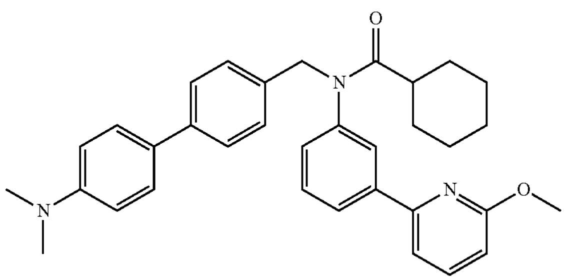 | N-((4'-(dimethylamino)-[1,1'-biphenyl]-4-yl)methyl)-N-(3-(6-methoxypyridin-2-yl)phenyl)cyclohexanecarboxamide | 520.8 |
| 26 | 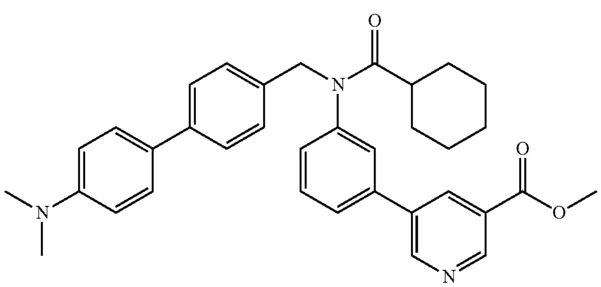 | Methyl 5-(3-(N-((4'-(dimethylamino)-[1,1'-biphenyl]-4-yl)methyl)cyclohexanecarboxamido)phenyl)nicotinate | 548.8 |

Compound 27

(E)-N-((4'-(Dimethylamino)-[1,1'-biphenyl]-4-yl)methyl)-N-(3-(2-(pyridin-2-yl)vinyl)phenyl)cyclohexanecarboxamide

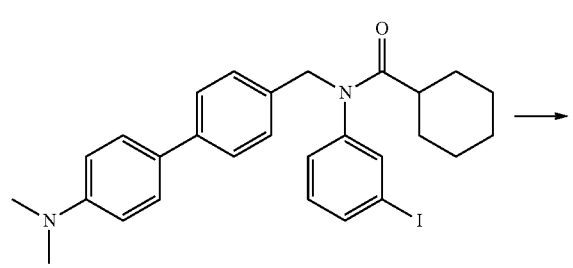

→

-continued

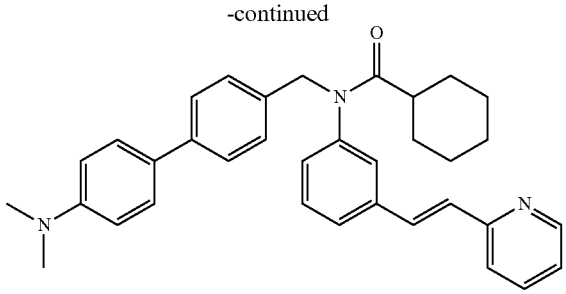

A mixture of Intermediate 2.4 (150 mg, 0.279 mmol), 2-vinylpyridine (0.06 mL, 0.556 mmol), palladium acetate (6 mg, 0.027 mmol), tri(o-tolyl)phosphine (34 mg, 0.112 mmol), triethylamine (1.5 mL), and DMF (1.5 mL) was degassed by bubbling N₂ for 10 min, heated at 80° C. for 1 h, and then allowed to cool to rt. Ethyl acetate was added to the mixture, and the solution was washed with water (2×20 mL), dried (Na$_2$SO$_4$), and concentrated. The crude material was purified by silica gel chromatography and then by reverse-phase HPLC. The resulting material was freebased with ethyl acetate and saturated NaHCO$_3$ to give Compound 27 as a yellow solid (97 mg, 68%). $^1$H NMR (400 MHz, DMSO-d$_6$): δ 8.56 (d, 1H), 7.77 (td, 1H), 7.66-7.63 (m, 1H), 7.61 (s, 1H), 7.53-7.47 (m, 6H), 7.40 (t, 1H), 7.32-7.24 (m, 2H), 7.19 (d, 2H), 7.09 (d, 1H), 6.77 (d, 2H), 4.87 (s, 2H), 2.92 (s, 6H), 2.27-2.16 (m, 1H), 1.74-1.58 (m, 4H), 1.54-1.37 (m, 3H), 1.15-1.05 (m, 1H), 0.97-0.82 (m, 2H); LCMS: 516.8 [M+H]$^+$.

The Compound below was synthesized from Intermediate 2.4 and 4-vinyl pyridine following the procedure described for Compound 27.

| Cmpd | Structure | Name | [M + H]$^+$ |
|---|---|---|---|
| 28 | 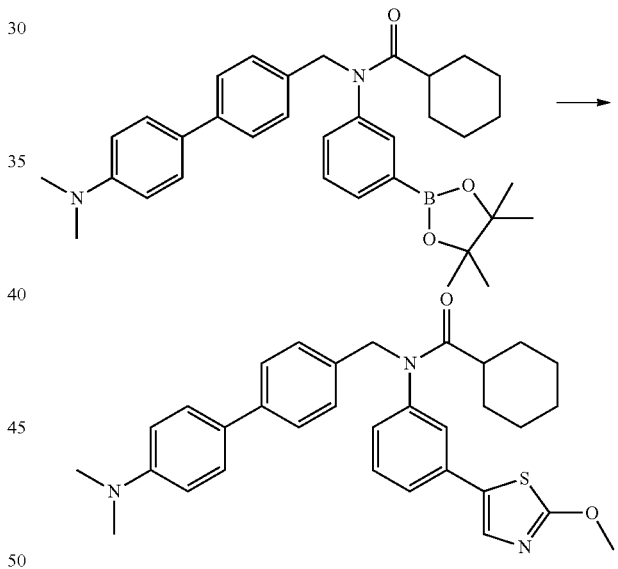 | (E)-N-((4'-(Dimethylamino)-[1,1'-biphenyl]-4-yl)methyl)-N-(3-(2-(pyridin-4-yl)vinyl)phenyl)cyclohexane-carboxamide | 516.8 |

Compound 29

N-((4'-(Dimethylamino)-[1,1'-biphenyl]-4-yl)methyl)-N-(3-(2-methoxythiazol-5-yl)phenyl)cyclohexanecarboxamide A mixture of Intermediate 9 (155 mg, 0.288 mmol), 5-bromo-2-methoxythiazole (89 mg, 0.489 mmol), Pd(dppf)Cl$_2$ (20 mg, 0.027 mmol), cesium carbonate (280 mg, 0.862 mmol), and DMF (1.5 mL) was degassed by bubbling N$_2$ for 10 min, heated at 80° C. for 2 h, and then allowed to cool to rt. Ethyl acetate was added to the mixture, and the solution was washed with water (2×20 mL), dried (Na$_2$SO$_4$), and concentrated. The crude material was purified by silica gel chromatography to give Compound 29 (63 mg, 42%). $^1$H NMR (400 MHz, DMSO-d$_6$): δ 7.69 (s, 1H), 7.52-7.45 (m, 5H), 7.38 (t, 1H), 7.34 (t, 1H), 7.17 (d, 2H), 7.04 (d, 1H), 6.77 (d, 2H), 4.56 (s, 2H), 4.02 (s, 3H), 2.92 (s, 6H), 2.25-2.14 (m, 1H), 1.72-1.58 (m, 4H), 1.55-1.36 (m, 3H), 1.15-1.08 (m, 1H), 0.98-0.82 (m, 2H); LCMS: 526.5 [M+H]$^+$.

The Compounds below were synthesized from Intermediate 9 and the appropriate aryl bromide or aryl iodide following the procedure described for Compound 29.

| Cmpd | Structure | Name | [M + H]+ |
|---|---|---|---|
| 30 | 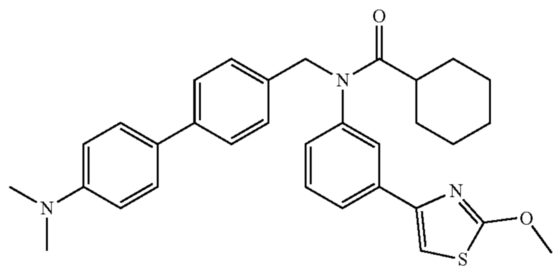 | N-((4'-(Dimethylamino)-[1,1'-biphenyl]-4-yl)methyl)-N-(3-(2-methoxythiazol-4-yl)phenyl)cyclohexanecarboxamide | 526.3 |
| 31 | 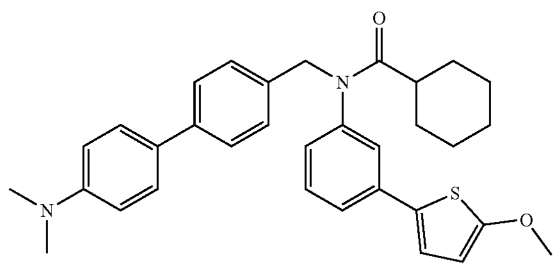 | N-((4'-(Dimethylamino)-[1,1'-biphenyl]-4-yl)methyl)-N-(3-(5-methoxythiophen-2-yl)phenyl)cyclohexanecarboxamide | 525.3 |
| 32 | 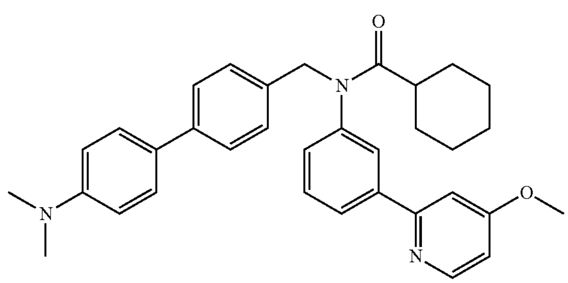 | N-((4'-(Dimethylamino)-[1,1'-biphenyl]-4-yl)methyl)-N-(3-(4-methoxypyridin-2-yl)phenyl)cyclohexanecarboxamide | 520.8 |
| 33 | 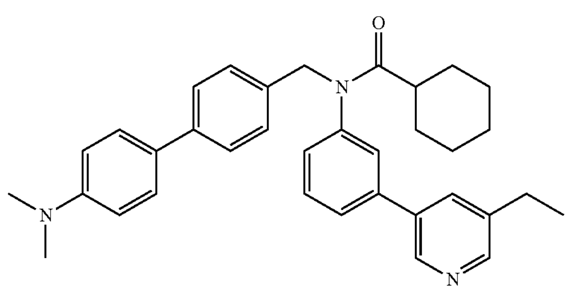 [SMILES: CCc1cncc(-c2cccc(N(Cc3ccc(-c4ccc(N(C)C)cc4)cc3)C(=O)C3CCCCC3)c2)c1] | N-((4'-(Dimethylamino)-[1,1'-biphenyl]-4-yl)methyl)-N-(3-(5-ethylpyridin-3-yl)phenyl)cyclohexanecarboxamide | 518.8 |
| 34 | 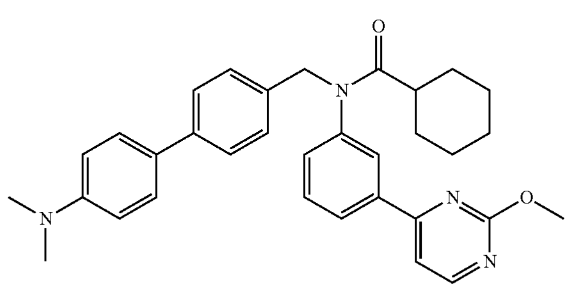 | N-((4'-(Dimethylamino)-[1,1'-biphenyl]-4-yl)methyl)-N-(3-(2-methoxypyrimidin-4-yl)phenyl)cyclohexanecarboxamide | 521.8 |

-continued

| Cmpd | Structure | Name | [M + H]+ |
|---|---|---|---|
| 35 | 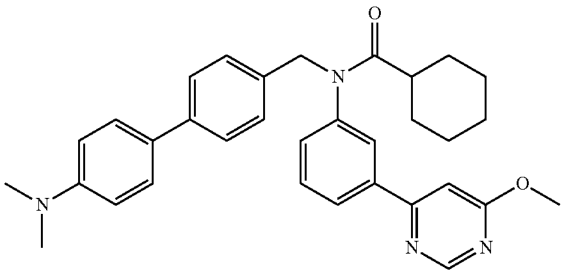 | N-((4'-(Dimethylamino)-[1,1'-biphenyl]-4-yl)methyl)-N-(3-(6-methoxypyrimidin-4-yl)phenyl)cyclohexanecarboxamide | 521.6 |
| 36 | 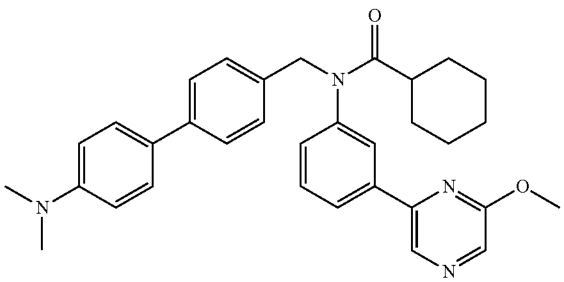 | N-((4'-(Dimethylamino)-[1,1'-biphenyl]-4-yl)methyl)-N-(3-(6-methoxypyrazin-2-yl)phenyl)cyclohexanecarboxamide | 521.6 |

Reaction conditions varied: 0.1-0.2 eq Pd(dppf)Cl$_2$; 3-4 eq. Cs$_2$CO$_3$; DMF or dioxane.

The Compounds below were synthesized from Intermediate 8.1 and the appropriate amine using standard HATU acylation conditions (HATU, iPr$_2$NEt, DMF, rt).

| Cmpd | Structure | Name | [M + H]+ |
|---|---|---|---|
| 37 | 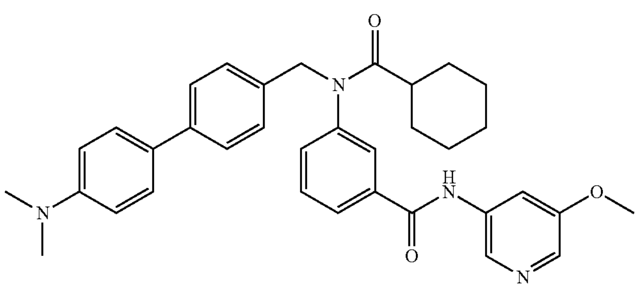 | 3-(N-((4'-(Dimethylamino)-[1,1'-biphenyl]-4-yl)methyl)cyclohexanecarboxamido)-N-(5-methoxypyridin-3-yl)benzamide | 563.8 |
| 38 | 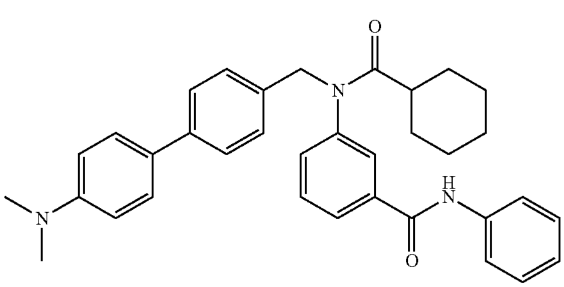 [SMILES: CN(C)c1ccc(-c2ccc(CN(C(=O)C3CCCCC3)c3cccc(C(=O)Nc4ccccc4)c3)cc2)cc1] | 3-(N-((4'-(Dimethylamino)-[1,1'-biphenyl]-4-yl)methyl)cyclohexanecarboxamido)-N-phenylbenzamide | 532.7 |

| Cmpd | Structure | Name | [M + H]⁺ |
|---|---|---|---|
| 39 | 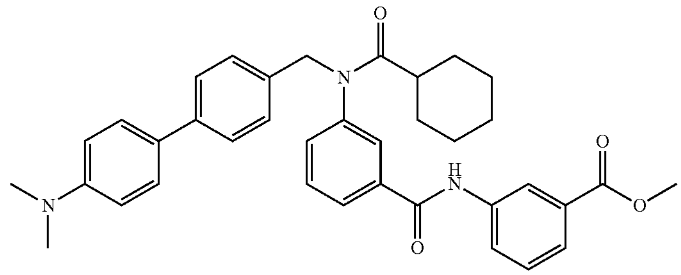 | Methyl 3-(3-(N-((4'-(dimethylamino)-[1,1'-biphenyl]-4-yl)methyl)cyclohexanecarboxamido)benzamido)benzoate | 590.7 |
| 40 | 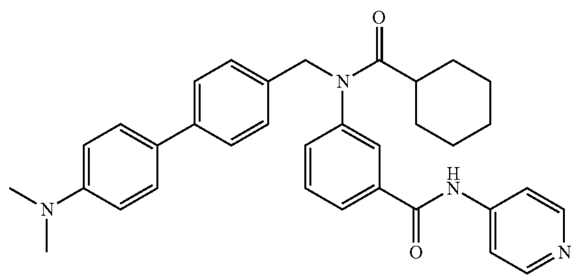 [SMILES: CN(C)c1ccc(-c2ccc(CN(C(=O)C3CCCCC3)c3cccc(C(=O)Nc4ccncc4)c3)cc2)cc1] | 3-(N-((4'-(Dimethylamino)-[1,1'-biphenyl]-4-yl)methyl)cyclohexanecarboxamido)-N-(pyridin-4-yl)benzamide | 533.6 |
| 41 | 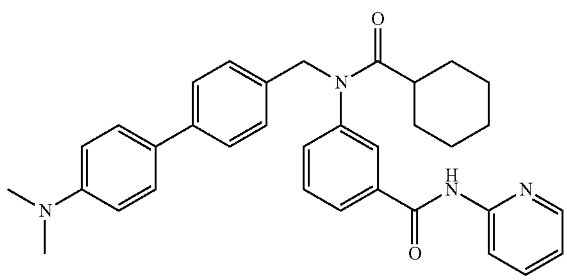 [SMILES: CN(C)c1ccc(-c2ccc(CN(C(=O)C3CCCCC3)c3cccc(C(=O)Nc4ccccn4)c3)cc2)cc1] | 3-(N-((4'-(Dimethylamino)-[1,1'-biphenyl]-4-yl)methyl)cyclohexanecarboxamido)-N-(pyridin-2-yl)benzamide | 533.6 |

Compound 42

(E)-N-((4'-(Dimethylamino)-[1,1'-biphenyl]-4-yl)methyl)-N-(3-(3-methylbut-1-en-1-yl)phenyl)cyclohexanecarboxamide

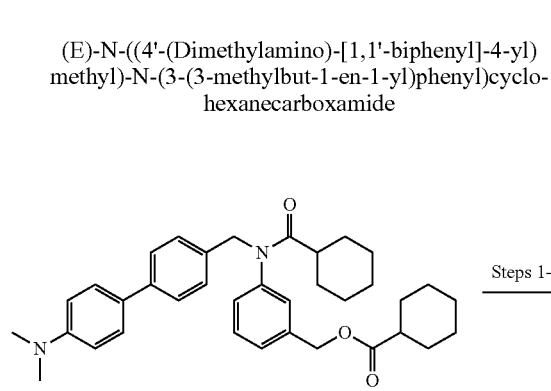

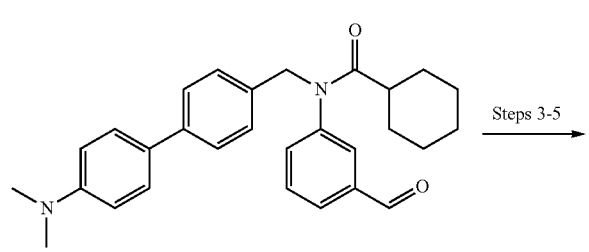

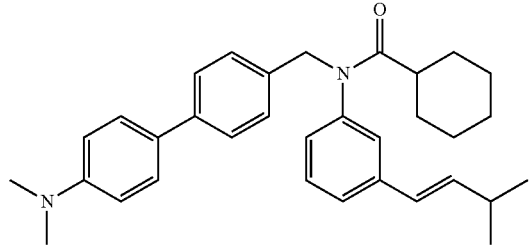

Step 2: N-((4'-(Dimethylamino)-[1,1'-biphenyl]-4-yl)methyl)-N-(3-formylphenyl)cyclohexanecarboxamide A mixture of N-((4'-(dimethylamino)-[1,1'-biphenyl]-4-yl)methyl)-N-(3-(hydroxymethyl)phenyl)cyclohexanecarboxamide (823.7 mg, 1.86 mmol) in DCM (20 mL) was stirred vigorously. Dess-Martin (928.9 mg, 2.19 mmol) was added, and the system was degassed with 3 vacuum/N₂ cycles. The mixture was stirred at rt for 2 h under N₂. Saturated aqueous NaHCO₃ solution (10 mL) and saturated aqueous Na₂S₂O₃ solution (10 mL) were added, and the mixture was stirred for 30 min before being extracted with DCM (20 mL×3). The combined organic layers were dried with MgSO₄, filtered, and concentrated to give a residue which was purified by chromatography on silica gel (Petroleum ether/Ethyl acetate; 2:1) to give N-((4'-(dimethylamino)-[1,1'-biphenyl]-4-yl)methyl)-N-(3-formylphenyl)cyclohexanecarboxamide (453.20 mg, 1.03 mmol, 55.34% yield) as a light yellow solid. $^1$H NMR (400 MHz, CDCl$_3$): δ 9.89 (s, 1H), 7.82-7.68 (m, 1H), 7.45-7.28 (m, 6H), 7.18-7.05 (m, 3H), 6.71 (d, 2H), 4.83 (s, 2H), 2.91 (s, 6H), 2.09-1.95 (m, 1H), 1.67-1.45 (m, 7H), 1.12-1.05 (m, 1H), 0.96-0.84 (m, 2H); MS: 441.2 [M+H]$^+$.

Step 3: 1-(3-(N-((4'-(Dimethylamino)-[1,1'-biphenyl]-4-yl)methyl)cyclohexanecarboxamido)phenyl)-3-methyl-2-(phenylsulfonyl)butyl acetate To a solution of Intermediate 11 (134.2 mg, 676.82 umol) in THF (1 mL) at −78° C., n-BuLi (2.5 M, 200 uL) was added. The mixture was stirred at −78° C. for 30 min, and then N-((4'-(dimethylamino)-[1,1'-biphenyl]-4-yl)methyl)-N-(3-formylphenyl)cyclohexanecarboxamide (177.6 mg, 403.10 umol) in THF (0.5 mL) was added. The mixture was stirred vigorously and kept at −78° C. for 3 h. Ac$_2$O (109.0 mg, 1.07 mmol) was added dropwise at −78° C. The mixture was kept at −78° C. for 1 h, the bath was removed, and the reaction was allowed to warm to rt overnight. The reaction was quenched with saturated aqueous NH$_4$Cl (5 mL) and extracted with EtOAc (15 mL×3). The combined organic layers were dried with MgSO$_4$, filtered, concentrated, and then purified by prep-TLC (EtOAc:PE=1:2) to give 1-(3-(N-((4'-(dimethylamino)-[1,1'-biphenyl]-4-yl)methyl)cyclohexanecarboxamido)phenyl)-3-methyl-2-(phenylsulfonyl)butyl acetate (61.6 mg, 90.47 umol, 22.89% yield) as white solid. $^1$H NMR (400 MHz, CDCl$_3$) δ: 7.77-7.70 (m, 2H), 7.56-7.49 (m, 1H), 7.45-7.34 (m, 6H), 7.18-7.14 (m, 1H), 7.05 (t, 2H), 6.98-6.87 (m, 1H), 6.79 (d, 1H), 6.75-6.69 (m, 2H), 6.19 (s, 1H), 6.02 (d, 1H), 4.95-4.82 (m, 1H), 4.61-4.58 (m, 1H), 3.10-3.05 (m, 1H), 2.92 (s, 6H), 2.38-2.23 (m, 1H), 2.19-2.09 (m, 1H), 1.96 (s, 3H), 1.58-1.49 (m, 6H), 1.11 (d, 6H), 0.90-0.77 (m, 4H); MS: 681.4 [M+H]$^+$.

Step 4: (Z)—N-((4'-(Dimethylamino)-[1,1'-biphenyl]-4-yl)methyl)-N-(3-(3-methyl-2-(phenylsulfonyl)but-1-en-1-yl)phenyl)cyclohexanecarboxamide To a solution of 1-(3-(N-((4'-(dimethylamino)-[1,1'-biphenyl]-4-yl)methyl)cyclohexanecarboxamido)phenyl)-3-methyl-2-(phenylsulfonyl)butyl acetate (93.2 mg, 136.88 umol) in THF (2 mL), DBU (128.4 mg, 843.41 umol) was added dropwise. The solution was stirred at rt overnight, concentrated, and then purified by prep-TLC (EtOAc:PE=1:2) to give (Z)—N-((4'-(dimethylamino)-[1,1'-biphenyl]-4-yl)methyl)-N-(3-(3-methyl-2-(phenyl sulfonyl)but-1-en-1-yl)phenyl)cyclohexanecarboxamide (67.8 mg, 109.21 umol, 79.78% yield) as a yellow solid. $^1$H NMR (400 MHz, CDCl$_3$): δ 7.80 (d, 1H), 7.73 (s, 1H), 7.54-7.29 (m, 8H), 7.18-7.14 (m, 1H), 7.09 (d, 2H), 7.02-6.91 (m, 2H), 6.83 (br s, 1H), 6.71 (d, 2H), 4.80 (br s, 2H), 2.92 (s, 6H), 2.84-2.74 (m, 1H), 2.13-1.98 (m, 1H), 1.70-1.53 (m, 8H), 1.23-1.09 (m, 2H), 0.85 (d, 6H); MS: 621.4 [M+H]$^+$.

Step 5: (E)-N-((4'-(Dimethylamino)-[1,1'-biphenyl]-4-yl)methyl)-N-(3-(3-methylbut-1-en-1-yl)phenyl)cyclohexanecarboxamide A mixture of (Z)—N-((4'-(dimethylamino)-[1,1'-biphenyl]-4-yl)methyl)-N-(3-(3-methyl-2-(phenylsulfonyl)but-1-en-1-yl)phenyl)cyclohexanecarboxamide (65.6 mg, 105.66 umol), 1,3-dimethyltetrahydropyrimidin-2(1H)-one (137.8 mg, 1.08 mmol) in THF (4 mL) was degassed with 3 vacuum/N$_2$ cycles. Methanol (34.8 mg, 1.09 mmol) was added followed by diiodosamarium (0.1 M, 9.00 mL, 0.9 mmol, THF solution). The mixture was stirred at rt for 2.5 h under N$_2$, concentrated, and purified by column chromatography on silica gel (Petroleum ether/Ethyl acetate; 2:1) to give (E)-N-((4'-(dimethylamino)-[1,1'-biphenyl]-4-yl)methyl)-N-(3-(3-methylbut-1-en-1-yl)phenyl)cyclohexanecarboxamide (29.3 mg, 60.96 umol, 57.69% yield) as a light yellow solid. $^1$H NMR (400 MHz, DMSO-d$_6$): δ: 7.46 (dd, 4H), 7.35-7.22 (m, 2H), 7.17-7.08 (m, 3H), 6.90 (d, 1H), 6.74 (d, 2H), 6.28 (d, 1H), 6.21 (dd, 1H), 4.79 (br s, 2H), 2.89 (s, 6H), 2.42-2.32 (m, 1H), 2.21-2.08 (m, 1H), 1.61 (t, 4H), 1.52-1.31 (m, 3H), 1.17-1.03 (m, 1H), 0.98 (d, 6H), 0.91-0.79 (m, 2H); MS: 481.4 [M+H]$^+$.

Compound 43

N-((4'-(Dimethylamino)-[1,1'-biphenyl]-4-yl)methyl)-N-(3-(3-methoxyisothiazol-5-yl)phenyl)cyclohexanecarboxamide

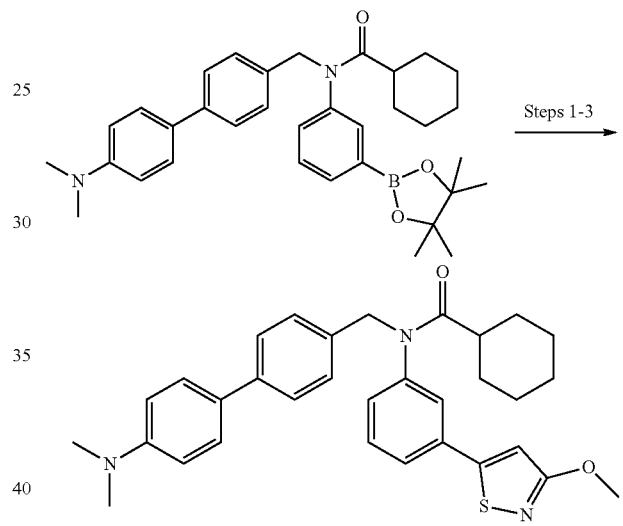

Step 1: N-((4'-(Dimethylamino)-[1,1'-biphenyl]-4-yl)methyl)-N-(3-(3-(methoxymethoxy)isothiazol-5-yl)phenyl)cyclohexanecarboxamide To a solution of Intermediate 9 (3.02 g, 5.61 mmol) and Intermediate 12 (1.51 g, 8.41 mmol) in dioxane (120 mL), Pd(dba)$_2$ (644.9 mg, 1.12 mmol), S-Phos (920.9 mg, 2.24 mmol) and K$_3$PO$_4$ (3.57 g, 16.82 mmol) were added. The mixture was refluxed for 6 h, EtOAc (300 mL) and water (150 mL) were added, and then the mixture was filtered. The organic layer was separated, washed with water (150 mL), dried over Na$_2$SO$_4$, filtered, concentrated, and purified by column chromatography on silica gel (petroleum ether/EtOAc=5/1) to give N-((4'-(dimethylamino)-[1,1'-biphenyl]-4-yl)methyl)-N-(3-(3-(methoxymethoxy)isothiazol-5-yl)phenyl)cyclohexanecarboxamide (2.03 g, 2.04 mmol, 36.36% yield, 55.79% purity) as yellow oil. MS: 556.4 [M+H]$^+$.

Step 2: N-((4'-(Dimethylamino)-[1,1'-biphenyl]-4-yl)methyl)-N-(3-(3-hydroxyisothiazol-5-yl)phenyl)cyclohexanecarboxamide To a solution of N-((4'-(dimethylamino)-[1,1'-biphenyl]-4-yl)methyl)-N-(3-(3-(methoxymethoxy)isothiazol-5-yl)

phenyl)cyclohexanecarboxamide (2.71 g, 4.88 mmol) in MeOH (100 mL) at rt, conc. HCl (13.4 mL, 12M, 161.43 mmol) was added. The reaction was stirred for 16 h, concentrated, and then dissolved in EtOAc (200 mL). This mixture was washed with aqueous NaHCO$_3$ solution (50 mL), dried over Na$_2$SO$_4$, filtered, concentrated, and then purified by column chromatography on silica gel (petroleum ether/EtOAc=2/1) to give N-((4'-(dimethylamino)-[1,1'-biphenyl]-4-yl)methyl)-N-(3-(3-hydroxyisothiazol-5-yl)phenyl)cyclohexanecarboxamide (924 mg, 1.77 mmol, 36.19% yield, 97.79% purity) as yellow oil. $^1$H NMR (400 MHz, DMSO-d$_6$): δ 11.63 (br s, 1H), 7.70-7.45 (m, 7H), 7.29-7.13 (m, 3H), 7.04 (s, 1H), 6.79 (d, 2H), 4.89 (s, 2H), 2.93 (s, 6H), 2.15-2.05 (m, 1H), 1.78-1.59 (m, 4H), 1.58-1.39 (m, 3H), 1.22-1.08 (m, 1H), 0.99-0.82 (m, 2H); MS: 512.2 [M+H]$^+$.

Step 3: N-((4'-(Dimethylamino)-[1,1'-biphenyl]-4-yl)methyl)-N-(3-(3-methoxyisothiazol-5-yl)phenyl)cyclohexanecarboxamide To a solution of N-((4'-(dimethylamino)-[1,1'-biphenyl]-4-yl)methyl)-N-(3-(3-hydroxyisothiazol-5-yl)phenyl)cyclohexanecarboxamide (462 mg, 902.91 umol) in THF (35 mL) and MeOH (5 mL) at 0° C. was added diazomethyl(trimethyl)silane (2M, 1.20 mL). The mixture was warmed to rt for 15 h, and then EtOAc (50 mL) was added. The solution was washed with 1N HCl solution (30 mL), washed with NaHCO$_3$ solution (30 mL), dried over Na$_2$SO$_4$, filtered, and concentrated to give crude material, which was purified by prep-HPLC (Reverse phase; water(10 mM NH$_4$HCO$_3$)—CH$_3$CN) to give N-((4'-(dimethylamino)-[1,1'-biphenyl]-4-yl)methyl)-N-(3-(3-methoxyisothiazol-5-yl)phenyl)cyclohexanecarboxamide (109.4 mg, 207.29 umol, 22.96% yield, 99.61% purity) as yellow solid. $^1$H NMR (400 MHz, DMSO-d$_6$): δ 7.78-7.70 (m, 1H), 7.66-7.56 (m, 6H), 7.40-7.23 (m, 4H), 6.87 (d, 2H), 4.97 (s, 2H), 4.03 (s, 3H), 3.02 (s, 6H), 2.35-2.20 (m, 1H), 1.86-1.66 (m, 4H), 1.65-1.45 (m, 3H), 1.28-1.16 (m, 1H), 1.06-0.91 (m, 2H); MS: 526.3 [M+H]$^+$.

Compound 44

N-((4'-(Dimethylamino)-[1,1'-biphenyl]-4-yl)methyl)-N-(3-(2-methyl-3-oxo-2,3-dihydroisothiazol-5-yl)phenyl)cyclohexanecarboxamide

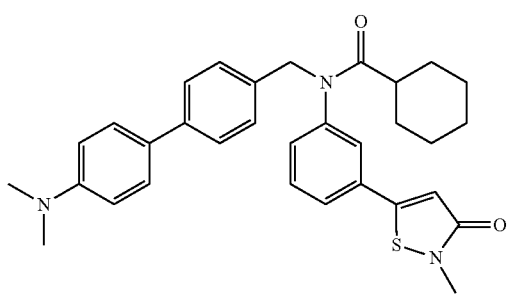 [SMILES: CN(C)c1ccc(-c2ccc(CN(C(=O)C3CCCCC3)c3cccc(-c4cc(=O)n(C)s4)c3)cc2)cc1]

During the purification of Compound 43, Compound 44 was isolated (108.8 mg, 205.64 umol, 22.78% yield, 99.36% purity) as white solid. $^1$H NMR (400 MHz, DMSO-d$_6$): δ 7.60 (d, 1H), 7.55-7.41 (m, 6H), 7.28 (d, 1H), 7.17 (d, 2H), 6.85-6.74 (m, 3H), 4.88 (s, 2H), 3.23 (s, 3H), 2.92 (s, 6H), 2.24-2.10 (m, 1H), 1.74-1.57 (m, 4H), 1.54-1.35 (m, 3H), 1.18-1.05 (m, 1H), 0.95-0.82 (m, 2H); MS: 526.3 [M+H]$^+$.

Compound 45 trans-4-Hydroxy-N-((trans-4-(4-methoxy-3-methylphenyl)cyclohexyl)methyl)-N-(3-(3-methoxyazetidin-1-yl)phenyl)cyclohexanecarboxamide

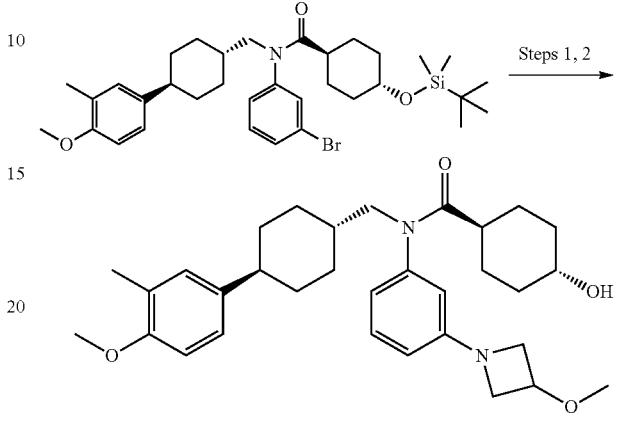

Step 1: trans-4-((tert-Butyldimethylsilyl)oxy)-N-((trans-4-(4-methoxy-3-methylphenyl)cyclohexyl)methyl)-N-(3-(3-methoxyazetidin-yl)phenyl)cyclohexanecarboxamide A mixture of Intermediate 2.6 (138 mg, 0.22 mmol), 3-methoxyazetidine hydrochloride (32 mg, 0.26 mmol), Cs$_2$CO$_3$ (215 mg, 0.66 mmol), Xantphos (17 mg, 0.029 mmol), Pd$_2$(dba)$_3$ (8 mg, 0.014 mmol) and dioxane (1.5 mL) was degassed with 3 vacuum/N$_2$ cycles, stirred at 100° C. for 3 h, and then allowed to cool to rt. The reaction mixture was poured into 20 mL saturated NaHCO$_3$ and extracted with 20 mL ethyl acetate. The organic layer was washed with 20 mL brine, dried (Na$_2$SO$_4$), filtered, concentrated and purified by silica gel chromatography (0-20% ethyl acetate in hexanes) to give trans-4-((tert-butyldimethylsilyl)oxy)-N-((trans-4-(4-methoxy-3-methylphenyl)cyclohexyl)methyl)-N-(3-(3-methoxyazetidin-1-yl)phenyl)cyclohexanecarboxamide (119 mg, 86%) as a pale yellow foam. $^1$H NMR (400 MHz, DMSO-d$_6$): δ 7.25 (t, 1H), 6.98-6.93 (m, 2H), 6.78 (d, 1H), 6.55 (d, 1H), 6.44 (d, 1H), 6.27 (br s, 1H), 4.35-4.28 (m, 1H), 4.05 (t, 2H), 3.72 (s, 3H), 3.64-3.58 (m, 2H), 3.54-3.45 (m, 3H), 3.24 (s, 3H), 2.37-2.28 (m, 1H), 2.09 (s, 3H), 2.13-2.03 (m, 1H), 1.78-1.68 (m, 6H), 1.65-1.57 (m, 2H), 1.50-1.38 (m, 3H), 1.35-1.22 (m, 2H), 1.09-0.96 (m, 2H), 0.80 (s, 9H), 0.92-0.77 (m, 2H), −0.013 (s, 6H); LCMS: 635.7 [M+H]$^+$.

Step 2: trans-4-Hydroxy-N-((trans-4-(4-methoxy-3-methylphenyl)cyclohexyl)methyl)-N-(3-(3-methoxyazetidin-1-yl)phenyl)cyclohexanecarboxamide Aqueous hydrochloric acid (6N, 0.24 mL, 1.4 mmol) was added to a solution of trans-4-((tert-butyldimethyl silyl)oxy)-N-((trans-4-(4-methoxy-3-methylphenyl)cyclohexyl)methyl)-N-(3-(3-methoxyazetidin-1-yl)phenyl)cyclohexanecarboxamide (113 mg, 0.178 mmol), THF (1 mL) and MeOH (1 mL) at rt. The reaction was stirred for 45 min, and then poured into a mixture of 20 mL saturated NaHCO$_3$ and 20 mL ethyl acetate. The separated organic layer was washed with 20 mL saturated NaHCO₃, washed with 20 mL brine, dried (Na₂SO₄), filtered, concentrated and purified by silica gel chromatography (40-80% ethyl acetate in hexanes) to give trans-4-hydroxy-N-((trans-4-(4-methoxy-3-methylphenyl)cyclohexyl)methyl)-N-(3-(3-methoxyazetidin-1-yl)phenyl)cyclohexanecarboxamide (61 mg, 66%) as a white foam. ¹H NMR (400 MHz, DMSO-d₆): δ 7.25 (t, 1H), 6.98-6.93 (m, 2H), 6.78 (d, 1H), 6.56 (d, 1H), 6.44 (d, 1H), 6.28 (br s, 1H), 4.43 (d, 1H), 4.36-4.29 (m, 1H), 4.09-4.03 (m, 2H), 3.72 (s, 3H), 3.64-3.58 (m, 2H), 3.52-3.45 (m, 2H), 3.24 (s, 3H), 3.30-3.22 (m, 1H), 2.38-2.28 (m, 1H), 2.09 (s, 3H), 2.10-2.00 (m, 1H), 1.78-1.67 (m, 6H), 1.63-1.55 (m, 2H), 1.47-1.34 (m, 3H), 1.34-1.22 (m, 2H), 1.09-0.97 (m, 2H), 0.84-0.72 (m, 2H); LCMS: 521.5 [M+H]⁺.

The Compounds below were synthesized from Intermediate 2.6 or 2.7 and the appropriate amine following the procedures described for Compound 45.

| Cmpd | Structure | Name | [M + H]⁺ |
|---|---|---|---|
| 46 | 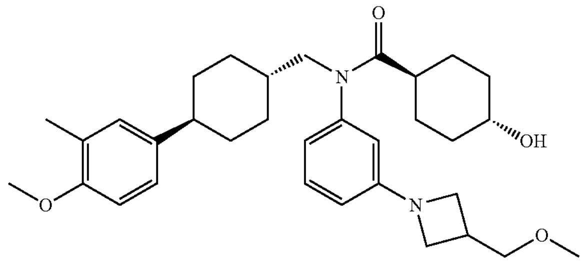 | trans-4-Hydroxy-N-((trans-4-(4-methoxy-3-methylphenyl)cyclohexyl)methyl)-N-(3-(3-(methoxymethyl)azetidin-1-yl)phenyl)cyclohexanecarboxamide | 535.9 |
| 47 | 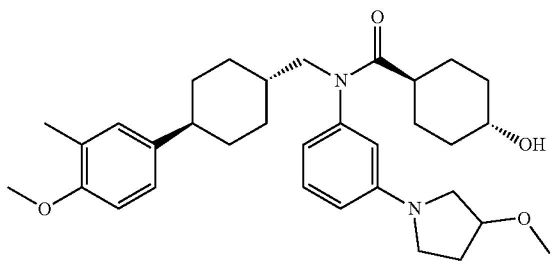 | trans-4-Hydroxy-N-((trans-4-(4-methoxy-3-methylphenyl)cyclohexyl)methyl)-N-(3-(3-methoxypyrrolidin-1-yl)phenyl)cyclohexanecarboxamide | 535.9 |
| 48 | 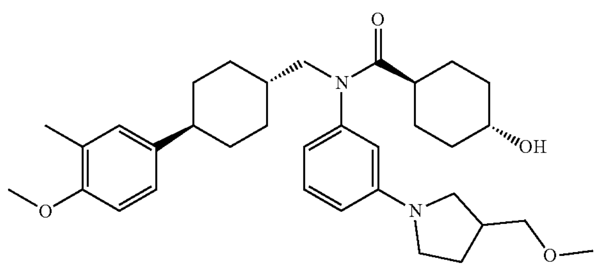 | trans-4-Hydroxy-N-((trans-4-(4-methoxy-3-methylphenyl)cyclohexyl)methyl)-N-(3-(3-(methoxymethyl)pyrrolidin-1-yl)phenyl)cyclohexanecarboxamide | 549.9 |
| 49 | 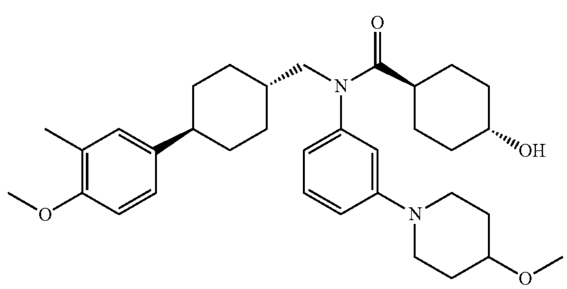 | trans-4-Hydroxy-N-((trans-4-(4-methoxy-3-methylphenyl)cyclohexyl)methyl)-N-(3-(4-methoxypiperidin-1-yl)phenyl)cyclohexanecarboxamide | 549.5 |
| 50 | 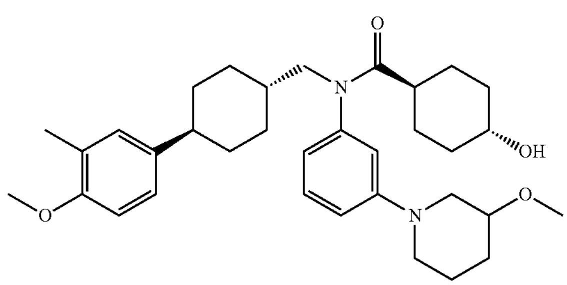 | trans-4-Hydroxy-N-((trans-4-(4-methoxy-3-methylphenyl)cyclohexyl)methyl)-N-(3-(3-methoxypiperidin-1-yl)phenyl)cyclohexanecarboxamide | 549.6 |

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection

Example A-2: Oral Solution

To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Example B-1: In Vitro FXR Assay (PGL3)

Seeding

CV-1 cells were seeded at a density of 2,000,000 cells in a T175 flask with DMEM+10% charcoal double-stripped FBS and incubated at 37° C. in a 5% $CO_2$ for 18 h (O/N).

Transfection

After 18 h of incubation, the medium in the T175 flask was changed with fresh DMEM+10% charcoal super-stripped serum.

To prepare the transfection reaction mixture, the transfection reagent (X-tremeGENE HP from Roche, Cat #06 366 236 001) was added in to a 1.5 mL microcentrifuge tube labelled "A" at a ratio of 1:3 (DNA in jag: transfection reagent in μL). OptiMEM medium (Life Technologies, Cat #31985-062) was added accordingly to provide a total volume of 1 mL. The transfection reaction mixture was then briefly vortexed and incubated at room temperature for 5 minutes.

In a separate 1.5 mL microcentrifuge tube labelled "B", 100 μL OptiMEM and plasmids XPD90Gal pCMXhFXRfl, pCMXhRXRfl+PGL3-ECRE*6-luc+CMX-YFP in the ratio 2 μg: 2 μg:18 μg:3 μg were added. This microcentrifuge tube "B" was then briefly vortexed and incubated at room temperature for 5 minutes.

The total volume in tube labelled "A" was then transferred in to tube labelled "B." The mixture was then briefly vortexed and the transfection:DNA complex was then incubated for about 15-20 minutes at room temperature.

Following incubation, the transfection reagent/DNA mixture complex was then added to cells in the T175 flask and the cells were incubated at 8 h (O/N) at 37° C. in 5% $CO_2$.

Test Compounds

In a 96 well plate, a half logarithmic serial dilution was prepared. OptiMEM was used as the diluent. Using any of one of the compounds described herein, a compound stock solution of 10 mM was prepared. An initial 1:100 dilution was made into the first well for a final concentration of 100 μM. The final concentrations in the 96-well plate was prepared by using a multichannel pipette to transfer 5 μL of the diluted compound to 384-well plate in quadruplicate.

Cells in T175 flask were trypsinized and cells were resuspending in 40 mL phenol red free DMEM+10% charcoal super-stripped FBS. Typically, one T175 flask was sufficient to seed two 384 well plates. CV-1 cells were seeded at 45 μL cell suspension/well using a multi-channel pipet or a 384 multidrop dispenser. The cells were then incubated for 18 hrs, overnight.

Reading

After removing the plates from the incubator, the medium was flicked out of plate and 384 well plate was turned upside down onto paper towel. The remaining medium was gently tapped out. 15 μL lysis buffer was then added to each well using a multichannel pipet or a 384 well multi-drop dispenser. After incubation for 10 minutes at room temperature on shaker, 30 μL Luciferase buffer was added to each well. Luminescence counts were taken immediately using the Perkin Elmer Envision.

The ability of the compounds disclosed herein to inhibit FXR activity was quantified and the respective $EC_{50}$ value was determined. Table 3 provides the activity of various compounds disclosed herein. Fex=fexaramine.

TABLE 3

| Compound No | Cmpd/Fex |
|---|---|
| 1 | +++ |
| 2 | ++ |
| 3 | +++ |
| 4 | +++ |
| 5 | + |
| 6 | + |
| 7 | ++ |
| 8 | + |
| 9 | ++ |
| 10 | + |
| 11 | + |
| 12 | ++ |
| 13 | + |
| 14 | +++ |

TABLE 3-continued

| Compound No | Cmpd/Fex |
|---|---|
| 15 | + |
| 16 | ++ |
| 17 | ++ |
| 18 | + |
| 19 | + |

Where 'Cmpd/Fex' denotes the ratio of the $EC_{50}$ for the test compound relative to the $EC_{50}$ of the Fexaramine control.
'+++' means Cmpd/Fex < 10;
'++' means Cmpd/Fex > 10 & <100;
'+' means Cmpd/Fex > 100.

Example B-2: In Vitro FXR Assay (TK)

Seeding

CV-1 cells were seeded at a density of 2,000,000 cells in a T175 flask with DMEM+10% charcoal double-stripped FBS and incubated at 37° C. in 5% $CO_2$ for 18 h (O/N).

Transfection

After 18 h of incubation, the medium in the T175 flask was changed with fresh DMEM+10% charcoal super-stripped serum. In a polypropylene tube, 2500 μL OptiMEM (Life Technologies, Cat #31985-062) was combined with expression plasmids for hFXR, hRXR, TK-ECRE-luc and pCMX-YFP. The tube was then briefly vortexed and incubated at room temperature for 5 minutes. Transfection reagent (X-tremeGENE HP from Roche, Cat #06 366 236 001) was added to the OptiMEM/plasmid mixture vortexed and incubated at room temperature for 20 minutes. Following incubation, the transfection reagent/DNA mixture complex was added to cells in the T175 flask and the cells were incubated at 37° C. in 5% $CO_2$ for 18 h (O/N).

Test Compounds

Compounds were serially diluted in DMSO and added to transfected CV-1 cells. The cells were then incubated for 18 hrs. The next day cells were lysed and examined for luminescence.

Representative data for exemplary compounds disclosed herein is presented in the following table.

TABLE 4

| Compound No | TK hFXR: $EC_{50}$ (μM) |
|---|---|
| 1 | +++ |
| 2 | + |
| 3 | + |
| 3.1 | +++ |
| 4 | ++ |
| 5 | + |
| 6 | + |
| 7 | ++ |
| 8 | + |
| 9 | +++ |
| 10 | + |
| 11 | + |
| 12 | + |
| 13 | +++ |
| 14 | +++ |
| 15 | +++ |
| 16 | ++ |
| 17 | + |
| 18 | ++ |
| 19 | + |
| 20 | + |
| 21 | + |
| 22 | +++ |
| 23 | ++ |
| 24 | ++ |
| 25 | + |
| 26 | + |
| 27 | +++ |
| 28 | ++ |
| 29 | +++ |
| 30 | + |
| 31 | +++ |
| 32 | + |
| 33 | ++ |
| 34 | + |
| 35 | +++ |
| 36 | + |
| 37 | + |
| 38 | + |
| 39 | + |
| 40 | + |
| 41 | + |
| 42 | + |
| 43 | +++ |
| 44 | + |
| 45 | +++ |
| 46 | +++ |
| 47 | ++ |
| 48 | ++ |
| 49 | +++ |
| 50 | + |

Where '+++' means $EC_{50} \leq 3$;
'++' means $EC_{50} > 3$ & <10;
'+' means $EC_{50} \geq 10$.
Compounds with a maximum efficacy of <25% of the Fexarmine control were classified as '+'

Example B-3: NASH Activity Study (STZ Model)

NASH can be induced in male C57BL/6 by a single subcutaneous injection of 200 ug STZ 2 days after birth followed by feeding high fat diet (HFD) ad libitum after 4 weeks of age. While continuing HFD, compounds can be dosed for 4-8 weeks to determine the effects on NASH. Fasting glucose can be measured throughout the study with a hand held glucose meter. Serum alanine aminotransferase (ALT), aspartate aminotransferase (AST) and triglyceride (TG) can be measured by a clinical chemistry analyzer. The contents of TG in the liver tissue can be measured using the Triglyceride E-test kit (Wako, Tokyo, Japan). Histological analysis of liver sections can be performed on tissue embedded in Tissue-TEK O.C.T. compound, snap frozen in liquid nitrogen, and stored at −80 C. The sections can be cut (5 um), air dried and fixed in acetone. For hematoxylin and eosin staining, liver sections can be prefixed by Bouin's solution and then stained with hematoxylin and eosin solution. The degree of (zone-3) liver fibrosis can be assessed with Sirius red staining.

Example B-4 NASH Activity Study (AMLN Model)

NASH is induced in male C57BL/6 mice by diet-induction with AMLN diet (DIO-NASH) (D09100301, Research Diet, USA) (40% fat (18% trans-fat), 40% carbohydrates (20% fructose) and 2% cholesterol). The animals are kept on the diet for 29 weeks. After 26 weeks of diet induction, liver biopsies are performed for base line histological assessment of disease progression (hepatosteatosis and fibrosis), stratified and randomized into treatment groups according to liver fibrosis stage, steatosis score, and body weight. Three weeks after biopsy the mice are stratified into treatment groups and dosed daily by oral gavage with FXR agonists for 8 weeks. At the end of the study liver biopsies are performed to assess hepatic steatosis and fibrosis by examining tissue sections stained with H&E and Sirius Red, respectively. Total collagen content in the liver is measured by colorimetric determination of hydroxyproline residues by acid hydrolysis of collagen. Triglycerides and total cholesterol content in liver homogenates are measured in single determinations using autoanalyzer Cobas C-111 with commercial kit (Roche Diagnostics, Germany) according to manufacturer's instructions.

Example B-5: Intrahepatic Cholestasis Model

Experimental intrahepatic cholestasis induced by 17a-ethynylestradiol (EE2) treatment in rodents is a widely used in vivo model to examine the mechanisms involved in estrogen-induced cholestasis. Intrahepatic cholestasis can be induced in adult male mice by subcutaneous injection of 10 mg/kg 17a-ethynylestradiol (E2) daily for 5 days. Testing of FXR ligands can be performed by administration of compounds during E2 induction of cholestasis. Cholestatic effects can be quantitated by assessing liver/body weight ratio and measuring serum total bile acids and alkaline phosphatase levels can be measured using reagents and controls from Diagnostic Chemicals Ltd. and the Cobas Mira plus CC analyzer (Roche Diagnostics). For histology and mitosis measurements, liver samples from each mouse can be fixed in 10% neutral buffered formalin. Slides are stained with hematoxylin and eosin using standard protocols and examined microscopically for structural changes. Hepatocyte proliferation is evaluated by immunohistochemical staining for Ki67.

Example B-6: Direct Target Gene Regulation

Direct target gene regulation by FXR ligands can be assessed by dosing mice either acutely or chronically with compounds and collecting tissues at various time points after dosing. RNA can be isolated from tissues such as the ileum and liver, and reverse transcribed to cDNA for quantitative PCR analysis of genes known in the literature to be directly and indirectly regulated by FXR such as SHP, BSEP, IBABP, FGF15, Cyp7a1, Cyp8b1 and C3.

Example B-7: Mouse PK Study

The plasma pharmacokinetics of any one of the compounds disclosed herein as a test article test article is measured following a single bolus intravenous and oral administration to mice (CD-1, C57BL, and diet induced obesity mice). Test article is formulated for intravenous administration in a vehicle solution of DMSO, PEG400, hydroxypropyl-β-cyclodextrin (HPβCD) and is administered at a dose volume of 3 mL/kg at selected dose levels. An oral dosing formulation is prepared in appropriate oral dosing vehicles (vegetable oils, PEG400, Solutol, citrate buffer, or carboxymethyl cellulose) and is administered at a dose volume of 5~10 mL/kg at selected dose levels. Blood samples (approximately 0.15 mL) are collected by cheek pouch method at pre-determined time intervals post intravenous or oral doses into tubes containing EDTA. Plasma is isolated by centrifugation of blood at 10,000 g for 5 minutes, and aliquots are transferred into a 96-well plate and stored at −60° C. or below until analysis.

Calibration standards of test article are prepared by diluting DMSO stock solution with DMSO in a concentration range. Aliquots of calibration standards in DMSO are combined with plasma from naïve mouse so that the final concentrations of calibration standards in plasma are 10-fold lower than the calibration standards in DMSO. PK plasma samples are combined with blank DMSO to match the matrix. The calibration standards and PK samples are combined with ice-cold acetonitrile containing an analytical internal standard and centrifuged at 1850 g for 30 minutes at 4° C. The supernatant fractions are analyzed by LC/MS/MS and quantitated against the calibration curve. Pharmacokinetic parameters (area under the curve (AUC), $C_{max}$, $T_{max}$, elimination half-life ($T_{1/2}$), clearance (CL), steady state volume of distribution ($V_{dss}$), and mean residence time (MRT)) are calculated via non-compartmental analysis using Microsoft Excel (version 2013).

Example B-8: Rat ANIT Model

A compound described herein is evaluated in a chronic treatment model of cholestasis over a range of doses from 0.01 to 10 mg/kg. This model is used to evaluate the suitability of the use of FXR agonists, e.g. a compound described herein, for the treatment of cholestatic liver disorders such as bile acid malabsorption (e.g., primary or secondary bile acid diarrhea), bile reflux gastritis, collagenous colitis, lymphocytic colitis, diversion colitis, indeterminate colitis, Alagille syndrome, biliary atresia, ductopenic liver transplant rejection, bone marrow or stem cell transplant associated graft versus host disease, cystic fibrosis liver disease, and parenteral nutrition-associated liver disease.

Rats are treated with alpha-naphthylisothiocyanate (ANIT) (0.1% w/w) in food for 3 days prior to treatment with a compound described herein, at doses from 0.01 to 10 mg/kg ("Veh"). A noncholestatic control group is fed standard chow diet without ANIT, and serves as the noncholestatic control animals ("Control"). After 14 days of oral dosing, rat serum is analyzed for levels of analytes. LLQ, lower limit of quantitation. Mean±SEM; n=5.

Levels of hepatobiliary injury indicators are measured in rat serum, such as elevated levels of circulating aspartate aminotransferase (AST), alanine aminotransferase (ALT), bilirubin and bile acids. ANIT exposure induces profound cholestasis and hepatocellular damage. A compound that improves many of these indicators is useful in the treatment of the aforementioned diseases or conditions.

Reductions in the accumulation of bile acids in the liver, enhancements in bile acid excretion in the biliary tract and inhibition of bile acid synthesis is consistent with the pharmacological action of a FXR agonist. An improvement in the serum conjugated bilirubin (a direct indicator for hepatic function) implies recovery from cholestasis with improved bile excretion.

Furthermore, an analysis is made to ascertain the effects of the compound described herein on serum FGF15 fibroblast growth factor 15 (FGF15 in rodent; FGF19 in human) expression, a hormone that is secreted in the portal blood and signals to the liver to repress Cyp7a1 expression synergistically with SHP. The direct FXR-dependent induction of FGF15/19 along with FGF15/19's anti-cholestatic properties makes it a convenient serum biomarker for detecting target engagement of FXR agonists.

Serum FGF15 levels are quantified using an FGF15 Meso Scale Discovery (MSD) assay. For example, Mouse FGF15 antibody from R&D Systems (AF6755) is used both as capture and detection antibody in the assay. MSD SULFO-TAG NHS-Ester is used to label the FGF15 antibody. MSD standard 96-well plates are coated with the FGF15 capture antibody and the plates are blocked with MSD Blocker A (R93AA-2). After washing the plate with PBS+0.05% Tween 20, MSD diluent 4 is dispensed into each well and incubated for 30 min. 25 pi of calibrator dilutions or samples (serum or EDTA plasma) are dispensed into each well and incubated with shaking at RT.

After washing, detection antibody is added and incubated with shaking for 1 h at RT. After washing and the addition of MSD Read buffer (R92TC-2), the plate is read on an MSD SECTOR Imager 6000. Plots of the standard curve and unknown samples are calculated using MSD data analysis software.

The examples and embodiments described herein are for illustrative purposes only and various modifications or changes suggested to persons skilled in the art are to be included within the spirit and purview of this application and scope of the appended claims.

What is claimed is:

1. A compound that has the structure of Formula (I), or a pharmaceutically acceptable salt or solvate thereof:

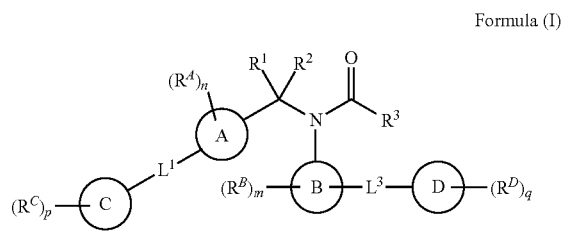

Formula (I)

wherein
$R^1$ and $R^2$ are each independently selected from H, D, F, $C_1$-$C_4$alkyl, and $C_1$-$C_4$fluoroalkyl;
or $R^1$ and $R^2$ are taken together with the carbon atom to which they are attached to form a substituted or unsubstituted $C_3$-$C_{10}$cycloalkyl, or substituted or unsubstituted $C_2$-$C_{10}$heterocycloalkyl;
$R^3$ is a substituted or unsubstituted $C_3$-$C_{10}$cycloalkyl, wherein
  if $R^3$ is substituted then $R^3$ is substituted with one or more $R^{12}$ groups;
  each $R^{12}$ is independently selected from D, halogen, —CN, —NO$_2$, —OR$^{10}$, —SR$^{10}$, —S(=O)R$^{11}$, —S(=O)$_2$R$^{11}$, —S(=O)$_2$N(R$^{10}$)$_2$, —NR$^{10}$S(=O)$_2$R$^{11}$, —C(=O)R$^{11}$, —OC(=O)R$^{11}$, —CO$_2$R$^{10}$, —OCO$_2$R$^{11}$, —N(R$^{10}$)$_2$, —C(=O)N(R$^{10}$)$_2$, —OC(=O)N(R$^{10}$)$_2$, —NR$^{10}$C(=O)R$^{11}$, —NR$^{10}$C(=O)OR$^{11}$, unsubstituted or substituted $C_1$-$C_{10}$alkyl, unsubstituted or substituted $C_1$-$C_{10}$fluoroalkyl, unsubstituted or substituted $C_2$-$C_{10}$alkenyl, unsubstituted or substituted $C_2$-$C_{10}$alkynyl, unsubstituted or substituted $C_1$-$C_{10}$heteroalkyl, unsubstituted or substituted $C_3$-$C_{10}$cycloalkyl, unsubstituted or substituted aryl, unsubstituted or substituted heteroaryl, and -$L^5$-$L^6$-$R^{13}$;
    $L^5$ is absent, —O—, —S—, —S(=O)—, —S(=O)$_2$—, —NR$^{10}$—, —C(=O)—, —C(=O)NH—, —NHC(=O)—, —C(=O)O—, —OC(=O)—, —OC(=O)NH—, —NHC(=O)NH—, —NHC(=O)O—, —(CH$_2$)$_r$—, or —(OCH$_2$CH$_2$)$_r$—, r is 1, 2, 3, or 4;
    $L^6$ is absent, unsubstituted or substituted $C_1$-$C_{10}$alkylene, unsubstituted or substituted $C_1$-$C_{10}$heteroalkylene, unsubstituted or substituted $C_2$-$C_{10}$alkenylene, unsubstituted or substituted $C_2$-$C_{10}$alkynylene, unsubstituted or substituted $C_3$-$C_{10}$cycloalkylene, unsubstituted or substituted $C_2$-$C_{10}$heterocycloalkylene, unsubstituted or substituted arylene, or unsubstituted or substituted heteroarylene;
    $R^{13}$ is H, halogen, —N(R$^{10}$)$_2$, unsubstituted or substituted $C_1$-$C_{10}$alkyl, unsubstituted or substituted $C_2$-$C_{10}$alkenyl, unsubstituted or substituted $C_2$-$C_{10}$alkynyl, unsubstituted or substituted $C_3$-$C_{10}$cycloalkyl, unsubstituted or substituted $C_2$-$C_{10}$heterocycloalkyl, unsubstituted or substituted aryl, or unsubstituted or substituted heteroaryl;
ring A is a monocyclic carbocycle that is phenyl or a $C_3$-$C_8$cycloalkyl, or monocyclic 5-membered or 6-membered heteroaryl;
each $R^A$ is independently selected from H, D, halogen, —CN, —OH, —OR$^{10}$, —SR$^{10}$, —S(=O)R$^{11}$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, and substituted or unsubstituted $C_1$-$C_6$heteroalkyl;
$L^1$ is absent;
ring C monocyclic carbocycle that is phenyl or a $C_3$-$C_8$cycloalkyl, bicyclic carbocycle that is indanyl, indenyl, or naphthyl, monocyclic $C_2$-$C_8$heterocycloalkyl, 5-membered or 6-membered heteroaryl, or bicyclic heterocycle that is a bicyclic $C_5$-$C_8$ heterocycloalkyl or a bicyclic $C_6$-$C_9$ heteroaryl;
each $R^C$ is independently selected from H, D, halogen, —CN, —OH, —OR$^{10}$, —SR$^{10}$, —S(=O)R$^{11}$, —NO$_2$, —N(R$^{10}$)$_2$, —S(=O)$_2$R$^{11}$, —NHS(=O)$_2$R$^{11}$, —S(=O)$_2$N(R$^{10}$)$_2$, —C(=O)R$^{11}$, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl, and substituted or unsubstituted phenyl;
ring B is a phenyl or monocyclic 5-membered or 6-membered heteroaryl
each $R^B$ is independently selected from H, D, halogen, —CN, —OH, —OR$^{10}$, —SR$^{10}$, —S(=O)R$^{11}$, —S(=O)$_2$R$^{11}$, —N(R$^{10}$)$_2$, —NHS(=O)$_2$R$^{11}$, —S(=O)$_2$N(R$^{10}$)$_2$, —C(=O)R, —OC(=O)R$^{11}$, —CO$_2$R$^{10}$, —OCO$_2$R$^{11}$, —C(=O)N(R$^{10}$)$_2$, —OC(=O)N(R$^{10}$)$_2$, —NR$^{10}$C(=O)N(R$^{10}$)$_2$, —NR$^{10}$C(=O)R$^{11}$, —NR$^{10}$C(=O)OR$^{11}$, substituted or unsubstituted $C_1$-$C_6$alkyl, substituted or unsubstituted $C_2$-$C_6$alkenyl, substituted or unsubstituted $C_2$-$C_6$alkynyl, substituted or unsubstituted $C_1$-$C_6$fluoroalkyl, substituted or unsubstituted $C_1$-$C_6$heteroalkyl;
$L^3$ is —$X^2$-$L^4$- or -$L^4$-$X^2$—;
$X^2$ is absent or —CH=CH—;
$L^4$ is absent;
ring D is phenyl, monocyclic N-containing $C_2$-$C_8$heterocycloalkyl, or monocyclic 5-membered or 6-membered heteroaryl
each $R^D$ is independently selected from H, D, halogen, —CN, —OH, —OR$^{10}$, —SR$^{10}$, —S(=O)R$^{11}$, —S(=O)₂R¹¹, —N(R¹⁰)₂, —NHS(=O)₂R¹¹, —S(=O)₂N(R¹⁰)₂, —C(=O)R¹, —OC(=O)R¹¹, —CO₂R¹⁰, —OCO₂R¹¹, —C(=O)N(R¹⁰)₂, —OC(=O)N(R¹⁰)₂, —NR¹⁰C(=O)N(R¹⁰)₂, —NR¹⁰C(=O)R¹¹, —NR¹⁰C(=O)OR¹¹, substituted or unsubstituted C₁-C₆alkyl, substituted or unsubstituted C₂-C₆alkenyl, substituted or unsubstituted C₂-C₆alkynyl, substituted or unsubstituted C₁-C₆fluoroalkyl, substituted or unsubstituted C₁-C₆heteroalkyl, unsubstituted or substituted C₃-C₁₀cycloalkyl, and substituted or unsubstituted C₂-C₁₀heterocycloalkyl;

each R¹⁰ is independently selected from H, substituted or unsubstituted C₁-C₆alkyl, substituted or unsubstituted C₁-C₆fluoroalkyl, substituted or unsubstituted C₃-C₆cycloalkyl, substituted or unsubstituted phenyl, substituted or unsubstituted monocyclic heteroaryl, and substituted or unsubstituted benzyl;

or two R¹⁰ on the same N atom are taken together with the N atom to which they are attached to form a N-containing heterocycle;

each R¹¹ is independently selected from substituted or unsubstituted C₁-C₆alkyl, substituted or unsubstituted C₁-C₆heteroalkyl, substituted or unsubstituted C₁-C₆fluoroalkyl, substituted or unsubstituted C₃-C₆cycloalkyl, substituted or unsubstituted phenyl, substituted or unsubstituted monocyclic heteroaryl, and substituted or unsubstituted benzyl;

m is 0, 1, or 2;

n is 0, 1, or 2;

p is 0, 1, 2, 3, or 4; and q is 0, 1, 2, 3, or 4.

2. The compound of claim 1, or a pharmaceutically acceptable salt or solvate thereof, wherein:

R¹ and R² are each independently selected from H and D; and wherein the groups

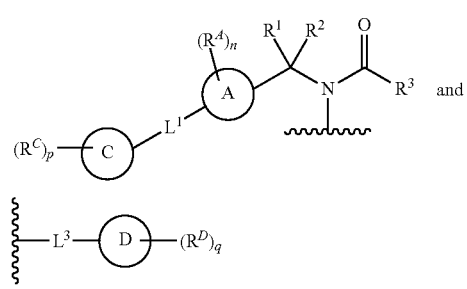

and are in a 1,3-relationship on ring B.

3. The compound of claim 2, or a pharmaceutically acceptable salt or solvate thereof, wherein:

ring B is phenyl; or ring B is monocyclic 6-membered heteroaryl selected from pyridinyl, pyrimidinyl, pyrazinyl, and pyridazinyl.

4. The compound of claim 3, or a pharmaceutically acceptable salt or solvate thereof, wherein:

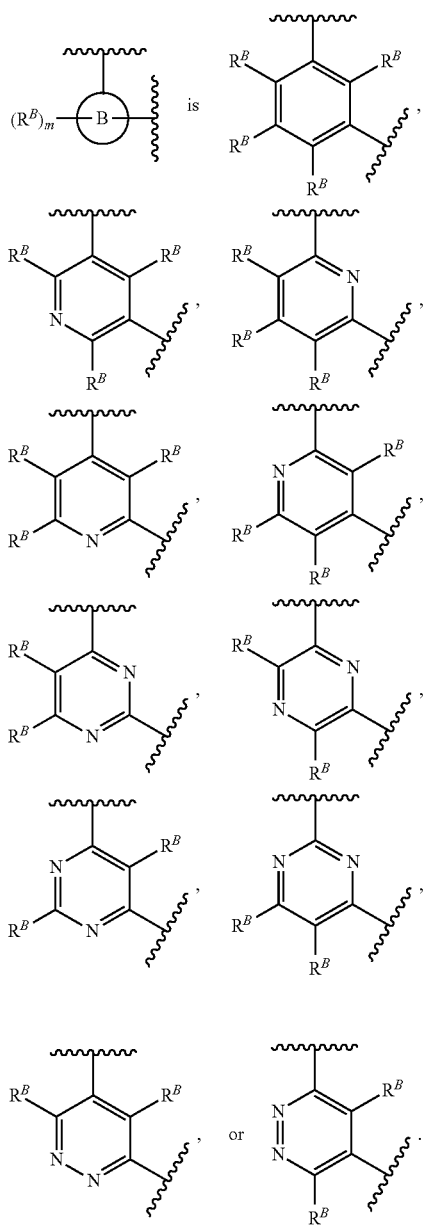

5. The compound of claim 4, or a pharmaceutically acceptable salt or solvate thereof, wherein:

ring D is phenyl; or ring D is monocyclic heteroaryl selected from furanyl, thienyl, pyrrolyl, oxazolyl, thiazolyl, imidazolyl, pyrazolyl, triazolyl, tetrazolyl, isoxazolyl, isothiazolyl, oxadiazolyl, thiadiazolyl, pyridinyl, pyrimidinyl, pyrazinyl, and pyridazinyl; or ring D is a monocyclic heterocycle that is a monocyclic C₂-C₈heterocycloalkyl containing at least 1 N atom in the ring that is selected from aziridinyl, azetidinyl, pyrrolidinyl, pyrrolidinonyl, pyrrolidine-2,5-dionyl, piperidinyl, piperidin-2-onyl, piperazinyl, morpholinyl, thiomorpholinyl, and azepanyl.

6. The compound of claim 5, or a pharmaceutically acceptable salt or solvate thereof, wherein:

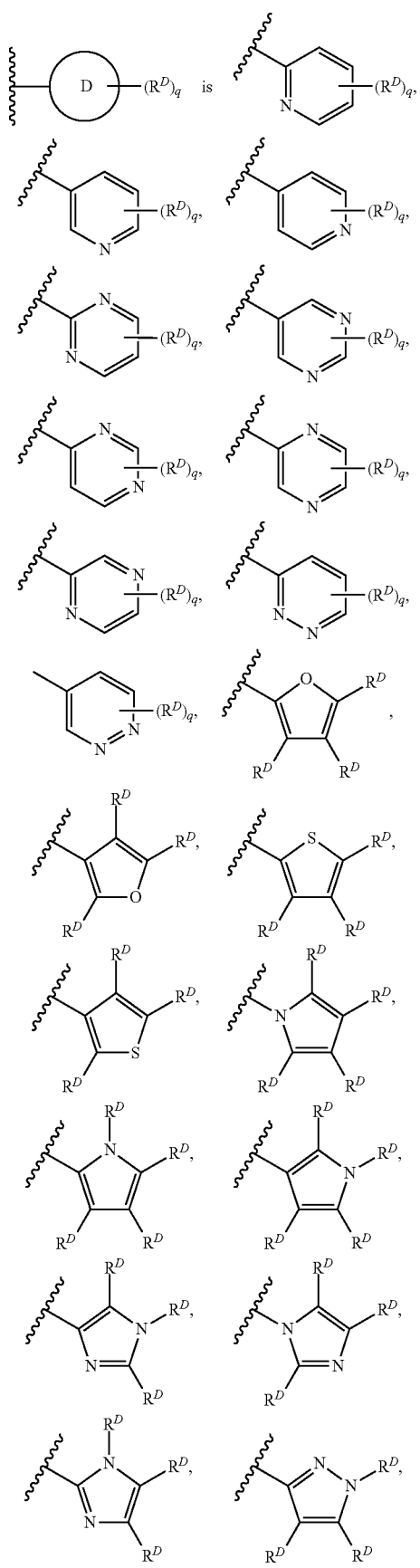
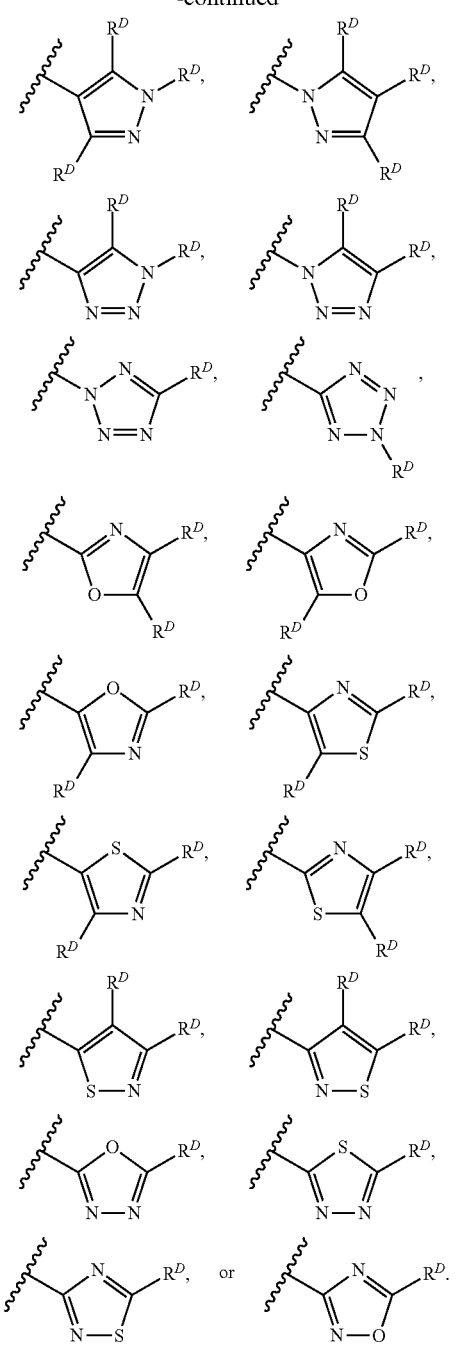

7. The compound of claim 6, or a pharmaceutically acceptable salt or solvate thereof, wherein:

$L^3$ is absent.

8. The compound of claim 7, or a pharmaceutically acceptable salt or solvate thereof, wherein:

ring A is monocyclic carbocycle that is phenyl or a $C_3$-$C_8$cycloalkyl that is selected from cyclopropyl, cyclobutyl, cyclopentyl, cyclohexyl, cycloheptyl, and cyclooctyl.

9. The compound of claim 8, or a pharmaceutically acceptable salt or solvate thereof, wherein the compound has the following structure:

Formula (II)

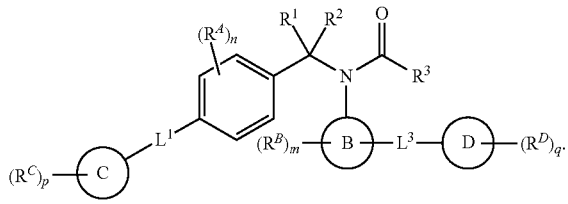

10. The compound of claim 9, or a pharmaceutically acceptable salt or solvate thereof, wherein:
   ring C is phenyl.

11. The compound of claim 10, or a pharmaceutically acceptable salt or solvate thereof, wherein:
   $R^3$ is a substituted or unsubstituted cyclohexyl.

12. The compound of claim 1, wherein the compound is:
   N-((4'-(Dimethylamino)-[1,1'-biphenyl]-4-yl)methyl)-N-(3-(5-methoxypyridin-3-yl)phenyl)cyclohexanecarboxamide;
   N-((4'-(Dimethylamino)-[1,1'-biphenyl]-4-yl)methyl)-N-(3'-methoxy-[1,1'-biphenyl]-3-yl)cyclohexanecarboxamide;
   N-((4'-(Dimethylamino)-[1,1'-biphenyl]-4-yl)methyl)-N-(3-(2-methoxypyridin-4-yl)phenyl)cyclohexanecarboxamide;
   N-((4'-(Dimethylamino)-[1,1'-biphenyl]-4-yl)methyl)-N-(4'-methoxy-[1,1'-biphenyl]-3-yl)cyclohexanecarboxamide;
   (E)-N-((4'-(Dimethylamino)-[1,1'-biphenyl]-4-yl)methyl)-N-(3-(2-(oxazol-2-yl)vinyl)phenyl)cyclohexanecarboxamide;
   N-([1,1'-Biphenyl]-3-yl)-N-((4'-fluoro-[1,1'-biphenyl]-4-yl)methyl)cyclohexanecarboxamide;
   N-([1,1'-Biphenyl]-3-yl)-N-((4'-(dimethylamino)-[1,1'-biphenyl]-4-yl)methyl)cyclohexanecarboxamide;
   N-((4'-(Dimethylamino)-[1,1'-biphenyl]-4-yl)methyl)-N-(3-(pyridin-3-yl)phenyl)cyclohexanecarboxamide;
   N-((4'-(Dimethylamino)-[1,1'-biphenyl]-4-yl)methyl)-N-(3-(5-methylpyridin-3-yl)phenyl)cyclohexanecarboxamide;
   N-((4'-(dimethylamino)-[1,1'-biphenyl]-4-yl)methyl)-N-(3-(6-methoxypyridin-2-yl)phenyl)cyclohexanecarboxamide;
   Methyl 5-(3-(N-((4'-(dimethylamino)-[1,1'-biphenyl]-4-yl)methyl)-cyclohexanecarboxamido)phenyl)nicotinate;
   (E)-N-((4'-(Dimethylamino)-[1,1'-biphenyl]-4-yl)methyl)-N-(3-(2-(pyridin-2-yl)vinyl)phenyl)cyclohexanecarboxamide;
   (E)-N-((4'-(Dimethylamino)-[1,1'-biphenyl]-4-yl)methyl)-N-(3-(2-(pyridin-4-yl)vinyl)phenyl)cyclohexanecarboxamide;
   N-((4'-(Dimethylamino)-[1,1'-biphenyl]-4-yl)methyl)-N-(3-(2-methoxythiazol-5-yl)phenyl)cyclohexanecarboxamide;
   N-((4'-(Dimethylamino)-[1,1'-biphenyl]-4-yl)methyl)-N-(3-(2-methoxythiazol-4-yl)phenyl)cyclohexanecarboxamide
   N-((4'-(Dimethylamino)-[1,1'-biphenyl]-4-yl)methyl)-N-(3-(5-methoxythiophen-2-yl)phenyl)cyclohexanecarboxamide;
   N-((4'-(Dimethylamino)-[1,1'-biphenyl]-4-yl)methyl)-N-(3-(4-methoxypyridin-2-yl)phenyl)cyclohexanecarboxamide;
   N-((4'-(Dimethylamino)-[1,1'-biphenyl]-4-yl)methyl)-N-(3-(5-ethylpyridin-3-yl)phenyl)cyclohexanecarboxamide;
   N-((4'-(Dimethylamino)-[1,1'-biphenyl]-4-yl)methyl)-N-(3-(2-methoxypyrimidin-4-yl)phenyl)cyclohexanecarboxamide;
   N-((4'-(Dimethylamino)-[1,1'-biphenyl]-4-yl)methyl)-N-(3-(6-methoxypyrimidin-4-yl)phenyl)cyclohexanecarboxamide;
   N-((4'-(Dimethylamino)-[1,1'-biphenyl]-4-yl)methyl)-N-(3-(6-methoxypyrazin-2-yl)phenyl)cyclohexanecarboxamide;
   N-((4'-(Dimethylamino)-[1,1'-biphenyl]-4-yl)methyl)-N-(3-(3-methoxyisothiazol-5-yl)phenyl)cyclohexanecarboxamide;
   N-((4'-(Dimethyl amino)-[1,1'-biphenyl]-4-yl)methyl)-N-(3-(2-methyl-3-oxo-2,3-dihydroisothiazol-5-yl)phenyl)cyclohexanecarboxamide;
   trans-4-Hydroxy-N-((trans-4-(4-methoxy-3-methylphenyl)cyclohexyl)methyl)-N-(3-(3-methoxyazetidin-1-yl)phenyl)cyclohexanecarboxamide;
   trans-4-Hydroxy-N-((trans-4-(4-methoxy-3-methylphenyl)cyclohexyl)methyl)-N-(3-(3-(methoxymethyl)azetidin-1-yl)phenyl)cyclohexanecarboxamide;
   trans-4-Hydroxy-N-((trans-4-(4-methoxy-3-methylphenyl)cyclohexyl)methyl)-N-(3-(3-methoxypyrrolidin-1-yl)phenyl)cyclohexanecarboxamide;
   trans-4-Hydroxy-N-((trans-4-(4-methoxy-3-methylphenyl)cyclohexyl)methyl)-N-(3-(3-(methoxymethyl)pyrrolidin-1-yl)phenyl)cyclohexanecarboxamide;
   trans-4-Hydroxy-N-((trans-4-(4-methoxy-3-methylphenyl)cyclohexyl)methyl)-N-(3-(4-methoxypiperidin-1-yl)phenyl)cyclohexanecarboxamide;
   trans-4-Hydroxy-N-((trans-4-(4-methoxy-3-methylphenyl)cyclohexyl)methyl)-N-(3-(3-methoxypiperidin-1-yl)phenyl)cyclohexanecarboxamide;
   or a pharmaceutically acceptable salt or solvate thereof.

13. A pharmaceutical composition comprising a compound of claim 1, or a pharmaceutically acceptable salt, or solvate thereof, and at least one pharmaceutically acceptable excipient.

14. A method of treating a liver disease or condition in a subject, comprising administering to the subject a therapeutically effective amount of one or more of the compounds of claim 1, or a pharmaceutically acceptable salt or solvate thereof.

15. The method of claim 14, wherein the liver disease or condition is primary biliary cirrhosis, primary sclerosing cholangitis, cholestasis, nonalcoholic steatohepatitis (NASH), or nonalcoholic fatty liver disease (NAFLD).

16. A method of treating inflammation in an intestinal region of a subject, comprising:
   administering to a gastrointestinal tract of the subject a therapeutically effective amount of one or more of the compounds of any one of claim 1, or a pharmaceutically acceptable salt or solvate thereof, thereby activating FXR receptors in the intestines, and thereby treating inflammation in the intestinal region of the subject; wherein the inflammation is associated with a condition selected from necrotizing enterocolitis, gastritis, ulcerative colitis, Crohn's disease, inflammatory bowel disease, irritable bowel syndrome, gastroenteritis, radiation induced enteritis, pseudomembranous colitis, chemotherapy induced enteritis, gastro-esophageal reflux disease (GERD), peptic ulcer, non-ulcer dyspepsia (NUD), celiac disease, intestinal celiac disease, post-surgical inflammation, gastric carcinogenesis or any combination thereof.

* * * * *